(12) United States Patent
Chan et al.

(10) Patent No.: US 11,230,599 B2
(45) Date of Patent: Jan. 25, 2022

(54) TUMOR MUTATIONAL LOAD

(71) Applicant: Memorial Sloan Kettering Cancer Center, New York, NY (US)

(72) Inventors: Timothy A. Chan, Cortlandt Manor, NY (US); Diego Chowell Puente, New York, NY (US); Robert M. Samstein, New York, NY (US); Luc Morris, New York, NY (US)

(73) Assignee: Memorial Sloan Kettering Cancer Center, New York, NY (US)

(*) Notice: Subject to any disclaimer, the term of this patent is extended or adjusted under 35 U.S.C. 154(b) by 339 days.

(21) Appl. No.: 16/141,528

(22) Filed: Sep. 25, 2018

(65) Prior Publication Data
US 2019/0092864 A1 Mar. 28, 2019

Related U.S. Application Data

(60) Provisional application No. 62/569,053, filed on Oct. 6, 2017, provisional application No. 62/562,977, filed on Sep. 25, 2017.

(51) Int. Cl.
| | |
|---|---|
| C07K 16/28 | (2006.01) |
| A61K 39/395 | (2006.01) |
| G16H 50/30 | (2018.01) |
| A61P 35/00 | (2006.01) |
| C12Q 1/6827 | (2018.01) |
| C12Q 1/6881 | (2018.01) |
| C12Q 1/6886 | (2018.01) |
| A61K 39/00 | (2006.01) |

(52) U.S. Cl.
CPC ........ *C07K 16/2827* (2013.01); *A61K 39/395* (2013.01); *A61P 35/00* (2018.01); *C07K 16/2818* (2013.01); *C07K 16/2896* (2013.01); *C12Q 1/6827* (2013.01); *C12Q 1/6881* (2013.01); *C12Q 1/6886* (2013.01); *G16H 50/30* (2018.01); *A61K 2039/505* (2013.01); *A61K 2039/507* (2013.01); *A61K 2039/80* (2018.08); *A61K 2039/812* (2018.08); *A61K 2039/86* (2018.08); *A61K 2039/868* (2018.08); *A61K 2039/876* (2018.08); *C07K 2317/76* (2013.01)

(58) Field of Classification Search
None
See application file for complete search history.

(56) References Cited

U.S. PATENT DOCUMENTS

| | | | |
|---|---|---|---|
| 2020/0109455 A1* | 4/2020 | Rabadan | C12Q 1/6886 |
| 2020/0258597 A1* | 8/2020 | Perera | G16B 20/20 |

FOREIGN PATENT DOCUMENTS

| | | | | |
|---|---|---|---|---|
| WO | WO 2016/081947 | * | 5/2016 | ............ A61K 39/00 |
| WO | WO-2016/081947 A2 | | 5/2016 | |
| WO | WO-2019/060894 A2 | | 3/2019 | |

OTHER PUBLICATIONS

Aptsiauri et al. (Role of Altered Expression of HLA Class I Molecules in Cancer Progression, p. 123-131 of Immune Mediated Diseases—From Theory to Therapy, Advances in Experimental Medicine and Biology, vol. 601, 2007).*
Cheng et al. (Journal of Molecular Diagnostics, 17(3): 215-264).*
Abraham, Mark, Performance enhancements for GROMACS nonbonded interactions on BlueGene, J Comput Chem, 32:2041-2046 (2011).
Alexandrov, L. et al., Signatures of mutational processes in human cancer, Nature, 500:415-421 (2013).
Anfossi, N. et al., Coordinated expression of Ig-like inhibitory MHC class I receptors and acquisition of cytotoxic function in human CD8+ T cells, J Immunol, 173:7223-7229 (2004).
Balachandran V. et al., Identification of unique neoantigen qualities in long-term survivors of pancreatic cancer, Nature, 551(7681):512-516 (2017).
Borghaei, H. et al., Nivolumab versus Docetaxel in Advanced Nonsquamous Non-Small-Cell Lung Cancer, N Engl J Med, 373(17):1627-1639 (2015).
Callahan, M. et al., Targeting T Cell Co-receptors for Cancer Therapy, Immunity, 44(5):1069-78 (2016).
Cao, H. et al., An integrated tool to study MHC region: accurate SNV detection and HLA genes typing in human MHC region using targeted high-throughput sequencing, PLoS One, 8:e69388 (2013).
Chalmers, Z. et al., Analysis of 100,000 human cancer genomes reveals the landscape of tumor mutational burden, Genome Med, 9:34 (2017).
Cheng, D. et al., Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology, J Mal Diagn, 17(3):251-264 (2015).
Chowell, D. et al., TCR contact residue hydrophobicity is a hallmark of immunogenic CD8(+) T cell epitopes, Proceedings of the National Academy of Sciences of the United States of America, 112:EI 754-EI 762 (2015).
Cibulskis, K. et al., Sensitive detection of somatic point mutations in impure and heterogeneous cancer samples, Nat. Biotechnol., 31(3):213-219 (2013).
Depristo, M. et al., A framework for variation discovery and genotyping using next-generation DNA sequencing data, Nature Genetics, 43(5):491-498 (2011).
Dyck, L. and Mills, KHG., Immune Checkpoints and their Inhibition in Cancer and Infectious Diseases, Eur J Immunol, 47(5):765-779 (2017).
Fellay, J. et al., A whole-genome association study of major determinants for host control of HIV-1, Science, 317:944-947 (2007).

(Continued)

*Primary Examiner* — Nelson B Moseley, II
(74) *Attorney, Agent, or Firm* — Choate, Hall & Stewart LLP; Brenda Herschbach Jarrell; Alexandra A. Bouza

(57) ABSTRACT

The present invention encompasses the discovery that the likelihood of a favorable response to cancer immunotherapy for a wide range of different cancers can be predicted through definition of a tumor mutational load threshold for the tumor (and/or the relevant immunotherapy).

16 Claims, 35 Drawing Sheets

(56) References Cited

OTHER PUBLICATIONS

Gao, K. et al., Effect of a single amino acid change in MHC class I molecules on the rate of progression to AIDS, New England Journal of Medicine, 344:1668-1675 (2001).
Gibney, G. et al., Predictive biomarkers for checkpoint inhibitor-based immunotherapy, Lancet Oncol., 17(12):e542-e551 (2016).
Goulder, P. and Walker, P., HIV and HLA Class I: An Evolving Relationship, Immunity, 37:426-440 (2012).
Gubin, M. et al., Checkpoint blockade cancer immunotherapy targets tumour-specific mutant antigens, Nature, 515:577-581 (2014).
H.I.V.C.S. International et al., The major genetic determinants of HIV-1 control affect HLA class I peptide presentation, Science, 330:1551-1557 (2010).
Hugo, W. et al., Genomic and Transcriptomic Features of Response to Anti-PD-1 Therapy in Metastatic Melanoma, Cell, 165(1):35-44 (2016).
Hyman, D. et al., Precision medicine at Memorial Sloan Kettering Cancer Center: clinical next-generation sequencing enabling next-generation targeted therapy trials, Drug Discov Today, 20:1422-1428 (2015).
International Search Report for PCT/US2018/052663 (Tumor Mutational Load and Checkpoint Immunotherapy, filed Sep. 25, 2018), issued by ISA/EP, 10 pages (dated Jun. 7, 2019).
Janjigian, Y. et al., Genetic Predictors of Response to Systemic Therapy in Esophagogastric Cancer, Cancer Discov, 8(1):49-58 (2018).
Johnson, D. et al., Targeted Next Generation Sequencing Identifies Markers of Response to PD-1 Blockade, Cancer Immunal Res, 4(11):959-967 (2016).
Jordan, E. et al., Prospective Comprehensive Molecular Characterization of Lung Adenocarcinomas for Efficient Patient Matching to Approved and Emerging Therapies, Cancer Discov, 7(6):596-609 (2017).
Kiyotani, K. et al., Comparison of exome-based HLA class I genotyping tools: identification of platform-specific genotyping errors. J Hum Genet, (2016).
Koboldt, D. et al., VarScan 2: somatic mutation and copy number alteration discovery in cancer by exome sequencing, Genome Res, 22(3):568-76 (2012).
Larson, D. et al., SomaticSniper: identification of somatic point mutations in whole genome sequencing data, Bioinformatics, 28(3):311-317 (2012).
Le, D. et al., PD-1 Blockade in Tumors with Mismatch-Repair Deficiency, N Engl J Med, 372:2509-2520 (2015).
Li, H. & Durbin, R., Fast and accurate short read alignment with Burrows-Wheeler transform, Bioinformatics, 25(14):1754-1760 (2009).
McGranahan, N. et al., Clonal neoantigens elicit T cell immunoreactivity and sensitivity to immune checkpoint blockade, Science, 351(6280):1463-1469 (2016).
McKenna, A. et al., The Genome Analysis Toolkit: a MapReduce framework for analyzing next-generation DNA sequencing data, Genome Res, 20:1297-1303 (2010).
Pearson, H. et al., MHC class I-associated peptides derive from selective regions of the human genome, J Clin Invest., 126(12):4690-4701 (2016).
Phillips, J. et al., Scalable molecular dynamics with NAMD, J Comput Chem, 26:1781-1802 (2005).
Riaz, N. et al., Recurrent SERPINB3 and SERPINB4 Mutations in Patients that Respond to Anti-CTLA4 Immunotherapy, Nat Genet., 48(11):1327-1329 (2016).
Riley, James L., PD-1 Signaling in Primary T Cells, Immunol Rev, 229(1): 114-125 (2009).
Rizvi, N. A. et al., Supplementary Materials for Mutational landscape determines sensitivity to PD-1 blockage in non-small cell lung cancer, Internet Citation (Apr. 3, 2015) retrieved from http://science.sciencemag.org/content/sci/suppl/2015/03/11/science.aaa1348.DC1/Rizvi-SM.pdf, pp. 1-31 (retrieved on Dec. 8, 2017).

Rizvi, N.A., et al., Mutational landscape determines sensitivity to PD-1 blockade in non-small cell lung cancer, Science, 348(6230):124-128 (2015).
Rooney, M. et al., Molecular and genetic properties of tumors associated with local immune cytolytic activity, Cell, 160(1-2):48-61 (2015).
Rosenberg, J. et al., Atezolizumab in patients with locally advanced and metastatic urothelial carcinoma who have progressed following treatment with platinum-based chemotherapy: a single-arm, multicentre, phase 2 trial, Lancet, 387(10031): 1909-1920 (2016).
Ross, D. et al., Next-Generation Assessment of Human Epidermal Growth Factor Receptor 2 (ERBB2) Amplification Status: Clinical Validation in the Context of a Hybrid Capture-Based, Comprehensive Solid Tumor Genomic Profiling Assay, J Mal Diagn, 19(2):244-254 (2017).
Saunders, C. et al., Strelka: accurate somaticsmall-variant calling from sequenced tumor-normal sample pairs, Bioinformatics, 28(14):1811-1817 (2012).
Schaefer, S. et al., A novel trafficking signal within the HLA-C cytoplasmic tail allows regulated expression upon differentiation of macrophages, J Immunol, 180:7804-7817 (2008).
Schumacher, T. and Schreiber, R., Neoantigens in cancer immunotherapy, Science, 348(6230):69-74 (2015).
Segal, N. et al., Epitope Landscape in Breast and Colorectal Cancer, Cancer Research, 68:889-892 (2008).
Shen, R. and Seshan, V., FACETS: allele-specific copy number and clonal heterogeneity analysis tool for high-throughput DNA sequencing, Nucleic Acids Research, 44, (2016).
Shukla, S. et al., Comprehensive analysis of cancer-associated somatic mutations in class I HLA genes, Nat Biotechnol, 33:1152-1158 (2015).
Sidney, J. et al., HLA class I supertypes: a revised and updated classification, BMC Immunol, 9:1 (2008).
Snyder, A. et al., Genetic Basis for Clinical Response to CTLA-4 Blockage in Melanoma, The New England Journal of Medicine, 371(23):2189-2199 (2014).
Szender, J. et al., HLA superfamily assignment is a predictor of immune response to cancer testis antigens and survival in ovarian cancer, Gynecol Oncol, 142(1):158-162 (2016).
Szolek, A. et al., OptiType: precision HLA typing from next-generation sequencing data, Bioinformatics, 30:3310-3316 (2014).
Topalian, S. et al., Safety, activity, and immune correlates of anti-PD-1 antibody in cancer, N Engl J Med, 366:2443-54 (2012).
Tran, E. et al., Immunogenicity of somatic mutations in human gastrointestinal cancers, Science, 350:1387-1390 (2015).
Tran, E. et al., T-Cell Transfer Therapy Targeting Mutant KRAS in Cancer, N Engl J Med, 375:2255-2262 (2016).
Van Allen, E.M. et al., Genomic correlates of response to CTLA-4 blockade in metastatic melanoma, Science, 350(6257):207-211 (2015).
Written Opinion for PCT/US2018/052663 (Tumor Mutational Load and Checkpoint Immunotherapy, filed Sep. 25, 2018), issued by ISA/EP, 11 pages (dated Jun. 7, 2019).
Zehir, A., et al., Mutational landscape of metastatic cancer revealed from prospective clinical sequencing of 10,000 patients, Nature Medicine, 23(6):703-713 (2017).
Bouffet, E. et al., Immune Checkpoint Inhibition for Hypermutant Glioblastoma Multiforme Resulting From Germline Biallelic Mismatch Repair Deficiency, J Clin Oneal, 34(19):2206-2211 (2016).
Carrington, M. et al., HLA and HIV-1: heterozygote advantage and B*35-Cw*04 disadvantage, Science, 283:1748-1752 (1999).
Chen, D. and Mellman, I., Elements of cancer immunity and the cancer-immune set point, Nature, 541:321-330 (2017).
Chowell, D. et al., Patient HLA class I genotype influences cancer response to checkpoint blockade immunotherapy, Science, 62:eaao4572 (2017).
Dibrino, M. et al., Identification of the peptide binding motif for HLA-B44, one of the most common HLA-B alleles in the Caucasian population, Biochemistry, 34(32):10130-8 (1995).
Doherty, P. and Zinkemagel, R., A biological role for the major histocompatibility antigens,. Lancet, 304(1):1406-1409 (1975).
Hill, A. et al., Common West African HLA Antigens Are Associated with Protection from Severe Malaria, Nature, 352:595-600 (1991).

(56) References Cited

OTHER PUBLICATIONS

Humphrey, W., et al., VMD: Visual molecular dynamics, J Mal Graph Model, 14(1):33-38 (1996).

Kiepiela, P. et al., Dominant influence of HLA-B in mediating the potential co-evolution of HIV and HLA, Nature, 432:769-774 (2004).

Larkin, A. et al., Combined Nivolumab and Ipilimumab or Monotherapy in Untreated Melanoma, N Engl J Med, 373(1):23-34 (2015).

Liu, P. et al., Observation of a dewetting transition in the collapse of the melittin tetramer, Nature, 437:159-162 (2005).

Parham, P. and Ohta, T., Population biology of antigen presentation by MHC class I molecules, Science, 272:67-74 (1996).

Riaz, N. et al., Tumor and Microenvironment Evolution during Immunotherapy with Nivolumab. In Review, 171(4):934-949, (2017).

Sette, A. and Sidney, J., Nine major HLA class I supertypes account for the vast preponderance of HLA-A and-B polymorphism, Immunogenetics, 50:201-212 (1999).

Snary, D. et al., Molecular structure of human histocompatibility antigens: the HLA-C series, Eur J Immunol, 7:580-585 (1977).

Thursz, M. et al., Heterozygote advantage for HLA class-II type in hepatitis B virus infection, Nat Genet, 17:11-12 (1997).

Trabace, S., HLA and disease associations, 1:S109-S113, Springer Science & Business Media, (2012).

Trachtenberg, E. et al., Advantage of rare HLA supertype in HIV disease progression, Nat Med, 9(7):928-935 (2003).

Tu, Y. et al., Destructive extraction of phospholipids from *Escherichia coli* membranes by graphene nanosheets, Nat Nanotechnol, 8:594-601 (2013).

Verdegaal E. et al., Neoantigen landscape dynamics during human melanoma-T cell interactions, Nature, 536(7614):91-5 (2016).

Zhou, R. et al., Hydrophobic collapse in multidomain protein folding, Science, 305:1605-1609 (2004).

Frampton G. et al., Assessment of tumor mutation burden from >60,000 clinical cancer patients using comprehensive genomic profiling. In: J Clin Oneal, vol. 34. 2016. 11558, Abstract Only Available.

Hellman, M. et al., Molecular determinants of response and resistance to anti-PD-(L) 1 blockade in patients with NSCLC profiled with targeted next-generation sequencing (NGS), J. Clin. Oncol., 35:9015-9015 (2017), Abstract Only Available.

\* cited by examiner

Figure 3
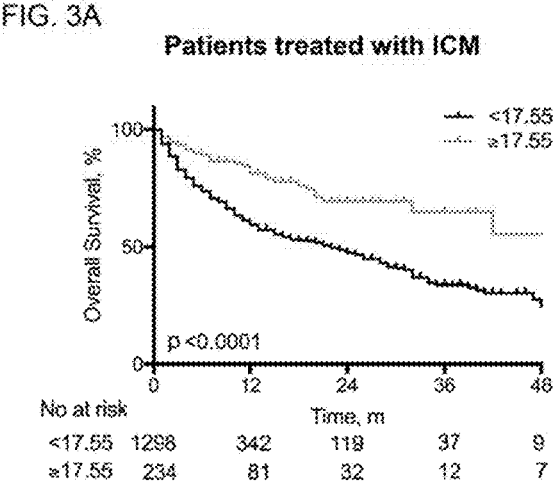
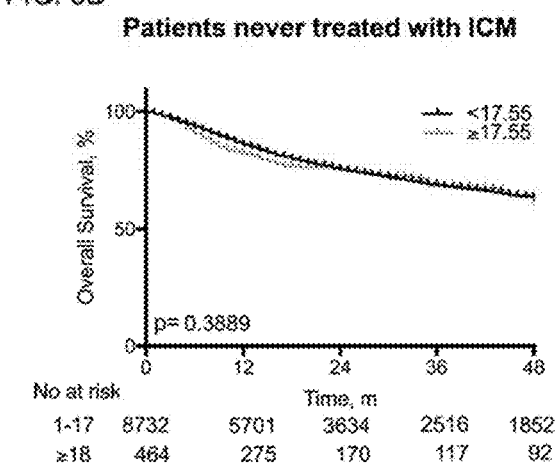

FIG. 6A
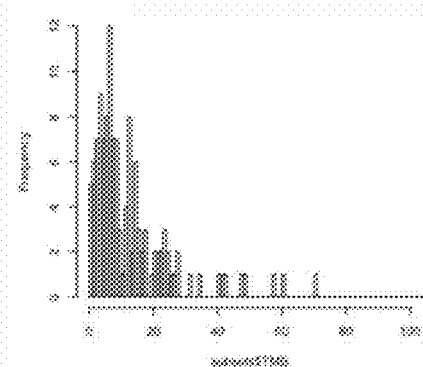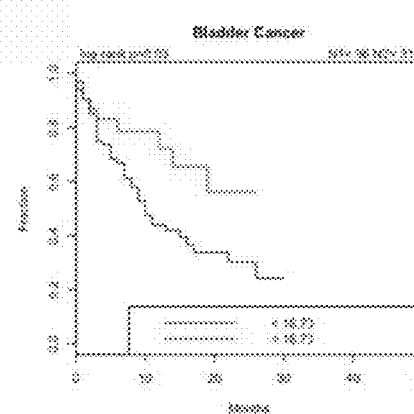
FIG. 6B
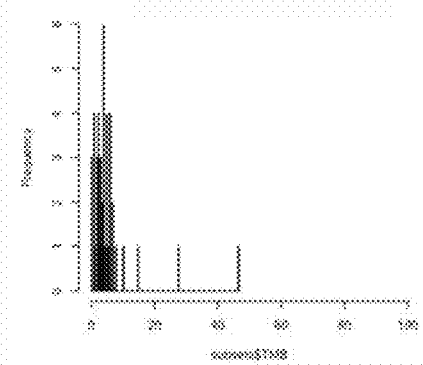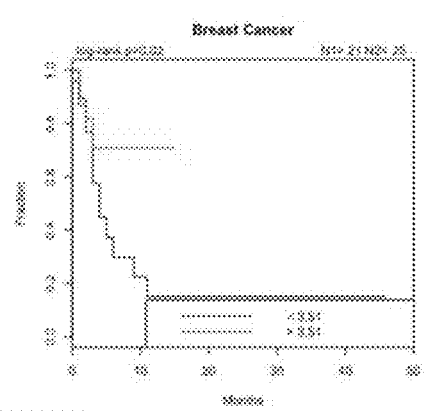
FIG. 6C
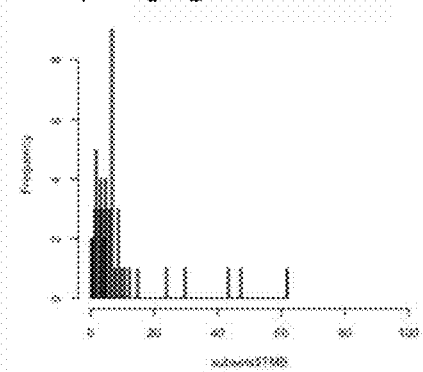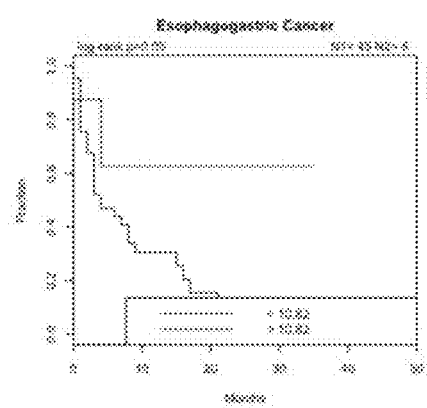
FIG. 6D
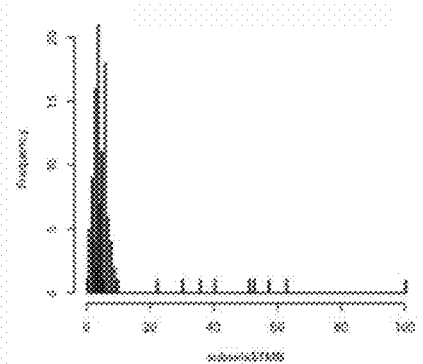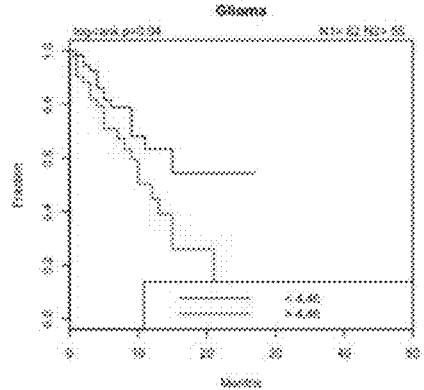

FIG. 6E
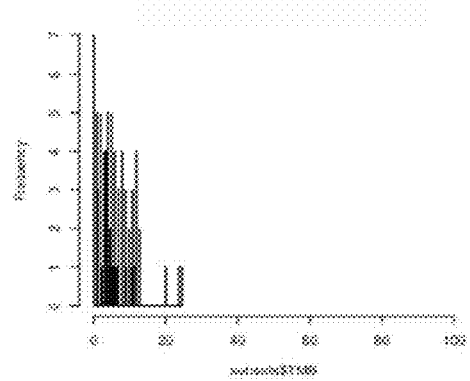 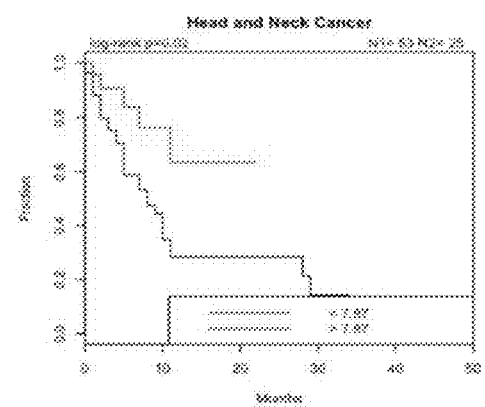
FIG. 6F
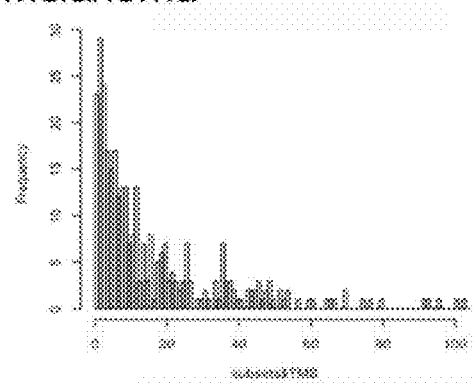 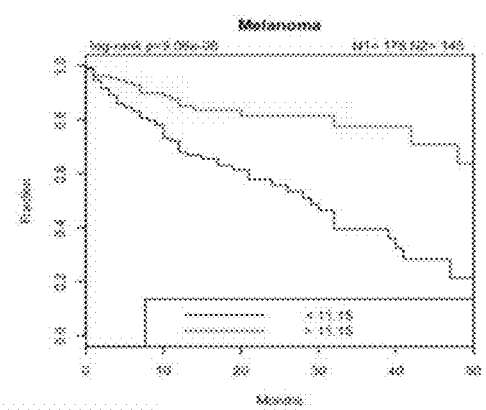
FIG. 6G
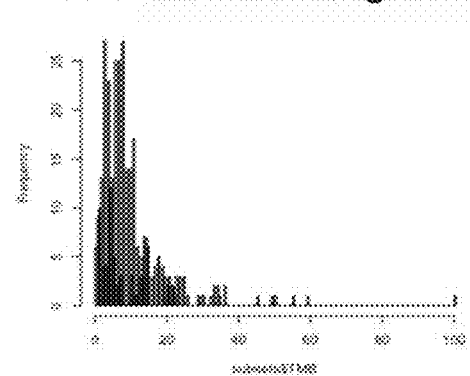 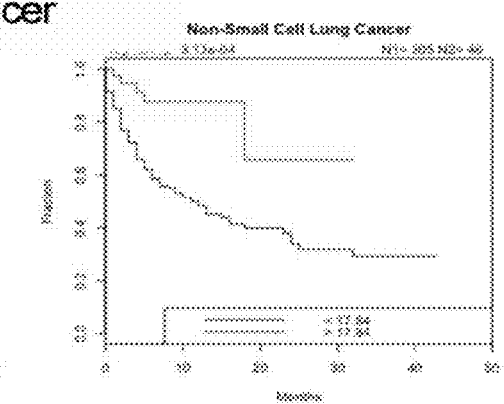
FIG. 6H
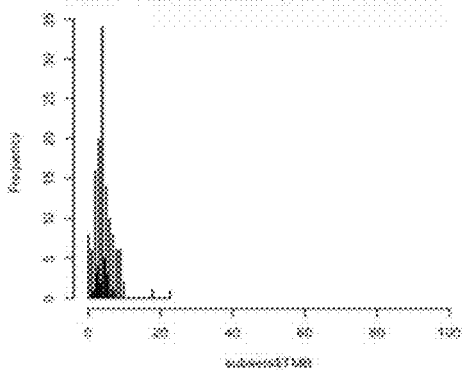 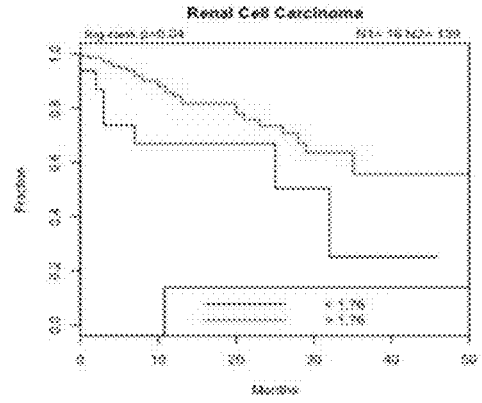

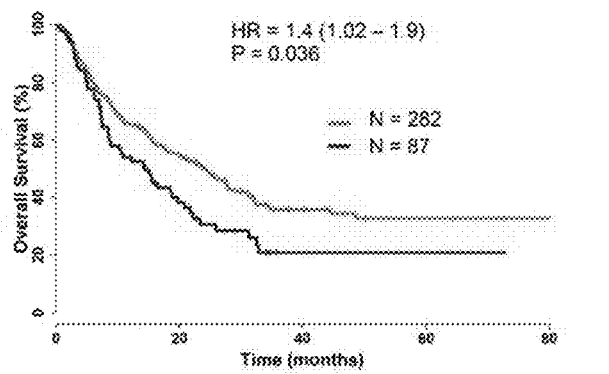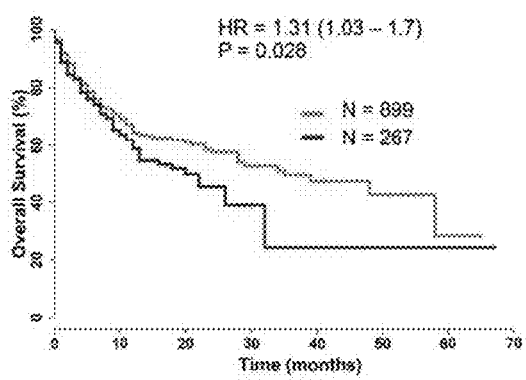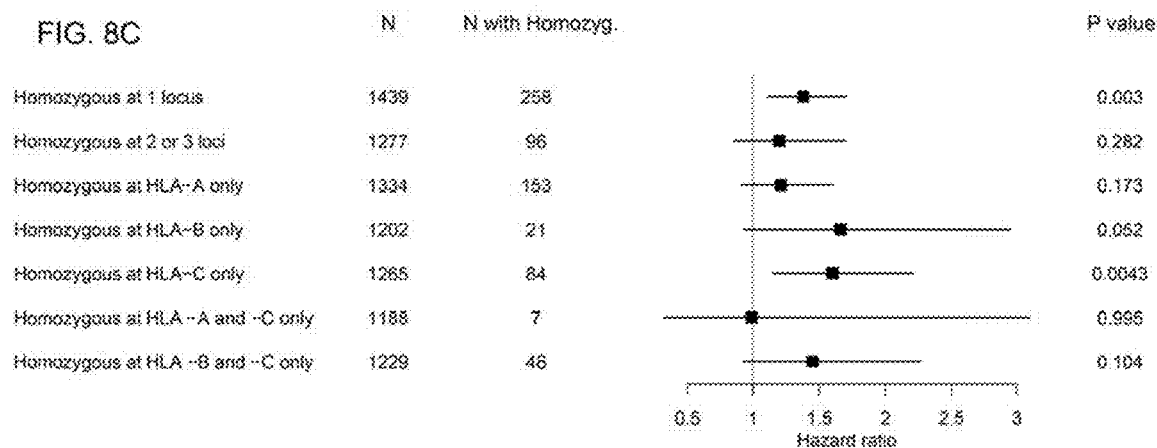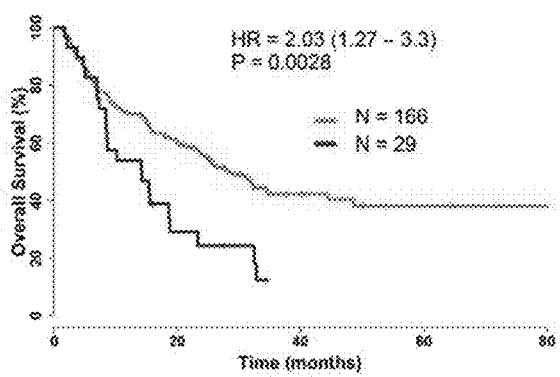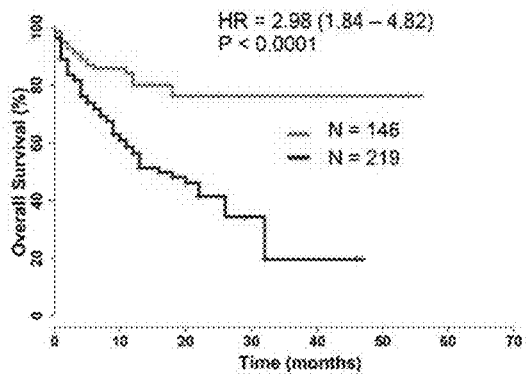

—— HLA-B44 (+)
—— HLA-B44 (−)

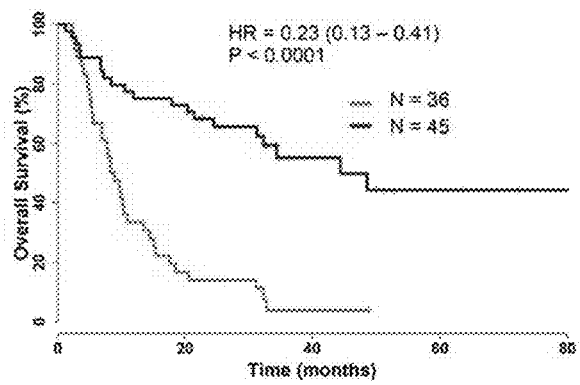
FIG. 9E
FIG. 9F
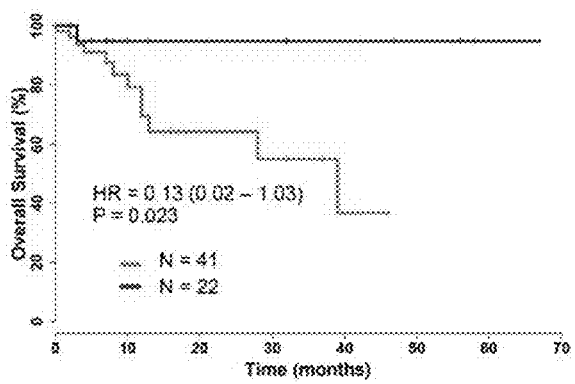
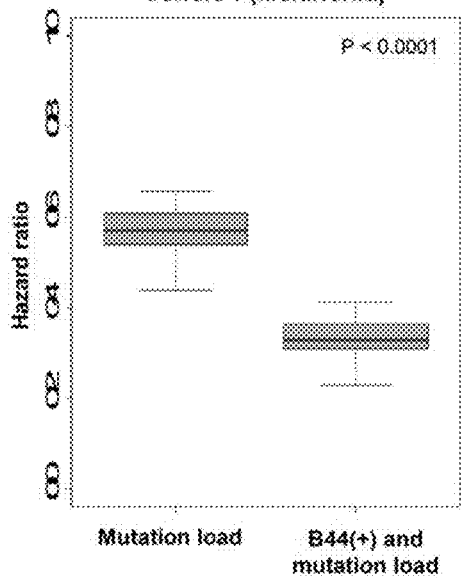
FIG. 9G
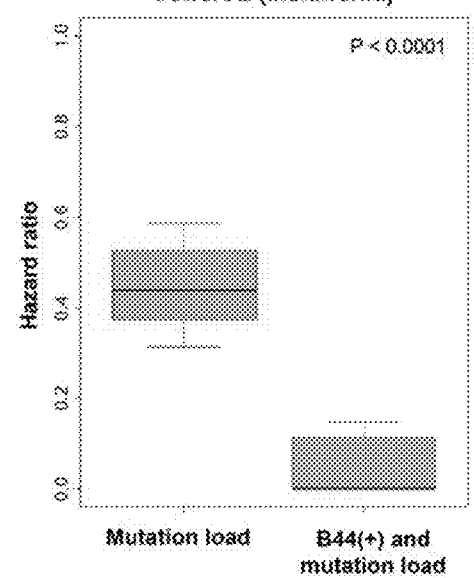
FIG. 9H

FIG. 10A
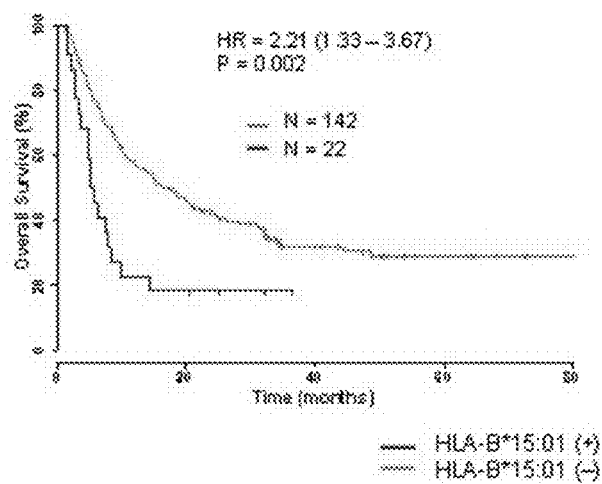
FIG. 10B
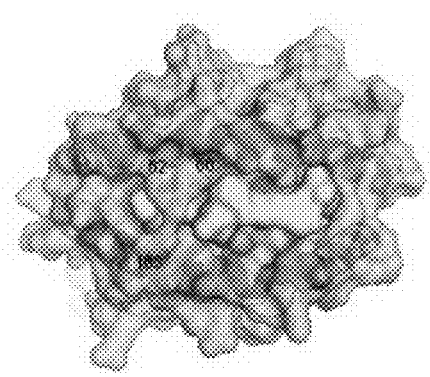
FIG. 10C
FIG. 10D
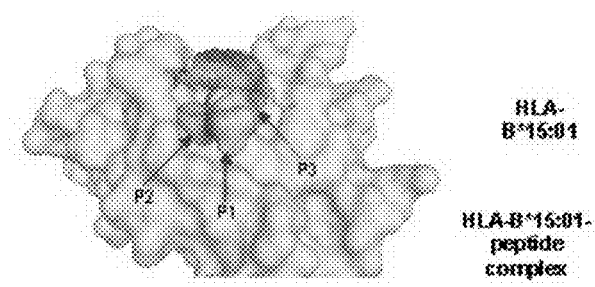
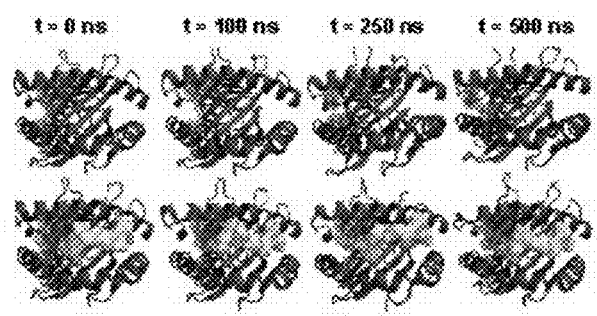
FIG. 10E
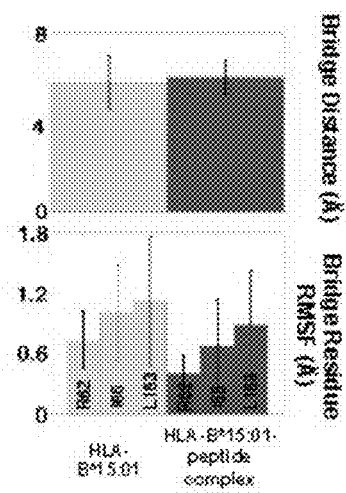

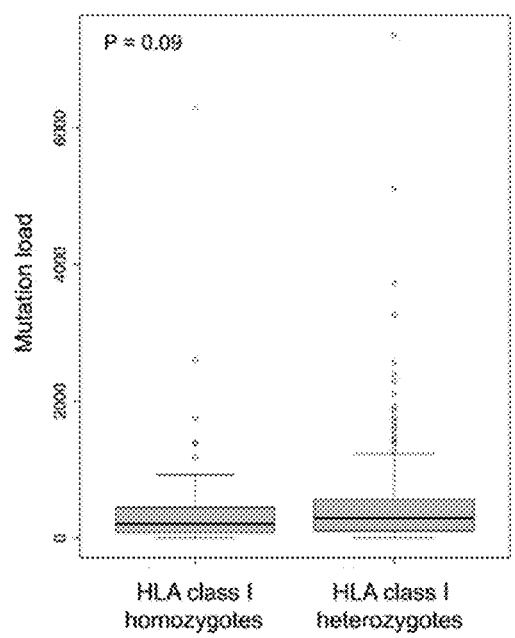
FIG. 11A Cohort 1
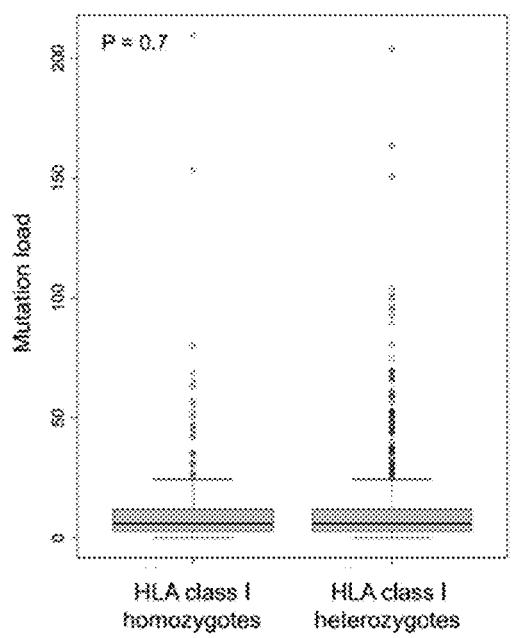
FIG. 11B Cohort 2

Figure 21
FIG. 21A  Non-Small Cell Lung Cancer
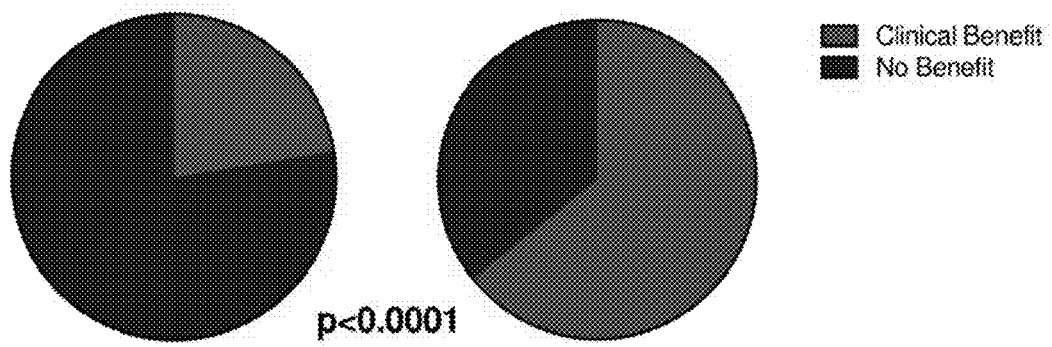
FIG. 21B  Head and Neck Cancer
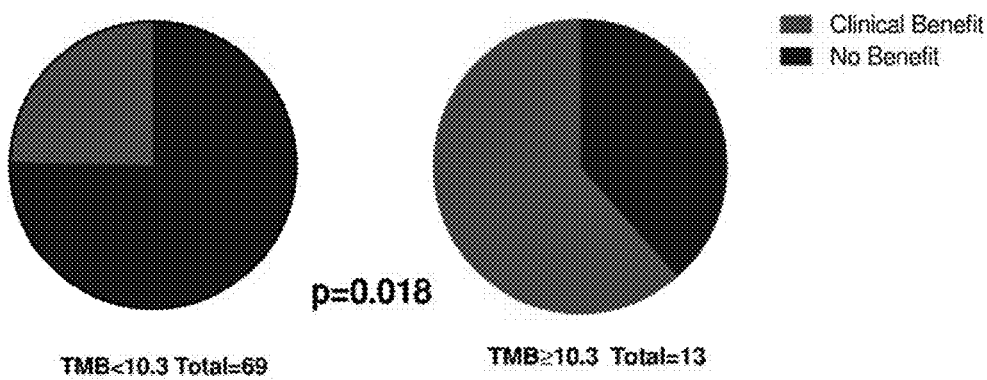
FIG. 21C  Esophagogastric Cancer
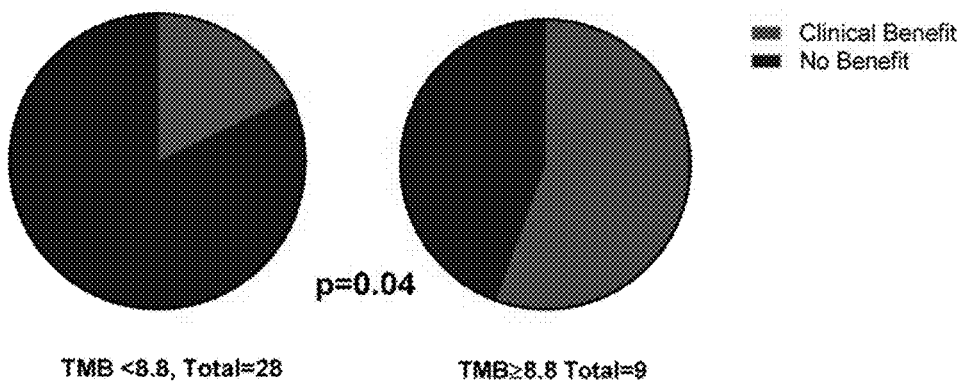

FIG. 22A  Melanoma
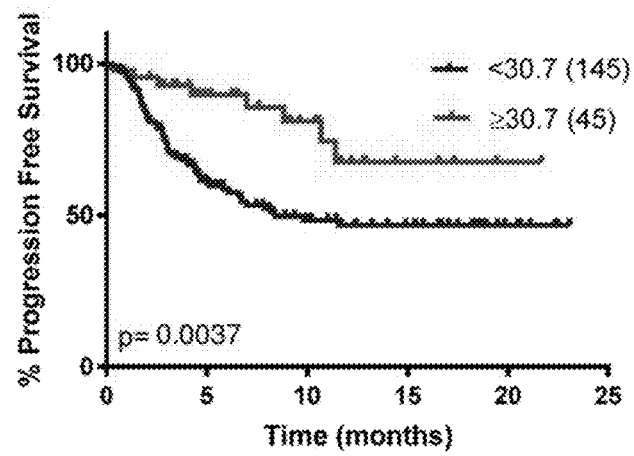
FIG. 22B  Head and Neck Cancer
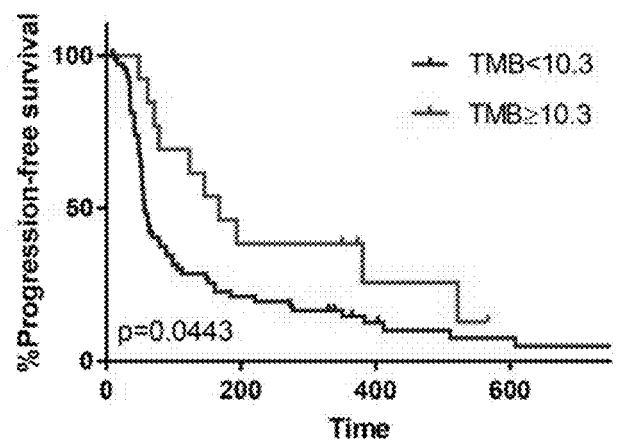
FIG. 22C  Esophagogastric Cancer
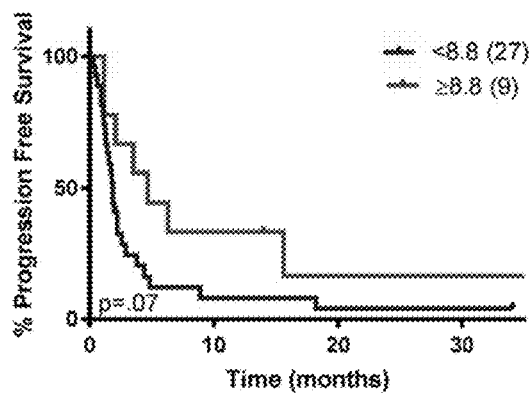

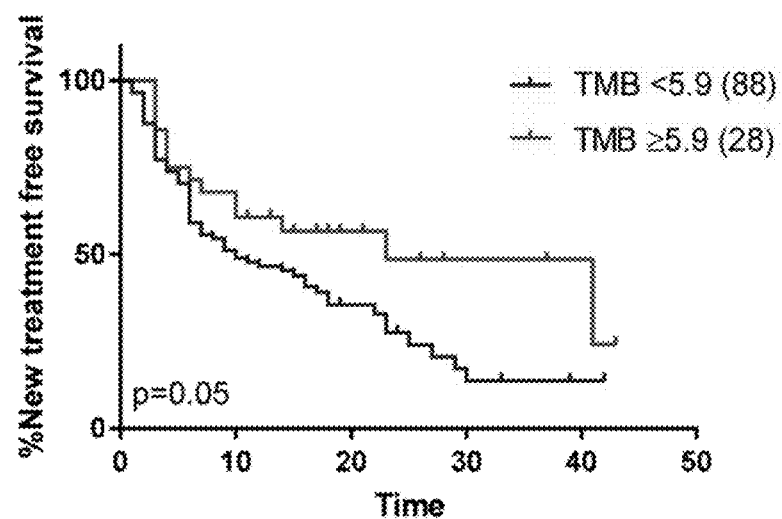
FIG. 22D  Renal Cell Carcinoma

Figure 24
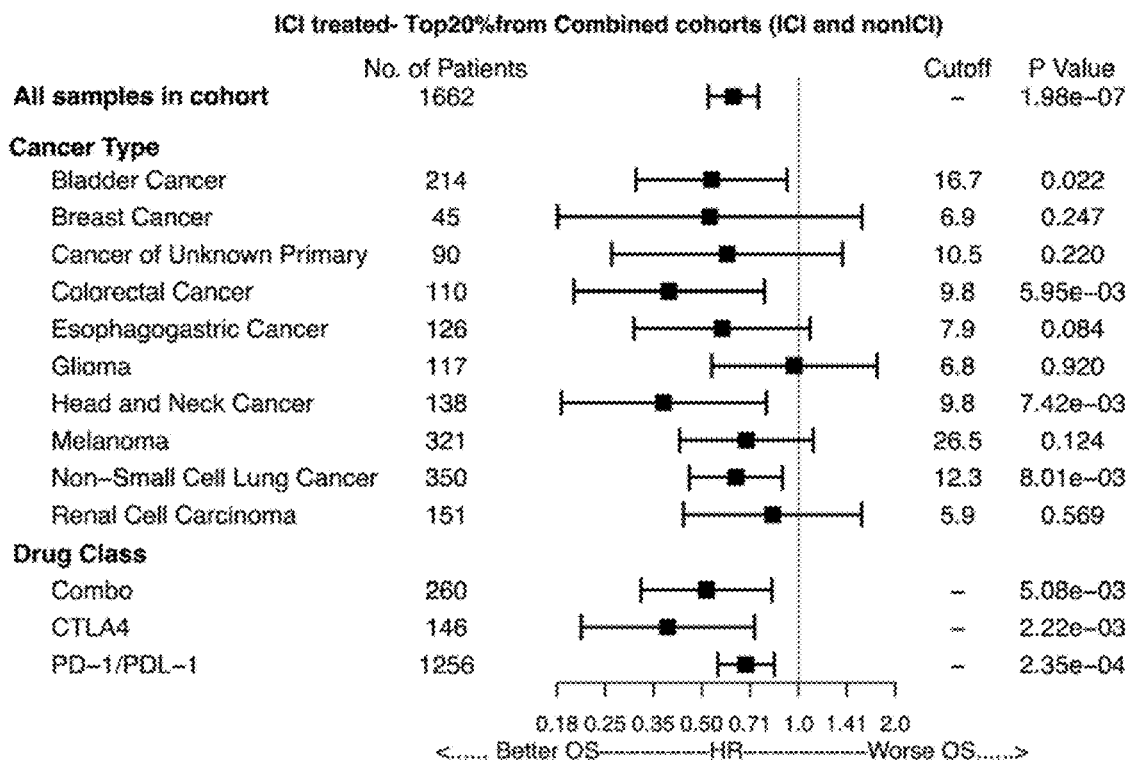
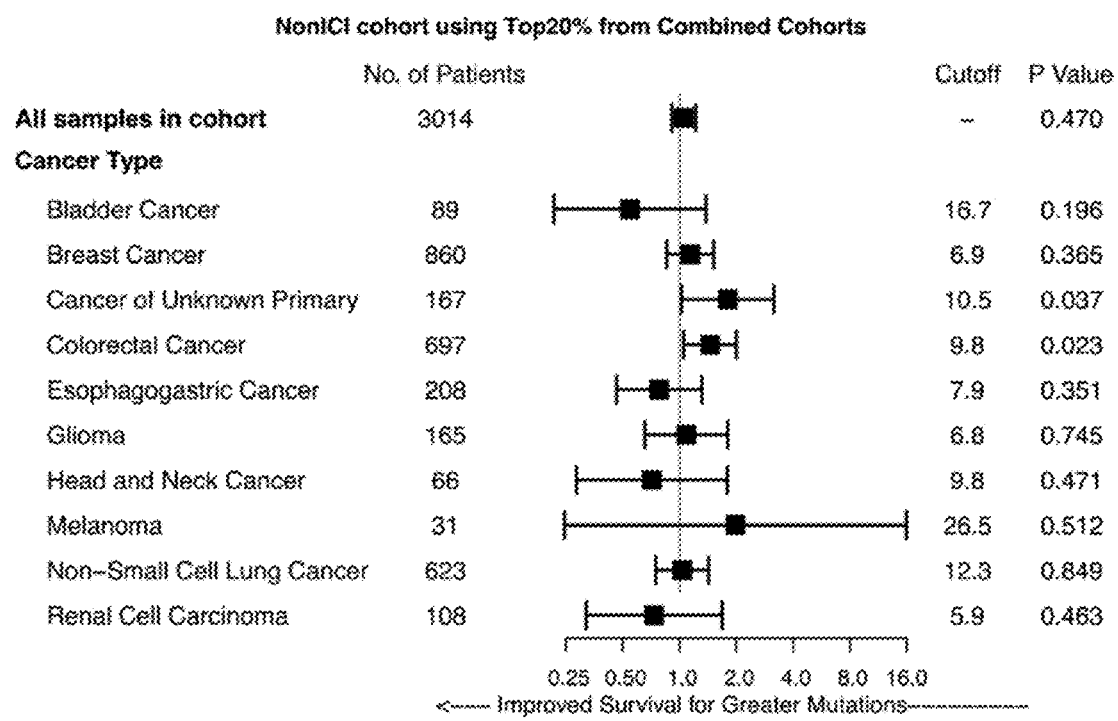

TUMOR MUTATIONAL LOAD

GOVERNMENT SUPPORT

This invention was made with government support under CA008748 awarded by the National Institutes of Health. The government has certain rights in the invention.

BACKGROUND

Cancer immunotherapy involves the attack of cancer cells by a patient's immune system. Regulation and activation of T lymphocytes depends on signaling by the T cell receptor and also cosignaling receptors that deliver positive or negative signals for activation. Immune responses by T cells are controlled by a balance of costimulatory and inhibitory signals, called immune checkpoints. It is predicted that worldwide cancer spending will exceed $150 billion by 2020, in significant part due to immunotherapy drug development.

SUMMARY

In recent years, immune checkpoint modulators have revolutionized treatment for patients with advanced stage solid tumors. These agents include antibodies that act as a CTLA-4 blockade or a PD-1/PD-L1 blockade, which can modulate immunoregulatory signals.[1]

The present disclosure recognizes the source of a problem that can arise with respect to immunotherapy regimens. In particular, it has been observed that durable benefit is often achieved in only a subset of patients.

Recent work has discovered that likelihood of a favorable response to cancer immunotherapy can often be predicted.[2] See, International Patent Application WO2016/081947 to Chan et al of the Memorial Sloan Kettering Cancer Center, incorporated herein by reference. In particular, it has been demonstrated that, for certain cancers, tumor mutational load can correlate with likely responsiveness to a particular therapy (e.g., to immunotherapy, and in particular to immune checkpoint modulator therapy), and also that certain cancer cells may harbor somatic mutations that result in neoepitopes that are recognizable by a patient's immune system as non-self, and that presence and/or identity of such neoepitopes may correlate with responsiveness to particular therapy. Further, the ability to present neoepitopes to the immune system, particularly through diverse HLA molecules, may correlate with responsiveness to particular therapy. Certain characteristics and/or mutational "signatures" that can be detected to predict responsiveness to immunotherapy, were defined, including specifically for lung cancer (e.g., small cell or non-small-cell carcinoma) and melanoma.

The present invention encompasses a discovery that likelihood of a favorable response to cancer immunotherapy for a wide range of different cancers can be predicted through definition of a tumor mutational load threshold for the tumor (and/or the relevant immunotherapy); in some embodiments, the present disclosure defines such thresholds and/or provides technologies that achieve such definition.

Moreover, in some embodiments, the present invention establishes that likelihood of durable responsiveness to cancer immunotherapy (and/or to a specific immunotherapy agent and/or regimen) can be predicted for tumors that have already been treated with prior immunotherapy. In particular, the present disclosure demonstrates that tumor mutational load thresholds can be defined for tumors that have already received prior immunotherapy, and that predict likely responsiveness to continued (and/or additional, extended, or modified) immunotherapy.

The present invention encompasses a discovery that likelihood of a favorable response to cancer immunotherapy for a wide range of different cancers can be predicted through HLA heterozygosity. In some embodiments, HLA heterozygosity alone is sufficient to determine likelihood of a favorable response to cancer immunotherapy. In some embodiments, FHA heterozygosity and tumor mutational load can be used in combination to determine likelihood of a favorable response to cancer immunotherapy.

Among other things, in some embodiments, the present disclosure provides technologies for defining tumor mutational load thresholds (and/or other characteristics—e.g., nature, level and/or frequency of neoantigens mutations) that predict ongoing responsiveness and/or durability of response to cancer immunotherapy. In some embodiments, the present disclosure defines such thresholds. Moreover, in some embodiments, the present disclosure provides technologies for treating tumors that have been exposed to cancer immunotherapy, for example by administering (e.g., continuing, supplementing, and/or initiating new) cancer immunotherapy to those tumors that display a mutational load characteristic (i.e., tumor mutational load above a defined threshold and/or neoantigen nature, level, and/or frequency) as described herein. In many embodiments, tumors that display a tumor mutational load above a threshold that has been correlated with a statistically significant probability of responding to immunotherapy are treated with such immunotherapy; in some embodiments, the tumors had previously been exposed to (the same or different) immunotherapy.

In some embodiments, the present disclosure provides technologies for treating tumors in subjects with a particular HLA class I genotype or HLA class I heterozygosity. Additionally, in some embodiments, the present disclosure provides technologies for treating tumors that have been exposed to cancer immunotherapy, for example by administering (e.g., continuing, supplementing, and/or initiating new) cancer immunotherapy to those tumors that display a mutational load characteristic (i.e., tumor mutational load above a defined threshold and/or neoantigen nature, level, and/or frequency) as described herein and are in a subject with a particular HLA class I genotype or HLA class I heterozygosity.

In some embodiments, a tumor mutational load characteristic may comprise (e.g., in addition or as an alternative to tumor mutational load) nature (e.g., identity or type), level, and/or frequency of neoepitopes that are recognizable by a patient's immune system as non-self. The present disclosure defines certain characteristics of particular tumor cells (e.g., cells that have been previously treated with cancer immunotherapy) that can be detected to predict responsiveness (e.g., continued responsiveness and/or durability of responsiveness) to immunotherapy, and particularly to therapy with immune checkpoint modulators. Among other things, the present disclosure provides tools and technologies that can be practically applied to define, characterize, and/or detect one or more tumor mutational load characteristics (e.g., tumor mutational load thresholds, neoepitope identity, type, level, and/or frequency, etc).

In some embodiments, HLA class I heterozygosity may comprise heterozygosity at a single HLA class I locus, two HLA class I loci, or at three HLA class I loci. In some embodiments, maximal heterozygosity is heterozygosity at three HLA class I loci (i.e., A, B, and C).

Among other things, the present disclosure demonstrates that a relevant tumor mutational load can be determined and/or detected using targeted gene panel technologies (e.g., assessed with next-generation sequencing), and do not necessarily require whole exome sequencing. The present disclosure recognizes the source of a problem with certain prior technologies for assessing tumor mutational load to the extent that they relied on and/or required whole exome sequencing, which is typically not broadly performed as part of routine clinical care.

In some embodiments of the present invention, tumor mutational load is or was determined and/or detected by use of a targeted sequence panel. In some embodiments, tumor mutational load is measured using next-generation sequencing. In some embodiments, tumor mutational load is measured using an Integrated Mutation Profiling of Actionable Cancer Targets (MSK-IMPACT) assay.[8,17]

In some embodiments, the step of determining comprises detecting at least one mutation characteristic by nucleic acid sequencing. In some embodiments, nucleic acid sequencing is or comprises whole exome sequencing. In some embodiments, nucleic acid sequencing does not involve whole exome sequencing. In some embodiments, nucleic acid sequencing is or comprises next generation sequencing.

In some embodiments, the present disclosure relates to administration of immunotherapy to a subject. In some embodiments, administration comprises steps of detecting a tumor mutational load characteristic (e.g., a tumor mutational load level relative to a threshold) in a cancer sample from a subject; and identifying the subject as a candidate for treatment (e.g. continued and/or extended or modified treatment) with an immunotherapy. In some embodiments, a tumor mutational load threshold is used to determine if a subject is a candidate for treatment (e.g., continued treatment and/or extended or modified treatment) with an immunotherapy. In some embodiments, the invention provides methods for detecting a low tumor mutational load, or a tumor mutational load below the defined tumor mutational load threshold, in a cancer sample from a subject; and identifying the subject as a poor candidate for treatment (e.g. continued treatment and/or extended or modified treatment) with an immune checkpoint modulator. In some embodiments, the step of detecting comprises sequencing one or more exomes from the cancer sample. In some embodiments, the step of detecting doesn't involve sequencing one or more exomes.

In some embodiments, the present disclosure relates to administration of immunotherapy to a subject. In some embodiments, such immunotherapy is or comprises immune checkpoint modulation therapy. In some embodiments, immunotherapy involves administration of one or more immunomodulatory agents; in some embodiments an immunomodulatory agent is or comprises an immune checkpoint modulator. In some embodiments, an immune checkpoint modulator is an agent (e.g., an antibody agent) that targets (i.e., specifically interacts with) an immune checkpoint target. In some embodiments, an immune checkpoint target is or comprises one or more of CTLA-4, PD-1, PD-L1, GITR, OX40, LAG-3, KIR, TIM-3, CD28, CD40, and CD137; in some embodiments, immune checkpoint modulator therapy is or comprises administration of an antibody agent that targets one or more such immune checkpoint targets. In some embodiments, the immune checkpoint modulator interacts with cytotoxic T-lymphocyte antigen 4 (CTLA4) or its ligands, and/or programmed death 1 (PD-1) or its ligands. In some embodiments, the antibody agent is or comprises a monoclonal antibody or antigen binding fragment thereof. In some embodiments, the antibody is selected from the group comprising of atezolizumab, avelumab, durvalumab, ipilimumab, nivolumab, pembrolizumab, or tremelimumab, and combinations therein.

In some embodiments, a cancer is selected from the group consisting of bladder cancer, bone cancer, breast cancer, cancer of unknown primary, esophagogastric cancer, gastrointestinal cancer, glioma, head and neck cancer, hepatobiliary cancer, melanoma, mesothelioma, non-hodgkin lymphoma, non-small cell lung cancer, pancreatic cancer, prostate cancer, renal cell carcinoma, skin cancer (non-melanoma), small cell lung cancer, soft tissue sarcoma, thyroid cancer, and combinations thereof.

In some embodiments, a cancer is selected from the group consisting of bladder cancer, breast cancer, esophagogastric cancer, glioma, head and neck cancer, melanoma, non-small cell lung cancer, renal cell carcinoma, and combinations thereof.

BRIEF DESCRIPTION OF THE DRAWING

The following figures are presented for the purpose of illustration only, and are not intended to be limiting.

FIG. 3A-3B shows overall survival in relation to pan-cancer tumor mutational load threshold (A) with and (B) without immune checkpoint modulator (ICM) therapy. Kaplan-Meier curves are shown for patients who were treated with ICM or never treated with ICM with the indicated number of normalized mutations identified on MSK-IMPACT testing. Overall survival is determined starting from the first dose of ICM or first dose of any chemotherapy.

FIG. 6A-6H shows the effect of tumor mutational load on overall survival after ICM therapy organized by cancer subtype. The first column in panels A-H demonstrates the distribution of normalized tumor mutational load frequency over subsets of tumor mutational load. The second column in panels A-H demonstrates Kaplan-Meier curves for patients who were treated with ICM therapy, with the indicated number of normalized mutations identified on MSK-IMPACT testing. Each panel represents a cancer subtype, with (A) bladder cancer, (B) breast cancer, (C) esophagogastric cancer, (D) glioma, (E) head and neck cancer, (F) melanoma, (G) non-small cell lung cancer (NSCLC), and (H) renal cell carcinoma.

FIG. 8A-8I shows the Effect of HLA class I homozygosity on survival in patients treated with immune check point modulator. (A) Association between homozygosity in at least one HLA class I locus and reduced overall survival in cohort 1, composed of 369 patients with melanoma or NSCLC treated with ICM therapy. (B) Association between homozygosity in at least one HLA class I locus and reduced survival in cohort 2, composed of 1,166 patients representing different cancer types treated with ICM therapy. (C) Association between homozygosity at one or more class I loci and for individual loci (HLA-A, HLA-B, and HLA-C) with decreased overall survival from all 1,535 patients. Indicated are the number of patients and hazard ratio (HR). Horizontal lines represent the 95% confidence interval. P value was calculated using the Log-rank test. Patients were divided into: individuals who were heterozygous at all three class I loci; individuals homozygous at one or more class I loci; individuals homozygous at the specified locus, but heterozygous at both of the other two loci; and individuals homozygous at the specified locus and also at one of the other two loci, but heterozygous at the other one. Homozygosity at HLA-A and HLA-B and homozygosity at HLA-A and HLA-C were rare in these patients, which limited the interpretability of analyses involving combinations of loci. (D) Improved survival in cohort 1 patients with heterozygosity at all HLA class I loci and a high tumor mutational load compared to patients that are homozygous for at least one HLA class I locus and have a low tumor mutational load. Mutational load was calculated from the total nonsynonymous mutational count from whole exome sequencing. High mutational load is defined here as tumors with >113 mutations. (E) Improved survival in cohort 2 patients with heterozygosity at all HLA class I loci and a high tumor mutational load compared to patients that are homozygous in at least one HLA class I locus and have a low tumor mutational load. Mutational load was calculated from the total nonsynonymous mutational count from MSK-IMPACT. High mutational load is defined here as tumors with >16.72 mutations. (F and G) Box plots illustrating the distribution of hazard ratios resulting from the survival analyses using a range of cutoffs to stratify patients based on their tumor mutational load. This analysis shows that the combined effect of HLA class I heterozygosity at all loci and mutation load on improved survival was greater compared to simply considering tumor mutational load alone in cohort 1 (F) and cohort 2 (G). For this analysis, we used a range of cutoffs across the quartiles of mutation load. P values were calculated using the Wilcoxon-rank sum test. (H) Survival analysis showing that LOH of heterozygous germline HLA class I is associated with decreased overall survival in patients treated with ICM immunotherapy. The number of patients who are of heterozygous germline at all HLA class I loci and without LOH is 199; the number of patients with heterozygous germline at all HLA class I loci and with LOH is 32. (I) Survival analysis showing that the effect of LOH of heterozygous germline HLA class I is enhanced in tumors with low mutation burden compared to tumors with high mutation load and without LOH. High mutation load is defined here as in (D). The number of patients who are of heterozygous germline at each HLA class I locus, without LOH, and with tumors containing high mutation load is 142; the number of patients with heterozygous germline at all HLA class I loci, with LOH, and with tumors having low mutation burden is 8.

FIGS. 9A-9J show the influence of HLA B44 supertype on survival in patients with advanced melanoma treated with ICM. (A) Prevalence of the different HLA supertypes in patients with melanoma from cohort 1. (B) Prevalence of the different HLA supertypes in the patients with melanoma from cohort 2. (C and D) Survival analysis showing the overall survival of advanced melanoma patients treated with ICM therapy possessing the B44 supertype [B44 (+)] compared with patients without the B44 supertype [B44 (−)] from cohort 1 (C) and cohort 2 (D). (E and F) Survival analysis of patients with the B44 supertype and high mutation burden versus patients without B44 and with low mutation burden, from cohort 1 (E) and cohort 2 (F). (G and H) Box plots illustrating the distribution of hazard ratios resulting from the survival analyses using different cutoffs to stratify patients based on their tumor mutational burden. This analysis shows that the combined effect of B44 and mutation load on increased survival was greater compared to simply considering tumor mutational load alone in patients with melanoma treated with ICM therapy from cohort 1 (G) and cohort 2 (H). For this analysis, we used a range of cutoffs across the quartiles of mutation load. P values were calculated using the Wilcoxon-rank sum test. (I) Survival analysis of melanoma patients with and without the B44 supertype from the TCGA cohort. (J) Left: Example of peptide motif common among B44 HLA alleles, docked in complex with HLA-B*44:02 based on an available crystal structure (PDB: 1M6O). The five common residues (E2, I3, P4, V6, and Y9) of the motif were reported in (45). Peptide residues are colored according to their properties as basic, acidic, polar, or hydrophobic. Center: Close up view of example peptide conforming to the B44 motif reported in the literature. Residues at positions 2 and 9 are particularly important for anchoring the peptide in the HLA peptide-binding groove. Right: Alignment between B44 peptide motif and known immunogenic neoantigens (table 8) within the B44 supertype expressed by melanomas. All neoepitopes feature a glutamate at position 2; neoantigens are also either identical or similar to the motif at one or two additional positions. The second neoantigen (FAM3C: TESPFEQHI) was identified in a melanoma patient with a long-term response to anti-CTLA-4 from cohort 1. Sequence similarity was determined using standard residue classes (GAVLI, FYW, CM, ST, KRH, DENQ, and P).

FIG. 10A-10E shows the effect of the HLA-B*15:01 allele on overall survival in patients with melanoma treated with ICM therapy. (A) Survival analysis showing reduced survival in ICM-treated melanoma patients from cohort 1 with and without the HLA-B*15:01 allele. (B) Overview of the three-dimensional structure of the peptide-binding groove of HLA-B*15:01, light purple; bound peptide, yellow; bridging residues, light pink. (C) Side view of the bridge-sequestration effect over bound-peptide residue positions P2 and P3 (light blue and red, respectively). (D) MD simulation snapshots of both the isolated HLA B*15:01 molecule and its complex with a 9-mer peptide; each trajectory was run over the course of 500 ns of simulation time. (E) Observables from the MD simulations described in (D). The mean bridge distances in the HLA-B*15:01 molecule and in the HLA-B*15:01-peptide complex are comparable. The residue-position root mean square fluctuations (RMSFs) indicate that each of the bridging residues becomes more rigid in the presence of the peptide.

FIGS. 11A-11B show the number of somatic coding mutations in the tumors between patients who were homozygous for at least one HLA class I locus and patients who are heterozygous at each class I locus in cohort 1 and cohort 2, respectively. The P value was calculated by Wilcoxon-rank sum test.

FIGS. 21A-21C show TMB as a predictor of clinical response to ICI. Pie charts demonstrating the relative proportion of patients with a clinical benefit (defined as radiographic response or stable disease for ≥6 months) with low or high TMB in A. NSCLC, B. Head and Neck, and C. Esophagogastric cancer. Fisher's exact test p values indicated. Similar data for the association between TMB and tumor response in MSK-IMPACT sequenced NSCLC patients have also been separately published.

FIGS. 22A-22D show TMB predicts for progression free survival progression free survival (A,B,C) or time to next treatment (D) in patients with high and low TMB (Top 20%) tumors in the indicated cancer types. Log-rank p values indicated.

FIG. 24 shows modified versions of FIG. 17 and FIG. 23, with the TMB cutoff instead defined as the top 20% among all patients in both ICI-treated and non-ICI treated cohorts.

DEFINITIONS

Figure 1:
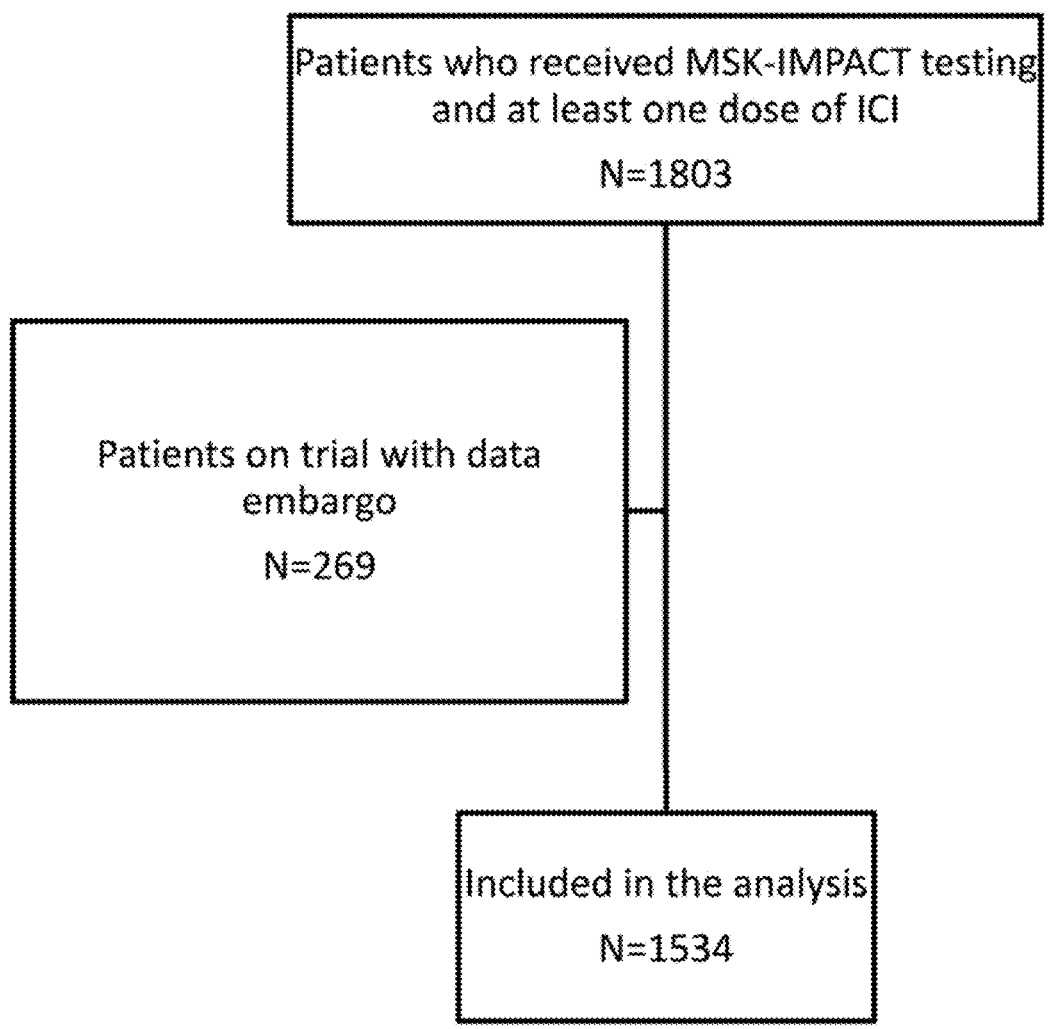
FIG. 1 shows a Consolidated Standard of Reporting Trials (CONSORT) diagram demonstrating the flow of patient selection for analysis.

In order for the present invention to be more readily understood, certain terms are defined below. Those skilled in the art will appreciate that definitions for certain terms may be provided elsewhere in the specification, and/or will be clear from context.

Administration: As used herein, the term "administration" refers to the administration of a composition to a subject. Administration may be by any appropriate route. For example, in some embodiments, administration may be bronchial (including by bronchial instillation), buccal, enteral, interdermal, intra-arterial, intradermal, intragastric, intramedullary, intramuscular, intranasal, intraperitoneal, intrathecal, intravenous, intraventricular, mucosal, nasal, oral, rectal, subcutaneous, sublingual, topical, tracheal (including by intratracheal instillation), transdermal, vaginal and vitreal.

Affinity: As is known in the art, "affinity" is a measure of the tightness with a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Amino acid: As used herein, term "amino acid," in its broadest sense, refers to any compound and/or substance that can be incorporated into a polypeptide chain. In some embodiments, an amino acid has the general structure H2N—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Antibody agent: As used herein, the term "antibody agent" refers to an agent that specifically binds to a particular antigen. In some embodiments, the term encompasses any polypeptide with immunoglobulin structural elements sufficient to confer specific binding. Suitable antibody agents include, but are not limited to, human antibodies, primatized antibodies, chimeric antibodies, bi-specific antibodies, humanized antibodies, conjugated antibodies (i.e., antibodies conjugated or fused to other proteins, radiolabels, cytotoxins), Small Modular Immuno Pharmaceuticals ("SMIPs™"), single chain antibodies, cameloid antibodies, and antibody fragments. As used herein, the term "antibody agent" also includes intact monoclonal antibodies, polyclonal antibodies, single domain antibodies (e.g., shark single domain antibodies (e.g., IgNAR or fragments thereof)), multispecific antibodies (e.g. bi-specific antibodies) formed from at least two intact antibodies, and antibody fragments so long as they exhibit the desired biological activity. In some embodiments, the term encompasses stapled peptides. In some embodiments, the term encompasses one or more antibody-like binding peptidomimetics. In some embodiments, the term encompasses one or more antibody-like binding scaffold proteins. In come embodiments, the term encompasses monobodies or adnectins. In many embodiments, an antibody agent is or comprises a polypeptide whose amino acid sequence includes one or more structural elements recognized by those skilled in the art as a complementarity determining region (CDR); in some embodiments an antibody agent is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody agent is or comprises a polypeptide whose amino acid sequence includes structural elements recognized by those skilled in the art as an immunoglobulin variable domain. In some embodiments, an antibody agent is a polypeptide protein having a binding domain which is homologous or largely homologous to an immunoglobulin-binding domain.

Antibody polypeptide: As used herein, the terms "antibody polypeptide" or "antibody", or "antigen-binding fragment thereof", which may be used interchangeably, refer to polypeptide(s) capable of binding to an epitope. In some embodiments, an antibody polypeptide is a full-length antibody, and in some embodiments, is less than full length but includes at least one binding site (comprising at least one, and preferably at least two sequences with structure of antibody "variable regions"). In some embodiments, the term "antibody polypeptide" encompasses any protein having a binding domain which is homologous or largely homologous to an immunoglobulin-binding domain. In particular embodiments, "antibody polypeptides" encompasses polypeptides having a binding domain that shows at least 99% identity with an immunoglobulin binding domain. In some embodiments, "antibody polypeptide" is any protein having a binding domain that shows at least 70%, 80%, 85%, 90%, or 95% identity with an immuglobulin binding domain, for example a reference immunoglobulin binding domain. An included "antibody polypeptide" may have an amino acid sequence identical to that of an antibody that is found in a natural source. Antibody polypeptides in accordance with the present invention may be prepared by any available means including, for example, isolation from a natural source or antibody library, recombinant production in or with a host system, chemical synthesis, etc., or combinations thereof. An antibody polypeptide may be monoclonal or polyclonal. An antibody polypeptide may be a member of any immunoglobulin class, including any of the human classes: IgG, IgM, IgA, IgD, and IgE. In certain embodiments, an antibody may be a member of the IgG immunoglobulin class. As used herein, the terms "antibody polypeptide" or "characteristic portion of an antibody" are used interchangeably and refer to any derivative of an antibody that possesses the ability to bind to an epitope of interest. In certain embodiments, the "antibody polypeptide" is an antibody fragment that retains at least a significant portion of the full-length antibody's specific binding ability. Examples of antibody fragments include, but are not limited to, Fab, Fab', F(ab')2, scFv, Fv, dsFv diabody, and Fd fragments. Alternatively or additionally, an antibody fragment may comprise multiple chains that are linked together, for example, by disulfide linkages. In some embodiments, an antibody polypeptide may be a human antibody. In some embodiments, the antibody polypeptides may be a humanized. Humanized antibody polypeptides include may be chimeric immunoglobulins, immunoglobulin chains or antibody polypeptides (such as Fv, Fab, Fab', F(ab')2 or other antigen-binding subsequences of antibodies) that contain minimal sequence derived from non-human immunoglobulin. In general, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In particular embodiments, antibody polypeptides for use in accordance with the present invention bind to particular epitopes of on immune checkpoint molecules.

Antigen: An "antigen" is a molecule or entity to which an antibody binds. In some embodiments, an antigen is or comprises a polypeptide or portion thereof. In some embodiments, an antigen is a portion of an infectious agent that is recognized by antibodies. In some embodiments, an antigen is an agent that elicits an immune response; and/or (ii) an agent that is bound by a T cell receptor (e.g., when presented by an MI-IC molecule) or to an antibody (e.g., produced by a B cell) when exposed or administered to an organism. In some embodiments, an antigen elicits a humoral response (e.g., including production of antigen-specific antibodies) in an organism; alternatively or additionally, in some embodiments, an antigen elicits a cellular response (e.g., involving T-cells whose receptors specifically interact with the antigen) in an organism. It will be appreciated by those skilled in the art that a particular antigen may elicit an immune response in one or several members of a target organism (e.g., mice, rabbits, primates, humans), but not in all members of the target organism species. In some embodiments, an antigen elicits an immune response in at least about 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99% of the members of a target organism species. In some embodiments, an antigen binds to an antibody and/or T cell receptor, and may or may not induce a particular physiological response in an organism. In some embodiments, for example, an antigen may bind to an antibody and/or to a T cell receptor in vitro, whether or not such an interaction occurs in vivo. In general, an antigen may be or include any chemical entity such as, for example, a small molecule, a nucleic acid, a polypeptide, a carbohydrate, a lipid, a polymer [in some embodiments other than a biologic polymer (e.g., other than a nucleic acid or amino acid polymer)] etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source). In some embodiments, antigens utilized in accordance with the present invention are provided in a crude form. In some embodiments, an antigen is or comprises a recombinant antigen.

Approximately: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Blockade": The term "blockade" as used herein, refers to an entity or event whose presence or level correlates with a reduction in level and/or activity of an indicated target. Thus, for example, "a PD-1 blockade" is an agent or event whose presence correlates with reduction in level and/or activity of PD-1. In some such embodiments, a relevant activity of PD-1 may be or comprise interaction with one of more of its ligands (e.g., PD-L1 and/or PD-L2) and/or a downstream effect thereof. In some embodiments, a PD-1 blockade may be achieved by administration of an agent, such as an antibody agent, that targets PD-1 and/or a PD-1 ligand (e.g., PD-L1 and/or PD-L2) and/or a complex thereof.

In some particular embodiments, a PD-1 blockade may be achieved through administration of an antibody agent that binds to PD-1. In some embodiments, a PD-1 blockade may be achieved through administration of one or more of nivolumab, pembrolizumab, atezolizumab, avelumab, and/or durvalumab. Analogously, a "CTL4-blockade is an agent or event whose presence correlates with reduction in level and/or activity of CTLA-4. In some such embodiments, a relevant activity of CTLA-4 may be or comprise interaction with one of more of its ligands (e.g., CD80 and/or CD86) and/or a downstream effect thereof. In some embodiments, a CTLA-4 blockade may be achieved by administration of an agent, such as an antibody agent, that targets CTLA-4 ligand (e.g., CD80 and/or CD86) and/or a complex thereof. In some particular embodiments, a CTLA-4 blockade may be achieved through administration of an antibody agent that binds to CTLA-4. In some embodiments, a CTLA-4 blockade may be achieved through administration of one or more of ipilimumab and/or tremelimumab.

Combination therapy: The term "combination therapy", as used herein, refers to those situations in which two or more different pharmaceutical agents are administered in overlapping regimens so that the subject is simultaneously exposed to both agents. When used in combination therapy, two or more different agents may be administered simultaneously or separately. This administration in combination can include simultaneous administration of the two or more agents in the same dosage form, simultaneous administration in separate dosage forms, and separate administration. That is, two or more agents can be formulated together in the same dosage form and administered simultaneously. Alternatively, two or more agents can be simultaneously administered, wherein the agents are present in separate formulations. In another alternative, a first agent can be administered just followed by one or more additional agents. In the separate administration protocol, two or more agents may be administered a few minutes apart, or a few hours apart, or a few days apart.

Comparable: The term "comparable" is used herein to describe two (or more) sets of conditions, circumstances, individuals, or populations that are sufficiently similar to one another to permit comparison of results obtained or phenomena observed. In some embodiments, comparable sets of conditions, circumstances, individuals, or populations are characterized by a plurality of substantially identical features and one or a small number of varied features. Those of ordinary skill in the art will appreciate that sets of circumstances, individuals, or populations are comparable to one another when characterized by a sufficient number and type of substantially identical features to warrant a reasonable conclusion that differences in results obtained or phenomena observed under or with different sets of circumstances, individuals, or populations are caused by or indicative of the variation in those features that are varied. Those skilled in the art will appreciate that relative language used herein (e.g., enhanced, activated, reduced, inhibited, etc) will typically refer to comparisons made under comparable conditions.

Consensus sequence: As used herein, the term "consensus sequence" refers to a core sequence that elicits or drives a physiological phenomenon (e.g., an immune response). It is to be understood by those of skill in the art that a a cancer cell that shares a "consensus sequence" with an antigen of an infectious agent shares a portion of amino acid sequence that affects the binding affinity of the antigen to an MHC molecule (either directly or allosterically), and/or facilitates recognition by T cell receptors. In some embodiments, a consensus sequence is a tetrapeptide. In some embodiments, a consensus sequence is a nonapeptide. In some embodiments, a consensus sequence is between four and nine amino acids in length. In some embodiments, a consensus sequence is greater than nine amino acids in length.

Diagnostic information: As used herein, diagnostic information or information for use in diagnosis is any information that is useful in determining whether a patient has a disease or condition and/or in classifying the disease or condition into a phenotypic category or any category having significance with regard to prognosis of the disease or condition, or likely response to treatment (either treatment in general or any particular treatment) of the disease or condition. Similarly, diagnosis refers to providing any type of diagnostic information, including, but not limited to, whether a subject is likely to have a disease or condition (such as cancer), state, staging or characteristic of the disease or condition as manifested in the subject, information related to the nature or classification of a tumor, information related to prognosis and/or information useful in selecting an appropriate treatment. Selection of treatment may include the choice of a particular therapeutic (e.g., chemotherapeutic) agent or other treatment modality such as surgery, radiation, etc., a choice about whether to withhold or deliver therapy, a choice relating to dosing regimen (e.g., frequency or level of one or more doses of a particular therapeutic agent or combination of therapeutic agents), etc.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which are separated from one another by a time period of the same length; in some embodiments, a dosing regimen comprises a plurality of doses and at least two different time periods separating individual doses. In some embodiments, a dosing regimen is or has been correlated with a desired therapeutic outcome, when administered across a population of patients.

Durable clinical benefit: As used herein, the term "durable clinical benefit" (DCB), has its art-understood meaning, referring to a clinical benefit that lasts for a relevant period of time. In some embodiments, such a clinical benefit is or comprises reduction in tumor size, increase in progression free survival, increase in overall survival, decrease in overall tumor burden, decrease in the symptoms caused by tumor growth such as pain, organ failure, bleeding, damage to the skeletal system, and other related sequelae of metastatic cancer and combinations thereof. In some embodiments, the relevant period of time is at least 1 month, 2 months, 3 months, 4 months, 5 months, 6 months, 7 months, 8 months, 9 months, 10 months, 11 months, 1 year, 2 years, 3 years, 4 years, 5 years, or longer. In some particular embodiments, the relevant period of time is 6 months.

Exome: As used herein, the term "exome" is used in accordance with its art-understood meaning referring to the set of exon sequences that are found in a particular genome.

Favorable response: As used herein, the term "favorable response" refers to a reduction in frequency and/or intensity of one or more symptoms, reduction in tumor burden, full or partial remission, or other improvement in disease pathophysiology. Symptoms are reduced when one or more symptoms of a particular disease, disorder or condition is reduced in magnitude (e.g., intensity, severity, etc.) and/or frequency. For purposes of clarity, a delay in the onset of a particular symptom is considered one form of reducing the frequency of that symptom. Many cancer patients with smaller tumors have no symptoms. It is not intended that the present invention be limited only to cases where the symptoms are eliminated. The present invention specifically contemplates treatment such that one or more symptoms is/are reduced (and the condition of the subject is thereby "improved"), albeit not completely eliminated. In some embodiments, a favorable response is established when a particular therapeutic regimen shows a statistically significant effect when administered across a relevant population; demonstration of a particular result in a specific individual may not be required. Thus, in some embodiments, a particular therapeutic regimen is determined to have a favorable response when its administration is correlated with a relevant desired effect.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4: 11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Immune checkpoint modulator: As used herein, the term "immune checkpoint modulator" refers to an agent that interacts directly or indirectly with an immune checkpoint. In some embodiments, an immune checkpoint modulator increases an immune effector response (e.g., cytotoxic T cell response), for example by stimulating a positive signal for T cell activation. In some embodiments, an immune checkpoint modulator increases an immune effector response (e.g., cytotoxic T cell response), for example by inhibiting a negative signal for T cell activation (e.g. disinhibition). In some embodiments, an immune checkpoint modulator interferes with a signal for T cell anergy. In some embodiments, an immune checkpoint modulator reduces, removes, or prevents immune tolerance to one or more antigens.

Long Term Benefit: In general, the term "long term benefit" refers to a desirable clinical outcome, e.g., observed after administration of a particular treatment or therapy of interest, that is maintained for a clinically relevant period of time. To give but one example, in some embodiments, a long term benefit of cancer therapy is or comprises (1) no evidence of disease ("NED", for example upon radiographic assessment) and/or (2) stable or decreased volume of diseases. In some embodiments, a clinically relevant period of time is at least 1 month, at least 2 months, at least 3 months, at least 4 months, at least 5 months or more. In some embodiments, a clinically relevant period of time is at least six months. In some embodiments, a clinically relevant period of time is at least 1 year.

Marker: A marker, as used herein, refers to an agent whose presence or level is a characteristic of a particular tumor or metastatic disease thereof. For example, in some embodiments, the term refers to a gene expression product that is characteristic of a particular tumor, tumor subclass, stage of tumor, etc. Alternatively or additionally, in some embodiments, a presence or level of a particular marker correlates with activity (or activity level) of a particular signaling pathway, for example that may be characteristic of a particular class of tumors. The statistical significance of the presence or absence of a marker may vary depending upon the particular marker. In some embodiments, detection of a marker is highly specific in that it reflects a high probability that the tumor is of a particular subclass. Such specificity may come at the cost of sensitivity (i.e., a negative result may occur even if the tumor is a tumor that would be expected to express the marker). Conversely, markers with a high degree of sensitivity may be less specific that those with lower sensitivity. According to the present invention a useful marker need not distinguish tumors of a particular subclass with 100% accuracy.

Modulator: The term "modulator" is used to refer to an entity whose presence in a system in which an activity of interest is observed correlates with a change in level and/or nature of that activity as compared with that observed under otherwise comparable conditions when the modulator is absent. In some embodiments, a modulator is an activator, in that activity is increased in its presence as compared with that observed under otherwise comparable conditions when the modulator is absent. In some embodiments, a modulator is an inhibitor, in that activity is reduced in its presence as compared with otherwise comparable conditions when the modulator is absent. In some embodiments, a modulator interacts directly with a target entity whose activity is of interest. In some embodiments, a modulator interacts indirectly (i.e., directly with an intermediate agent that interacts with the target entity) with a target entity whose activity is of interest. In some embodiments, a modulator affects level of a target entity of interest; alternatively or additionally, in some embodiments, a modulator affects activity of a target entity of interest without affecting level of the target entity. In some embodiments, a modulator affects both level and activity of a target entity of interest, so that an observed difference in activity is not entirely explained by or commensurate with an observed difference in level.

Mutation: As used herein, the term "mutation" refers to permanent change in the DNA sequence that makes up a gene. In some embodiments, mutations range in size from a single DNA building block (DNA base) to a large segment of a chromosome. In some embodiments, mutations can include missense mutations, frameshift mutations, duplications, insertions, nonsense mutation, deletions and repeat expansions. In some embodiments, a missense mutation is a change in one DNA base pair that results in the substitution of one amino acid for another in the protein made by a gene. In some embodiments, a nonsense mutation is also a change in one DNA base pair. Instead of substituting one amino acid for another, however, the altered DNA sequence prematurely signals the cell to stop building a protein. In some embodiments, an insertion changes the number of DNA bases in a gene by adding a piece of DNA. In some embodiments, a deletion changes the number of DNA bases by removing a piece of DNA. In some embodiments, small deletions may remove one or a few base pairs within a gene, while larger deletions can remove an entire gene or several neighboring genes. In some embodiments, a duplication consists of a piece of DNA that is abnormally copied one or more times. In some embodiments, frameshift mutations occur when the addition or loss of DNA bases changes a gene's reading frame. A reading frame consists of groups of 3 bases that each code for one amino acid. In some embodiments, a frameshift mutation shifts the grouping of these bases and changes the code for amino acids. In some embodiments, insertions, deletions, and duplications can all be frameshift mutations. In some embodiments, a repeat expansion is another type of mutation. In some embodiments, nucleotide repeats are short DNA sequences that are repeated a number of times in a row. For example, a trinucleotide repeat is made up of 3-base-pair sequences, and a tetranucleotide repeat is made up of 4-base-pair sequences. In some embodiments, a repeat expansion is a mutation that increases the number of times that the short DNA sequence is repeated.

"Mutational Load": The term "mutational load" is used herein to refer to the number of mutations detected in a sample (e.g., a tumor sample) at a given point in time. Those skilled in the art will appreciate that "mutational load" may also be referred to as "mutational burden". In some embodiments, mutations included in an assessment of mutational load may be neoantigen mutations (i.e., mutations that give rise to neoantigens). In some embodiments, a sample in which mutational load is assessed is from a single tumor. In some embodiments, a sample is pooled from multiple tumors, either from a single individual subject, or from a plurality of subjects.

Neoepitope: A "neoepitope" is understood in the art to refer to an epitope that emerges or develops in a subject after exposure to or occurrence of a particular event (e.g., development or progression of a particular disease, disorder or condition, e.g., infection, cancer, stage of cancer, etc). As used herein, a neoepitope is one whose presence and/or level is correlated with exposure to or occurrence of the event. In some embodiments, a neoepitope is one that triggers an immune response against cells that express it (e.g., at a relevant level). In some embodiments, a neopepitope is one that triggers an immune response that kills or otherwise destroys cells that express it (e.g., at a relevant level). In some embodiments, a relevant event that triggers a neoepitope is or comprises somatic mutation in a cell. In some embodiments, a neoepitope is not expressed in non-cancer cells to a level and/or in a manner that triggers and/or supports an immune response (e.g., an immune response sufficient to target cancer cells expressing the neoepitope). In some embodiments, a neoepitope is a neoantigen.

No Benefit: As used herein, the phrase "no benefit" is used to refer to absence of detectable clinical benefit (e.g., in response to administration of a particular therapy or treatment of interest). In some embodiments, absence of clinical benefit refers to absence of statistically significant change in any particular symptom or characteristic of a particular disease, disorder, or condition. In some embodiments, absence of clinical benefit refers to a change in one or more symptoms or characteristics of a disease, disorder, or condition, that lasts for only a short period of time such as, for example, less than about 6 months, less than about 5 months, less than about 4 months, less than about 3 months, less than about 2 months, less than about 1 month, or less. In some embodiments, no benefit refers to no durable benefit.

Objective Response: As used herein, the phrase "objective response" refers to size reduction of a cancerous mass by a defined amount. In some embodiments, the cancerous mass is a tumor. In some embodiments, confirmed objective response is response confirmed at least four (4) weeks after treatment.

Objective Response Rate: As used herein, the term "objective response rate" ("ORR") has its art-understood meaning referring to the proportion of patients with tumor size reduction of a predefined amount and for a minimum time period. In some embodiments, response duration usually measured from the time of initial response until documented tumor progression. In some embodiments, ORR involves the sum of partial responses plus complete responses.

Patient: As used herein, the term "patient" or "subject" refers to any organism to which a provided composition is or may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. In some embodiments, a patient is suffering from or susceptible to one or more disorders or conditions. In some embodiments, a patient displays one or more symptoms of a disorder or condition. In some embodiments, a patient has been diagnosed with one or more disorders or conditions. In some embodiments, the disorder or condition is or includes cancer, or presence of one or more tumors. In some embodiments, the disorder or condition is metastatic cancer.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Prognostic and predictive information: As used herein, the terms prognostic and predictive information are used interchangeably to refer to any information that may be used to indicate any aspect of the course of a disease or condition either in the absence or presence of treatment. Such information may include, but is not limited to, the average life expectancy of a patient, the likelihood that a patient will survive for a given amount of time (e.g., 6 months, 1 year, 5 years, etc.), the likelihood that a patient will be cured of a disease, the likelihood that a patient's disease will respond to a particular therapy (wherein response may be defined in any of a variety of ways). Prognostic and predictive information are included within the broad category of diagnostic information.

Progression Free Survival: As used herein, the term "progression free survival" (PFS) has its art-understood meaning relating to the length of time during and after the treatment of a disease, such as cancer, that a patient lives with the disease but it does not get worse. In some embodiments, measuring the progression-free survival is utilized as an assessment of how well a new treatment works. In some embodiments, PFS is determined in a randomized clinical trial; in some such embodiments, PFS refers to time from randomization until objective tumor progression and/or death.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids.

Reference: Those of skill in the art will appreciate that, in many embodiments described herein, a determined value or characteristic of interest is compared with an appropriate reference. In some embodiments, a reference value or characteristic is one determined for a comparable cohort, individual, population, or sample. In some embodiments, a reference value or characteristic is tested and/or determined substantially simultaneously with the testing or determination of the characteristic or value of interest. In some embodiments, a reference characteristic or value is or comprises a historical reference, optionally embodied in a tangible medium. Typically, as would be understood by those skilled in the art, a reference value or characteristic is determined under conditions comparable to those utilized to determine or analyze the characteristic or value of interest.

Response: As used herein, the term "response" may refer to an alteration in a subject's condition that occurs as a result of or correlates with treatment. In some embodiments, a response is or comprises a beneficial response. In some embodiments, a beneficial response may include stabilization of the condition (e.g., prevention or delay of deterioration expected or typically observed to occur absent the treatment), amelioration (e.g., reduction in frequency and/or intensity) of one or more symptoms of the condition, and/or improvement in the prospects for cure of the condition, etc. In some embodiments, "response" may refer to response of an organism, an organ, a tissue, a cell, or a cell component or in vitro system. In some embodiments, a response is or comprises a clinical response. In some embodiments, presence, extent, and/or nature of response may be measured and/or characterized according to particular criteria; in some embodiments, such criteria may include clinical criteria and/or objective criteria. In some embodiments, techniques for assessing response may include, but are not limited to, clinical examination, positron emission tomography, chest X-ray CT scan, MRI, ultrasound, endoscopy, laparoscopy, presence or level of a particular marker in a sample, cytology, and/or histology. Where a response of interest is or comprises response of a tumor to therapy, those of ordinary skill will be aware of a variety of established techniques for assessing such response, including, for example, for determining tumor burden, tumor size, tumor stage, etc. For example, certain technologies for assessing response of solid tumors to treatment are discussed in Therasse et. al., "New guidelines to evaluate the response to treatment in solid tumors", European Organization for Research and Treatment of Cancer, National Cancer Institute of the United States, National Cancer Institute of Canada, *J. Natl. Cancer Inst.*, 2000, 92(3):205-216. Those of ordinary skill in the art will be aware of, and/or will appreciate in light of the present disclosure, strategies for determining particular response criteria for individual tumors, tumor types, patient populations or cohorts, etc, as well as for determining appropriate references therefor.

Sample: As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Specific: The term "specific", when used herein with reference to an agent having an activity, is understood by those skilled in the art to mean that the agent discriminates between potential target entities or states. For example, an in some embodiments, an agent is said to bind "specifically" to its target if it binds preferentially with that target in the presence of one or more competing alternative targets. In many embodiments, specific interaction is dependent upon the presence of a particular structural feature of the target entity (e.g., an epitope, a cleft, a binding site). It is to be understood that specificity need not be absolute. In some embodiments, specificity may be evaluated relative to that of the binding agent for one or more other potential target entities (e.g., competitors). In some embodiments, specificity is evaluated relative to that of a reference specific binding agent. In some embodiments specificity is evaluated relative to that of a reference non-specific binding agent. In some embodiments, the agent or entity does not detectably bind to the competing alternative target under conditions of binding to its target entity. In some embodiments, binding agent binds with higher on-rate, lower off-rate, increased affinity, decreased dissociation, and/or increased stability to its target entity as compared with the competing alternative target(s).

Specific binding: As used herein, the terms "specific binding" or "specific for" or "specific to" refer to an interaction (typically non-covalent) between a target entity (e.g., a target protein or polypeptide) and a binding agent (e.g., an antibody, such as a provided antibody). As will be understood by those of ordinary skill, an interaction is considered to be "specific" if it is favored in the presence of alternative interactions. In many embodiments, an interaction is typically dependent upon the presence of a particular structural feature of the target molecule such as an antigenic determinant or epitope recognized by the binding molecule. For example, if an antibody is specific for epitope A, the presence of a polypeptide containing epitope A or the presence of free unlabeled A in a reaction containing both free labeled A and the antibody thereto, will reduce the amount of labeled A that binds to the antibody. It is to be understood that specificity need not be absolute. For example, it is well known in the art that numerous antibodies cross-react with other epitopes in addition to those present in the target molecule. Such cross-reactivity may be acceptable depending upon the application for which the antibody is to be used. In particular embodiments, an antibody specific for receptor tyrosine kinases has less than 10% cross-reactivity with receptor tyrosine kinase bound to protease inhibitors (e.g., ACT). One of ordinary skill in the art will be able to select antibodies having a sufficient degree of specificity to perform appropriately in any given application (e.g., for detection of a target molecule, for therapeutic purposes, etc.). Specificity may be evaluated in the context of additional factors such as the affinity of the binding molecule for the target molecule versus the affinity of the binding molecule for other targets (e.g., competitors).

Stage of cancer: As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

Subject: As used herein, the term "subject" or "patient" refers to any organism upon which embodiments of the invention may be used or administered, e.g., for experimental, diagnostic, prophylactic, and/or therapeutic purposes. Typical subjects include animals (e.g., mammals such as mice, rats, rabbits, non-human primates, and humans; insects; worms; etc.).

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Suffering from: An individual who is "suffering from" a disease, disorder, or condition (e.g., a cancer) has been diagnosed with and/or exhibits one or more symptoms of the disease, disorder, or condition. In some embodiments, an individual who is suffering from cancer has cancer, but does not display any symptoms of cancer and/or has not been diagnosed with a cancer.

Susceptible to: An individual who is "susceptible to" a disease, disorder, or condition (e.g., cancer) is at risk for developing the disease, disorder, or condition. In some embodiments, an individual who is susceptible to a disease, disorder, or condition does not display any symptoms of the disease, disorder, or condition. In some embodiments, an individual who is susceptible to a disease, disorder, or condition has not been diagnosed with the disease, disorder, and/or condition. In some embodiments, an individual who is susceptible to a disease, disorder, or condition is an individual who displays conditions associated with development of the disease, disorder, or condition. In some embodiments, a risk of developing a disease, disorder, and/or condition is a population-based risk.

Target cell or target tissue: As used herein, the terms "target cell" or "target tissue" refer to any cell, tissue, or organism that is affected by a condition described herein and to be treated, or any cell, tissue, or organism in which a protein involved in a condition described herein is expressed. In some embodiments, target cells, target tissues, or target organisms include those cells, tissues, or organisms in which there is a detectable amount of immune checkpoint signaling and/or activity. In some embodiments, target cells, target tissues, or target organisms include those cells, tissues or organisms that display a disease-associated pathology, symptom, or feature.

Therapeutic regimen: As used herein, the term "therapeutic regimen" refers to any method used to partially or completely alleviate, ameliorate, relieve, inhibit, prevent, delay onset of, reduce severity of and/or reduce incidence of one or more symptoms or features of a particular disease, disorder, and/or condition. It may include a treatment or series of treatments designed to achieve a particular effect, e.g., reduction or elimination of a detrimental condition or disease such as cancer. The treatment may include administration of one or more compounds either simultaneously, sequentially or at different times, for the same or different amounts of time. Alternatively, or additionally, the treatment may include exposure to radiation, chemotherapeutic agents, hormone therapy, or surgery. In addition, a "treatment regimen" may include genetic methods such as gene therapy, gene ablation or other methods known to reduce expression of a particular gene or translation of a gene-derived mRNA.

Therapeutic agent: As used herein, the phrase "therapeutic agent" refers to any agent that, when administered to a subject, has a therapeutic effect and/or elicits a desired biological and/or pharmacological effect.

Therapeutically effective amount: As used herein, the term "therapeutically effective amount" refers to an amount of an agent (e.g., an immune checkpoint modulator) that confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). In particular, the "therapeutically effective amount" refers to an amount of a therapeutic agent or composition effective to treat, ameliorate, or prevent a desired disease or condition, or to exhibit a detectable therapeutic or preventative effect, such as by ameliorating symptoms associated with the disease, preventing or delaying the onset of the disease, and/or also lessening the severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the subject; the time of administration, route of administration, and/or rate of excretion or metabolism of the specific fusion protein employed; the duration of the treatment; and like factors as is well known in the medical arts.

Treatment: As used herein, the term "treatment" (also "treat" or "treating") refers to any administration of a substance (e.g., provided compositions) that partially or completely alleviates, ameliorates, relieves, inhibits, delays onset of, reduces severity of, and/or reduces incidence of one or more symptoms, features, and/or causes of a particular disease, disorder, and/or condition (e.g., cancer). Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

Wild-type: As used herein, the term "wild-type" has its art-understood meaning that refers to an entity having a structure and/or activity as found in nature in a "normal" (as contrasted with mutant, diseased, altered, etc.) state or context. Those of ordinary skill in the art will appreciate that wild-type genes and polypeptides often exist in multiple different forms (e.g., alleles).

DETAILED DESCRIPTION OF CERTAIN EMBODIMENTS

Cancers

In some embodiments, the present disclosure relates to treatment of cancer. Certain exemplary cancers that may, in some embodiments, be treated in accordance with the present disclosure include, for example, adrenocortical carcinoma, astrocytoma, basal cell carcinoma, carcinoid, cardiac, cholangiocarcinoma, chordoma, chronic myeloproliferative neoplasms, craniopharyngioma, ductal carcinoma in situ, ependymoma, intraocular melanoma, gastrointestinal carcinoid tumor, gastrointestinal stromal tumor (GIST), gestational trophoblastic disease, glioma, histiocytosis, leukemia (e.g., acute lymphoblastic leukemia (ALL), acute myeloid leukemia (AML), chronic lymphocytic leukemia (CLL), chronic myelogenous leukemia (CML), hairy cell leukemia, myelogenous leukemia, and myeloid leukemia), lymphoma (e.g., Burkitt lymphoma (non-Hodgkin lymphoma), cutaneous T-cell lymphoma, Hodgkin lymphoma, mycosis fungoides, Sezary syndrome, AIDS-related lymphoma, follicular lymphoma, diffuse large B-cell lymphoma), melanoma, merkel cell carcinoma, mesothelioma, myeloma (e.g., multiple myeloma), myelodysplastic syndrome, papillomatosis, paraganglioma, pheochromacytoma, pleuropulmonary blastoma, retinoblastoma, sarcoma (e.g., Ewing sarcoma, Kaposi sarcoma, osteosarcoma, rhabdomyosarcoma, uterine sarcoma, vascular sarcoma), Wilms' tumor, and/or cancer of the adrenal cortex, anus, appendix, bile duct, bladder, bone, brain, breast, bronchus, central nervous system, cervix, colon, endometrium, esophagus, eye, fallopian tube, gall bladder, gastrointestinal tract, germ cell, head and neck, heart, intestine, kidney (e.g., Wilms' tumor), larynx, liver, lung (e.g., non-small cell lung cancer, small cell lung cancer), mouth, nasal cavity, oral cavity, ovary, pancreas, rectum, skin, stomach, testes, throat, thyroid, penis, pharynx, peritoneum, pituitary, prostate, rectum, salivary gland, ureter, urethra, uterus, vagina, or vulva.

In some embodiments, a cancer may involve one or more tumors. In some embodiments, a tumor comprises a solid tumor. In some embodiments, solid tumors include but are not limited to tumors of the bladder, breast, central nervous system, cervix, colon, esophagus, endometrium, head and neck, kidney, liver, lung, ovary, pancreas, skin, stomach, uterus, or upper respiratory tract.

In some embodiments, a cancer is selected from the group consisting of bladder cancer, bone cancer, breast cancer, cancer of unknown primary, esophagogastric cancer, gastrointestinal cancer, glioma, head and neck cancer, hepatobiliary cancer, melanoma, mesothelioma, non-hodgkin lymphoma, non-small cell lung cancer, pancreatic cancer, prostate cancer, renal cell carcinoma, skin cancer (non-melanoma), small cell lung cancer, soft tissue sarcoma, thyroid cancer, and combinations thereof.

In some embodiments, a cancer is selected from the group consisting of bladder cancer, breast cancer, esophagogastric cancer, glioma, head and neck cancer, melanoma, non-small cell lung cancer, renal cell carcinoma, and combinations thereof.

In some embodiments, a cancer that may be treated in accordance with the present disclosure is one that has been exposed to immunotherapy as described herein.

In some embodiments, a cancer that may be treated in accordance with the present disclosure is one that has been exposed to immunotherapy, which in some embodiments may be or include therapy with one or more immune checkpoint inhibitor modulators.

In some embodiments, a cancer that may be treated in accordance with the present disclosure is one characterized by high tumor mutational load (i.e., tumor mutational load above a relevant threshold) as described herein. Alternatively or additionally, a cancer that may be treated in accordance with the present disclosure is one characterized by neoantigens.

In some embodiments, a cancer that may be treated in accordance with the present disclosure is characterized by both prior exposure to immunotherapy comprising immune checkpoint modulators and high tumor mutational load; in some such embodiments, the cancer shows higher tumor mutational load than was present prior to its exposure to the immunotherapy.

Immunotherapy

In some embodiments, the present disclosure relates to administration of immunotherapy to a subject. In some embodiments, immunotherapy is or comprises immune checkpoint modulation therapy. In some embodiments, immunotherapy involves administration of one or more immunomodulatory agents; in some embodiments an immunomodulatory agent is or comprises an immune checkpoint modulator. In some embodiments, an immune checkpoint modulator is an agent (e.g., an antibody agent) that targets (i.e., specifically interacts with) an immune checkpoint target. In some embodiments, an immune checkpoint target is or comprises one or more of CTLA-4, PD-1, PD-L1, GITR, OX40, LAG-3, KIR, TIM-3, CD28, CD40, and CD137; in some embodiments, immune checkpoint modulator therapy is or comprises administration of an antibody agent that targets one or more such immune checkpoint targets.

In some embodiments, immune checkpoint refers to inhibitory pathways of an immune system that are responsible for maintaining self-tolerance and modulating duration and amplitude of physiological immune responses. Certain cancer cells thrive by taking advantage of immune checkpoint pathways as a major mechanism of immune resistance, particularly with respect to T cells that are specific for tumor antigens. For example, certain cancer cells may overexpress one or more immune checkpoint proteins responsible for inhibiting a cytotoxic T cell response. Thus, among other things, immune checkpoint modulators may be administered to overcome inhibitory signals and permit and/or augment an immune attack against cancer cells. Immune checkpoint modulators may facilitate immune cell responses against cancer cells by decreasing, inhibiting, or abrogating signaling by negative immune response regulators (e.g. CTLA-4), or may stimulate or enhance signaling of positive regulators of immune response (e.g. CD28).

Advances in understanding of molecular mechanisms of T cell activation and inhibition and immune homeostasis have allowed for rational development of immunologically targeted therapies for cancer. The best known of these are immune checkpoint modulator monoclonal antibodies that block CTLA-4 and PD-1 pathways, representing critical inhibitory checkpoints that restrain T cells from full and persistent activation and proliferation under normal physiologic conditions. Blockade of CTLA-4 and/or PD-1 pathways can result in durable regressions for patients with a widening spectrum of malignancies. In some embodiments, an immunotherapy is or comprises administration of one or more of PD-1 or PD-L1 blockade therapies. In some embodiments, an immunotherapy is or comprises administration of one or more of CTLA-4 blockade therapies. In some embodiments, an immunotherapy can include any of ipilumimab and tremelimumab which target CTLA-4; pembrolizumab, nivolumab, avelumab, durvalumab, and atezoluzumab, which target PD-1; or combinations thereof.

Teachings of the present disclosure, among other things, predict responsiveness to immune checkpoint modulators, and particularly to therapeutic modalities or regimens targeting immune checkpoint regulators. The present disclosure, among other things, demonstrates that tumor mutational load threshold correlates with responsiveness to immune checkpoint modulators. In some embodiments, the present disclosure demonstrates that tumor mutational load threshold correlates with an increased likelihood of clinical efficacy from immune checkpoint regulators for those cancers responsive to immunotherapy (e.g., to PD-1 blockade and/or to CTLA-4 blockade). In some embodiments, immunotherapy (e.g. immune checkpoint modulator therapy) involves administration of an agent that acts as a blockade of cytotoxic T-lymphocyte-associated protein 4 (CTLA-4). In certain embodiments, immunotherapy involves treatment with an agent that interferes with an interaction involving CTLA-4 (e.g., with CD80 or CD86). In some embodiments, immunotherapy involves administration of one or more of tremelimumab and/or ipilimumab. In some embodiments, immunotherapy (e.g. immune checkpoint modulator therapy) involves administration of an agent (e.g. antibody agent) that acts as a blockade of programmed cell death 1 (PD-1). In certain embodiments, immunotherapy involves treatment with an agent that interferes with an interaction involving PD-1 (e.g., with PD-L1). In some embodiments, immunotherapy involves administration of an agent (e.g. antibody agent) that specifically interacts with PD-1 or with PD-L1. In some embodiments, immunotherapy (e.g. immune checkpoint modulator therapy) involves administration of one or more of nivolumab, pembrolizumab, atezolizumab, avelumab, and/or durvalumab.

CTLA-4

CTLA-4 is a member of the immunoglobulin superfamily that is expressed by activated T cells and transmits an inhibitory signal to T cells. CTLA-4 is structurally similar to T cell co-stimulatory protein, CD28, and both molecules bind to CD80 and CD86 on antigen-presenting cells.[18] CTLA-4 binds CD80 and CD86 with greater affinity than CD28, thus enabling it to outcompete CD28 for its ligands.[18] CTLA-4 transmits an inhibitory signal to T cells, whereas CD28 transmits a stimulatory signal. T cell activation through T cell receptor and CD28 leads to increased expression of CTLA-4.

The mechanism by which CTLA-4 acts in T cells remains somewhat elusive. Biochemical evidence suggests that CTLA-4 recruits a phosphatase to a T cell receptor, thus attenuating the signal. It has also been suggested that CTLA-4 may function in vivo by capturing and removing CD80 and CD86 from membranes of antigen-presenting cells, thus making these antigens unavailable for triggering of CD28.

CTLA-4 protein contains an extracellular V domain, a transmembrane domain, and a cytoplasmic tail. CTLA-4 has an intracellular domain that is similar to that of CD28, in that it has no intrinsic catalytic activity and contains one YVKM motif able to bind PI3K, PP2A and SHP-2, as well as one proline-rich motif able to bind SH3-containing proteins. One role of CTLA-4 in inhibiting T cell responses seems to directly involve SHP-2 and PP2A dephosphorylation of T cell receptor-proximal signaling proteins, such as CD3 and LAT. CTLA-4 can also affect signaling indirectly, via competition with CD28 for CD80 and/or CD86 binding.

The first clinical evidence that modulation of T cell activation could result in effective anti-cancer therapy came from development of CTLA-4 blockade antibody ipilimumab.[18] In some embodiments, ipilimumab is a human IgG1 antibody with specificity for CTLA-4. In some embodiments, another CTLA-4 blockade therapy, tremelimumab, is a human IgG2 antibody.

PD-1

PD-1 is expressed on T cells, B cells, and certain myeloid cells; however, its role is best characterized in T cells. PD-1 expression on T cells is induced by antigen stimulation. Unlike CTLA-4, which limits early T-cell activation, PD-1 mainly exerts its inhibitory effect on T cells in the periphery where T cells encounter PD-1 ligands. Two ligands of PD-1 have been identified so far, PD-L1 and PD-L2, which are expressed by a large range of cell types, including tumor cells, monocyte-derived myeloid dendritic cells, epithelial cells, T cells, and B cells.[18] In cancer, tumor cells and myeloid cells are thought to be main cell types mediating T-cell suppression through PD-1 ligation. It is still unclear whether effects of PD-L1 and PD-L2 on PD-1 downstream signaling are dependent on cell type that expresses a given ligand. Moreover, there are differences between PD-L1- versus PD-L2-induced effects, which remain to be fully elucidated.

Several mechanisms of PD-1-mediated T cell suppression have been proposed.[18] One mechanism suggests that PD-1 ligation inhibits T cell activation only upon T cell receptor engagement. PD-1 has an intracellular "immunoreceptor tyrosine-based inhibition motif" or (ITIM) and an immunoreceptor tyrosine-based switch motif. It has been shown that PD-1 ligation leads to recruitment of phosphatases called "src homology 2 domain-containing tyrosine phosphatases," or SHP-1 and SHP-2, to immunoreceptor tyrosine-based switch motif. Moreover, PD-1 ligation has been shown to interfere with signaling molecules, such as phosphatidylinositol-4,5-bisphosphate 3-kinase and Ras, which are important for T-cell proliferation, cytokine secretion, and metabolism. Analysis of human immunodeficiency virus (HIV)-specific T cells has also demonstrated PD-1-dependent basic leucine zipper transcription factor upregulation, which inhibits T cell function. Ligation of PD-1 has also been shown to induce metabolic alterations in T cells. Metabolic reprogramming of T cells from glycolysis to lipolysis is a consequence of PD-1-mediated impairment of T-cell effector function. Furthermore, PD-1-induced defects in mitochondrial respiration and glycolysis leads to impaired T-cell effector function that could be reversed by a mammalian target of rapamycin inhibition. Since most of the identified mechanisms of PD-1-mediated T-cell suppression are based on in vitro or ex vivo experiments, it remains to be demonstrated that these same mechanisms are responsible for T-cell exhaustion in vivo.

PD-1 is a type I membrane protein of 288 amino acids and is a member of the extended CD28/CTLA-4 family of T cell regulators.[19] PD-1 protein structure includes an extracellular IgV domain followed by a transmembrane region and an intracellular tail, which contains two phosphorylation sites located in an immunoreceptor tyrosine-based inhibitory motif (ITIM) and an immunoreceptor tyrosine-based switch motif, which suggests that PD-1 negatively regulates T cell receptor signals. This is consistent with binding of SHP-1 and SHP-2 phosphatases to PD-1 cytoplasmic tail upon ligand binding. In addition, PD-1 ligation up-regulates E3-ubiquitin ligases CBL-b and c-CBL that trigger T cell receptor down-modulation. PD-1 is expressed on the surface of activated T cells, B cells, and macrophages, suggesting that compared to CTLA-4, PD-1 more broadly negatively regulates immune responses.

CTLA-4 and PD-1 in Combination

Although monotherapies with CTLA-4- or PD-1-blocking antibodies have significantly prolonged survival of some patients with certain cancers, there are cases where some patients do not respond to therapy. A previous study has shown that combined treatment with ipilimumab (CTLA-4 blockade) and nivolumab (PD-1 blockade) induced better responses than either treatment alone.[18,20] In some embodiments, immunotherapy, in accordance with the present disclosure, comprises both PD-1 blockade therapy and CTLA-4 blockade therapy. In certain embodiments, immunotherapy (e.g. immune checkpoint modulator therapy) involves treatment with an agent (e.g. antibody agent) that interferes with an interaction involving CTLA-4 and/or PD-1. In some embodiments, immunotherapy (e.g. immune checkpoint modulator therapy) involves administration of an agent (e.g. antibody agent) that specifically interacts with one or more of CTLA-4, CD80, CD86, PD-1 or PD-L1. In some embodiments, such therapy involves administration of one or more of atezolizumab, avelumab, durvalumab, ipilimumab, nivolumab, pembrolizumab, and/or tremelimumab.

Tumor Mutational Load

Among other things, the present disclosure demonstrates a that tumor mutational load can predict clinical efficacy of immunotherapy treatment for certain cancers. The present disclosure establishes, among other things, that in certain cases, individuals with higher tumor mutational loads are more likely to respond positively to immunotherapy than individuals with significantly lower tumor mutational loads. The present disclosure, among other things, establishes that, in certain cases, individuals with higher tumor mutational loads and who have already received immunotherapy, are more likely to respond positively to immunotherapy, than individuals with significantly lower tumor mutational loads.

In some embodiments, tumor mutational load comprises a number of somatic mutations within a region of a tumor genome. In some embodiments, somatic mutations comprise DNA alterations in non-germline cells and commonly occur in cancer cells. In some embodiments, a somatic mutation results in a neoantigen or neoepitope. It has been discovered that certain somatic mutations in cancer cells result in expression of neoepitopes, that in some embodiments transition a stretch of amino acids from being recognized as "self" to "non-self". A cancer cell harboring a "non-self" antigen is typically more likely to elicit an immune response against a cancer cell. The identification of multiple mutations in a cancer sample as described herein can be useful for determining which cancer patients are likely to respond favorably to immunotherapy (e.g. continued and/or extended or modified immunotherapy); in some embodiments, such identification can be useful for determining which cancer patients are likely to respond, in particular, to treatment with an immune checkpoint modulator and/or otherwise to PD-1 and/or CTLA-4 blockade.

The present disclosure, among other things, demonstrates that, for certain cancers, patients with high numbers of somatic mutations, or a high tumor mutational load, are more likely to benefit from treatment with immune checkpoint modulators than those patients with lower tumor mutational loads. In some embodiments, patients with a high tumor mutational load respond better to PD-1 (programmed cell death 1) blockade than those patients with a significantly lower tumor mutational load. In some embodiments, individuals with a high tumor mutational load respond better to treatment with anti-PD-1 antibodies than those individuals with a low tumor mutational load. In some embodiments, individuals with a high tumor mutational load respond better to treatment with CTLA-4 blockade than those individuals with a low tumor mutational load. In some embodiments, individuals with a high tumor mutational load respond better to treatment with CTLA-4 antibodies than those individuals with a low tumor mutational load.

Tumor Mutational Load Threshold

The present disclosure, among other things, encompasses an insight that meaningful limits can be imposed on mutational analysis of cancer cells and, moreover, that use of such limits surprisingly defines and/or provides tumor mutational load thresholds that effectively predict responsiveness to treatment (e.g., continued and/or extended or modified immunotherapy). In some embodiments, a tumor mutational load threshold as described herein correlates with and/or predicts response to immunotherapy (e.g., immune checkpoint modulator therapy, e.g. PD-1 blockade or CTLA-4 blockade).

Moreover, the present disclosure, among other things, encompasses the discovery that a tumor mutational load threshold that predicts likelihood of responsiveness to cancer immunotherapy (and/or to a specific immunomodulatory agent and/or regimen) can be defined for tumors that have already received prior immunotherapy. In some embodiments, the number of mutations in a given tumor correlates with and/or is predictive of positive response to immunotherapy. Moreover, the present disclosure demonstrates that tumor mutational load level relative to a threshold, can be detected and effectively utilized to predict tumor responsiveness for a wide variety of cancers.

In some embodiments, as described herein, the present disclosure provides technologies for defining tumor mutational load thresholds that predict responsiveness to immunotherapy (e.g. continued and/or extended or modified), and particularly to immune checkpoint modulator therapy. In some embodiments, the present disclosure describes and/or establishes effective use of such thresholds in predicting therapeutic responsiveness.

The present disclosure demonstrates that a mutational landscape and/or tumor mutational load threshold of a particular tumor can predict the likelihood of clinical benefit from immunotherapy (e.g., PD-1 blockade or CTLA-4 blockade). The disclosure also teaches that a tumor mutational load threshold can predict likelihood of positive response to immunotherapy with immune checkpoint modulators. Furthermore, the nature of the somatic mutations present can predict response to immunotherapy with immune checkpoint modulators.

In some embodiments, tumor mutational load level relative to a threshold, can be determined and/or detected using targeted gene panel technologies (e.g., assessed with next-generation sequencing), and do not necessarily require whole exome sequencing.

Thus, among other things, the present disclosure establishes that relevant thresholds for these cancers may be, for example:

| Cancer Type | Threshold |
|---|---|
| Bladder Cancer | Within a range of about 7 to about 27; in some embodiments about 17. |
| Breast Cancer | Within a range of about 1 to about 14; in some embodiments about 4. |
| Esophagogastric Cancer | Within a range of about 1 to about 21; in some embodiments about 11. |
| Glioma | Within a range of about 1 to about 15; in some embodiments about 5. |
| Head and Neck Cancer | Within a range of about 1 to about 18; in some embodiments about 8. |
| Melanoma | Within a range of about 1 to about 21; in some embodiments about 11. |
| Non-Small Cell Lung Cancer | Within a range of about 1 to about 29; in some embodiments about 18. |

-continued

| Cancer Type | Threshold |
|---|---|
| Renal Cell Carcinoma | Within a range of about 1 to about 12; in some embodiments about 2. |

Detection of Tumor Mutational Load and/or Neoepitopes

Cancers may be screened to detect mutations and/or neoepitopes (e.g., to detect tumor mutational load and/or neoepitope load and/or neoantigen identity, and/or neopitope nature, level, and/or frequency) as described herein using any of a variety of known technologies. In some embodiments, particular mutations or neoepitopes, or expression thereof, is/are detected at the nucleic acid level (e.g., in DNA or RNA). One of skill in the art would recognize that mutations or neoepitopes, or expression thereof, can be detected in a sample comprising DNA or RNA from cancer cells. Further, one of skill in the art would understand that a sample comprising DNA or RNA from cancer cells can include but is not limited to circulating tumor DNA (ctDNA), cell free DNA (cfDNA), cells, tissues, or organs. In some embodiments, mutations or neopeitopes, or expression thereof, is detected at the protein level (e.g., in a sample comprising polypeptides from cancer cells, which sample may be or comprise polypeptide complexes or other higher order structures including but not limited to cells, tissues, or organs).

In some particular embodiments, detection involves nucleic acid sequencing. In some embodiments, detection involves whole exome sequencing. In some embodiments, detection involves an immunoassay. In some embodiments, detection involves use of a microarray. In some embodiments, detection involves massively parallel exome sequencing. In some embodiments, detection involves genome sequencing. In some embodiments, detection involves RNA sequencing. In some embodiments, detection involves standard DNA or RNA sequencing. In some embodiments, detection involves mass spectrometry.

In some embodiments, detection involves next generation sequencing (DNA and/or RNA). In some embodiments, detection involves genome sequencing, genome resequencing, targeted sequencing panels, transcriptome profiling (RNA-Seq), DNA-protein interactions (ChIP-sequencing), and/or epigenome characterization. In some embodiments, re-sequencing of a patient's genome may be utilized, for example to detect genomic variations.

In some embodiments, detection involves using a technique such as ELISA, Western Transfer, immunoassay, mass spectrometry, microarray analysis, etc.

In some embodiments, detection involves next generation sequencing (DNA and/or RNA). In some embodiments, detection involves next generation sequencing of targeted gene panels (e.g. MSK-IMPACT or FoundationOne 8). In some embodiments, detection involves genomic profiling. In some embodiments, detection involves genomic profiling using Integrated Mutation Profiling of Actionable Cancer Targets (MSK-IMPACT).[8,17] MSK-IMPACT is a comprehensive molecular profiling assay that involves hybridization capture and deep sequencing of all exons and selected introns of multiple oncogenes and tumor-suppressor genes, allowing for detection of point mutations, small and large insertions or deletions, and rearrangements. MSK-IMPACT also captures intergenic and intronic single-nucleotide polymorphisms (e.g., tiling probes), interspersed across a genome, aiding in accurate assessment of genome-wide copy number. In some embodiments, probes may target a megabase.

In some embodiments, detection may involve sequencing of exon and/or intron sequences from at least 100, 150, 200, 250, 300, 350, 400, 450, 500, 550, 600, 650, 700, 750, 800, 850, 900, 950, 1000 or more genes (e.g., oncogenes and/or tumor-suppressor genes). For example, literature reports indicate that MSK-IMPACT has been used to achieve deep sequencing of all exons and selected introns of 468 oncogenes and tumor-suppressor genes.

Alternatively or additionally, in some embodiments, detection may involve sequencing of intergenic and/or intronic single-nucleotide polymorphisms. For example, literature reports indicate that MSK-IMPACT has been used to achieve deep sequencing of >1000 intergenic and intronic single-nucleotide polymorphisms.

In some embodiments, administering immunotherapy to a subject who has received prior immunotherapy displays a tumor mutational load above a threshold that has been correlated with a statistically significant probability of responding to immunotherapy.

In some embodiments, a method of administering immunotherapy to a subject comprises a further step of measuring tumor mutational load level relative to a threshold in the subject, which measuring step is performed at a time selected from the group consisting of prior to the administering, during the administering, after the administering, and combinations thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

Human Leukocyte Antigen

Prior to the present disclosure, there has been little understanding of how host genetics impact response to cancer immunotherapy. One factor that has been repeatedly associated with modulating the immune response during bacterial or viral infection, inflammatory conditions, and autoimmune diseases, is HLA class I genotype (21-29). The human leukocyte antigen (HLA) complex is a gene complex encoding the major histocompatibility complex (MHC) proteins. The major histocompatibility complex (MEC) class I coding region in humans is central to the immune response. Each HLA class I molecule binds specific peptides derived from intracellular proteins that have been processed and transported into the endoplasmic reticulum by the TAP proteins, where they are bound to the MHC class I molecules for presentation on the cell surface (30).

MHC molecules are extremely polymorphic, and over a thousand allelic variants have already been described at the class I A and B loci. Most of the polymorphism is located in the peptide-binding region, and as a result each variant is believed to bind a unique repertoire of peptide ligands. Despite this polymorphism, HLA class I molecules can be clustered into groups, designated as supertypes (a.k.a. superfamilies), representing sets of molecules that share largely overlapping peptide binding specificity. Exemplary supertypes include but are not limited to A02, A24, A03, B07, B27, B44, Each supertype can be described by a supermotif that reflects the broad main anchor motif recognized by molecules within the corresponding supertype. For example, molecules of the A02-supertype share specificity for peptides with aliphatic hydrophobic residues in position 2 and at the C-terminus, while A03-supertype molecules recognize peptides with small or aliphatic residues in position 2 and basic residues at the C-terminus.

Typically, in the case of human leukocyte antigen (HLA) class I, the main binding energy is provided by the interaction of residues in position 2 and the C-terminus of the peptide with the B and F binding pockets of the MHC molecule, respectively although side chains throughout the ligand can have a positive or negative influence on binding capacity. Once pathogen or tumor-derived epitopes are presented on the cell surface, CD8+ T-cells must be able to recognize them to subsequently elicit an immune response and eliminate cells bearing those same epitopes (31, 32). Some tumor cells have reduced ability to present epitopes on the surface due to genetic alterations resulting in loss of heterozygosity (LOH) in the HLA locus. LOH is a gross chromosomal event that results in loss of an entire gene and surrounding chromosomal region. The anti-tumor activity of immune checkpoint treatment has been shown to depend on CD8+ T cell, MHC class I-dependent immune activity (33-35).

Among other things, the present disclosure demonstrates that HLA class I genotype can influence clinical efficacy of immunotherapy treatment for certain cancers. The present disclosure establishes, among other things, that heterozygosity at one or more HLA class I loci (e.g., A, B, or C) can influence clinical efficacy of immunotherapy treatment. In some embodiments, heterozygosity at all three HLA class I loci (i.e., maximum heterozygosity) can influence clinical efficacy of immunotherapy treatment.

The present disclosure establishes, among other things, that in certain cases, individuals with heterozygosity at one or more HLA class I loci (e.g., A, B, or C) are more likely to respond positively to immunotherapy. In some embodiments, individuals with heterozygosity at all three HLA class I loci (i.e., maximum heterozygosity) are more likely to respond positively to immunotherapy.

In some embodiments, the present disclosure establishes that individuals with particular HLA class I superfamily alleles are more likely to respond positively to immunotherapy. In some embodiments, individuals with HLA class I B44 allele are more likely to respond positively to immunotherapy. In some embodiments, individuals with HLA class I B62 allele are more likely to respond positively to immunotherapy.

Further, the present disclosure establishes, among other things, that in certain cases, individuals with heterozygosity at one or more HLA class I loci (e.g., A, B, or C) and higher tumor mutational loads as described herein are more likely to respond positively to immunotherapy than individuals with significantly lower tumor mutational loads and/or no or less heterozygosity at HLA class I loci. In some embodiments, individuals with heterozygosity at all three HLA class I loci and higher tumor mutational loads as described herein are more likely to respond positively to immunotherapy than individuals with significantly lower tumor mutational loads and/or no or less heterozygosity at HLA class I loci.

In some embodiments, a subject's HLA class I genotype can be determined sequencing. Sequencing can be performed by methods known in the art. In some embodiments, for example, HLA class I genotype can be determined by exome sequencing. In some embodiments, a subject's HLA class I genotype can be determined using a clinically validated HLA typing assay.

Treatment

In some embodiments, the invention relates to treatment of tumors that display a tumor mutational load above a relevant threshold. In some embodiments, such tumors have previously received immunotherapy. In some embodiments, such immunotherapy is an immune checkpoint modulator.

Administration of Immune Checkpoint Modulators

In accordance with certain methods of the invention, an immunomodulatory agent (e.g. immune checkpoint modulator) is and/or has been administered to an individual. In some embodiments, treatment with an immunomodulatory agent (e.g. immune checkpoint modulator) is utilized as a sole therapy. In some embodiments, treatment with an immunomodulatory agent (e.g. immune checkpoint modulator) is used in combination with one or more other therapies.

Those of ordinary skill in the art will appreciate that appropriate formulations, indications, and dosing regimens are typically analyzed and approved by government regulatory authorities such as the Food and Drug Administration in the United States. For example, Examples 4 and 5 present certain FDA-approved dosing information for PD-1 and CTLA-4 blockade regimens, respectively. In some embodiments, an immunomodulatory agent (e.g. immune checkpoint modulator) is administered in accordance with the present invention according to such an approved protocol. However, the present disclosure, among other things, provides certain technologies for identifying, characterizing, and/or selecting particular patients to whom an immunomodulatory agent (e.g.immune checkpoint modulator) may be desirably administered. In some embodiments, insights provided by the present disclosure permit dosing of a given an immunomodulatory agent (e.g. immune checkpoint modulator) with greater frequency and/or greater individual doses (e.g., due to reduced susceptibility to and/or incidence or intensity of undesirable effects) relative to that recommended or approved based on population studies that include both individuals identified as described herein (e.g., expressing neoepitopes or having a tumor mutational load above the threshold) and other individuals. In some embodiments, insights provided by the present disclosure permit dosing of a given an immunomodulatory agent (e.g. immune checkpoint modulator) with reduced frequency and/or reduced individual doses (e.g., due to increased responsiveness) relative to that recommended or approved based on population studies that include both individuals identified as described herein (e.g., expressing neoepitopes or having a tumor mutational load above the threshold) and other individuals.

In some embodiments, an immunomodulatory agent (e.g. immune checkpoint modulator) is administered in a pharmaceutical composition that also comprises a physiologically acceptable carrier or excipient. In some embodiments, a pharmaceutical composition is sterile. In many embodiments, a pharmaceutical composition is formulated for a particular mode of administration.

In some embodiments, suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrrolidone, etc., as well as combinations thereof. In some embodiments, a pharmaceutical preparation can, if desired, comprise one or more auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In some embodiments, a water-soluble carrier suitable for intravenous administration is used.

In some embodiments, a pharmaceutical composition or medicament, if desired, can contain an amount (typically a minor amount) of wetting or emulsifying agents, and/or of pH buffering agents. In some embodiments, a pharmaceutical composition can be a liquid solution, suspension, emulsion, tablet, pill, capsule, sustained release formulation, or powder. In some embodiments, a pharmaceutical composition can be formulated as a suppository, with traditional binders and carriers such as triglycerides. In some embodiments, oral formulation can include standard carriers such as pharmaceutical grades of mannitol, lactose, starch, magnesium stearate, polyvinyl pyrrolidone, sodium saccharine, cellulose, magnesium carbonate, etc.

In some embodiments, a pharmaceutical composition can be formulated in accordance with routine procedures as a pharmaceutical composition adapted for administration to human beings. For example, in some embodiments, a composition for intravenous administration typically is a solution in sterile isotonic aqueous buffer. In some embodiments, where necessary, a composition may also include a solubilizing agent and a local anesthetic to ease pain at the site of the injection. In some embodiments, generally, ingredients are supplied either separately or mixed together in unit dosage form, for example, as a dry lyophilized powder or water free concentrate in a hermetically sealed container such as an ampule or sachet indicating the quantity of active agent. In some embodiments, where a composition is to be administered by infusion, it can be dispensed with an infusion bottle containing sterile pharmaceutical grade water, saline or dextrose/water. In some embodiments, where a composition is administered by injection, an ampule of sterile water for injection or saline can be provided so that the ingredients may be mixed prior to administration.

In some embodiments, an immunomodulatory agent (e.g. immune checkpoint modulator) can be formulated in a neutral form; in some embodiments it may be formulated in a salt form. In some embodiments, pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Pharmaceutical compositions for use in accordance with the present invention may be administered by any appropriate route. In some embodiments, a pharmaceutical composition is administered intravenously. In some embodiments, a pharmaceutical composition is administered subcutaneously. In some embodiments, a pharmaceutical composition is administered by direct administration to a target tissue, such as heart or muscle (e.g., intramuscular), or nervous system (e.g., direct injection into the brain; intraventricularly; intrathecally). Alternatively or additionally, in some embodiments, a pharmaceutical composition is administered parenterally, transdermally, or transmucosally (e.g., orally or nasally). More than one route can be used concurrently, if desired.

In some embodiments, an immunomodulatory agent (e.g. immune checkpoint modulator (or a composition or medicament containing an immune checkpoint modulator)), can be administered alone, or in conjunction with other immunomodulatory agents. The term, "in conjunction with," indicates that a first immune checkpoint modulator is administered prior to, at about the same time as, or following another immune checkpoint modulator. In some embodiments, a first immunomodulatory agent (e.g. immune checkpoint modulator) can be mixed into a composition containing one or more different immunomodulatory agents (e.g. immune checkpoint modulators), and thereby administered contemporaneously; alternatively, in some embodiments, the agent can be administered contemporaneously, without mixing (e.g., by "piggybacking" delivery of the agent on the intravenous line by which the immunomodulatory agent (e.g. immune checkpoint modulator) is also administered, or vice versa). In some embodiments, an immunomodulatory agent (e.g. immune checkpoint modulator) can be administered separately (e.g., not admixed), but within a short time frame (e.g., within 24 hours) of administration of another immunomodulatory agent (e.g. immune checkpoint modulator).

In some embodiments, subjects treated with an immunomodulatory agent (e.g. immune checkpoint modulator) are administered one or more immunosuppressants. In some embodiments, one or more immunosuppressants are administered to decrease, inhibit, or prevent an undesired autoimmune response (e.g., enterocolitis, hepatitis, dermatitis (including toxic epidermal necrolysis), neuropathy, and/or endocrinopathy), for example, hypothyroidism. In some embodiments, exemplary immunosuppressants include steroids, antibodies, immunoglobulin fusion proteins, and the like. In some embodiments, an immunosuppressant inhibits B cell activity (e.g. rituximab). In some embodiments, an immunosuppressant is a decoy polypeptide antigen.

In some embodiments, an immunomodulatory agent (e.g. immune checkpoint modulators (or a composition or medicament containing immune checkpoint modulators)) are administered in a therapeutically effective amount (e.g., a dosage amount and/or according to a dosage regimen that has been shown, when administered to a relevant population, to be sufficient to treat cancer, such as by ameliorating symptoms associated with the cancer, preventing or delaying the onset of the cancer, and/or also lessening the severity or frequency of symptoms of cancer). In some embodiments, long term clinical benefit is observed after treatment with an immunomodulatory agent (e.g. immune checkpoint modulators), including, for example, PD-1 blockade such as pembrolizumab, CTLA-4 blockade such as ipilimumab, and/or other agents. Those of ordinary skill in the art will appreciate that a dose which will be therapeutically effective for the treatment of cancer in a given patient may depend, at least to some extent, on the nature and extent of cancer, and can be determined by standard clinical techniques. In some embodiments, one or more in vitro or in vivo assays may optionally be employed to help identify optimal dosage ranges. In some embodiments, a particular dose to be employed in the treatment of a given individual may depend on the route of administration, the extent of cancer, and/or one or more other factors deemed relevant in the judgment of a practitioner in light of patient's circumstances. In some embodiments, effective doses may be extrapolated from dose-response curves derived from in vitro or animal model test systems (e.g., as described by the U.S. Department of Health and Human Services, Food and Drug Administration, and Center for Drug Evaluation and Research in "Guidance for Industry: Estimating Maximum Safe Starting Dose in Initial Clinical Trials for Therapeutics in Adult Healthy Volunteers", Pharmacology and Toxicology, July 2005).

In some embodiments, a therapeutically effective amount of an immunomodulatory agent (e.g. immune checkpoint modulator) can be, for example, more than about 0.01 mg/kg, more than about 0.05 mg/kg, more than about 0.1 mg/kg, more than about 0.5 mg/kg, more than about 1.0 mg/kg, more than about 1.5 mg/kg, more than about 2.0 mg/kg, more than about 2.5 mg/kg, more than about 5.0 mg/kg, more than about 7.5 mg/kg, more than about 10 mg/kg, more than about 12.5 mg/kg, more than about 15 mg/kg, more than about 17.5 mg/kg, more than about 20 mg/kg, more than about 22.5 mg/kg, or more than about 25 mg/kg body weight. In some embodiments, a therapeutically effective amount can be about 0.01-25 mg/kg, about 0.01-20 mg/kg, about 0.01-15 mg/kg, about 0.01-10 mg/kg, about 0.01-7.5 mg/kg, about 0.01-5 mg/kg, about 0.01-4 mg/kg, about 0.01-3 mg/kg, about 0.01-2 mg/kg, about 0.01-1.5 mg/kg, about 0.01-1.0 mg/kg, about 0.01-0.5 mg/kg, about 0.01-0.1 mg/kg, about 1-20 mg/kg, about 4-20 mg/kg, about 5-15 mg/kg, about 5-10 mg/kg body weight. In some embodiments, a therapeutically effective amount is about 0.01 mg/kg, about 0.05 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1.0 mg/kg, about 1.1 mg/kg, about 1.2 mg/kg, about 1.3 mg/kg about 1.4 mg/kg, about 1.5 mg/kg, about 1.6 mg/kg, about 1.7 mg/kg, about 1.8 mg/kg, about 1.9 mg/kg, about 2.0 mg/kg, about 2.5 mg/kg, about 3.0 mg/kg, about 4.0 mg/kg, about 5.0 mg/kg, about 6.0 mg/kg, about 7.0 mg/kg, about 8.0 mg/kg, about 9.0 mg/kg, about 10.0 mg/kg, about 11.0 mg/kg, about 12.0 mg/kg, about 13.0 mg/kg, about 14.0 mg/kg, about 15.0 mg/kg, about 16.0 mg/kg, about 17.0 mg/kg, about 18.0 mg/kg, about 19.0 mg/kg, about 20.0 mg/kg, body weight, or more. In some embodiments, the therapeutically effective amount is no greater than about 30 mg/kg, no greater than about 20 mg/kg, no greater than about 15 mg/kg, no greater than about 10 mg/kg, no greater than about 7.5 mg/kg, no greater than about 5 mg/kg, no greater than about 4 mg/kg, no greater than about 3 mg/kg, no greater than about 2 mg/kg, or no greater than about 1 mg/kg body weight or less.

In some embodiments, the administered dose for a particular individual is varied (e.g., increased or decreased) over time, depending on the needs of the individual.

In some embodiments, a loading dose (e.g., an initial higher dose) of a therapeutic composition may be given at the beginning of a course of treatment, followed by administration of a decreased maintenance dose (e.g., a subsequent lower dose) of the therapeutic composition. Without wishing to be bound by any theories, it is contemplated that a loading dose may clear out an initial and, in some cases massive, accumulation of undesirable materials (e.g., fatty materials and/or tumor cells, etc) in tissues (e.g., in the liver), and maintenance dosing may delay, reduce, or prevent buildup of fatty materials after initial clearance.

In some embodiments, it will be appreciated that a loading dose and maintenance dose amounts, intervals, and duration of treatment may be determined by any available method, such as those exemplified herein and those known in the art. In some embodiments, a loading dose amount is about 0.01-1 mg/kg, about 0.01-5 mg/kg, about 0.01-10 mg/kg, about 0.1-10 mg/kg, about 0.1-20 mg/kg, about 0.1-25 mg/kg, about 0.1-30 mg/kg, about 0.1-5 mg/kg, about 0.1-2 mg/kg, about 0.1-1 mg/kg, or about 0.1-0.5 mg/kg body weight. In some embodiments, a maintenance dose amount is about 0-10 mg/kg, about 0-5 mg/kg, about 0-2 mg/kg, about 0-1 mg/kg, about 0-0.5 mg/kg, about 0-0.4 mg/kg, about 0-0.3 mg/kg, about 0-0.2 mg/kg, about 0-0.1 mg/kg body weight. In some embodiments, a loading dose is administered to an individual at regular intervals for a given period of time (e.g., 1, 2, 3, 4, 5, 6, 7, 8, 9, 10, 11, 12 or more months) and/or a given number of doses (e.g., 1, 2, 3, 4, 5, 6, 7, 8, 9, 10, 15, 20, 25, 30 or more doses), followed by maintenance dosing. In some embodiments, a maintenance dose ranges from 0-2 mg/kg, about 0-1.5 mg/kg, about 0-1.0 mg/kg, about 0-0.75 mg/kg, about 0-0.5 mg/kg, about 0-0.4 mg/kg, about 0-0.3 mg/kg, about 0-0.2 mg/kg, or about 0-0.1 mg/kg body weight. In some embodiments, a maintenance dose is about 0.01, 0.02, 0.04, 0.06, 0.08, 0.1, 0.2, 0.3, 0.4, 0.5, 0.6, 0.7, 0.8, 0.9, 1.0, 1.2, 1.4, 1.6, 1.8, or 2.0 mg/kg body weight. In some embodiments, maintenance dosing is administered for 1, 2, 3, 4, 5, 6, 7, 8, 9, 10, 11, 12 or more months. In some embodiments, maintenance dosing is administered for 1, 2, 3, 4, 5, 6, 7, 8, 9, 10 or more years. In some embodiments, maintenance dosing is administered indefinitely (e.g., for life time).

In some embodiments, a therapeutically effective amount of an immunomodulatory agent (e.g. an immune checkpoint modulator) may be administered as a one-time dose or administered at intervals, depending on the nature and extent of the cancer, and on an ongoing basis. Administration at an "interval," as used herein indicates that the therapeutically effective amount is administered periodically (as distinguished from a one-time dose). In some embodiments, an interval can be determined by standard clinical techniques. In some embodiments, an immunomodulatory agent (e.g. immune checkpoint modulator) is administered bimonthly, monthly, twice monthly, triweekly, biweekly, weekly, twice weekly, thrice weekly, or daily. In some embodiments, the administration interval for a single individual need not be a fixed interval, but can be varied over time, depending on the needs and rate of recovery of the individual.

As used herein, those of skill in the art are familiar with certain terms commonly used to describe dosing regimens. For example, the term "bimonthly" has its art understood meaning, referring to administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

The invention, among other things, additionally pertains to a pharmaceutical composition comprising an immunomodulatory agent (e.g. immune checkpoint modulator), as described herein; in some embodiments in a container (e.g., a vial, bottle, bag for intravenous administration, syringe, etc.) with a label containing instructions for administration of the composition for treatment of cancer.

Combination Therapy

In some embodiments, an immunomodulatory agent can be used in combination with another therapeutic agent to treat diseases such as cancer. In some embodiments, an immunomodulatory agent, or a pharmaceutical composition comprising immunotherapy as described herein can optionally contain, and/or be administered in combination with, one or more additional therapeutic agents, such as a cancer therapeutic agent, e.g., a chemotherapeutic agent or a biological agent. An additional agent can be, for example, a therapeutic agent that is art-recognized as being useful to treat the disease or condition being treated by the immunomodulatory agent, e.g., an anti-cancer agent, or an agent that ameliorates a symptom associated with the disease or condition being treated. The additional agent also can be an agent that imparts a beneficial attribute to the therapeutic composition (e.g., an agent that affects the viscosity of the composition). For example, in some embodiments, immunotherapy is administered to a subject who has received, is receiving, and/or will receive therapy with another therapeutic agent or modality (e.g., with a chemotherapeutic agent, surgery, radiation, or a combination thereof).

Some embodiments of combination therapy modalities provided by the present disclosure provide, for example, administration of an immunomodulatory agent and additional agent(s) in a single pharmaceutical formulation. Some embodiments provide administration of an immunomodulatory agent and administration of an additional therapeutic agent in separate pharmaceutical formulations.

Examples of chemotherapeutic agents that can be used in combination with an immunomodulatory agent described herein include platinum compounds (e.g., cisplatin, carboplatin, and oxaliplatin), alkylating agents (e.g., cyclophosphamide, ifosfamide, chlorambucil, nitrogen mustard, thiotepa, melphalan, busulfan, procarbazine, streptozocin, temozolomide, dacarbazine, and bendamustine), antitumor antibiotics (e.g., daunorubicin, doxorubicin, idarubicin, epirubicin, mitoxantrone, bleomycin, mytomycin C, plicamycin, and dactinomycin), taxanes (e.g., paclitaxel and docetaxel), antimetabolites (e.g., 5-fluorouracil, cytarabine, premetrexed, thioguanine, floxuridine, capecitabine, and methotrexate), nucleoside analogues (e.g., fludarabine, clofarabine, cladribine, pentostatin, and nelarabine), topoisomerase inhibitors (e.g., topotecan and irinotecan), hypomethylating agents (e.g., azacitidine and decitabine), proteosome inhibitors (e.g., bortezomib), epipodophyllotoxins (e.g., etoposide and teniposide), DNA synthesis inhibitors (e.g., hydroxyurea), vinca alkaloids (e.g., vicristine, vindesine, vinorelbine, and vinblastine), tyrosine kinase inhibitors (e.g., imatinib, dasatinib, nilotinib, sorafenib, and sunitinib), nitrosoureas (e.g., carmustine, fotemustine, and lomustine), hexamethylmelamine, mitotane, angiogenesis inhibitors (e.g., thalidomide and lenalidomide), steroids (e.g., prednisone, dexamethasone, and prednisolone), hormonal agents (e.g., tamoxifen, raloxifene, leuprolide, bicalutamide, granisetron, and flutamide), aromatase inhibitors (e.g., letrozole and anastrozole), arsenic trioxide, tretinoin, nonselective cyclooxygenase inhibitors (e.g., nonsteroidal anti-inflammatory agents, salicylates, aspirin, piroxicam, ibuprofen, indomethacin, naprosyn, diclofenac, tolmetin, ketoprofen, nabumetone, and oxaprozin), selective cyclooxygenase-2 (COX-2) inhibitors, or any combination thereof.

Examples of biological agents that can be used in the compositions and methods described herein include monoclonal antibodies (e.g., rituximab, cetuximab, panetumumab, tositumomab, trastuzumab, alemtuzumab, gemtuzumab ozogamicin, bevacizumab, catumaxomab, denosumab, obinutuzumab, ofatumumab, ramucirumab, pertuzumab, ipilimumab, nivolumab, nimotuzumab, lambrolizumab, pidilizumab, siltuximab, BMS-936559, RG7446/MPDL3280A, MEDI4736, tremelimumab, or others known in the art), enzymes (e.g., L-asparaginase), cytokines (e.g., interferons and interleukins), growth factors (e.g., colony stimulating factors and erythropoietin), cancer vaccines, gene therapy vectors, or any combination thereof.

In some embodiments, an immunomodulatory agent is administered to a subject in need thereof in combination with another agent for the treatment of cancer, either in the same or in different pharmaceutical compositions. In some embodiments, the additional agent is an anticancer agent. In some embodiments, the additional agent affects (e.g., inhibits) histone modifications, such as histone acetylation or histone methylation. In certain embodiments, an additional anticancer agent is selected from the group consisting of chemotherapeutics (such as 2CdA, 5-FU, 6-Mercaptopurine, 6-TG, Abraxane™, Accutane®, Actinomycin-D, Adriamycin®, Alimta®, all-trans retinoic acid, amethopterin, Ara-C, Azacitadine, BCNU, Blenoxane®, Camptosar®, CeeNU®, Clofarabine, Clolar™, Cytoxan®, daunorubicin hydrochloride, DaunoXome®, Dacogen®, DIC, Doxil®, Ellence®, Eloxatin®, Emcyt®, etoposide phosphate, Fludara®, FUDR®, Gemzar®, Gleevec®, hexamethylmelamine, Hycamtin®, Hydrea®, Idamycin®, Ifex®, ixabepilone, Ixempra®, L-asparaginase, Leukeran®, liposomal Ara-C, L-PAM, Lysodren, Matulane®, mithracin, Mitomycin-C, Myleran®, Navelbine®, Neutrexin®, nilotinib, Nipent®, Nitrogen Mustard, Novantrone®, Oncaspar®, Panretin®, Paraplatin®, Platinol®, prolifeprospan 20 with carmustine implant, Sandostatin®, Targretin®, Tasigna®, Taxotere®, Temodar®, TESPA, Trisenox®, Valstar®, Velban®, Vidaza™, vincristine sulfate, VM 26, Xeloda® and Zanosar®), biologics (such as Alpha Interferon, Bacillus Calmette-Guerin, Bexxar®, Campath®, Ergamisol®, Erlotinib, Herceptin®, Interleukin-2, Iressa®, lenalidomide, Mylotarg®, Ontak®, Pegasys®, Revlimid®, Rituxan®, Tarceva™, Thalomid®, Velcade® and Zevalin™); small molecules (such as Tykerb®); corticosteroids (such as dexamethasone sodium phosphate, DeltaSone® and Delta-Cortef®); hormonal therapies (such as Arimidex®, Aromasin®, Casodex®, Cytadren®, Eligard®, Eulexin®, Evista®, Faslodex®, Femara®, Halotestin®, Megace®, Nilandron®, Nolvadex®, Plenaxis™ and Zoladex®); and radiopharmaceuticals (such as Iodotope®, Metastron®, Phosphocol® and Samarium SM-153).

The additional agents that can be used in combination with immunotherapy as set forth above are for illustrative purposes and not intended to be limiting. The combinations embraced by this disclosure, include, without limitation, one or more immunomodulatory agent(s) as provided herein or otherwise known in the art, and at least one additional agent selected from the lists above or otherwise provided herein. Immunomodulatory agents can also be used in combination with one or with more than one additional agent, e.g., with two, three, four, five, or six, or more, additional agents.

In some embodiments, treatment methods described herein are performed on subjects for which other treatments of the medical condition have failed or have had less success in treatment through other means, e.g., in subjects having a cancer refractory to standard-of-care treatment. Additionally, the treatment methods described herein can be performed in conjunction with one or more additional treatments of the medical condition, e.g., in addition to or in combination with standard-of-care treatment. For instance, the method can comprise administering a cancer regimen, e.g., nonmyeloablative chemotherapy, surgery, hormone therapy, and/or radiation, prior to, substantially simultaneously with, or after the administration of an immunomodulatory agent described herein, or composition thereof. In certain embodiments, a subject to which an immunomodulatory agent described herein is administered can also be treated with antibiotics and/or one or more additional pharmaceutical agents.

EXEMPLIFICATION

Example 1. Pan-Cancer Analysis of Tumor Mutational Load Threshold and Survival after Immunotherapy with Immune Checkpoint Modulators This example illustrates the association between tumor mutational load, as measured by a targeted sequencing panel, and overall survival after treatment with immune checkpoint modulators (ICM).

In prior studies, the data on tumor mutational load were primarily based on whole exome sequencing, which is typically not broadly performed as part of routine clinical care. Currently, the most widely used precision oncology platforms utilize next-generation sequencing of targeted gene panels. An association between higher tumor mutational load and clinical benefit from ICM were observed in melanoma patients treated with CTLA4 blockade,[3,4] as well as non-small cell lung cancer (NSCLC), melanoma, and bladder cancer patients treated with PD-1/PD-L1 inhibitors.[5-7] Importantly, it remains unknown how broadly tumor mutational load predicts clinical benefit across different human cancers.

At Memorial Sloan Kettering Cancer Center, over 15,000 patients have undergone genomic profiling using an assay termed "Integrated Mutation Profiling of Actionable Cancer Targets" (MSK-IMPACT), which identifies somatic exonic mutations in a pre-defined subset of 341, 410 or in its most updated version, 468 cancer-related genes, using both tumor-derived and matched germline normal DNA.[8,17]

Specifically, MSK-IMPACT was used to analyze a cohort of 1534 patients treated at Memorial Sloan Kettering Cancer Center (MSKCC) who previously received at least one dose of an ICM (FIG. 1). Patients who previously received atezolizumab, avelumab, durvalumab, ipilimumab, nivolumab, pembrolizumab, or tremelimumab as monotherapy or in combination were included in the study. In total, 130 patients received anti-CTLA-4 immunotherapy, 1166 anti-PD-1 or PD-L1 immunotherapy, and 228 received both anti-CTL A-4 and anti-PD-1 or PD-immunotherapy. The total number of somatic mutations was calculated for all patient samples in the cohort and normalized to the total number of megabases sequenced. Tumor mutational load, as measured by targeted next-generation sequencing (NGS) panels, including MSK-IMPACT, has been previously validated as a means to estimate total tumor mutational load of tumors by multiple investigators.[9,10,11] Overall survival (OS) was measured from the date of first ICM treatment to time of death or last follow-up. Median followup was 11 months with 984 (64%) patients alive at last followup.

Figure 4A:
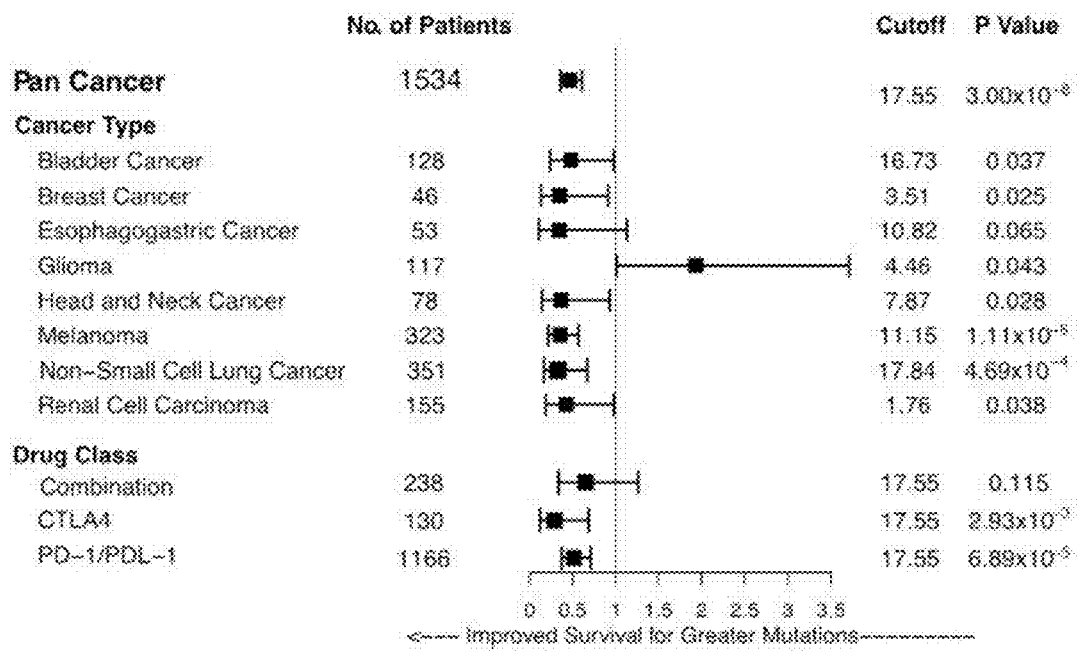
FIG. 4A-4B shows the effect of tumor mutational load on overall survival (A) after ICM therapy by cancer subtype and drug class. A Forest plot is shown for all patients in the identified cohort ("Pan Cancer") or individual cancer subtypes. Indicated are the number of patients and hazard ratio. Horizontal lines represent the 95% confidence interval. The threshold used of normalized tumor mutational load from MSK-IMPACT for that particular subtype to select high tumor mutational load is shown, as well as the log-rank p value for the comparison of high and low tumor mutational load survival curves. All cancer types tested with a patient number of N>35 are displayed. (B) shows the effect of tumor mutational load on overall survival by cancer subtype without ICM therapy. A Forest plot is shown for all patients in the cohort of patients who did not receive ICM ("Pan Cancer") or individual cancer subtypes. Indicated are the number of patients and hazard ratio. Horizontal lines represent the 95% confidence interval. The thresholds used are the optimal cutoff for that particular subtype in the ICM cohort. Log-rank p value are indicated for the comparison of high and low tumor mutational load survival curves. All cancer types tested with a patient number of N>35 are displayed. In both panels A and B, the term "cutoff" is used to denote a tumor mutational load threshold determined herein.
Figure 4B:
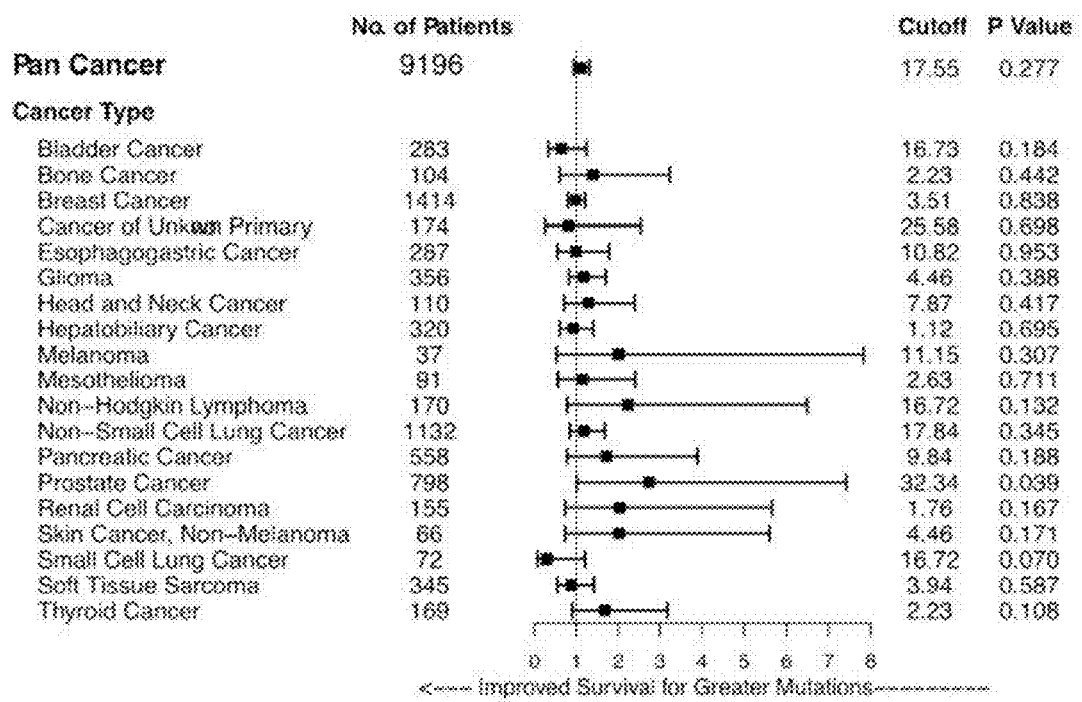

The largest number of patients had tumors with histologies for which use of an ICM is FDA approved: 351 patients with non-small cell lung cancer (NSCLC), 323 with melanoma, 155 with renal cell carcinoma (RCC), 127 with bladder cancer and 78 with head and neck squamous cell cancer (Table 1). Patients with other tumor types such as breast cancer, glioma and gastrointestinal cancers were also included in the study. Multivariable analysis of all patients using Cox proportional-hazards regression demonstrated that the normalized number of somatic, exonic non-synonymous mutations discovered using MSK-IMPACT, or tumor mutational load relative to a threshold, was significantly associated with overall survival (as a continuous variable: HR=0.987, p=0.001; binary cutoff: HR 0.524, p=5.0×10$^{-5}$), adjusting for cancer type, age, and drug class of ICM (Table 2). In the table, the term "cutoff" is used to signify tumor mutational load threshold, as used herein. As one of skill in the art will appreciate, a hazard ratio (HR) in survival analysis is the ratio of the hazard rates corresponding to conditions described by two levels of an explanatory variable. For example, in a drug study, if a treated population survives at twice the rate per unit time as a control population, the hazard ratio would be 0.5, indicating higher hazard of death from no treatment.

did not receive ICM therapy (n=9196), there was no association between higher tumor mutational load and improved overall survival (FIGS. 3B and 4B).

A significant association with improved overall survival and higher tumor mutational load was observed with CTLA-4 and PD-1/PD-L1 blockade targeted therapy while a similar non-significant trend was observed with combination therapy. It is intriguing that combination therapy appears to lessen the significance of tumor mutational load

TABLE 1

Hazard ratios of OS for normalized tumor mutational load threshold across histologies tested

| Histology | HR | CIlo | CIhi | pvalue | N | Threshold | Med OS< | Med OS> |
|---|---|---|---|---|---|---|---|---|
| Pan Cancer | 0.44 | 0.32 | 0.60 | $3.00 \times 10^{-8}$ | 1551 | 17.55 | 20 | NA |
| Bladder Cancer | 0.48 | 0.23 | 0.98 | 0.038 | 127 | 16.73 | 10 | NA |
| Breast Cancer | 0.35 | 0.13 | 0.91 | 0.025 | 46 | 3.51 | 4 | NA |
| Cancer of Unknown Primary | 4.71 | 0.42 | 52.75 | 0.166 | 29 | 25.58 | 9 | 1 |
| Esophagogastric Cancer | 0.34 | 0.1 | 1.13 | 0.065 | 53 | 10.82 | 4 | NA |
| Glioma | 1.93 | 1.01 | 3.71 | 0.043 | 117 | 4.46 | NA | 12 |
| Head and Neck Cancer | 0.36 | 0.14 | 0.93 | 0.028 | 78 | 7.87 | 8 | NA |
| Hepatobiliary Cancer | 0.43 | 0.07 | 2.65 | 0.352 | 23 | 1.12 | 5 | NA |
| Melanoma | 0.35 | 0.21 | 0.57 | $1.11 \times 10^{-5}$ | 323 | 11.15 | 29 | NA |
| Non-Small Cell Lung Cancer | 0.23 | 0.10 | 0.57 | $4.69 \times 10^{-4}$ | 351 | 17.84 | 12 | NA |
| Pancreatic Cancer | 0 | | | 0.084 | 23 | 9.84 | 3 | NA |
| Prostate Cancer | 4.55 | 0.75 | 27.44 | 0.07 | 23 | 32.34 | NA | 20 |
| Renal Cell Carcinoma | 0.43 | 0.19 | 0.98 | 0.038 | 155 | 1.76 | 32 | NA |
| Skin Cancer, Non-Melanoma | 1.86 | 0.57 | 6.1 | 0.3 | 30 | 4.46 | NA | 15 |
| Drug Class | | | | | | | | |
| Combination | 0.54 | 0.25 | 1.18 | 0.115 | 238 | 17.55 | 32 | NA |
| CTLA4 | 0.29 | 0.12 | 0.68 | 0.003 | 130 | 17.55 | 34 | NA |
| PD-1/PD-L1 | 0.49 | 0.35 | 0.70 | $6.89 \times 10^{-5}$ | 1166 | 17.55 | 13 | NA |

*Other rare and miscellaneous cancers are included in the overall analysis but limited numbers (<20) did not allow analysis individually.

TABLE 2

Multivariate analysis of factors associated with overall survival.

| | HR | 95% CI | P value |
|---|---|---|---|
| Normalized Mutation Count | | | |
| Continuous | 0.987 | 0.979-0.995 | .001 |
| Binary (>17.55) | 0.524 | 0.384-0.716 | $5.0 \times 10^{-5}$ |
| Cancer Type Melanoma (reference) | | | |
| NSCLC | 1.803 | 1.329-2.444 | $1.5 \times 10^{-4}$ |
| Not Melanoma/NSCLC | 1.445 | 1.101-1.898 | .008 |
| Age | 1.003 | 0.997-1.010 | 0.340 |
| Drug Class PD-1/PD-L1 (reference) | | | |
| CTLA4 | 0.619 | 0.441-0.866 | .005 |
| Combo | 0.701 | 0.541-0.908 | .007 |

Figure 2:
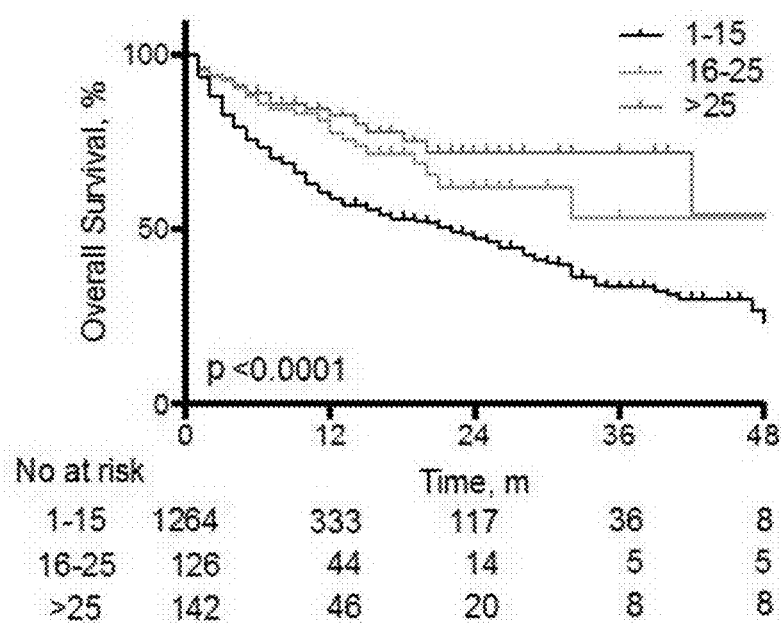
FIG. 2 shows the effect of tumor mutational load on overall survival after immune checkpoint modulator therapy. Kaplan-Meier curves are shown for the number of patients with the indicated number of mutations (1-15, 16-25, or greater than 25) identified from MSK-IMPACT testing. Overall survival is determined from the first dose of immune checkpoint modulator therapy. M, months. $P<0.05$ for all pairwise comparisons.
Figure 5A:
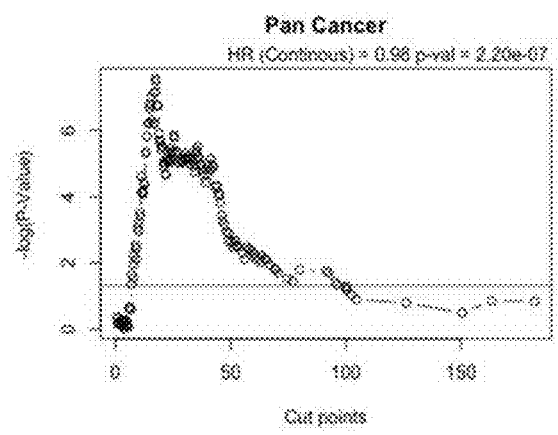
FIG. 5 shows selection of tumor mutational load threshold values used for analysis. (A) demonstrates the use of maximum chi-squared analysis for optimal threshold with individual cut points of normalized tumor mutational load on the x-axis and the p value. (B) demonstrates the hazard ratio at each cut point.
Figure 5B:
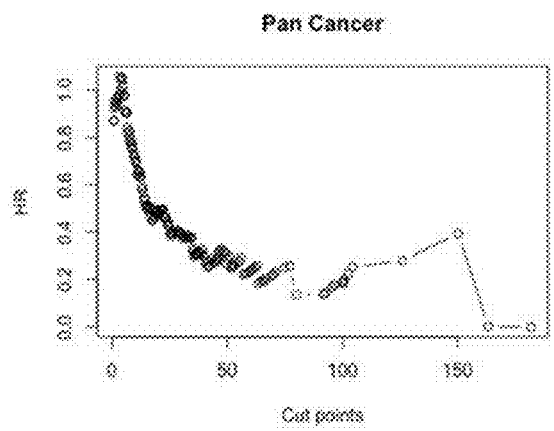
Figure 7:
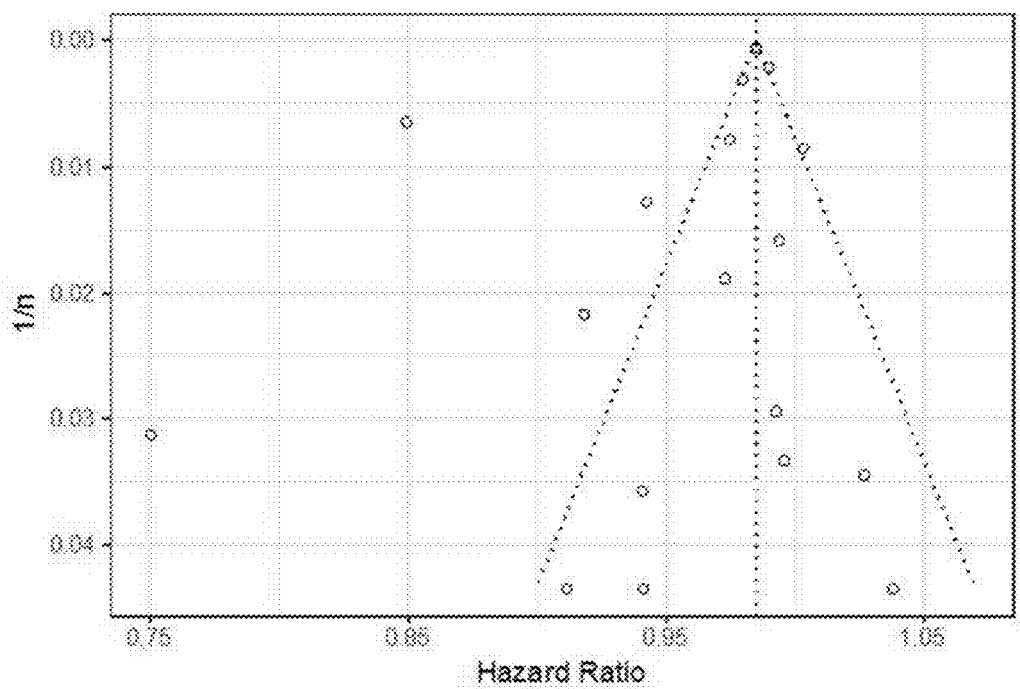
FIG. 7 shows a funnel plot of hazard ratio for all cancer subtypes. The funnel plot is of the reciprocal of the number of patients (y-axis) and hazard ratios for normalized tumor mutational load (x-axis) as a continuous variable for particular histologies.

In pan-cancer analysis, a higher number of somatic mutations, or high tumor mutational load, was associated with proportionally improved overall survival (FIG. 2). As expected, distribution of tumor mutational load varied across diverse histologies.[12] More importantly, optimal tumor mutational load thresholds were identified that predict overall survival after ICM therapy for each cancer subtype using maximum chi-squared analysis (FIGS. 4A and 5A-B).[13] A significant association or strong trend was observed with increased tumor mutational load and improved overall survival from immunotherapy treatment across many histologies, concordant with the number of patients in the subgroup (FIGS. 6A-H and 7). Importantly, in patients who on outcome. This relationship suggests that abrogating multiple immune checkpoints may enable the immune system to target a broader set of potential neoantigens more effectively, increasing the likelihood of establishing an effective anti-tumor response.

Glioma was an outlier in the study (FIG. 4A), as increased tumor mutational load, or a high tumor mutational load threshold was associated with a trend towards poorer overall survival. This is in contrast to reports of dramatic responses to immune checkpoint modulators in patients with glioblastoma associated with childhood biallelic mismatch repair deficiency.[14] This discrepancy may reflect the fact that mismatch repair is very rare in GBM and tumor mutational load in these patients may reflect prior exposure to the alkylating agent temozolomide, which has been shown to promote the expansion of subclonal mutations that have been suggested to be less immunogenic.[15] It should be noted, as anticipated from a large pan-cancer analysis, that the patients included were heterogeneous, with some having been heavily pre-treated whereas others were treated with a variety of combination therapies.

Figure 13:
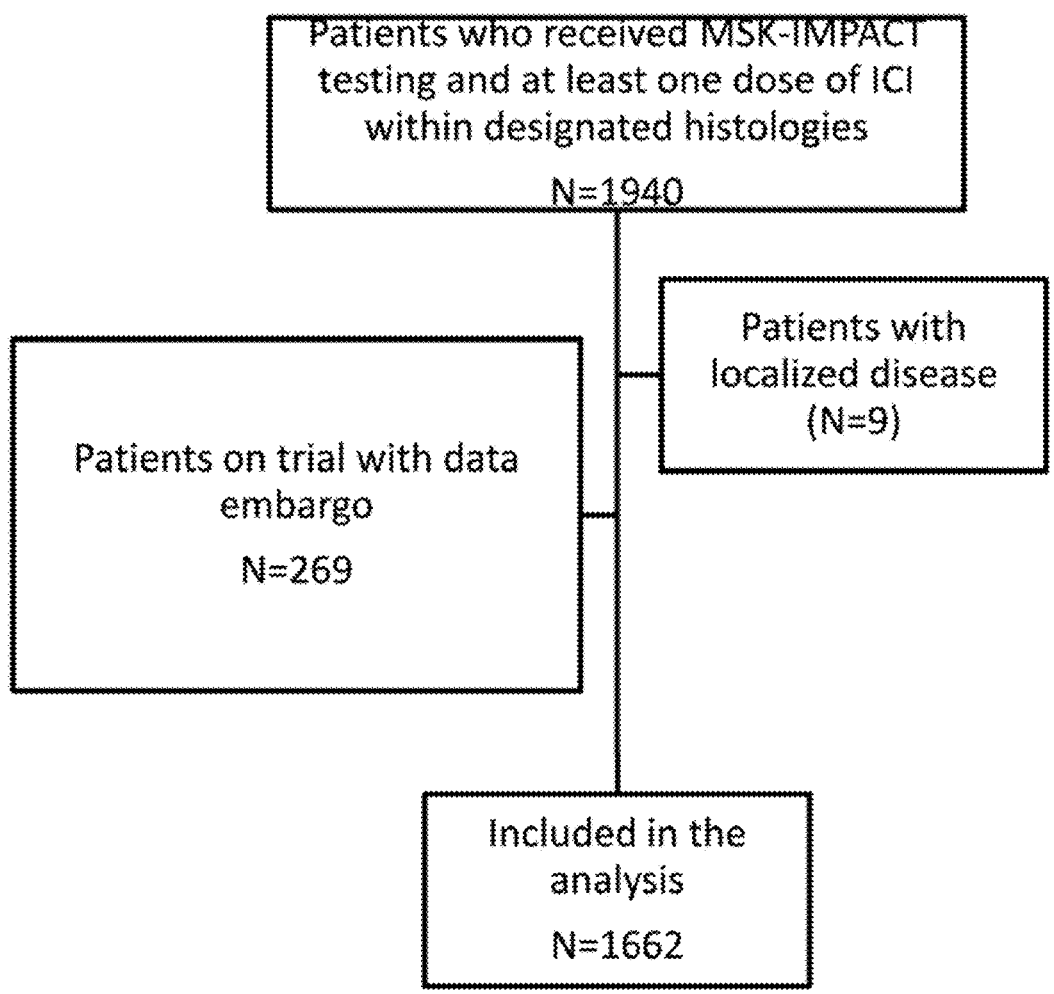
FIG. 13 shows a Consolidated Standard of Reporting Trials (CONSORT) diagram demonstrating the flow of patient selection for analysis for a confirmatory cohort.

These findings are confirmed by additional analysis of a larger cohort in the MSK-IMPACT study. The cohort included 1662 patients whose tumors were profiled by next generation sequencing and who received at least one dose of ICI therapy, representing a variety of cancer types with sufficient number of patients for analysis (FIG. 13). Patients who received atezolizumab, avelumab, durvalumab, ipilimumab, nivolumab, pembrolizumab, or tremelimumab as monotherapy or in combination were included in the study. The vast majority of patients (1446, 94% of tumors excluding glioma) had stage IV or metastatic disease. A small number of patients had locally recurrent disease (n=10), or were melanoma patients with regionally advanced unresectable disease (stage III, n=89 (Table 3). In total, 146 received anti-CTLA4, 1447 received anti-PD1 or PD-L1, and 189 received both. A large number of patients had cancers for which ICI is FDA-approved, including 350 NSCLCs, 321 melanomas, 151 renal cell carcinomas (RCC), 214 bladder cancers and 138 head and neck squamous cell cancers (Table 4). To calculate tumor mutational burden (TMB), the total number of somatic non-synonymous mutations was normalized to the total number of megabases sequenced. OS was measured from the date of first ICI treatment to time of death or last follow-up. The median followup was 19 months (range 0-80, with 830 [50%] patients alive and censored at last followup.

TABLE 3

Patient Clinical Characteristics

| | N (%) |
|---|---|
| Gender | |
| Male | 1034 (62) |
| Female | 628 (38) |
| Cancer Type | |
| See FIG. 1 | |
| Cancer Disease State | |
| Metastatic | 1446 (87) |
| Unresectable locally recurrent | 10 (0.7) |
| Melanoma stage III | 89 (6) |
| Glioma | 117 (7) |
| Drug Class | |
| CTLA4 targeted | 146 (9) |
| PD-1/PD-L1 targeted | 1256 (76) |
| Combination of above | 260 (16) |
| Year of ICI start | |
| 2011-2012 | 26 (2) |
| 2013-2014 | 189 (11) |
| 2015-2017 | 1447 (87) |
| | Median (range) |
| Age | 62 (4-93) |
| Tumor Mutational Burden | 5.9 (0-210) |

TABLE 4

Multivariable analysis of TMB association with removal of Melanoma and NSCLC patients

| | HR | 95% CI | P value |
|---|---|---|---|
| Normalized Mutation Count | | | |
| Continuous | 0.982 | 0.974-0.990 | $1.7 \times 10^{-5}$ |
| Cancer Type | | | |
| Bladder Cancer (reference) | | | |
| Glioma | 1.25 | 0.91-1.72 | 0.17 |
| Esophagogastric Cancer | 1.28 | 0.91-1.79 | 0.16 |
| Renal Cell Carcinoma | 0.41 | 0.29-0.58 | $5.1 \times 10^{-7}$ |
| Head and Neck Cancer | 1.20 | 0.88-1.64 | 0.24 |
| Other | 1.17 | 0.87-1.57 | 0.30 |
| Age | 0.993 | 0.986-1.00 | 0.05 |

TABLE 4-continued

Multivariable analysis of TMB association with removal of Melanoma and NSCLC patients

| | HR | 95% CI | P value |
|---|---|---|---|
| Drug Class | | | |
| PD-1/PD-L1 (reference) | | | |
| CTLA4 | 1.41 | 0.85-2.34 | 0.18 |
| Combo | 0.78 | 0.57-1.06 | 0.11 |
| Year of ICI start | | | 0.02 |

Figure 14A:
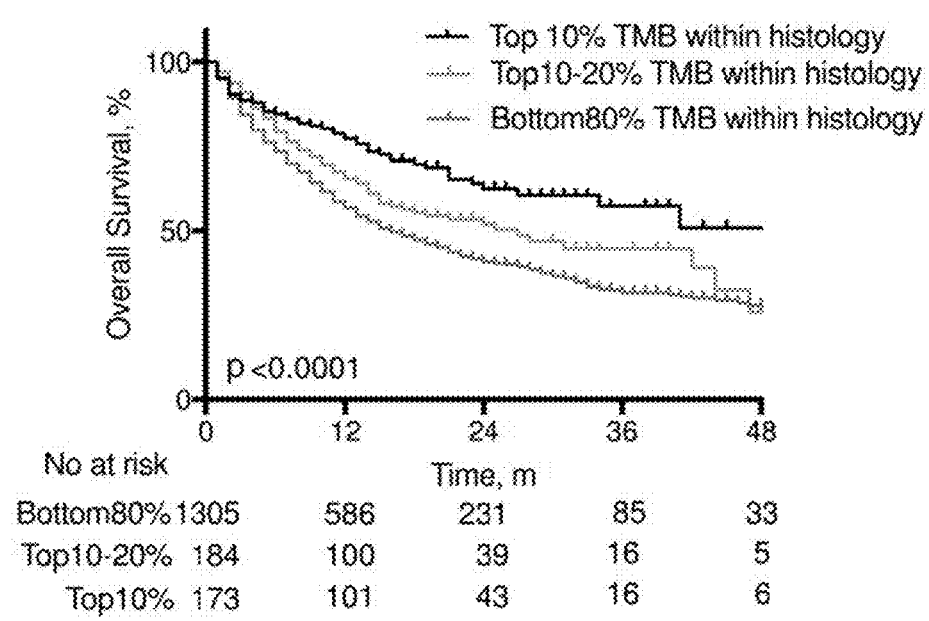
FIGS. 14A and 14B show effect of mutational load on overall survival after ICI treatment. A. Kaplan-Meier curves for patients with tumors falling into the depicted deciles of tumor mutational burden (TMB) within each histology. TMB is defined as normalized somatic mutations per MB identified on MSK-IMPACT testing. Overall survival is from the first dose of ICI. Log-rank p value indicated for all patients, with univariate Cox regression hazard ratio of 0.76 (95% CI 0.62-0.94) and 0.52 (95% CI 0.42-0.64) for the 10-20% and Top 10% groups, respectively, compared to Bottom 80% group. m, months B. Cox regression hazard ratios for overall survival, at depicted cutoffs of tumor mutational burden (TMB) measured in mutations per MB across all cancer subtypes. Solid black circles represent hazard ratios with p-values <0.05.
Figure 14B:
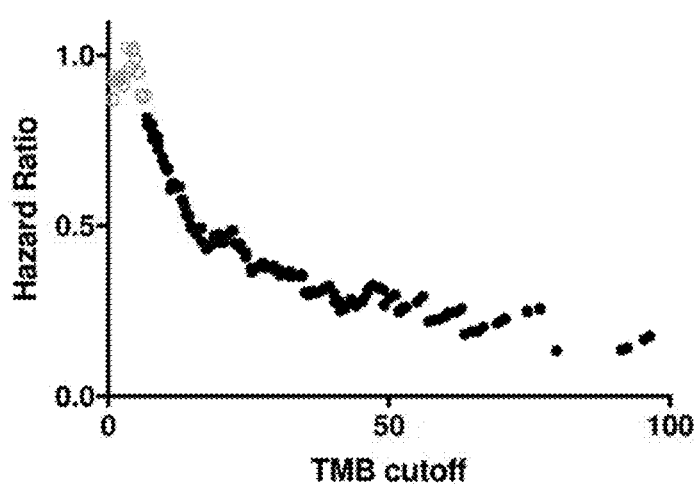
Figure 15:
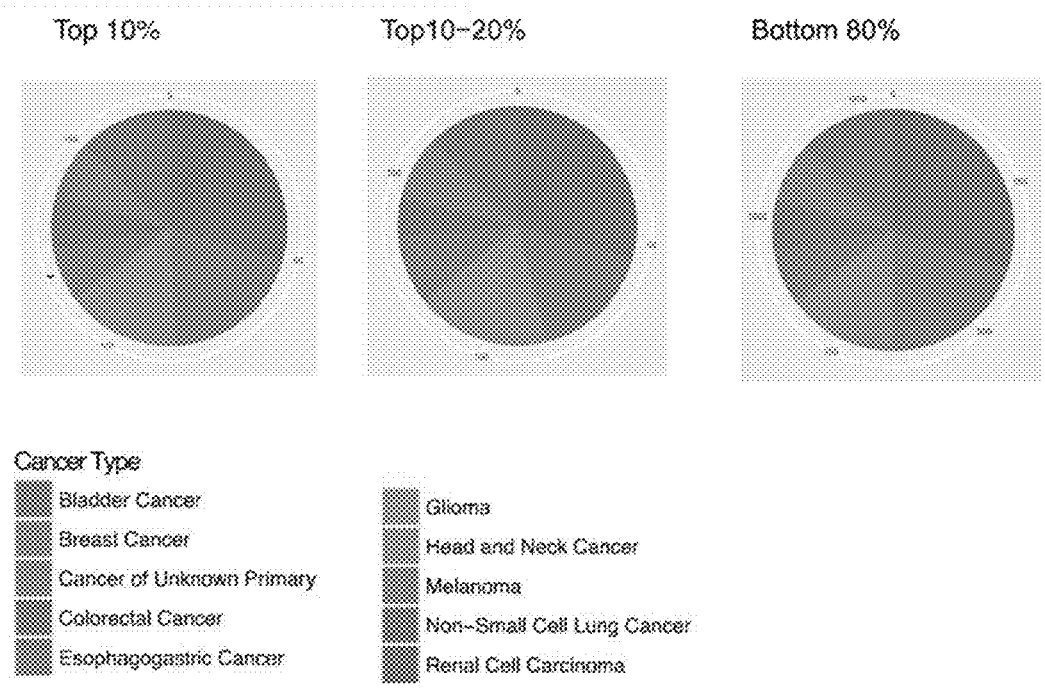
FIG. 15 demonstrates the distribution of cancer types within the groups demonstrated in FIG. 14A.
Figure 16A:
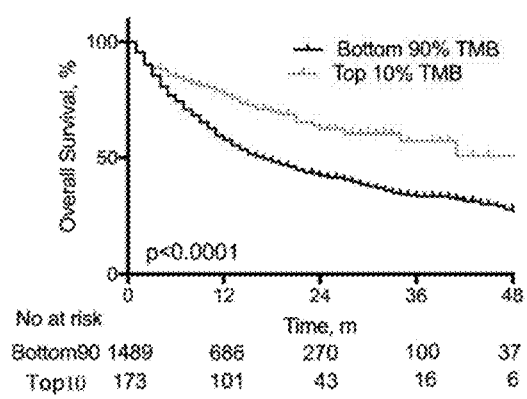
FIGS. 16A-16D demonstrates overall survival of high TMB patients by quantiles across cancer types. Kaplan Meier survival analysis of high vs. low TMB defined by the top indicated percentage of patients from each cancer type. P values indicate log rank test.
Figure 16B:
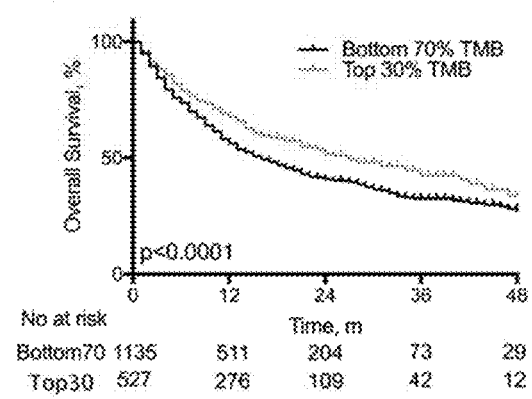
Figure 16C:
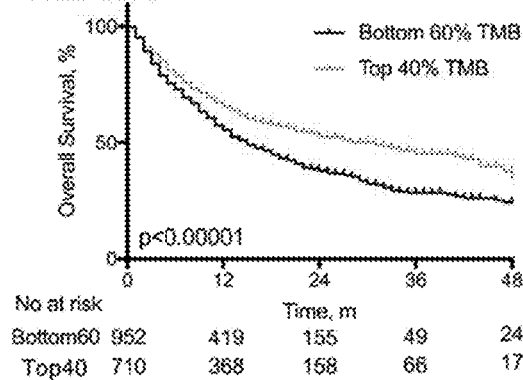
Figure 16D:
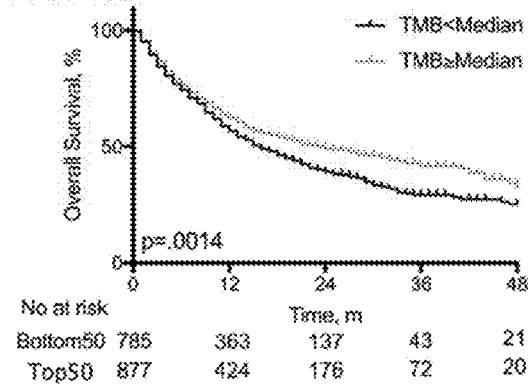

TMB subgroups were defined by percentiles within each histology. This approach was used because the median and range of mutational load has been shown to vary across tumor types[13]; therefore, a universal cutoff for "high TMB" would be enriched for tumor types with higher mutation load. Across the entire cohort, stratifying tumors by TMB decile within histology revealed that a higher number of mutations was associated with improved OS. This significant association, stratified by histology, was seen across a variety of cutpoints chosen to define the high TMB group (ranging from top 10-50%; FIGS. 14A, 15, 16). A clear trend toward decreasing hazard ratio (HR) of death with increasing TMB cutoff was observed across cancer types demonstrating increasing benefit from ICI with higher TMB (FIGS. 14B, 16).[13]

To confirm that these results were present across multiple cancer types, two additional analyses were performed. First, a multivariable analysis across the entire cohort using Cox proportional-hazards regression demonstrated that the tumor mutation burden was significantly associated with OS both as a continuous variable (HR=0.985, p=$3.4 \times 10^{-7}$) and with a binary cutoff (top 20% of each histology, HR 0.61 p=$1.3 \times 10^{-7}$), adjusting for cancer type, age, drug class of ICI, and year of ICI start (Table 5). Furthermore, this association remained significant with removal of melanoma and NSCLC patients from the cohort (Table 4), indicating that this effect was not solely driven by these histologies.

TABLE 5

Multivariable analysis of factors associated with overall survival.

| | HR | 95% CI | P value |
|---|---|---|---|
| Normalized Mutation Count | | | |
| Continuous | 0.985 | 0.979-0.991 | $3.4 \times 10^{-7}$ |
| Binary (Top 20% of each histology) | 0.61 | 0.508-0.733 | $1.3 \times 10^{-7}$ |
| Cancer Type | | | |
| Melanoma (reference) | | | |
| NSCLC | 2.08 | 1.61-2.68 | $1.9 \times 10^{-8}$ |
| Not Melanoma/NSCLC | 1.52 | 1.21-1.92 | $3.7 \times 10^{-4}$ |
| Age | 0.995 | 0.990-1.004 | 0.07 |
| Drug Class | | | |
| PD-1/PD-L1 (reference) | | | |
| CTLA4 | 1.18 | 0.846-1.66 | 0.32 |
| Combo | 0.67 | 0.534-0.844 | $6.6 \times 10^{-4}$ |
| Year of ICI start | | | $2.3 \times 10^{-8}$ |

Figure 17:
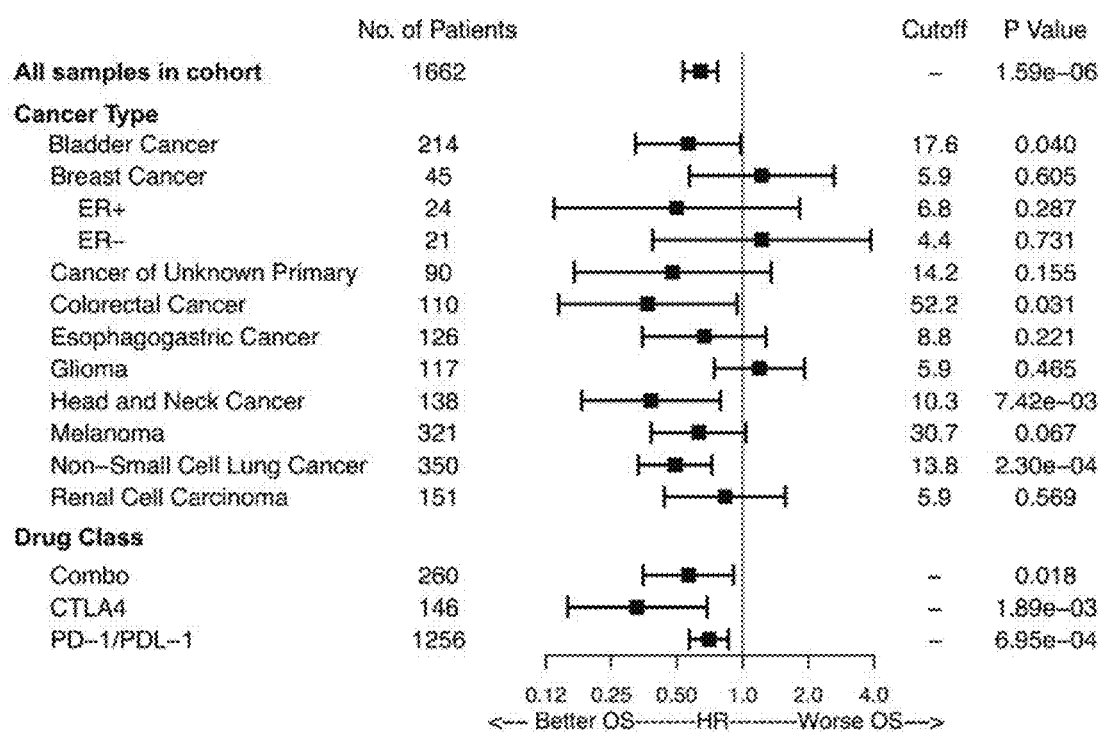
FIG. 17 demonstrates effect of non-synonymous mutational load on overall survival after ICI Treatment by cancer subtype and drug class. Forest plot for all patients in the identified cohort or individual cancer subtypes. Indicated are the number of patients and hazard ratio comparing overall survival after ICI in patients in the highest 20th percentile TMB within each histology. Horizontal lines represent the 95% confidence interval. The cutoff defining top 20% of normalized mutational burden from MSK-IMPACT for each cancer type is shown, as well as the log-rank p value for the comparison of high and low mutational burden survival curves. All cancer types in analysis are displayed.
Figure 18A:
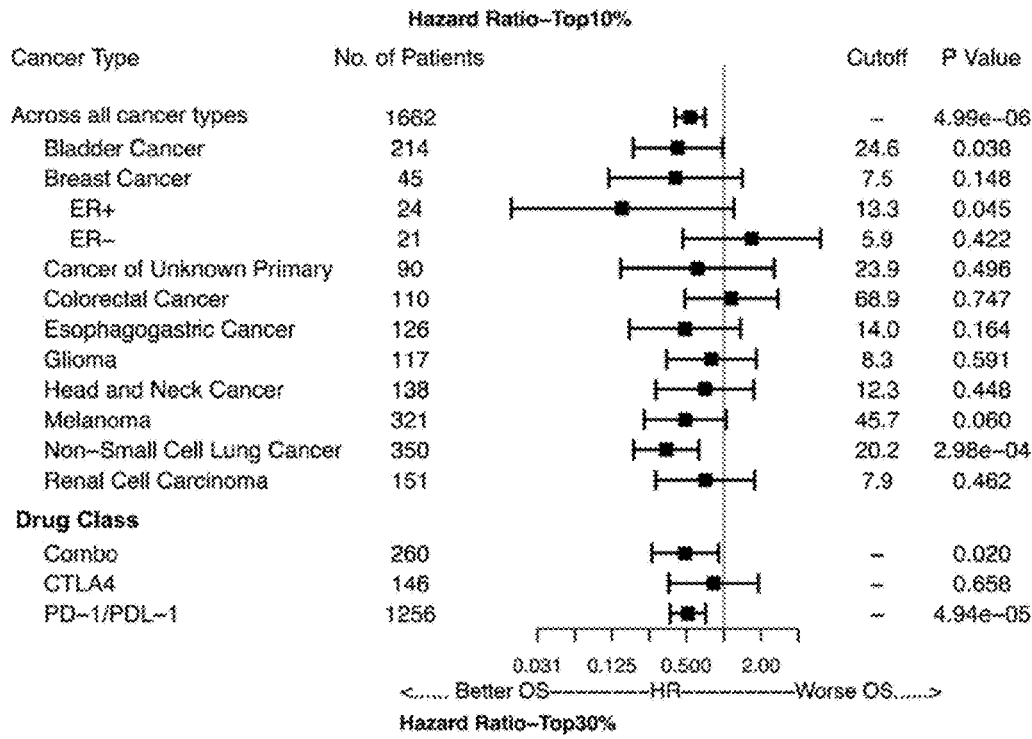
FIGS. 18A and 18B show forest plot for all patients in the cohort and individual cancer histologies. Indicated are the number of patients and hazard ratio comparing overall survival after ICI in patients with z 10% highest TMB (A) or 30% (B) for each histology. Horizontal lines represent the 95% confidence interval. The cutoff used of normalized mutational burden from MSK-IMPACT for that particular subtype to select high mutational burden is shown, as well as the log-rank p value for the comparison of high and low mutational burden survival curves.
Figure 18B:
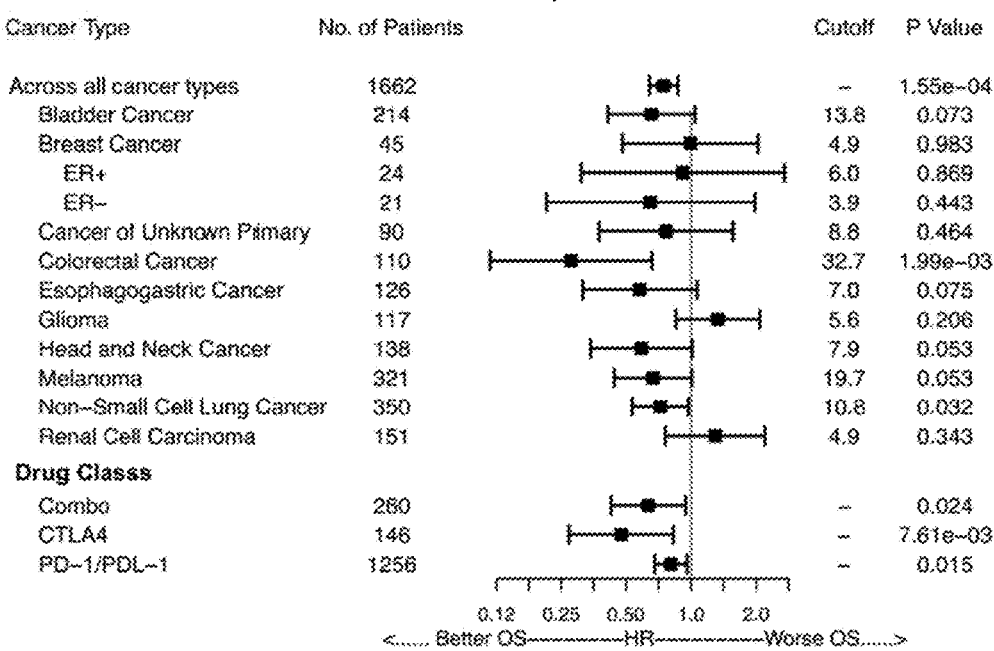

A stratified analysis within each cancer type was also performed, by selecting the higher mutation load quintile (top 20%) in each histology as the TMB-high group. Using this approach, a similar association of longer OS with higher TMB (top 20% within each histology) across multiple cancer types was observed (FIGS. 17, 18). Although the effect for some individual cancers did not reach statistical significance, possibly due to smaller sample size, the numerical trend of better OS (HR<1) was observed in nearly all cancer types, with glioma the clearest exception. Taken together, these data indicate that the association between TMB and improved survival after ICI is likely to be present in the majority of cancer histologies.

Figure 19:
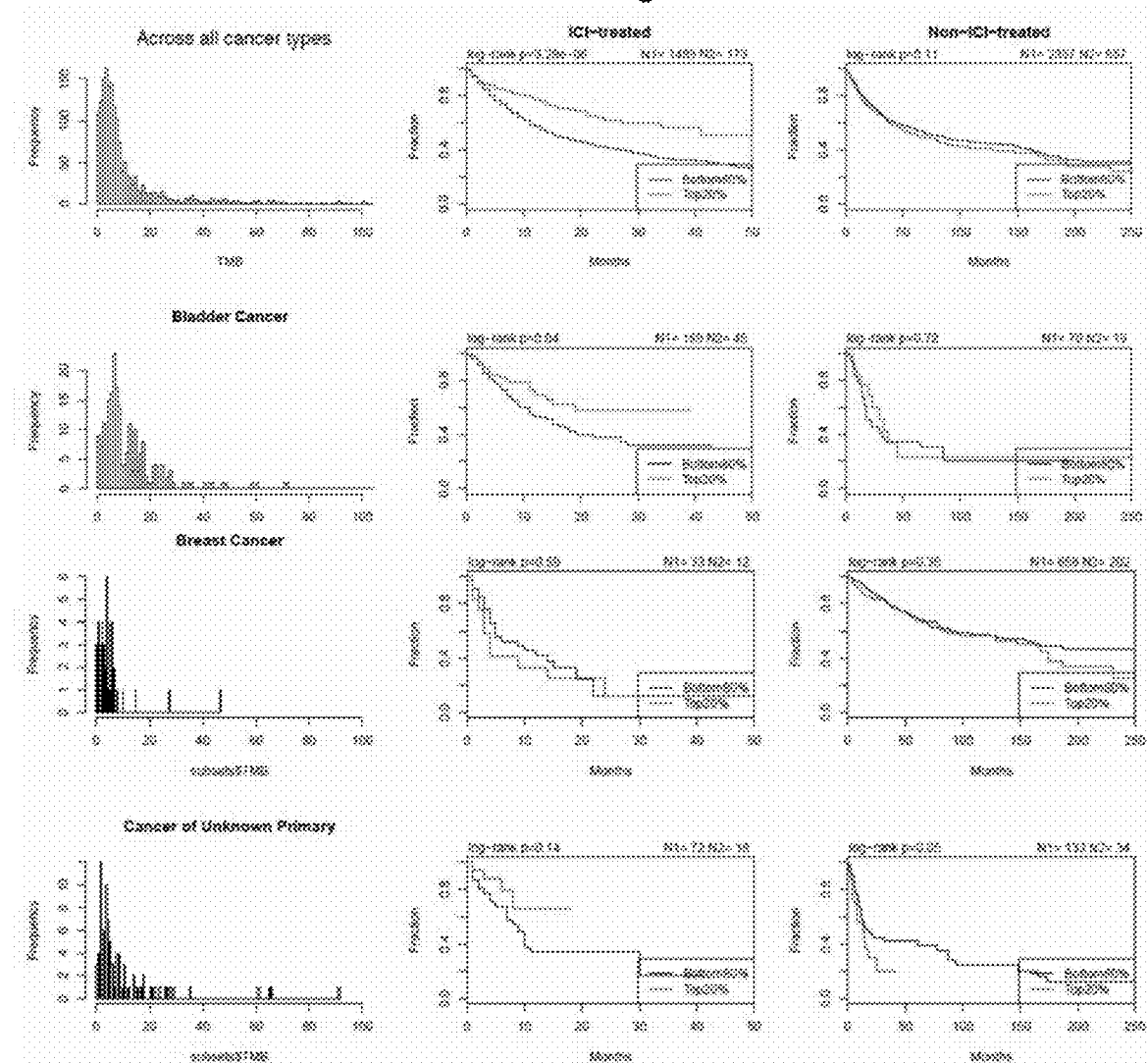
FIG. 19 shows effect of non-synonymous mutational load on overall survival after ICI Treatment, or in non-ICI treated patients, by cancer subtype. Individual plots for all patients in the identified cohort ("All cancer types") or individual cancer subtypes. The first column demonstrates the distribution of normalized mutational load frequency. The second column demonstrates Kaplan-Meier curves for patients who were treated with ICI with the top 20% TMB within each histology identified on MSK-IMPACT testing. The third column represents OS comparing the top 20% of tumors in the cohort of patients never treated with ICI from date of diagnosis.
Figure 19:
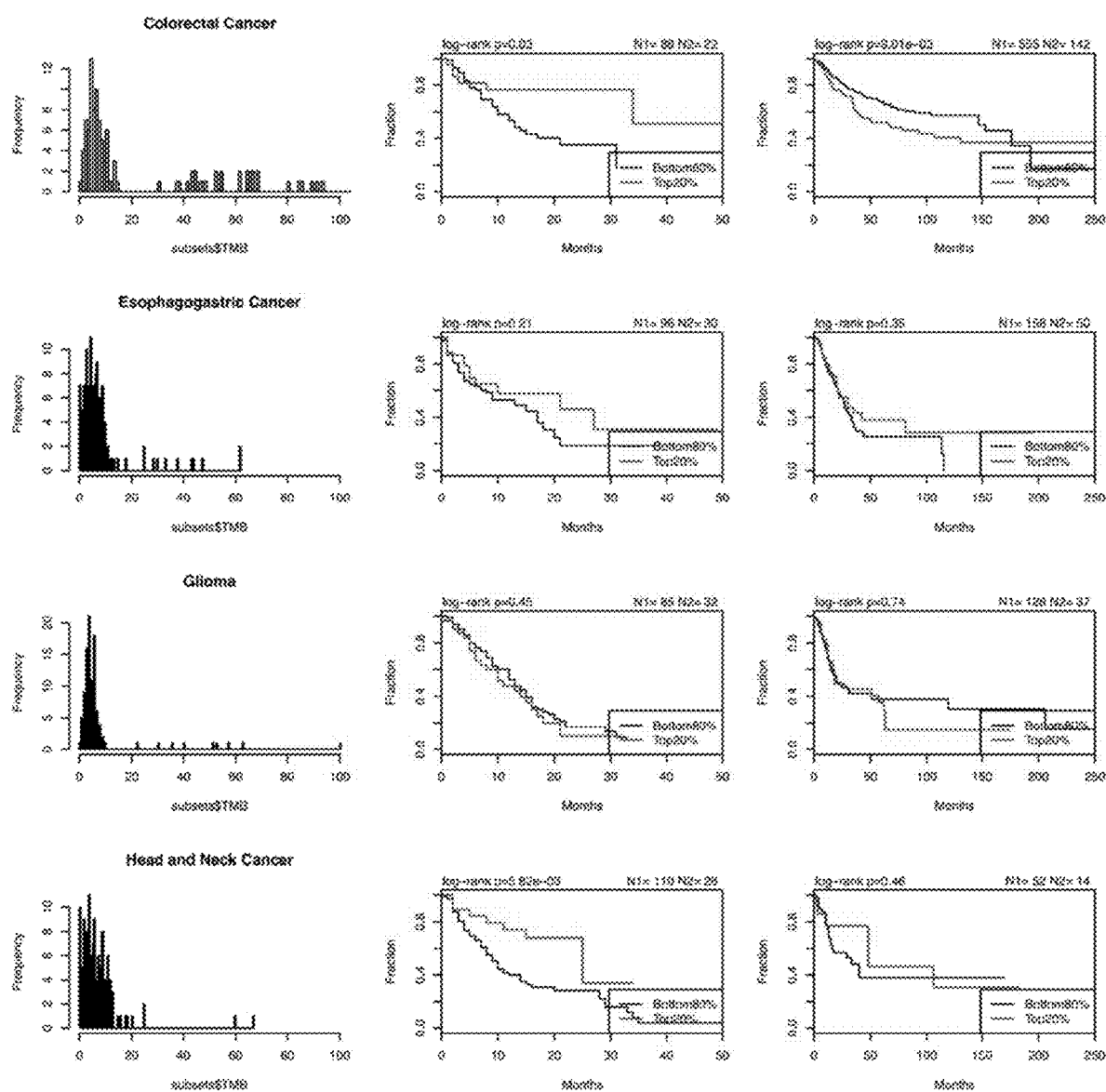
Figure 19:
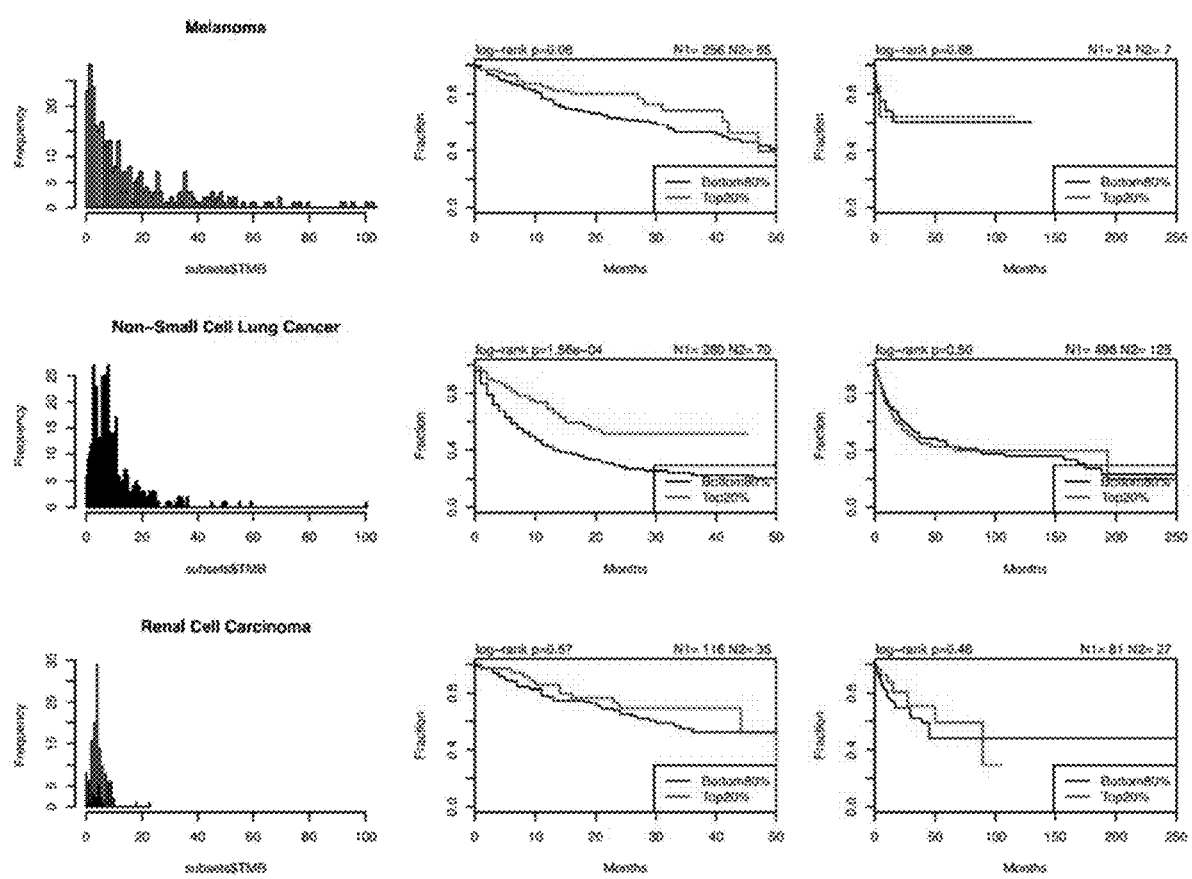

Consistent with varying distributions of TMB across histologies, the TMB cutoff associated with the top 20% of each cancer type varied markedly (FIGS. 17, 19). Importantly, this suggests that there is not likely to be a universal number defining high TMB that is predictive of clinical benefit to ICI across all cancer types, and that the optimal cutpoint is likely to vary for different cancers.

Figure 20:
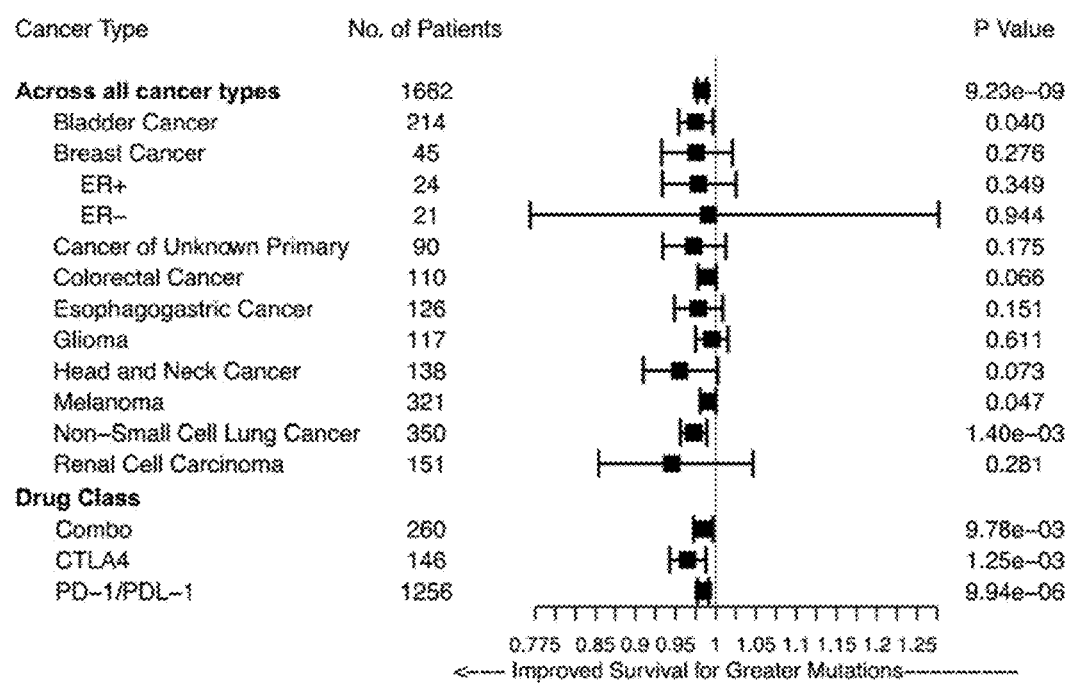
FIG. 20 shows forest plot depicting the Cox proportional hazards model across all cancer types and individual histologies demonstrating the hazard ratio for TMB as a continuous variable.

A similar numerical trend was observed for longer OS with TMB measured as a continuous variable, across many histologies, concordant with the number of patients in the subgroup (FIG. 20). Consistent with the differences in OS, similar associations between TMB and rates of clinical benefit to ICI, or progression free survival, was observed in patients with cancer types for which response data was available—NSCLC, melanoma, esophagogastric, head and neck, and renal cell cancer (FIGS. 21-22).[72-74]

Figure 23:
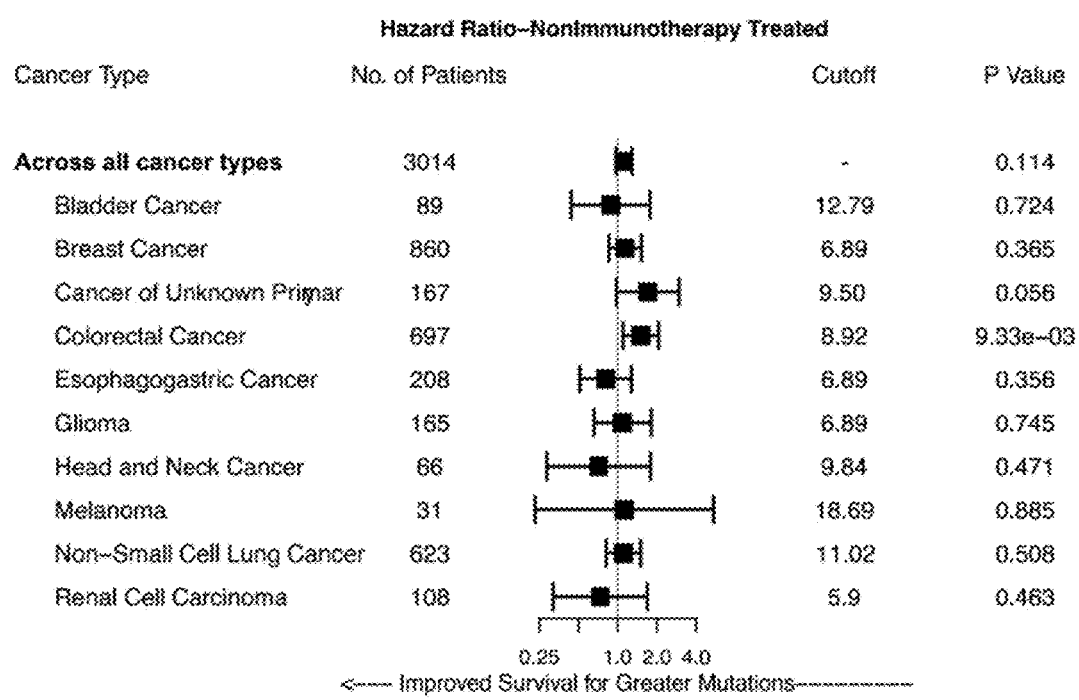
FIG. 23 shows effect of non-synonymous mutational load on OS by cancer Subtype in Patients Not Treated with ICI. Forest plot for all metastatic patients in the cohort of patients who did not receive ICI ("All cancer types") or individual cancer subtypes. Indicated are the number of patients and hazard ratio. Horizontal lines represent the 95% confidence interval. The cutoffs used are the top 20% in this cohort. Log-rank p value are indicated for the comparison of high and low mutational burden survival curves.

To investigate the possibility that the observed survival differences among patients with higher TMB tumors could simply be attributable to a general prognostic benefit of high mutational load, unrelated to ICI, the outcomes of 5371 patients with metastatic cancers who did not receive ICI, and whose tumors were sequenced with MSK-IMPACT was measured. In these patients, there was no association between higher TMB and improved OS (HR 1.12, p=0.11). This lack of prognostic benefit was also observed within each histology (FIGS. 17, 23).

Figure 25:
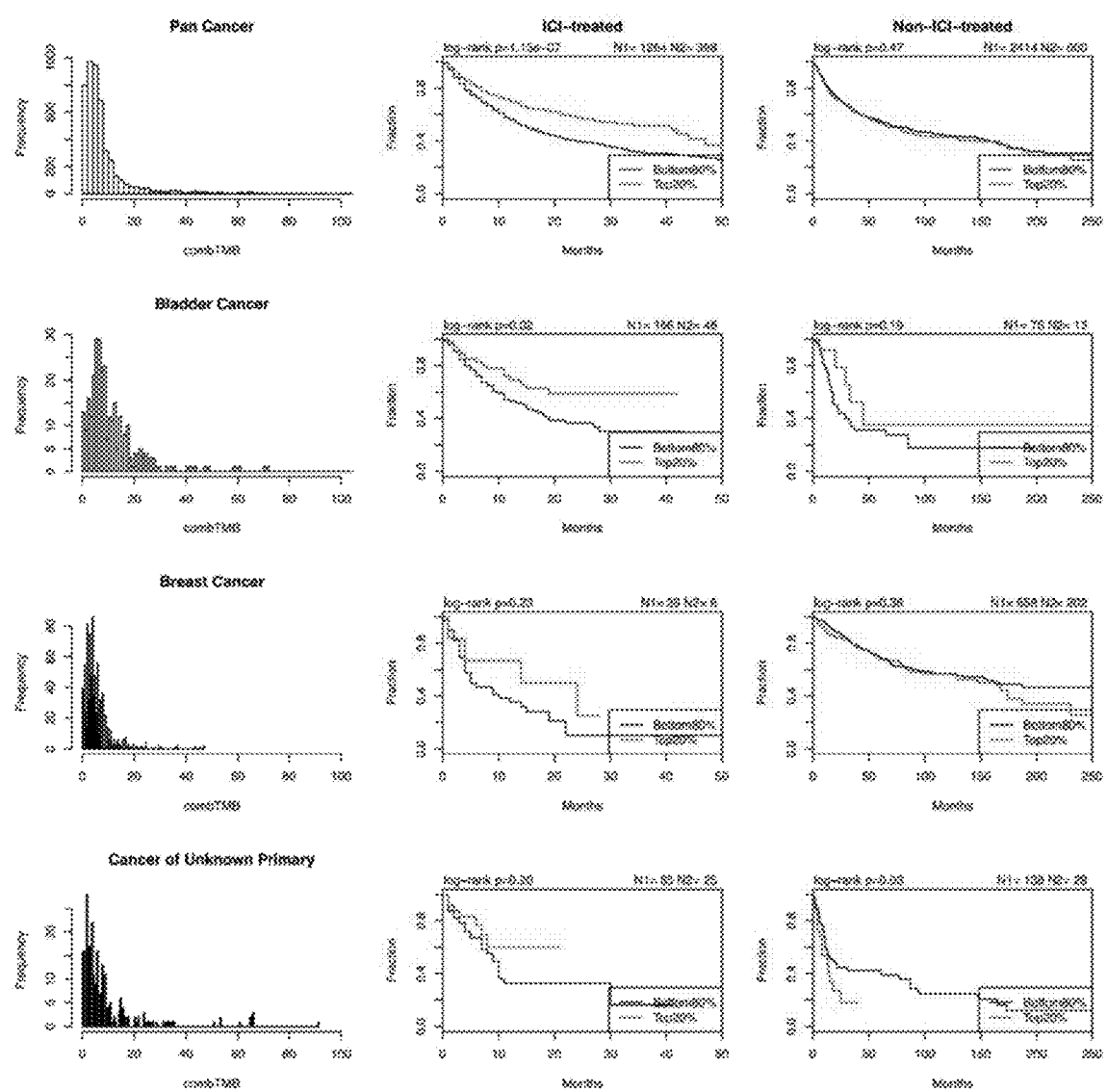
FIG. 25 shows a modified version of FIG. 19, with TMB cutoff instead defined as the top 20% from all patients in both the ICI-treated and non-ICI treated cohorts. The first column demonstrates the distribution of normalized mutational load frequency across the combined ICI treated and non-ICI treated cohorts in that histology. The second column demonstrates Kaplan-Meier curves for patients who were treated with ICI with the top 20% TMB (across the combined cohorts) within each histology identified on MSK-IMPACT testing. The third column represents OS comparing the top 20% TMB (across the combined cohorts) in the cohort of patients never treated with ICI from date of diagnosis.
Figure 25:
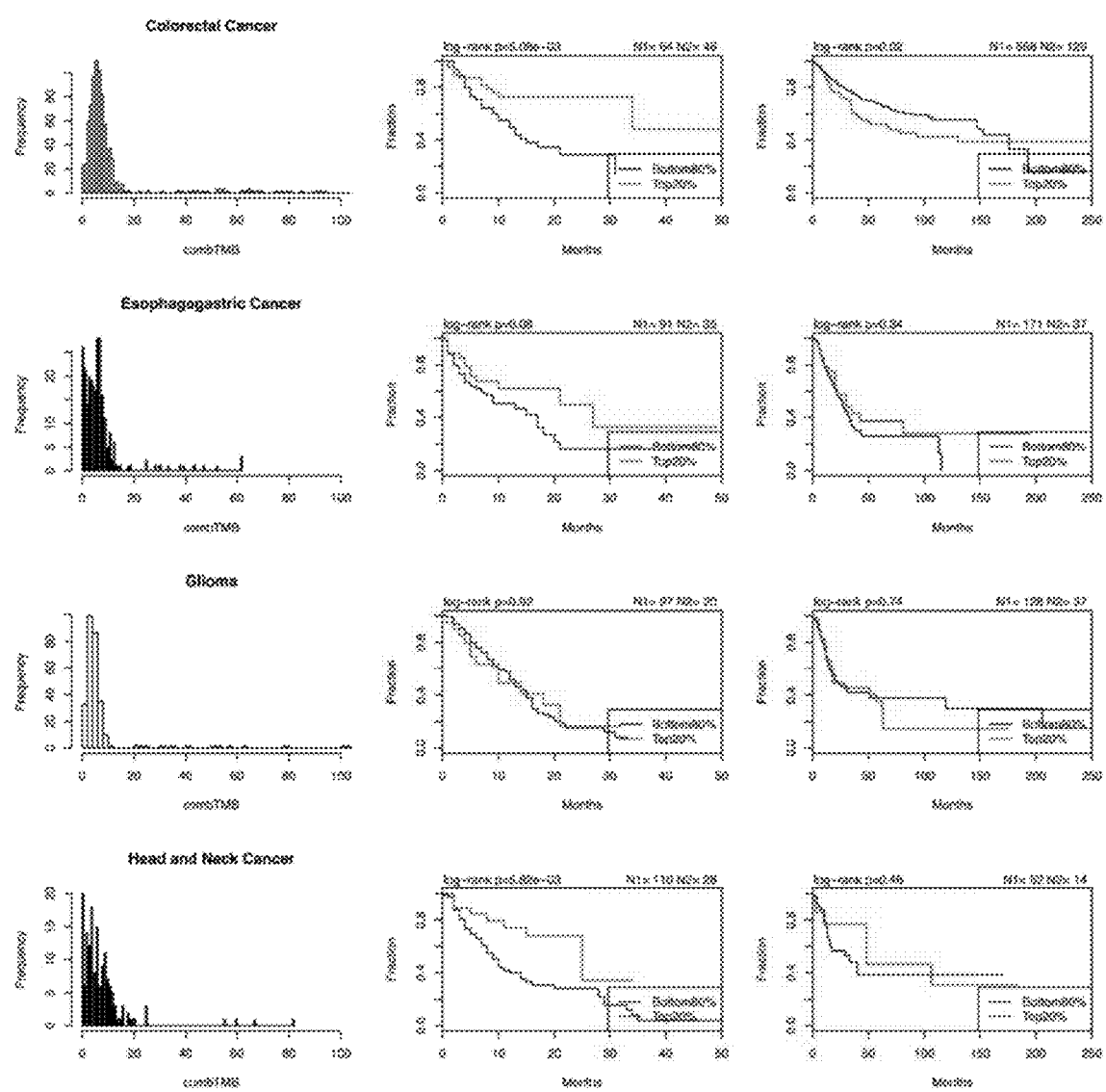
Figure 25:
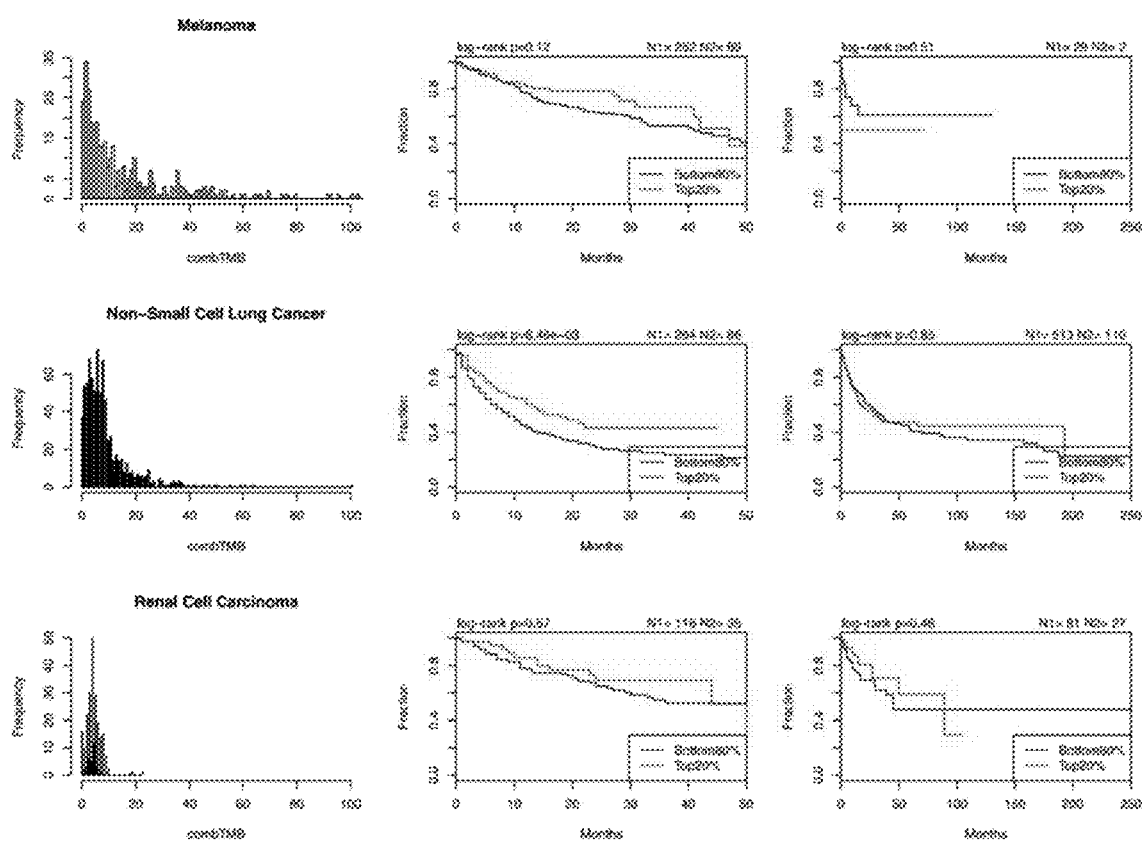

Of note, the TMB cutpoint for the top 20% of colorectal cancer patients was high (52.2/MB), potentially consistent with many MSI-high colorectal tumors receiving ICI treatment. To evaluate the possibility that the ICI-treated cohort of patients might be enriched for patients with higher TMB—if, for example, clinicians were more likely to triage higher TMB patients to ICI therapy—the survival analyses was repeated, instead calculating the top 20% of TMB among all (both ICI and non-ICI treated) patients. The TMB cutpoints in other cancer types were not changed with this calculation, and the associations with survival in each cancer type remained very similar, in both the ICI and non-ICI treated cohorts (FIGS. 24, 25).

Distinct from the other cancer types, there was no association between higher TMB and improved survival in patients with glioma; in fact, the trend was toward poorer survival. Although there have been case reports of dramatic responses to ICI in patients with glioblastoma associated with childhood biallelic mismatch repair deficiency[14], mismatch repair is very rare in GBM, and higher TMB in many glioma patients may reflect prior exposure to the alkylating agent temozolomide, which can promote the expansion of less immunogenic subclonal mutations.[15] Alternatively, anti-tumor immune responses in the CNS may be distinct and less dependent on TMB.

As would be expected in a large multi-cancer analysis of tumors sequenced as part of clinical care, the patients included were heterogeneous, with some having been heavily pre-treated whereas others were treated with a variety of combination therapies. The timing of MSK-IMPACT testing relative to ICI start was also variable. Nevertheless, the finding of a significant association with OS in a heterogeneous cohort underscores the robustness of TMB as a predictive biomarker, suggesting it is likely to be clinically meaningful.

The variable threshold of TMB across histologies can likely be attributed to distinct tumor microenvironments as well as the numerous other factors shows to independently predict response to ICI including clonality, immune infiltration, immune cell exclusion, HLA genotype and alterations, expression levels of checkpoint molecules, as well as others.[15,75-78] Our data overall suggest that TMB is associated with increasing OS in a dose-dependent fashion. The pan-cancer nature of this biomarker likely reflects fundamental mechanisms by which ICI functions. Our data are also consistent with the hypothesis that higher mutation load is associated with a higher number of tumor neoantigens presented on MEC molecules that facilitate immune recognition as foreign and the development of an anti-tumor immune response.[79,80]

This finding is in line with the observation that patients with hypermutated tumors as a result of defective mismatch repair have high response rates to pembrolizumab, a finding that had led to the FDA's tissue/site-agnostic approval of this agent for microsatellite instability-high or mismatch repair deficient tumors[65]. Mutational load can predict survival across diverse types of human cancers and is relevant in patients treated with either anti-CTLA4 or anti-PD1 therapies. Second, previous studies on the association between mutational load and survival after ICI had examined small cohorts and therefore, the effects of TMB on clinical benefit could not be quantified in a precise manner. This study presents genomic data from the largest cohort of patients treated with ICI to date and demonstrates the continuous association between higher TMB and superior OS. Capturing as little as 3% of the coding exome using targeted panels such as MSK IMPACT appears to provide a sufficient estimation of total tumor mutational load to confer predictive value for patients in whom ICI treatment is being considered. Finally, the mutational number defining TMB high appears to vary across cancer types, and there is unlikely to be a universal number that defines the likelihood of benefit from ICI across all histologies.

Example 2: Patient Population Selection Criteria for Example 1

The present example describes the criteria in which a patient was selected for analysis in predicting overall survival based on tumor mutational load threshold.

After receiving institutional review board approval from the Memorial Sloan Kettering Cancer Center, institutional pharmacy records were used to identify patients who received at least one dose of an immune checkpoint modulator (e.g. tezolizumab, avelumab, durvalumab, ipilimumab, nivolumab, pembrolizumab, or tremelimumab) and then cross-referenced with patients who had MSK-IMPACT testing done in the context of routine clinical care. Importantly, concurrent sequencing of germline DNA from peripheral blood is performed for all samples to identify somatic tumor mutations. Patients enrolled in ongoing clinical trials for which publication of outcomes data was prohibited were removed. Other preceding or concurrent non-ICM treatments were not recorded or accounted for in the analysis. The timing of tissue pathology on which MSK-IMPACT was performed relative to ICM administration is also heterogeneous with a small portion of patients with testing after ICM administration.

For analysis of patients who did not receive ICM, all patients for whom MSK-IMPACT data was available across all histologies were included. Overall survival analysis was performed from the start of first chemotherapy.

This study addresses several fundamentally important questions in immune-oncology. First, it had previously been unclear how broadly tumor mutational load thresholds predicted for clinical benefit from immune checkpoint modulators across human cancers. Our study suggests that tumor mutational load threshold can predict survival across many diverse types of human cancers, in patients treated with both CTLA-4 blockade or PD-1 blockade therapies. Second, previous studies on the association between tumor mutational load and survival after ICM therapy had examined smaller cohorts and therefore, the effects of tumor mutational load on clinical benefit could not be quantified in a precise manner. This study presents genomic data from the largest cohort of patients treated with ICM to date (over 1500 patients) and also expands upon and validates earlier data from smaller studies. Lastly, the MSK-IMPACT targeted panel captures approximately 3% of the coding exome and our data indicate that this profiling strategy provides sufficient representation of total tumor mutational load to have predictive value in patients treated with ICM. Taken together, these data collectively indicate that tumor mutational load and tumor mutational load threshold is a predictive biomarker for ICM response across multiple human cancer types and could potentially have value in concert with PD-L1 immunohistochemistry.[16] The pan-cancer nature of this biomarker likely reflects fundamental mechanisms by which ICM functions. Our data is thus consistent with the theory that higher tumor mutation load is presumed to be associated with a higher number of tumor neoantigens presented on MHC molecules that facilitate immune recognition as foreign and development of an anti-tumor immune response.

Example 3: Calculation of Tumor Mutational Load Threshold for Example 1

The present example describes how tumor mutational load is calculated from collected patient data.

The total number of somatic mutations, or tumor mutational load, identified was normalized to the exonic coverage of the respective MSK-IMPACT panel in megabases. Overall survival analysis on ICM therapy patients was performed from the date of first infusion of any ICM. For patients who received multiple courses of ICM, the first treatment was used for analysis. Patients were censored at the date of last attended appointment. For non-ICM patients, the date of first dose of any chemotherapy was used for overall survival analysis.

Survival analysis was performed using Kaplan Meier with log-rank p values reported. Multivariable analysis was performed using Cox proportional hazard regression. These data analysis methods are known to one of skill in the art. Optimal tumor mutational load cutoffs, or tumor mutational load thresholds as used herein, were determined by maximum chi-squared analysis as known to one of skill in the art, as the distribution of tumor mutational load varied significantly by histology. Statistical analysis was performed in R using the survival package.

Example 4 HLA Class I Genotype Influences Survival with Immune Checkpoint Modulators Materials and Methods
Study Design and Description of Patient Sets For the analyses presented in this study, we used two different sets of cancer patients who were treated with immune checkpoint inhibitors. For cohort 1, we obtained exome sequencing data and clinical data from 371 patients who were treated with anti-CTLA-4 or anti-PD-1 therapy. Two patients did not have overall survival data and they were not included in the analyses. Out of the 369 patients with complete clinical data, 269 patients had advanced melanoma and 100 patients had advanced non-small cell lung cancer (NSCLC). The melanoma data are from four previously reported studies (3, 4, 7, 36). The NSCLC data are from patients with metastatic disease treated mainly with anti-PD-1 monotherapy. The patients are from a prospective trial that we reported previously (5) and from NewYork-Presbyterian/Columbia University Medical Center. Exome sequencing data were not available for 67 patients with NSCLC. All patients were treated under institutional review approved prospective protocols. For cohort 2, we obtained independent next-generation sequencing data using a targeted gene panel (MSK-IMPACT) and clinical data from 1,166 patients representing different cancer types on an institutional IRB-approved research protocol (NCT01775072). These patients were treated with anti-CTLA-4, or PD-1/PD-L1 blockade, or a combination of both drugs at the Memorial Sloan Kettering Cancer Center (32). Clinical characteristics of patient cohorts are provided in Appendix 1. For analysis of germline variants, original sequencing files and relevant clinical data were anonymized by a third party without investigator access to the original patient identification according the protocol design. Additional details regarding these tumors can be found in the original publications (3-5, 7,11, 36). The results published here are in part based on data generated by TCGA pilot project established by the National Cancer Institute and National Human Genome Research Institute. Information about TCGA and the investigators and institutions that constitute the TCGA research network can be found at cancergenome.nih.gov/. The TCGA exome data for the patients with melanoma was obtained from the Cancer Genome Atlas (TCGA) (N=378).

Overall Survival and Clinical Response Data

The clinical endpoint used in these analyses was overall survival, defined as the length of time from treatment start to time to event (survival or censor). All clinical data were obtained from the original studies (3-5, 7, 11, 36). Clinical data for the TCGA patients with melanoma were accessed through the TCGA data portal.

HLA Class I Genotyping Data

We performed high-resolution HLA class I genotyping from germline normal DNA exome sequencing data directly or using a clinically validated HLA typing assay (LabCorp). Patient exome data or targeted gene panels were obtained and the well-validated tool Polysolver was used to identify HLA class I alleles with default parameter settings (38). It has previously been shown that Polysolver is highly accurate compared to serology or PCR-based methods (37, 38). For quality assurance, a subset of these patients (N=22) was molecularly HLA typed at a CLIA-certified center (New York Blood Center) and typed using Polysolver. The overall concordance between Polysolver and the molecular typing was 96%. Concordance is defined as [(6−number of allele mismatches between Polysolver and molecular typing)/6]× 100. Furthermore, HLA class I homozygosity detected by Polysolver was confirmed by two additional computational tools, OptiType and HLA-SOAP (39,40). For the 67 patients with NSCLC with no available exome sequencing data, HLA class I molecular typing was done at LabCorp. For quality assurance of MSK-IMPACT (CLIA-certified hybridization-capture based assay) captures HLA class I (8, 11, 41), we compared HLA class I typing by Polysolver between 37 samples that we sequenced with MSK-IMPACT and whole exome. The MSK-IMPACT panel successfully captured HLA-A, -B, and -C. To make sure that HLA class I genes have adequate coverage in MSK-IMPACT bam files, we also applied bedtools multicov tool (//bedtools.readthedocs.io/en/latest/content/tools/multicov.html), which reports the count of alignments from multiple position-sorted and indexed BAM files that overlap with targets intervals in a BED format. Only high quality reads were counted and only samples with sufficient coverage were used. The overall concordance of class I typing between the MSK-IMPACT samples and their matched WES samples was 96%.

Statistical Analysis

Figure 8F:
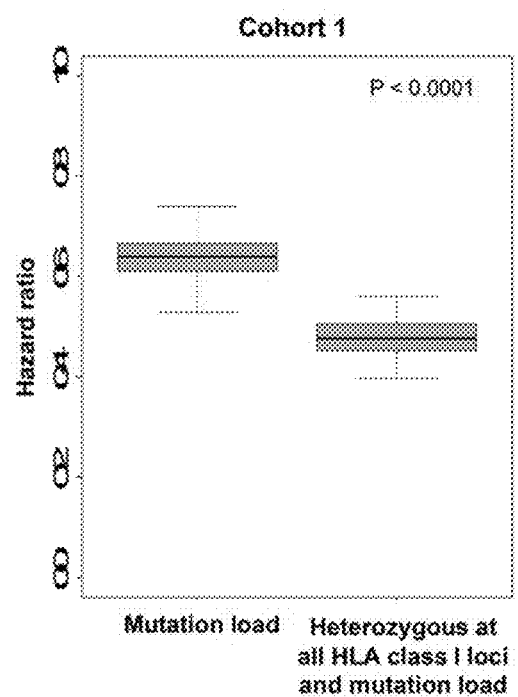
Figure 8G:
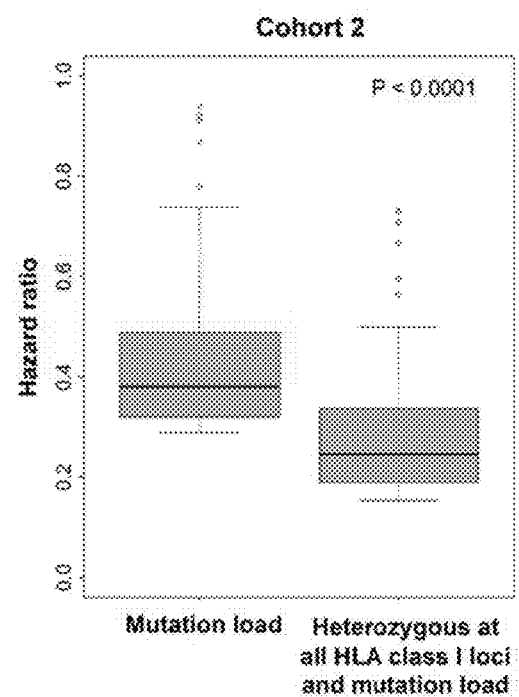

We performed survival analyses using the Kaplan-Meier estimator. The log-rank test was used to determine statistical significance of the survival distributions between patients with a specific genotyping and patients without it. We computed hazard ratios using univariate or multivariable Cox regression. To stratify patients into two groups, with high and low tumor mutational load, we used cutoffs calculated by the R function maxstat.test (//cran.r-project.org/web/packages/maxstat/vignettes/maxstat.pdf). In FIG. 8F, FIG. 8G, FIG. 9G, and FIG. 9H we used a range of cutoffs across the quartiles of the distribution of the number of somatic mutations of the specific cohort analyzed. The cutoffs were used to stratify patients into two groups, high or low tumor mutational load, and to generate the box plot showing the distribution of hazard ratios resulting from the survival analyses using the multiple cutoffs. In FIG. 8F, we used the range [80, 542]. For FIG. 8G, we used [5, 65]. For FIG. 9G, we used the range [108, 569]. And for FIG. 9H, we used [5, 25]. Comparison of number of somatic mutations between HLA class I homozygotes and heterozygotes groups was performed with the Wilcoxon-rank sum test. All statistical analysis was performed in the R Statistical Computing environment version 3.3.1 (www.r-project.org).

Mutational Analysis Pipeline

For cohort 1, whole-exome sequencing for all data sets was previously completed (3-5, 36). Analysis was performed as described by DePristo et al. (42, 43) As previously described (42), paired-end reads in FASTQ format were aligned to the reference human genome GRCh37 using the Burrows-Wheeler aligner (BWA; v0.7.10) (44). Local realignment was performed using the Genome Analysis Toolkit (GATK 3.2.2) (45). Duplicate reads were removed using Picard version 1.119. To identify somatic single nucleotide variants (SNVs), we used a pipeline that integrates mutation calls from four different mutation callers: MuTect 1.1.4, Strelka 1.0.3, SomaticSniper 1.0.4, and Varscan 2.3.7 (46-49). Insertions and deletions were determined using Strelka 1.0.3 with default settings (42,43). SNVs with an allele read count of less than 4 or with corresponding normal coverage of less than 7 reads were filtered out. For cohort 2, relative mutational load was determined using MSK-IMPACT consistent with targeted panels as a validated method to determine relative mutational load (8, 11, 41, 50).

Loss of Heterozygosity of HLA Class I Analysis

Copy number variation analysis was performed using FACETS 0.5.6 (51) to determine allele specific copy number. Segments within the chromosome 6p locus were identified containing the HLA-A, HLA-B and HLA-C loci. Loss of heterozygosity (LOH) was defined as a minor allele copy number estimate of 0 for any of the HLA loci using the expectation-maximization model.

HLA Class I Structural Analysis and Molecular Dynamics Simulations

The neoantigen structure within the pHLA complex presented in PDB 1M6O was mutated to conform to the desired B44 motif (F3I, P4G, A6V, F9Y) using the VMD Mutator plugin. All images were rendered using the VMD 1.9.2 software package (52).

Molecular dynamics (MD) simulations of isolated HLA class I alleles and HLA-peptide complexes were initiated from configurations drawn from crystal structures at the highest available resolutions: HLA-B*15:01 (PDB ID: 1XR9); HLA-B*07:02 (PDB ID: 5EO0); and HLA-B*53:01 (PDB ID: 1A1M). To generate isolated HLA configurations, atoms corresponding to bound peptides were removed. After the addition of hydrogen atom and disulfide bond patches, each system was solvated in TIP3P water molecules and brought to a physiological concentration (150 mM) of $Na^+$ and $Cl^-$ ions. Following similar protocols used in our previous studies (53-55), the resulting protein-water systems were minimized for 25000 steps by steepest descent, and then equilibrated with and without harmonic protein restraints in separate 5 ns simulations. Configurations taken from the ends of equilibration runs were used to seed production simulations, which were extended to 500 ns in duration for HLA-B*15:01 and 300 ns in length for HLA-B*07:02 and HLA-B*53:01. In all equilibration and production runs, temperature and pressure were constrained at 310 K and 1 atm using a Langevin thermostat and Parrinello-Rahman barostat, respectively. All MD simulations were conducted with the NAMD 2.11 simulation package (56). Inter-residue separations and residue-position root mean square fluctuations (RMSFs) were computed using standard utilities included in the GROMACS 5.1 software suite (57). Simulation snapshots were generated with VMD (52).

Results

We performed survival and genetic association analyses to address two hypotheses: (i) heterozygosity at HLA class I genes confers a selective advantage on survival with the administration of immune checkpoint inhibitors in cancer patients, and (ii) individual HLA class I germline alleles vary in their influence on survival after ICM therapy.

To examine these hypotheses, we scrutinized two sets of cancer patients (henceforth called cohort 1 and cohort 2) who were treated with ICM therapy. Cohort 1 was comprised of 369 patients who were treated with anti-CTLA-4 or anti-PD-1 drugs, for which exome sequencing data and clinical data were obtained. Out of these 369 patients, 269 patients had advanced melanoma, previously reported by Snyder et al. (3), Van Allen et al. (4), Hugo et al. (7), and Riaz et al. (36), and 100 patients had advanced non-small cell lung cancer (NSCLC) (5) (Appendix 1). The patients with NSCLC were treated mainly with anti-PD-1 monotherapy. Cohort 2 was comprised of 1,166 patients representing different cancer types including melanoma and NSCLC (Appendix 1), whose tumors were subjected to targeted next-generation sequencing (MSK-IMPACT) (11). These patients were treated with drugs targeting CTLA-4, PD-1/PD-L1, or a combination of both, at the Memorial Sloan Kettering Cancer Center (11). For all patients in both cohorts, we performed high-resolution HLA class I genotyping from normal DNA using DNA sequencing data or a clinically validated HLA typing assay (LabCorp). HLA typing from sequencing data was done using Polysolver, which has been extensively validated (33, 34). For quality assurance, a subset of these patients (N=22) were HLA typed using a CLIA-certified assay (at the New York Blood Center) and typed using Polysolver (38). As expected and previously shown, the overall concordance between Polysolver and the HLA-typing assay was very high (96%).

MHC class I molecules are extremely polymorphic with most of the polymorphism located in the peptide-binding region; each variant binds a select repertoire of peptide ligands. As such, a person who is homozygous in at least one HLA class I locus would be predicted to present a smaller, less diverse repertoire of tumor-derived peptides that are recognized by cytotoxic T lymphocytes (CTLs) compared to a person who is heterozygous at each class I locus (32). We thus reasoned that, greater diversity (heterozygosity) in the repertoire of antigen-presenting HLA class I molecules would be associated with better survival following ICM treatment. Conversely, less diversity (homozygosity) at these class I genes would be associated with poorer survival. We tested this hypothesis by examining HLA zygosity at each of the HLA class I genes (HLA-A, -B, and -C) in cohort 1 and cohort 2, independently. For this analysis, we employed a Cox proportional hazard regression model to examine the probability of overall survival. The results showed a statistically significant association between HLA class I homozygosity and reduced survival in the 369 patients from cohort 1 treated with ICM therapy (FIG. 8A). The association was apparent when at least one HLA class I locus was homozygous (cohort 1; P=0.036, HR=1.40, 95% CI 1.02-1.9; FIG. 8A). We validated this finding in the independent cohort of 1,166 patients treated with ICM therapy (cohort 2; P=0.028, HR=1.31, 95% CI 1.03-1.70; FIG. 8B). The number of somatic mutations in tumors was not statistically different between homozygotes and heterozygotes patients in either cohort 1 (Wilcoxon rank-sum test P=0.09; FIG. 11A) or cohort 2 (Wilcoxon rank-sum test P=0.7; FIG. 11B). Furthermore, the association of homozygosity with reduced survival remained significant in multivariable Cox regression modeling when including mutation load, tumor stage, age, and drug class in cohort 1 (P=0.02, HR=1.50, 95% CI 1.07-2.10) (Table 4) and in cohort 2 (P=0.028, HR=1.31, 95% CI 1.03-1.67) (table 5).

TABLE 4

Multivariable survival analysis incorporating homozygosity for at least one HLA class I locus, mutation burden (as a continuous variable), age, tumor stage, and drug class from cohort 1

| Covariate | HR | 95% CI | P value |
| --- | --- | --- | --- |
| Homozygosity for at least one HLA-I locus | 1.50 | 1.07-2.10 | 0.02 |
| Mutation load (Continuous) | 1.00 | 0.98-0.99 | 0.004 |
| Age | 1.00 | 0.99-1.01 | 0.96 |
| Stage M0 (reference) | | | |
| Stage M1a | 2.30 | 0.75-6.70 | 0.15 |
| Stage M1b | 2.70 | 0.91-7.77 | 0.08 |
| Stage M1c | 4.06 | 1.49-11.08 | 0.006 |
| Drug class: CTLA-4 (reference) | | | |
| Drug class: PD-1 | 0.64 | 0.47-0.87 | 0.004 |

TABLE 5

Multivariable survival analysis incorporating homozygosity for at least one HLA class I locus, mutation burden (as a continuous variable), age, tumor stage, and drug class from cohort 2

| Covariate | HR | 95% CI | P value |
| --- | --- | --- | --- |
| Homozygosity for at least one HLA-I locus | 1.31 | 1.03-1.67 | 0.028 |
| Mutation load (Continuous) | 0.99 | 0.98-0.99 | 0.003 |
| Age group <30 (reference) | | | |
| Age group >71 | 0.94 | 0.44-2.02 | 0.88 |
| Age group 31-50 | 0.90 | 0.44-1.84 | 0.78 |
| Age group 50-60 | 0.77 | 0.37-1.59 | 0.47 |
| Age group 61-70 | 0.76 | 0.36-1.61 | 0.48 |
| Drug class: Combo (reference) | | | |
| Drug class: CTLA-4 | 0.52 | 0.28-0.96 | 0.036 |
| Drug class: PD-1/PDL-1 | 1.53 | 1.12-2.08 | 0.007 |

The generation of HLA class I-restricted T-cell responses has been shown to be important in the clinical response of cancer patients treated with immunotherapies (3, 5, 34, 35). These results suggest that by limiting the number of HLA class I-restricted tumor-derived epitopes that can be presented to T cells, HLA homozygosity may impair a patient's survival after ICM therapy perhaps by decreasing the chance that antigens needed for anti-tumor immunity will be presented. Interestingly, these data are consistent with the association of rapid progression to AIDS of HIV-infected patients having HLA class I homozygosity (22, 25), and with the association of HLA class II with persistent hepatitis B virus infection (58).

We next examined all 1,535 patients from cohort 1 and 2 together, to determine whether the effect of homozygosity may be due to a single class I locus, or a combination of different loci. This analysis revealed that homozygosity at one HLA class I locus (A, or B, or C) was associated with significant reduction of overall survival (P=0.003, HR=1.38, 95% CI 1.11-1.70; FIG. 8C). Interestingly, the effect of homozygosity on survival due to specific HLA class I locus seemed mostly associated with HLA-B (P=0.052, HR=1.66, 95% CI 0.93-2.94; FIG. 8C) and HLA-C (P=0.004, HR=1.60, 95% CI 1.16-2.21; FIG. 8C). Of note, the number of patients available likely limited the interpretability of analyses involving combinations of loci (HLA-A and -B, etc.).

Without wishing to be bound by any particular theory, there are two possible explanations for the significant association of homozygosity at the HLA-B locus with decreased survival. First, HLA-B is expressed at higher levels on the cell surface than HLA-A and HLA-C, and HLA-B alleles bind to greater diversity of peptides (59,60). Amino acids that bind to the B pocket of HLA-A alleles are broadly hydrophobic residues. In contrast, the B pocket of HLA-B alleles can accommodate a greater variety of residues (proline, positively and negatively charged residues, and histidine and glutamine) (60). The principal source of HLA-B diversity arises from intralocus recombination events within exon 3, primarily affecting the F, C, and D pockets (60) and the HLA-B locus is dominant in determining clinical outcomes in infectious diseases such as HIV and malaria (21-28). Similarly, heterozygosity at HLA-C loci may enable greater peptide ligand diversity. Although HLA-C also has the ability to present peptides to cytotoxic CD8+ T cells, antigen-presenting cells (APCs) express higher levels of HLA-C on the cell surface than other cell types (61). Because HLA-C molecules bind to inhibitory killer cell immunoglobulin-like receptors (KIRs) that are up regulated upon acquisition of effector functions (62), heterozygous HLA-C locus may more effectively limit CTL lysis of cross-presenting APCs. This may, therefore, facilitate continuous priming of naïve CTLs during treatment with ICM therapy (63).

Previous reports have shown that the total number of somatic coding mutations in a cancer genome correlates with response to ICM therapy (6, 3-5, 65). An explanation for this observation is that the number of neopeptides presented by the tumor increases with the number of somatic mutations, which in turn also increases the probability that $CD8^+$ T cells recognize a neoepitope following ICM therapy (64). Therefore, we assessed the effect of zygosity at the HLA class I loci in combination with mutation burden. This analysis revealed that HLA class I homozygosity and low mutation burden were strongly associated with decreased survival compared to patients who were heterozygous at each class I locus and whose tumors had high mutation burden. This effect was seen in both in cohort 1 (P=0.003, HR=2.03, 95% CI 1.27-3.30; FIG. 8D) and in cohort 2 (P<0.0001, HR=2.98, 95% CI 1.84-4.82; FIG. 8E). Notably, the combined effect of HLA class I heterozygosity and mutation load on survival was greater compared with mutation load alone in both cohort 1 and cohort 2 (FIGS. 8, F and G).

Figure 8H:
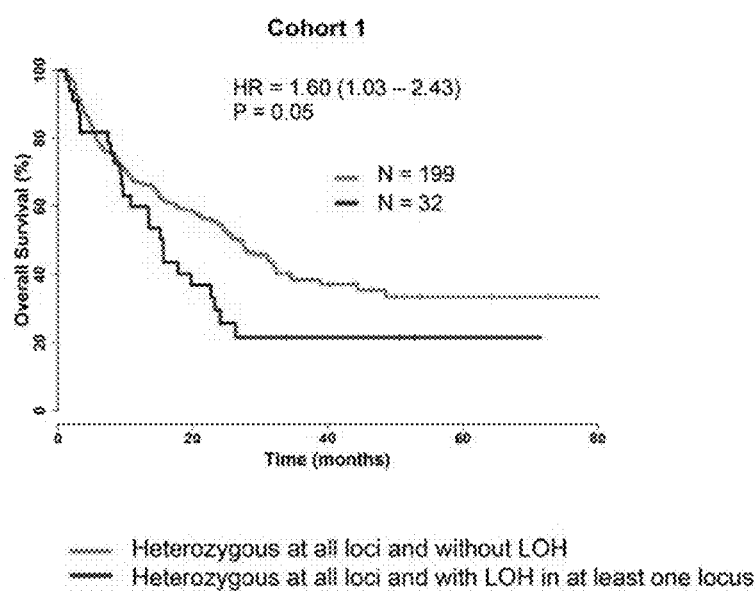
Figure 8I:
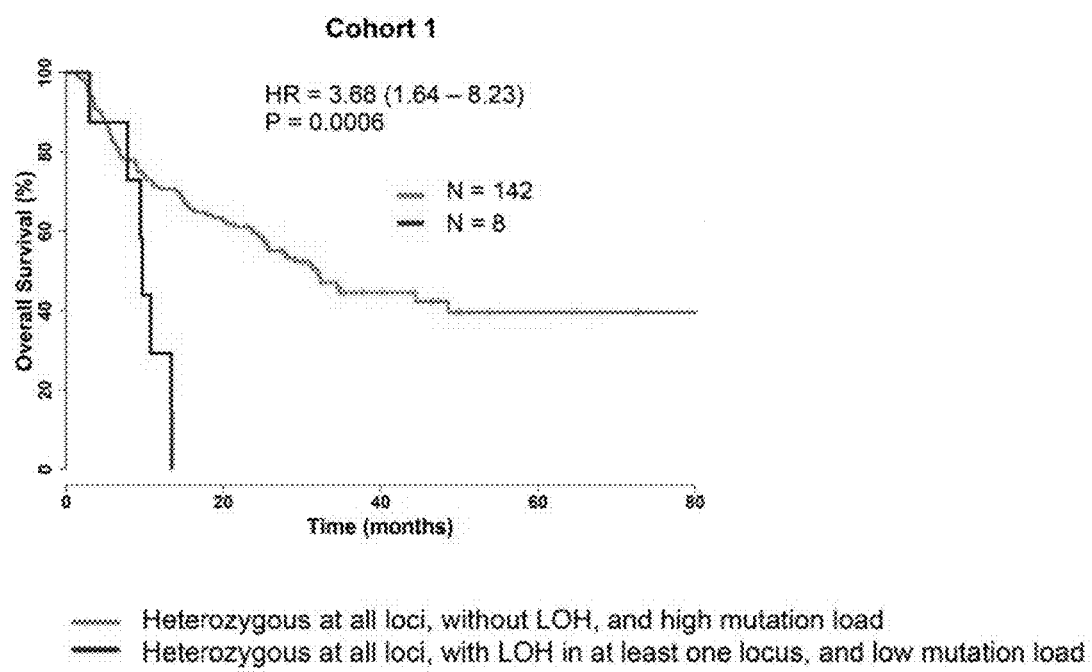

Previous work has reported the presence of loss of heterozygosity (LOH) of HLA class I genes in cancer (66). We therefore examined whether LOH of HLA class I in the tumor may have a similar effect on survival outcome after ICM therapy as in the case of germline HLA class I homozygosity. We analyzed all tumor exomes from cohort 1 and identified 32 patients who were heterozygous at all HLA class I loci, but had LOH in at least one HLA class I locus in their tumors (Appendix 1). We found that patients with LOH of HLA class I were associated with reduced survival compared to patients who were heterozygous at each HLA class I locus and without LOH (P=0.05, HR=1.60, 95% CI 1.03-2.43; FIG. 8H). Consistent with the above results, the effect of LOH of HLA class I on survival was enhanced in patients whose tumors contained low mutation load compared to patients who were heterozygous at all HLA class I loci, without LOH, and whose tumors had high mutation burden (P=0.0006, HR=3.68, 95% CI 1.64-8.23; FIG. 8I). Taken together, these results indicate that patient-specific diversity of antigen-presenting HLA class I molecules and mutation burden in the tumor may both impact the number of immunogenic neoantigens that are presented on the cell surface, which in turn, influences response to ICM therapy. Furthermore, the demonstration of a significant survival advantage to HLA class I heterozygosity in patients treated with ICM therapy both at the germline and somatic level highlights its importance in the dynamic anti-tumor immune response and its evasion.

To investigate the clinical relevance of individual HLA class I alleles after anti-PD-1 or anti-CTLA-4 therapy, we examined the effects of HLA class I supertypes on overall survival after ICM treatment. Individual HLA class I alleles are classified into twelve discrete supertypes (or superfamilies) (67,68). HLA alleles within the same supertype are expected to present similar peptides and this classification is supported by strong evidence for shared-presentation of peptide-binding motifs by different HLA class I molecules (25, 67, 68). Importantly, these supertypes together cover most HLA-A and HLA-B alleles found in distinct populations (67, 68).

Figure 9A:
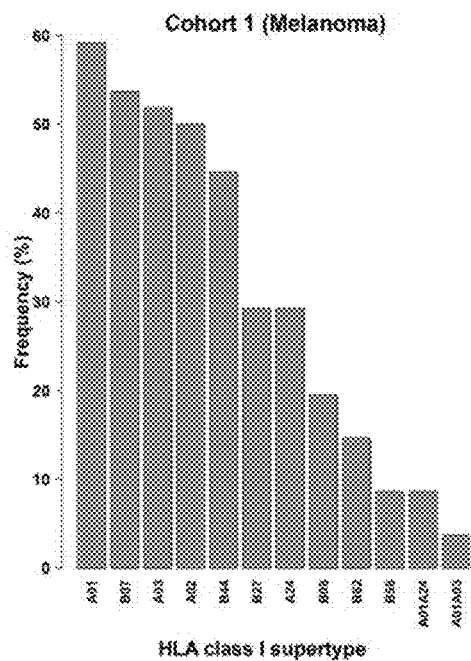
Figure 9B:
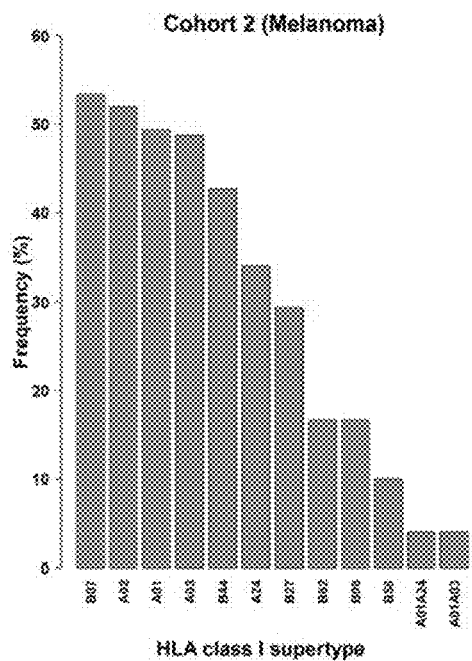

To assess the effect of HLA supertype on survival, we focused on melanoma patients, as we had enough patients in the two patient sets for meaningful analysis given HLA allelic diversity. Based on the biological definition of supertypes, we classified the 27 HLA-A alleles present in the patients with melanoma into six A supertypes, and the 50 HLA-B alleles into six B supertypes (Appendix 1 and FIG. 9A). We determined whether each HLA superfamily was associated with survival following ICM treatment. Strikingly, this analysis identified two supertypes, both B supertypes, associated with survival outcome in patients with advanced melanoma treated with anti-CTLA-4. Patients with B44 superfamily alleles had significantly better overall survival (P=0.01, HR=0.61, 95% CI 0.42-0.89) (Table 3) and patients with B62 alleles had significantly decreased survival (P=0.0007, HR=2.29, 95% CI 1.40-3.7) (Table 3). In these patients, the B44 supertype was present at a prevalence of 45%; the B62 supertype, 15% (FIG. 9A). We did not find any supertype significantly associated with overall survival in patients with NSCLC, likely due to the limited sample size.

TABLE 3

HLA supertype association with overall survival in patients with melanoma from cohort 1 treated with ICM and influence of specific alleles on the associations

| HLA class I supertype | Frequency | HR | P value |
| --- | --- | --- | --- |
| A24 | 0.29 | 0.67 (0.44-1.03) | 0.07 |
| A01 | 0.59 | 0.87 (0.60-1.27) | 0.47 |
| A03 | 0.52 | 1.39 (0.96-2.03) | 0.08 |
| A02 | 0.5 | 1.13 (0.76-1.63) | 0.53 |
| B58 | 0.09 | 0.98 (0.51-1.88) | 0.96 |
| B62 | 0.15 | 2.29 (1.40-3.74) | 0.0007 |
| B27 | 0.29 | 1.09 (0.73-1.63) | 0.67 |
| B44 | 0.45 | 0.61 (0.42-0.89) | 0.009 |
| B07 | 0.54 | 1.35 (0.92-1.97) | 0.12 |
| B08 | 0.2 | 0.85 (0.52-1.39) | 0.51 |
| A01A03 | 0.04 | 1.20 (0.49-2.94) | 0.69 |
| A01A24 | 0.09 | 0.89 (0.43-1.83) | 0.76 |

TABLE 3-continued

HLA supertype association with overall survival in patients with melanoma from cohort 1 treated with ICM and influence of specific alleles on the associations

| HLA class I supertype | Frequency | HR | P value |
|---|---|---|---|
| Alleles influencing the significant associations | | | |
| B44s, B*18:01, B*44:02, B*44:03, B*44:05, B*50:01 | 0.34 | 0.5 (0.32-0.76) | 0.001 |
| B62s, B*15:01 | 0.13 | 2.21 (1.33-3.7) | 0.002 |

Figure 9C:
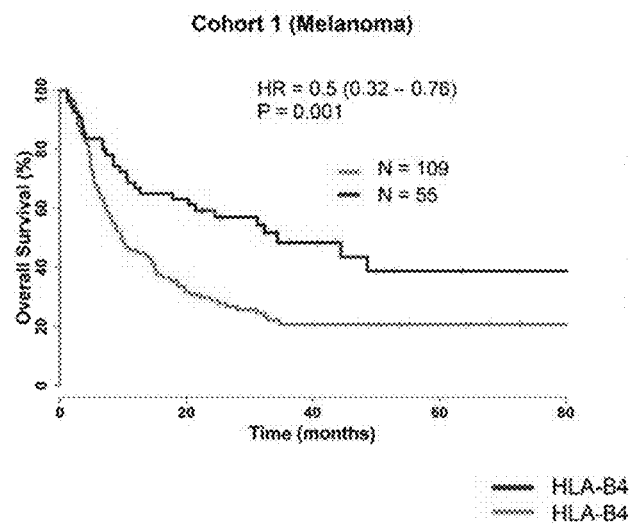
Figure 9D:
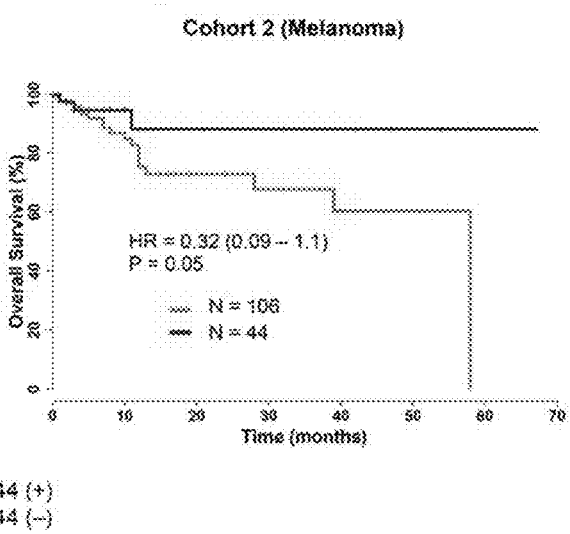

We then examined whether these supertype associations were influenced by the presence of specific component HLA class I alleles. The B44 association was influenced by HLA-B*18:01, HLA-B*44:02, HLA-B*44:03, HLA-B*44:05, and HLA-B*50:01 (P=0.001, HR=0.49, 95% CI 0.32-0.76; FIG. 9C) (Table 3). And, the B62 association was significantly driven by HLA-B*15:01 (P=0.002, HR=2.21, 95% CI 1.33-3.7; FIG. 10A) (Table 3). Both of these B44 and B62 supertype allele associations remained statistically significant (P=0.01 and P=0.02, respectively) after a conservative Bonferroni correction for multiple comparisons.

Figure 9I:
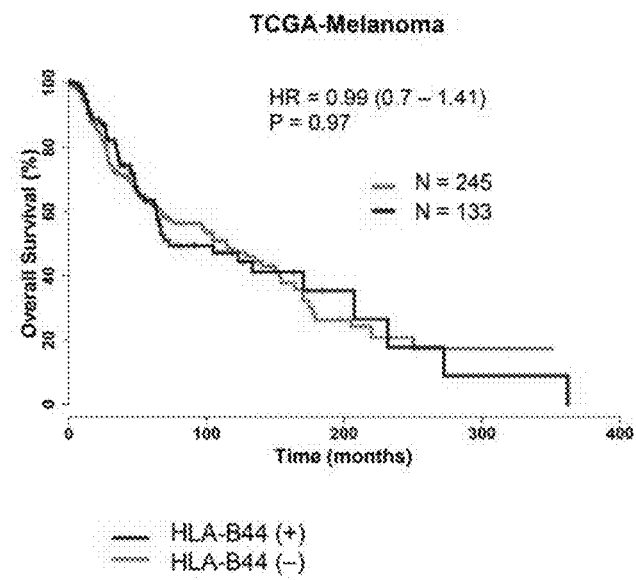

In the independent set of patients, cohort 2, melanoma patients treated with anti-PD-1 or anti-CTLA-4 who had the B44 supertype alleles had significantly better overall survival (P=0.05, HR=0.32, 95% CI 0.09-1.1; FIGS. 9, B and D). The association of the B44s with increased survival remained significant in multivariable analysis when including mutation load, tumor stage, age, and drug class (anti-CTLA-4 or anti-PD-1) in both cohort 1 (table 6) and in cohort 2 (table 7). Furthermore, the effect of B44s on extended survival was enhanced when somatic mutational load in the tumor was also considered. Patients with melanoma possessing B44s and whose tumors also contained high mutation burden had significantly prolonged survival compared to patients who did not carry B44s and having tumors that contained low mutation load in cohort 1 (P<0.0001, HR=0.23, 95% CI 0.13-0.41; FIG. 9E) and in cohort 2 (P=0.023, HR=0.13, 95% CI 0.02-1.07; FIG. 9F). The combined effect of the B44s and mutation load was greater than simply considering mutation burden alone in both cohort 1 and cohort 2 (FIGS. 9, G and H). We note that, in general, outcomes of melanoma patients in cohort 2 tended to be better than in cohort 1 because patients who received ICM therapy and were accrued to our protocol for MSK-IMPACT testing tended to have lived longer. Yet, despite this trend, we still observed a significant effect from the B44 superfamily alleles. Notably, the B44 supertype did not associate with overall survival in patients with melanoma from The Cancer Genome Atlas (TCGA), suggesting that the presence of B44 is predictive of response to ICM therapy and is not prognostic (FIG. 9I).

TABLE 6

Multivariable survival analysis incorporating presence of B44s, mutation burden (as a continuous variable), age, tumor stage, and drug class from patients with melanoma from cohort 1

| Covariate | HR | 95% CI | P value |
|---|---|---|---|
| HLA-B44(+) | 0.54 | 0.34-0.84 | 0.013 |
| Mutation load (Continuous) | 1.00 | 0.98-0.99 | 0.007 |
| Age | 1.00 | 0.99-1.01 | 0.5 |

TABLE 6-continued

Multivariable survival analysis incorporating presence of B44s, mutation burden (as a continuous variable), age, tumor stage, and drug class from patients with melanoma from cohort 1

| Covariate | HR | 95% CI | P value |
|---|---|---|---|
| Stage M0 (reference) | | | |
| Stage M1a | 1.91 | 0.62-5.87 | 0.26 |
| Stage M1b | 2.14 | 0.73-6.25 | 0.16 |
| Stage M1c | 3.53 | 1.30-9.64 | 0.01 |
| Drug class: CTLA-4 (reference) | | | |
| Drug class: PD-1 | 0.73 | 0.52-1.02 | 0.07 |

TABLE 7

Multivariable survival analysis incorporating presence of B44s, mutation burden (as a continuous variable), age, and drug class from patients with melanoma from cohort 2

| Covariate | HR | 95% CI | P value |
|---|---|---|---|
| HLA-B44(+) | 0.27 | 0.07-0.95 | 0.04 |
| Mutation load (continuous variable) | 0.99 | 0.97-1.01 | 0.4 |
| Age group <30 (reference) | | | |
| Age group >71 | 0 | 0- | 1.00 |
| Age group 31-50 | 0.25 | 0.06-1.01 | 0.05 |
| Age group 50-60 | 0.7 | 0.17-2.97 | 0.63 |
| Age group 61-70 | 0.64 | 0.12-3.46 | 0.60 |
| Drug class: CTLA-4 (reference) | | | |
| Drug class: PD-1/PDL-1 | 4.36 | 1.35-14.10 | 0.01 |

Figure 9J:
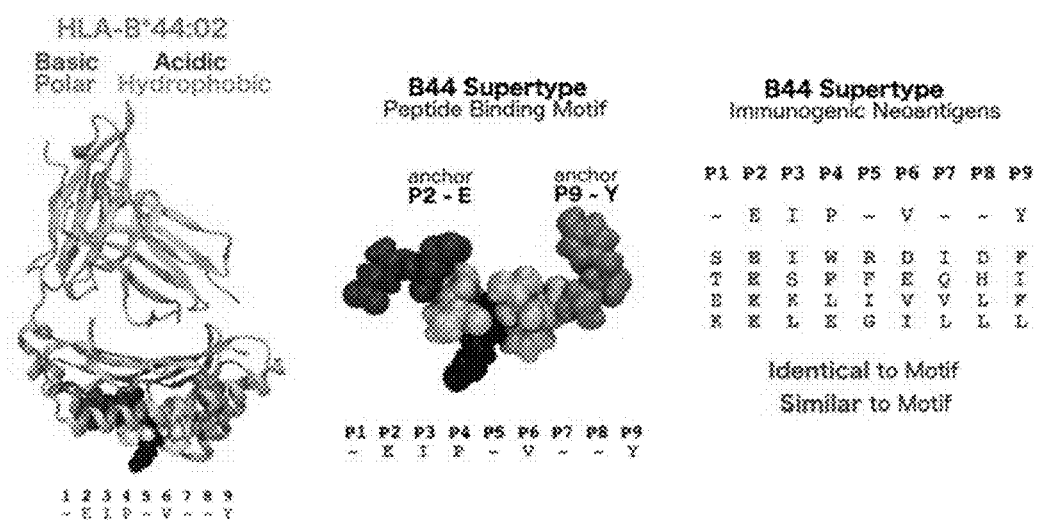
Figure 12A:
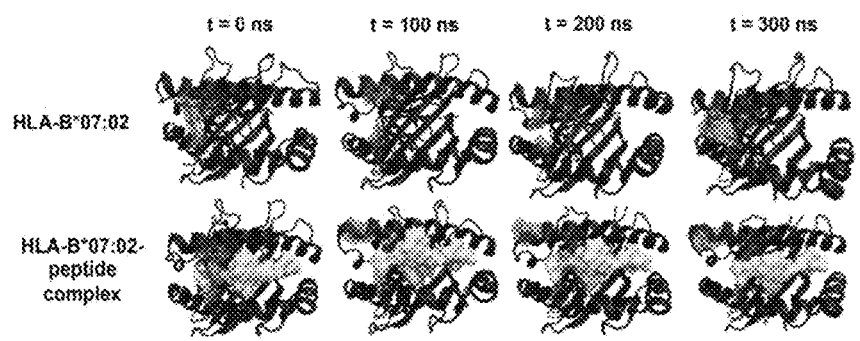
FIGS. 12A-12D show molecular dynamics simulations for HLA-B*07:02 and HLA-B*53:01. (A and C) MD simulation snapshots of both the isolated HLA B*07:02 and HLA B*53:01 molecules, respectively, and their complexes with a 9-mer peptide; each trajectory was run over the course of 300 ns of simulation time. (B and D) Observables from the MD simulations described in (A and C). Both mean bridge distances and bridging residues RMSFs in the HLA B*07:02 and HLA B*53:01 molecules and in their corresponding HLA-peptide complexes are shown.
Figure 12B:
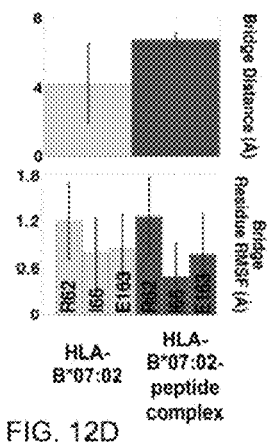
Figure 12C:
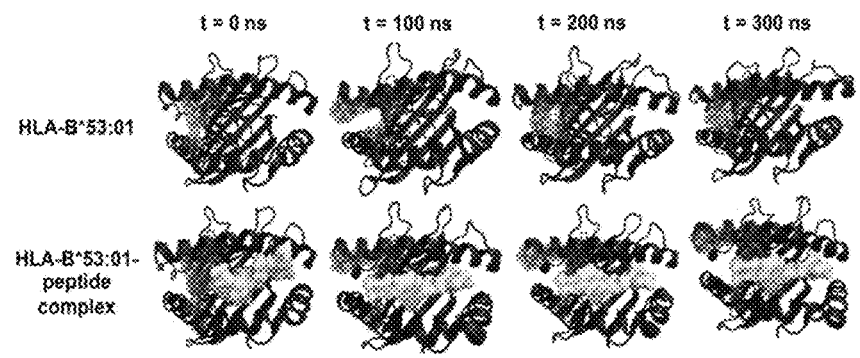
Figure 12D:
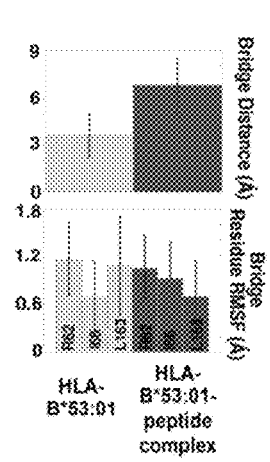

Members of the B44 supertype share a preference for peptides with negatively charged residues at anchor position P2 (Glu) near the N-terminus and polar residues at the C-terminus (69) (FIG. 9J). A number of previously identified immunogenic antigens expressed by melanomas are HLA-B44 restricted (FIG. 9J and table 8), including the testis antigen MAGEA3 epitope, which has been shown to be restricted to HLA-B*44:03 and HLA-B*18:01 (both members of B44), and an immunogenic clonal neoantigen (FAM3C: TESPFEQHI) identified in a melanoma patient who derived a long-term response to CTLA-4 blockade from cohort 1 (table 8) (3, 15). Additionally, an association of B44 with spontaneous immune response in NY-ESO-1 expressing tumors has been recently reported (70). Taken together, these data suggest that the B44s may facilitate presentation of tumor-derived antigens that are recognized by CD8+ T cells, which in turn contribute to the improved survival outcome following ICM therapy.

TABLE 8

Some experimentally identified immunogenic HLA-B44 restricted neoantigens expressed by melanomas reported in the literature

| Gene | WT Peptide | Neoantigen | HLA-B44 allele | WT score | Neo-antigen score | Reference |
|---|---|---|---|---|---|---|
| MAGE3 | — | MEVDPIGHLY | B*44:03 | — | 0.01 | (67, 68) |
| MAGE3 | — | MEVDPIGHLY | B*18:01 | — | 0.10 | (67, 68) |
| TYR | — | SEIWRDIDF | B*44:03 | — | 0.25 | (69) |
| FAM3C | TKSPFEQHI | TESPFEQHI | B*44:02 | 16 | 0.6 | (10) |
| MUM1 | EEKLSVVLF | EEKLIVVLF | B*44:02 | 0.09 | 0.1 | (70) |
| MUM2 | SELFRSRLDSY | SELFRSGLDSY | B*44:02 | 0.7 | 2.5 | (71) |
| OS9 | KELEGILLP | KELEGILLL | B*44:03 | 2.5 | 0.6 | (72) |

The WT score and the neoantigen score refer to the binding strengths of the wild type peptide and its mutated peptide, respectively, predicted by NetMHC version 4.0 (73).

In contrast, the B62 association with poor survival driven by the HLA-B*15:01 allele was intriguing (FIG. 10A) (Table 3). In an exploratory analysis, we sought to determine whether any molecular features in the HLA-B*15:01 allele are associated with its effect on survival following immunotherapy. Out of all the HLA-B alleles that were available for three-dimensional structural analysis (N=119; Appendix 2), we identified three alleles at their highest resolutions, HLA-B*15:01 (PDB ID: 1XR9); HLA-B*07:02 (PDB ID: 5EO0); and HLA-B*53:01 (PDB ID: 1A1M), as possessing a structural bridge in the peptide-binding grooves at positions 62, 66, and 163. The bridge in HLA-B*15:01 apparently sequesters bound-peptide residue positions P2 and P3 (FIGS. 10, B and C).

The poor survival associated with the HLA-B*15:01 allele may not reflect simple failure to present peptides, because significant peptide presentation has been reported for this allele (71). We thus postulated that this specific structural feature may modulate the effective T cell recognition of neoepitopes presented on the HLA-B*15:01 molecule. To evaluate the validity of this hypothesis, we conducted molecular dynamics (MD) simulations on these three HLA class I molecules following similar protocols used in previous studies (53-55).

In the case of HLA-B*07:02 and HLA-B*53:01, molecular dynamics simulations demonstrated that the bound peptide expands the respective HLA binding cleft, effectively breaking the bridge (FIG. 12, A to D). Conversely, in the HLA-B*15:01 molecule, the bridge was largely maintained with the peptide present, and the bridging residues were also made much less flexible (FIGS. 10, D and E). FIG. 10D shows MD simulation snapshots of both the isolated HLA B*15:01 and its complex with a 9-mer UBCH6 peptide, each over the course of 500 ns of dynamics. In both cases, the bridging residues (Arg62, Ile66, and Leu163) separated somewhat when their crystal coordinates were relaxed, and bridging residue positions fluctuated as the trajectories proceeded. However, the general bridge configuration seen in the crystal structure was conserved in our simulated conformational ensembles (FIGS. 10, D and E). As FIG. 10E illustrates, the occupation of the peptide-binding groove in HLA-B*15:01 had the effect of arresting bridging residue dynamics. While the mean bridge separation remained nearly constant (~6 Å) in both systems of HLA B*15:01 (FIG. 10E), the fluctuations in this distance were less dramatic in the peptide-bound complex. The residue-position root mean square fluctuations (RMSFs) indicate that each of the bridging residues was more rigid with the presence of peptide (FIG. 10E). Altogether, these unique structural and dynamical elements of the HLA-B*15:01 molecule may impair the total strength of the interaction for effective antigen recognition between the HLA-B*15:01-neoepitope complex and T-cell receptor. However, further experimental work will be necessary to test this hypothesis.

Thus, results presented here show that HLA class I genes influence survival outcome with ICM therapy. Our data indicate that patient-specific HLA class I genotype and somatic alterations, in combination or in the alternative, in tumors impact clinical outcomes following ICM therapy. Both can be considered during the design of future clinical trials and/or recommended therapeutic dosing. The observation that the B44 superfamily is associated with extended overall survival may provide an opportunity for the development of therapeutic vaccines that potentially target immunodominant HLA-B44-restricted neoantigens expressed by melanomas. Additionally, our findings suggest that HLA class I homozygosity and LOH of HLA class I represent a genetic barrier that can be considered to enhance immunotherapeutic efficacy.

Example 5: Exemplary Dosing Regimens for Approved PD-1 Immune Checkpoint Modulators The present Example sets forth certain dosing regimens that have been approved by the United States Food and Drug Administration for the indicated immune checkpoint modulator agents.

Atezolizumab (TECENTRIQ™)

- - - Indications and Usage - - -
TECENTRIQ is a programmed death-ligand 1 (PD-L1) blocking antibody indicated for the treatment of patients with locally advanced or metastatic urothelial carcinoma who:

Have disease progression during or following platinum-containing chemotherapy;

Have disease progression within 12 months of neoadjuvant or adjuvant treatment with platinum-containing chemotherapy.

This indication is approved under accelerated approval based on tumor response rate and duration of response. Continued approval for this indication may be contingent upon verification and description of clinical benefit in confirmatory trials.

- - - Dosage and Administration - - -

Administer 1200 mg as an intravenous infusion over 60 minutes every 3 weeks.

Dilute prior to intravenous infusion.

- - - Dosage Forms and Strengths - - -

Injection: 1200 mg/20 mL (60 mg/mL) solution in a single-dose vial.

- - - Contraindications - - -

None.

- - - Warnings and Precautions - - -

Immune-Related Pneumonitis: Withhold for moderate and permanently discontinue for severe or life-threatening pneumonitis. (5.1)

Immune-Related Hepatitis: Monitor for changes in liver function. Withhold for moderate and permanently discontinue for severe or life-threatening transaminase or total bilirubin elevation.

Immune-Related Colitis: Withhold for moderate or severe, and permanently discontinue for life-threatening colitis.

Immune-Related Endocrinopathies:

Hypophysitis: Withhold for moderate or severe and permanently discontinue for life-threatening hypophysitis.

Thyroid Disorders: Monitor for changes in thyroid function. Withhold for symptomatic thyroid disease.

Adrenal Insufficiency: Withhold for symptomatic adrenal insufficiency.

Type 1 Diabetes Mellitus: Withhold for ≥Grade 3 hyperglycemia.

Immune-Related Myasthenic Syndrome/Myasthenia Gravis, Guillain-Barré or Meningoencephalitis: Permanently discontinue for any grade.

Ocular Inflammatory Toxicity: Withhold for moderate and permanently discontinue for severe ocular inflammatory toxicity.

Immune-Related Pancreatitis: Withhold for moderate or severe, and permanently discontinue for life-threatening pancreatitis, or any grade of recurring pancreatitis.

Infection: Withhold for severe or life-threatening infection.

Infusion Reaction: Interrupt or slow the rate of infusion for mild or moderate infusion reactions and discontinue for severe or life-threatening infusion reactions.

Embryo-Fetal Toxicity: TECENTRIQ can cause fetal harm. Advise females of reproductive potential of the potential risk to a fetus and use of effective contraception.

Avelumab (BAVENCIO®)

- - - Indications and Usage - - -

BAVENCIO is a programmed death ligand-1 (PD-L1) blocking antibody indicated for the treatment of adults and pediatric patients 12 years and older with metastatic Merkel cell carcinoma (MCC).

This indication is approved under accelerated approval. Continued approval for this indication may be contingent upon verification and description of clinical benefit in confirmatory trials.

- - - Dosage and Administration - - -

Administer 10 mg/kg as an intravenous infusion over 60 minutes every 2 weeks.

Premedicate with acetaminophen and an antihistamine for the first 4 infusions and subsequently as needed.

- - - Dosage Forms and Strengths - - -

Injection: 200 mg/10 mL (20 mg/mL) solution in single-dose vial.

- - - Contraindications - - -

None. (4)

- - - Warnings and Precautions - - -

Immune-mediated pneumonitis: Withhold for moderate pneumonitis; permanently discontinue for severe, life-threatening or recurrent moderate pneumonitis.

Immune-mediated hepatitis: Monitor for changes in liver function. Withhold for moderate hepatitis; permanently discontinue for severe or life-threatening hepatitis.

Immune-mediated colitis: Withhold for moderate or severe colitis; permanently discontinue for life-threatening or recurrent severe colitis.

Immune-mediated endocrinopathies: Withhold for severe or life-threatening endocrinopathies.

Immune-mediated nephritis and renal dysfunction: Withhold for moderate or severe nephritis and renal dysfunction; permanently discontinue for life-threatening nephritis or renal dysfunction.

Infusion-related reactions: Interrupt or slow the rate of infusion for mild or moderate infusion-related reactions. Stop the infusion and permanently discontinue BAVENCIO for severe or life-threatening infusion-related reactions.

Embryo-fetal toxicity: BAVENCIO can cause fetal harm. Advise of potential risk to a fetus and use of effective contraception.

Durvalumab (IMFINZI™)

- - - Indications and Usage - - -

IMFINZI is a programmed death-ligand 1 (PD-L1) blocking antibody indicated for the treatment of patients with:

Locally advanced or metastatic urothelial carcinoma who:

have disease progression during or following platinum-containing chemotherapy.

have disease progression within 12 months of neoadjuvant or adjuvant treatment with platinum-containing chemotherapy.

This indication is approved under accelerated approval based on tumor response rate and duration of response. Continued approval for this indication may be contingent upon verification and description of clinical benefit in confirmatory trials.

- - - Dosage and Administration - - -

Administer 10 mg/kg as an intravenous infusion over 60 minutes every 2 weeks.

Premedicate with acetaminophen and an antihistamine for the first 4 infusions and subsequently as needed.

- - - Dosage Forms and Strengths - - -

Administer 10 mg/kg as an intravenous infusion over 60 minutes every 2 weeks and dilute prior to intravenous infusion.

- - - Contraindications - - -

None.

- - - Warnings and Precautions - - -

Immune-Mediated Pneumonitis: Withhold for moderate and permanently discontinue for severe or life-threatening pneumonitis.

Immune-Mediated Hepatitis: Monitor for changes in liver function.

Withhold for moderate and permanently discontinue for severe or life-threatening transaminase or total bilirubin elevation.

Immune-Mediated Colitis: Withhold for moderate and permanently discontinue for severe or life-threatening colitis.

Immune-Mediated Endocrinopathies: Adrenal Insufficiency, Hypophysitis, or Type 1 Diabetes Mellitus: Withhold for moderate, severe or life-threatening.

Immune-Mediated Nephritis: Monitor for changes in renal function. Withhold for moderate and permanently discontinue for severe or life-threatening nephritis.

Infection: Withhold for severe or life-threatening infection.

Infusion-Related Reactions: Interrupt infusion or slow the rate of infusion for mild or moderate and permanently discontinue for severe or life-threatening infusion-related reactions.

Embryo-Fetal Toxicity: Can cause fetal harm. Advise females of reproductive potential of the potential risk to a fetus and use of effective contraception.

Nivolumab (OPDIVO®)

- - - Indications and Usage - - -

OPDIVO is a human programmed death receptor-1 (PD-1) blocking antibody indicated for the treatment of patients with unresectable or metastatic melanoma and disease progression following ipilimumab and, if BRAF V600 mutation positive, a BRAF inhibitor.

This indication is approved under accelerated approval based on tumor response rate and durability of response. Continued approval for this indication may be contingent upon verification and description of clinical benefit in the confirmatory trials. (1, 14)

- - - Dosage and Administration - - -

Administer 3 mg/kg as an intravenous infusion over 60 minutes every 2 weeks.

- - - Dosage Forms and Strengths - - -

Injection: 40 mg/4 mL and 100 mg/10 mL solution in a single-use vial.

- - - Contraindications - - -

None.

- - - Warnings and Precautions - - -

Immune-mediated adverse reactions: Administer corticosteroids based on the severity of the reaction Immune-mediated pneumonitis: Withhold for moderate and permanently discontinue for severe or life-threatening pneumonitis.

Immune-mediated colitis: Withhold for moderate or severe and permanently discontinue for life-threatening colitis.

Immune-mediated hepatitis: Monitor for changes in liver function. Withhold for moderate and permanently discontinue for severe or life-threatening transaminase or total bilirubin elevation.

Immune-mediated nephritis and renal dysfunction: Monitor for changes in renal function. Withhold for moderate and permanently discontinue for severe or life-threatening serum creatinine elevation.

Immune-mediated hypothyroidism and hyperthyroidism: Monitor for changes in thyroid function. Initiate thyroid hormone replacement as needed.

Embryofetal toxicity: Can cause fetal harm. Advise of potential risk to a fetus and use of effective contraception.

Pembrolizumab (KEYTRUDA®)

- - - Indications and Usage - - -

KEYTRUDA is a human programmed death receptor-1 (PD-1)-blocking antibody indicated for the treatment of patients with unresectable or metastatic melanoma and disease progression following ipilimumab and, if BRAF V600 mutation positive, a BRAF inhibitor.

This indication is approved under accelerated approval based on tumor response rate and durability of response. An improvement in survival or disease-related symptoms has not yet been established. Continued approval for this indication may be contingent upon verification and description of clinical benefit in the confirmatory trials.

- - - Dosage and Administration - - -

Administer 2 mg/kg as an intravenous infusion over 30 minutes every 3 weeks.

Reconstitute and dilute prior to intravenous infusion.

- - - Dosage Forms and Strengths - - -

For injection: 50 mg, lyophilized powder in single-use vial for reconstitution.

- - - Contraindications - - -

None.

- - - Warnings and Precautions - - -

Immune-mediated adverse reactions: Administer corticosteroids based on the severity of the reaction.

Immune-mediated pneumonitis: Withhold for moderate, and permanently discontinue for severe or life-threatening pneumonitis.

Immune-mediated colitis: Withhold for moderate or severe, and permanently discontinue for life-threatening colitis.

Immune-mediated hepatitis: Monitor for changes in hepatic function. Based on severity of liver enzyme elevations, withhold or discontinue.

Immune-mediated hypophysitis: Withhold for moderate, withhold or discontinue for severe, and permanently discontinue for life-threatening hypophysitis.

Immune-mediated nephritis: Monitor for changes in renal function. Withhold for moderate, and permanently discontinue for severe or life-threatening nephritis.

Immune-mediated hyperthyroidism and hypothyroidism: Monitor for changes in thyroid function. Withhold for severe and permanently discontinue for life-threatening hyperthyroidism.

Embryofetal Toxicity: KEYTRUDA may cause fetal harm. Advise females of reproductive potential of the potential risk to a fetus.

Example 6: Exemplary Dosing Regimens for Approved CTLA-4 Immune Checkpoint Modulators The present Example sets forth certain dosing regimens that have been approved by the United States Food and Drug Administration for the indicated immune checkpoint modulator agents.

Ipilimumab (YERVOY™)

- - - Indications and Usage - - -

YERVOY is a human cytotoxic T-lymphocyte antigen 4 (CTLA-4)-blocking antibody indicated for:

Treatment of unresectable or metastatic melanoma.

Adjuvant treatment of patients with cutaneous melanoma with pathologic involvement of regional lymph nodes of more than 1 mm who have undergone complete resection, including total lymphadenectomy.

- - - Dosage and Administration - - -

Unresectable or metastatic melanoma: 3 mg/kg administered intravenously over 90 minutes every 3 weeks for a total of 4 doses.

Adjuvant melanoma: 10 mg/kg administered intravenously over 90 minutes every 3 weeks for 4 does, followed by 10 mg/kg every 12 weeks for up to 3 years or until documented disease recurrence or unacceptable toxicity.

Permanently discontinue for severe adverse reactions.

- - - Dosage Forms and Strengths - - -

Injection: 50 mg/10 mL (5 mg/mL)

Injection: 200 mg/40 mL (5 mg/mL)

- - - Contraindications - - -

None.

- - - Warnings and Precautions - - -

Immune-mediated adverse reactions: Permanently discontinue for severe reactions. Withhold dose for moderate immune-mediated adverse reactions until return to baseline, improvement to mild severity, or complete resolution, and patient is receiving less than 7.5 mg prednisone or equivalent per day. Administer systemic high-dose corticosteroids for severe, persistent, or recurring immune-mediated reactions.

Immune-mediated hepatitis: Evaluate liver function tests before each dose of YERVOY.

Immune-mediated endocrinopathies: Monitor clinical chemistries, ACTH level, and thyroid function tests prior to each dose. Evaluate at each visit for signs and symptoms of endocrinopathy. Institute hormone replacement therapy as needed.

Embryo-fetal toxicity: Can cause fetal harm. Advise of potential risk to a fetus and use of effective contraception.

Tremelimumab

- - - Indications and Usage - - -

Tremelimumab is a human cytotoxic T-lymphocyte antigen 4 (CTLA-4)-blocking antibody, still in clinical trials for the following:

Treatment of Head and Neck Cancer, HR+/HER2 Breast Cancer, Malignant Mesothelioma, Melanoma, Metastatic Renal Cell Carcinoma, Unresectable Malignant Melanoma, Urothelial Cancer, NSCLC, etc.

- - - Dosage and Administration - - -

In combination with one or more other drugs, Tremelimumab is given via IV over one hour on day 29 of the dosing cycle, which repeats once a month three of the treatment regimen. Doses range from 6 mg/kg to 15 mg/kg. Alternatively, in combination with one or more other drugs or given alone, Tremelimumab is given via IV every 90 days for four cycles at a concentration of 15 mg/kg; or IV infusions every 3 weeks for 12 weeks for four cycles with an additional dose administered at week 16.

APPENDIX 1

Cohort 1

| Sample | OS_Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| CR0095 | 67.93688479 | 0 | CTLA-4 | M1b | Stage 4 | 74 | M | 282 | Melanoma | Snyder et al. 2014 | A0201,A3101,B3502,B3906,C0702,C0401 | A02,A03,B07,B27,UNK,UNK | 0 | 0 |
| CR04885 | 25.61752464 | 0 | CTLA-4 | M0 | Stage 3 | 49 | F | 2102 | Melanoma | Snyder et al. 2014 | A0201,A3201,B0702,B1801,C0701,C0702 | A02,A01,B07,B44,UNK,UNK | 0 | 0 |
| CR06670 | 444.303943 | 1 | CTLA-4 | M0 | Stage 3 | 79 | F | 590 | Melanoma | Snyder et al. 2014 | A2402,A2601,B1801,B4403,C1601,C1203 | A24,A01,B44,B44,UNK,UNK | 0 | 0 |
| CR1509 | 53.88891476 | 0 | CTLA-4 | M1c | Stage 4 | 54 | F | 539 | Melanoma | Snyder et al. 2014 | A3301,A2601,B3801,B3501,C1203,C0401 | A03,A01,B27,B44,UNK,UNK | 0 | 0 |
| CR22640 | 51.23504928 | 0 | CTLA-4 | M1c | Stage 4 | 71 | M | 334 | Melanoma | Snyder et al. 2014 | A0301,A0201,B4101,B5001,C1701,C0602 | A03,A02,B44,B44,UNK,UNK | 0 | 0 |
| CR3665 | 31.87933827 | 0 | CTLA-4 | M1b | Stage 4 | 70 | M | 141 | Melanoma | Snyder et al. 2014 | A0205,A6801,B1402,B1801,C0701,C0802 | A02,A03,B27,B44,UNK,UNK | 0 | 0 |
| CR4880 | 64.35087166 | 0 | CTLA-4 | M1b | Stage 4 | 63 | M | 2570 | Melanoma | Snyder et al. 2014 | A0101,A0201,B4001,B0801,C0701,C0304 | A01,A02,B44,B08,UNK,UNK | 0 | 0 |
| CR6126 | 22.81560788 | 0 | CTLA-4 | M1b | Stage 4 | 66 | F | 562 | Melanoma | Snyder et al. 2014 | A0301,A3201,B5101,B4402,C0501,C1502 | A03,A01,B07,B44,UNK,UNK | 0 | 0 |
| CR6161 | 31.32142661 | 1 | CTLA-4 | M1b | Stage 4 | 81 | M | 930 | Melanoma | Snyder et al. 2014 | A0201,A0201,B1801,B5701,C0602,C1203 | A02,A02,B44,B58,UNK,UNK | 1 | 0 |
| CR7623 | 64.84435925 | 0 | CTLA-4 | M1c | Stage 4 | 62 | M | 503 | Melanoma | Snyder et al. 2014 | A0201,A6801,B3501,B5101,C0602,C0401 | A02,A03,B07,B07,UNK,UNK | 0 | 0 |
| CR9306 | 63.56129152 | 0 | CTLA-4 | M1c | Stage 4 | 65 | M | 1389 | Melanoma | Snyder et al. 2014 | A2402,A2402,B3502,B4402,C1604,C0401 | A24,A24,B07,B44,UNK,UNK | 1 | 0 |
| CR9699 | 52.83614457 | 0 | CTLA-4 | M1c | Stage 4 | 70 | M | 1226 | Melanoma | Snyder et al. 2014 | A2301,A2601,B4403,B2705,C0102,C0401 | A24,A01,B44,B27,UNK,UNK | 0 | 1 |
| CRNR0244 | 25.21725082 | 0 | CTLA-4 | M1c | Stage 4 | 49 | M | 543 | Melanoma | Snyder et al. 2014 | A0101,A0301,B0702,B4402,C0702,C0501 | A01,A03,B07,B44,UNK,UNK | 0 | 0 |
| CRNR2472 | 20.41396495 | 0 | CTLA-4 | M1c | Stage 4 | 71 | M | 627 | Melanoma | Snyder et al. 2014 | A3002,A3201,B1801,B1501,C0501,C0303 | A01,A01,B44,B62,UNK,UNK | 0 | 0 |
| CRNR4941 | 86.45914566 | 0 | CTLA-4 | M1c | Stage 4 | 40 | F | 117 | Melanoma | Snyder et al. 2014 | A6802,A0206,B4801,B1801,C0501,C0803 | A02,A02,B27,B44,UNK,UNK | 0 | 0 |
| LSD0167 | 32.42217962 | 0 | CTLA-4 | M1c | Stage 4 | 33 | M | 399 | Melanoma | Snyder et al. 2014 | A0301,A0101,B0801,B0702,C0701,C0702 | A03,A01,B08,B07,UNK,UNK | 0 | 0 |
| LSD2057 | 40.12745071 | 0 | CTLA-4 | M1c | Stage 4 | 36 | F | 171 | Melanoma | Snyder et al. 2014 | A1101,A2402,B3501,B5101,C0102,C0401 | A03,A24,B07,B07,UNK,UNK | 0 | 0 |
| LSD3484 | 34.82382256 | 0 | CTLA-4 | M1c | Stage 4 | 74 | M | 531 | Melanoma | Snyder et al. 2014 | A0201,A1101,B4402,B3501,C0501,C0401 | A02,A03,B07,B44,UNK,UNK | 0 | 0 |
| LSD4691 | 87.65996713 | 0 | CTLA-4 | M1c | Stage 4 | 62 | M | 393 | Melanoma | Snyder et al. 2014 | A0101,A2402,B3508,B4402,C0501,C0401 | A01,A24,B07,B44,UNK,UNK | 0 | 0 |
| LSD4744 | 25.21725082 | 0 | CTLA-4 | M1c | Stage 4 | 52 | M | 1124 | Melanoma | Snyder et al. 2014 | A2402,A0201,B0702,B3901,C0702,C1203 | A24,A02,B07,B27,UNK,UNK | 0 | 0 |
| LSD6819 | 40.8279299 | 0 | CTLA-4 | M1c | Stage 4 | 55 | M | 216 | Melanoma | Snyder et al. 2014 | A0101,A2902,B0801,B4403,C0701,C1601 | A01,A01,A24,B08,B44,UNK,UNK | 0 | 0 |
| LSDNR1120 | 55.23778751 | 0 | CTLA-4 | M1a | Stage 4 | 68 | M | 537 | Melanoma | Snyder et al. 2014 | A0301,A0201,B0801,B0801,C0702,C0701 | A03,A02,B08,B08,UNK,UNK | 1 | 0 |
| LSDNR1650 | 32.42217962 | 1 | CTLA-4 | M1c | Stage 4 | 71 | F | 25 | Melanoma | Snyder et al. 2014 | A0301,A3201,B4101,B3501,C1701,C0401 | A03,A01,B44,B07,UNK,UNK | 0 | 0 |

APPENDIX 1-continued

Cohort 1

| Sample | OS Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| LSDNR3086 | 31.22135816 | 1 | CTLA-4 | M1c | Stage 4 | 43 | M | 54 | Melanoma | Snyder et al. 2014 | A3001,A0201,B4001, B1302,C0602,C0304 | A01,A03,A02,B44, UNK,UNK,UNK | 0 | 0 |
| LSDNR9298 | 50.03422781 | 0 | CTLA-4 | M1c | Stage 4 | 82 | F | 1277 | Melanoma | Snyder et al. 2014 | A3201,A2902,B4501, B4402,C0602,C0501 | A01,A01,A24,B44, B44,UNK,UNK | 0 | 0 |
| NR1867 | 18.52226085 | 1 | CTLA-4 | M1c | Stage 4 | 68 | M | 80 | Melanoma | Snyder et al. 2014 | A6801,A3402,B1503, B1503,C0210,C0210 | A03,A03,B27, B27,UNK,UNK | 1 | 1 |
| NR2137 | 9.806708651 | 0 | CTLA-4 | M1c | Stage 4 | 18 | M | 635 | Melanoma | Snyder et al. 2014 | A0101,A0201,B0702, B3901,C0702,C1203 | A01,A02,B07, B27,UNK,UNK | 0 | 0 |
| NR3156 | 12.63330229 | 1 | CTLA-4 | M1b | Stage 4 | 68 | F | 6 | Melanoma | Snyder et al. 2014 | A6801,A3201,B4402, B1401,C0704,C0802 | A03,A01,B44, B27,UNK,UNK | 1 | 0 |
| NR3549 | 6.18505312 | 0 | CTLA-4 | M1c | Stage 4 | 50 | M | 365 | Melanoma | Snyder et al. 2014 | A1101,A0301,B0702, B0702,C0702,C0702 | A03,A03,B07, B07,UNK,UNK | 1 | 0 |
| NR4018 | 3.302258036 | 1 | CTLA-4 | M1c | Stage 4 | 55 | M | 146 | Melanoma | Snyder et al. 2014 | A0201,A2601,B3501, B1801,C1203,C0401 | A02,A01,B07, B44,UNK,UNK | 0 | 0 |
| NR4045 | 20.41396495 | 1 | CTLA-4 | M1c | Stage 4 | 42 | M | 451 | Melanoma | Snyder et al. 2014 | A0201,A2601,B0702, B1801,C0702,C1203 | A02,A01,B07, B44,UNK,UNK | 0 | 0 |
| NR4083 | 2.701848302 | 1 | CTLA-4 | M1c | Stage 4 | 54 | M | 444 | Melanoma | Snyder et al. 2014 | A0101,A3101,B2705, B3701,C0602,C0202 | A01,A03,B27, B44,UNK,UNK | 0 | 0 |
| NR4631 | 6.004107338 | 1 | CTLA-4 | M1c | Stage 4 | 59 | M | 1165 | Melanoma | Snyder et al. 2014 | A0101,A0301,B4201, B0702,C0702,C0701 | A01,A03,B07, B07,UNK,UNK | 0 | 0 |
| NR4810 | 4.80328587 | 1 | CTLA-4 | M1c | Stage 4 | 48 | F | 358 | Melanoma | Snyder et al. 2014 | A0201,A3301,B1402, B1501,C0202,C0802 | A02,A03,B27, B62,UNK,UNK | 0 | 0 |
| NR4949 | 8.356401514 | 1 | CTLA-4 | M1c | Stage 4 | 79 | F | 513 | Melanoma | Snyder et al. 2014 | A0301,A0201,B4402, B2705,C0501,C0102 | A03,A02,B44, B27,UNK,UNK | 0 | 1 |
| NR5784 | 5.494169495 | 1 | CTLA-4 | M1c | Stage 4 | 58 | F | 39 | Melanoma | Snyder et al. 2014 | A2403,A0201,B0702, B5107,C0702,C1402 | A24,A02,B07, UNK,UNK,UNK | 0 | NA |
| NR6689 | 15.01026834 | 1 | CTLA-4 | M1c | Stage 4 | 46 | F | 6 | Melanoma | Snyder et al. 2014 | A0301,A1101,B0801, B3501,C0701,C0401 | A03,A03,B08, B07,UNK,UNK | 0 | 0 |
| NR6721 | 9.60657174 | 1 | CTLA-4 | M1a | Stage 4 | 64 | M | 128 | Melanoma | Snyder et al. 2014 | A0301,A1101,B5501, B5101,C0102,C0303 | A03,A03,B07, B07,UNK,UNK | 0 | 0 |
| NR6842 | 9.806708651 | 1 | CTLA-4 | M1c | Stage 4 | 64 | F | 3 | Melanoma | Snyder et al. 2014 | A2402,A0201,B1502, B3503,C0303,C0401 | A24,A02,B62, B07,UNK,UNK | 0 | 0 |
| NR8727 | 5.198076941 | 1 | CTLA-4 | M1b | Stage 4 | 69 | M | 2 | Melanoma | Snyder et al. 2014 | A6802,A2901,B3502, B1402,C0401,C0802 | A02,A01,A24,B07, B27,UNK,UNK | 0 | 0 |
| NR8815 | 14.91019989 | 1 | CTLA-4 | M1a | Stage 4 | 67 | F | 1699 | Melanoma | Snyder et al. 2014 | A0301,A0201,B2702, B5101,C0102,C0202 | A03,A02,B27, B07,UNK,UNK | 0 | 0 |
| NR9341 | 12.1398147 | 1 | CTLA-4 | M1c | Stage 4 | 77 | M | 323 | Melanoma | Snyder et al. 2014 | A0301,A0301,B1402, B0702,C0702,C0802 | A03,A03,B27, B07,UNK,UNK | 1 | 0 |
| NR9445 | 2.501711391 | 1 | CTLA-4 | M1c | Stage 4 | 50 | M | 267 | Melanoma | Snyder et al. 2014 | A0201,A2601,B5701, B2705,C0102,C0602 | A02,A01,B58, B27,UNK,UNK | 0 | 0 |
| NR9449 | 7.204928805 | 1 | CTLA-4 | M1c | Stage 4 | 64 | F | 295 | Melanoma | Snyder et al. 2014 | A0301,A0201,B4402, B5701,C0602,C0501 | A03,A02,B44, B58,UNK,UNK | 0 | 0 |
| NR9521 | 32.4221796 | 1 | CTLA-4 | M1b | Stage 4 | 74 | M | 1061 | Melanoma | Snyder et al. 2014 | A2402,C0102,C0501 B4402,C0102,C0501 | A24,A02,B07, B44,UNK,UNK | 0 | 0 |
| NR9705 | 14.40985761 | 1 | CTLA-4 | M1c | Stage 4 | 63 | F | 37 | Melanoma | Snyder et al. 2014 | A0101,A2402,B0801, B1501,C0701,C0303 | A01,A24,B08, B62,UNK,UNK | 0 | 0 |
| NR9765 | 25.01711391 | 1 | CTLA-4 | M1b | Stage 4 | 38 | F | 1148 | Melanoma | Snyder et al. 2014 | A0101,A0301,B0702, B1517,C0702,C0701 | A01,A03,B07, B58,UNK,UNK | 0 | 0 |

APPENDIX 1-continued

Cohort 1

| Sample | OS Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| PR03803 | 94.66475902 | 1 | CTLA-4 | M0 | Stage 3 | 90 | M | 269 | Melanoma | Snyder et al. 2014 | A2301,A0201,B5001,B4002,C0701,C0202 | A24,A02,B44,B44,UNK,UNK | 0 | 0 |
| PR12117 | 18.7128012 | 1 | CTLA-4 | M1c | Stage 4 | 66 | M | 1081 | Melanoma | Snyder et al. 2014 | A0301,A0201,B4001,B3501,C0304,C0401 | A03,A02,B44,B07,UNK,UNK | 0 | 0 |
| PR4035 | 50.23436472 | 0 | CTLA-4 | M1c | Stage 4 | 78 | M | 525 | Melanoma | Snyder et al. 2014 | A0101,A0201,B3901,B3906,C1203,C0602 | A01,A02,B27,B27,UNK,UNK | 0 | 0 |
| PR4046 | 25.31731927 | 0 | CTLA-4 | M1a | Stage 4 | 44 | M | 139 | Melanoma | Snyder et al. 2014 | A0201,A0205,B1501,B4901,C0701,C0303 | A02,A02,B62,UNK,UNK,UNK | 0 | 0 |
| PR4077 | 72.74976724 | 0 | CTLA-4 | M1a | Stage 4 | 75 | M | 1741 | Melanoma | Snyder et al. 2014 | A0101,A0101,B0801,B5701,C0701,C0602 | A01,A01,B08,B58,UNK,UNK | 1 | 0 |
| PR4081 | 72.44956187 | 0 | CTLA-4 | M1a | Stage 4 | 65 | F | 277 | Melanoma | Snyder et al. 2014 | A0101,A0201,B3701,B4402,C0602,C0501 | A01,A02,B44,B44,UNK,UNK | 0 | 0 |
| PR4092 | 72.8498357 | 0 | CTLA-4 | M1a | Stage 4 | 57 | F | 3267 | Melanoma | Snyder et al. 2014 | A0402,A2601,B3801,B4901,C0701,C1203 | A24,A01,B27,UNK,UNK,UNK | 0 | 0 |
| SD0346 | 34.77446881 | 1 | CTLA-4 | M1b | Stage 4 | 43 | F | 537 | Melanoma | Snyder et al. 2014 | A0301,A201,B0702,B1402,C0702,C0802 | A03,A02,B07,B27,UNK,UNK | 0 | 0 |
| SD1494 | 23.7203368 | 0 | CTLA-4 | M1c | Stage 4 | 70 | M | 915 | Melanoma | Snyder et al. 2014 | A0101,A2902,B4403,B0801,C0701,C1601 | A01,A01,A24,B44,B08,UNK,UNK | 1 | 0 |
| SD2051 | 10.16585434 | 1 | CTLA-4 | M1c | Stage 4 | 61 | M | 38 | Melanoma | Snyder et al. 2014 | A3601,A2301,B5301,B5301,C0401,C0401 | A01,A24,B07,B07,UNK,UNK | 0 | 0 |
| SD2056 | 47.27618107 | 0 | CTLA-4 | M1b | Stage 4 | 39 | F | 136 | Melanoma | Snyder et al. 2014 | A0301,A2402,B2705,B3906,C0702,C0401 | A03,A24,B27,B27,UNK,UNK | 0 | 0 |
| SD5038 | 13.98216503 | 1 | CTLA-4 | M1c | Stage 4 | 55 | M | 256 | Melanoma | Snyder et al. 2014 | A0201,A3301,B1402,B3901,C0802,C1203 | A02,A03,B27,B27,UNK,UNK | 0 | 0 |
| SD5118 | 32.86632346 | 1 | CTLA-4 | M1c | Stage 4 | 55 | F | 74 | Melanoma | Snyder et al. 2014 | A0101,A0101,B0702,B0702,C0702,C0702 | A01,A01,B07,B07,UNK,UNK | 1 | 0 |
| SD5934 | 19.80532859 | 1 | CTLA-4 | M1c | Stage 4 | 52 | M | 156 | Melanoma | Snyder et al. 2014 | A2402,A2402,B3502,B3502,C0401,C0401 | A24,A24,B07,B07,UNK,UNK | 1 | 0 |
| SD6336 | 83.4324151 | 0 | CTLA-4 | M1c | Stage 4 | 53 | M | 338 | Melanoma | Snyder et al. 2014 | A3001,A3301,B1302,B1402,C0602,C0802 | A01,A03,A03,UNK,B27,UNK | 0 | 0 |
| SD6494 | 8.718293078 | 1 | CTLA-4 | M1c | Stage 4 | 63 | F | 594 | Melanoma | Snyder et al. 2014 | A6802,A2402,B3501,B1402,C0802,C0401 | A02,A24,B07,B27,UNK,UNK | 0 | 0 |
| SD7357 | 24.50991694 | 1 | CTLA-4 | M1c | Stage 4 | 50 | F | 1148 | Melanoma | Snyder et al. 2014 | A2402,A0201,B5501,B1801,C1203,C0303 | A24,A02,B07,B44,UNK,UNK | 0 | 0 |
| Pat02 | 53.6547744 | 0 | CTLA-4 | M1c | Stage 4 | 42 | F | 233 | Melanoma | Van Allen et al. 2015 | A0201,A2601,B0702,B0801,C0702,C0701 | A02,A01,B08,B07,UNK,UNK | 0 | 0 |
| Pat03 | 3.28767 | 1 | CTLA-4 | M1c | Stage 4 | 61 | F | 372 | Melanoma | Van Allen et al. 2015 | A0301,A2901,B0705,B3501,C1505,C0401 | A03,A01,A24,B07,B07,UNK,UNK | 0 | 1 |
| Pat04 | 32.4493029 | 0 | CTLA-4 | M1b | Stage 4 | 71 | F | 336 | Melanoma | Van Allen et al. 2015 | A0101,A0201,B1501,B4405,C0202,C0303 | A01,A02,B62,B44,UNK,UNK | 0 | 0 |
| Pat06 | 5.2931487 | 1 | CTLA-4 | M1c | Stage 4 | 33 | M | 174 | Melanoma | Van Allen et al. 2015 | A1101,A0201,B2702,B5501,C0303,C0202 | A03,A02,B27,B07,UNK,UNK | 0 | 0 |
| Pat07 | 34.520535 | 0 | CTLA-4 | M0 | Stage 3 | 36 | M | 148 | Melanoma | Van Allen et al. 2015 | A0101,A0101,B0702,B0801,C0702,C0701 | A01,A01,B07,B08,UNK,UNK | 1 | 0 |
| Pat08 | 4.602738 | 1 | CTLA-4 | M1c | Stage 4 | 73 | M | 265 | Melanoma | Van Allen et al. 2015 | A8801,A2601,B3501,B3801,C1203,C0401 | A03,A01,B07,B27,UNK,UNK | 0 | 0 |
| Pat100 | 11.835612 | 1 | CTLA-4 | M1c | Stage 4 | 70 | M | 519 | Melanoma | Van Allen et al. 2015 | A0301,A0201,B4001,B4403,C1601,C0304 | A03,A02,B44,B44,UNK,UNK | 0 | 0 |

APPENDIX 1-continued

Cohort 1

| Sample | OS Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| Pat101 | 9.4484896 | 1 | CTLA-4 | M1c | Stage 4 | 75 | M | 50 | Melanoma | Van Allen et al. 2015 | A0301,A2902,B0702, B4403,C0702,C1601 | A03,A01,A24,B07, B44,UNK,UNK | 0 | 1 |
| Pat103 | 34.4547816 | 1 | CTLA-4 | M1c | Stage 4 | 70 | M | 630 | Melanoma | Van Allen et al. 2015 | A0101,A2301,B0801, B5001,C0701,C0602 | A01,A24,B08, B44,UNK,UNK | 0 | 0 |
| Pat104 | 7.7917779 | 1 | CTLA-4 | M1c | Stage 4 | 45 | F | 35 | Melanoma | Van Allen et al. 2015 | A0301,A0201,B0702, B1501,C0702,C0304 | A03,A02,B07, B62,UNK,UNK | 0 | 1 |
| Pat105 | 34.4210049 | 0 | CTLA-4 | M0 | Stage 3 | 41 | M | 125 | Melanoma | Van Allen et al. 2015 | A0101,A201,B0801, B4402,C0701,C0501 | A01,A02,B08, B44,UNK,UNK | 0 | 0 |
| Pat106 | 8.239175 | 1 | CTLA-4 | M1b | Stage 4 | 43 | F | 30 | Melanoma | Van Allen et al. 2015 | A1101,A0201,B1501, B1302,C0602,C0304 | A03,A02,B62, UNK,UNK,UNK | 0 | 0 |
| Pat109 | 2.7287661 | 1 | CTLA-4 | M1b | Stage 4 | 69 | M | 286 | Melanoma | Van Allen et al. 2015 | A0301,A0201,B4001, B1501,C0102,C0304 | A03,A02,B44, B62,UNK,UNK | 0 | 0 |
| Pat110 | 10.520544 | 1 | CTLA-4 | M1b | Stage 4 | 76 | M | 6301 | Melanoma | Van Allen et al. 2015 | A0201,A3201,B4002, B4405,C0202,C0202 | A02,A01,B44, B44,UNK,UNK | 1 | 0 |
| Pat113 | 9.8958667 | 1 | CTLA-4 | M1c | Stage 4 | 68 | M | 317 | Melanoma | Van Allen et al. 2015 | A0101,A2301,B0801, B1402,C0701,C0802 | A01,A24,B08, B27,UNK,UNK | 0 | 0 |
| Pat115 | 4.7671215 | 1 | CTLA-4 | M1c | Stage 4 | 45 | M | 76 | Melanoma | Van Allen et al. 2015 | A0201,A0201,B0702, B1501,C0702,C0303 | A02,A02,B07, B62,UNK,UNK | 1 | 0 |
| Pat117 | 30.0493038 | 0 | CTLA-4 | M1c | Stage 4 | 73 | M | 689 | Melanoma | Van Allen et al. 2015 | A1101,A0201,B0801, B2702,C0701,C0202 | A03,A02,B08, B27,UNK,UNK | 0 | 0 |
| Pat118 | 10.2904071 | 1 | CTLA-4 | M1c | Stage 4 | 43 | F | 113 | Melanoma | Van Allen et al. 2015 | A0301,A0201,B3501, B5101,C0102,C0401 | A03,A02,B07, B07,UNK,UNK | 0 | 0 |
| Pat121 | 4.0109574 | 1 | CTLA-4 | M1c | Stage 4 | 46 | M | 63 | Melanoma | Van Allen et al. 2015 | A0201,A2601,B1509, B4402,C0704,C0501 | A02,A01,B27, B44,UNK,UNK | 0 | 0 |
| Pat123 | 28.0438251 | 1 | CTLA-4 | M1c | Stage 4 | 50 | F | 482 | Melanoma | Van Allen et al. 2015 | A0101,A3101,B5101, B3501,C0202,C0401 | A01,A03,B07, B07,UNK,UNK | 0 | 0 |
| Pat124 | 4.7999982 | 1 | CTLA-4 | M1b | Stage 4 | 78 | M | 441 | Melanoma | Van Allen et al. 2015 | A3201,A0201,B1302, B5101,C1502,C0602 | A01,A02,UNK, B07,UNK,UNK | 0 | 0 |
| Pat126 | 21.0739647 | 0 | CTLA-4 | M1b | Stage 4 | 77 | M | 397 | Melanoma | Van Allen et al. 2015 | A0101,A0201,B4001, B0801,C0701,C0304 | A01,A02,B44, B08,UNK,UNK | 0 | 0 |
| Pat127 | 10.9150644 | 1 | CTLA-4 | M1c | Stage 4 | 25 | F | 109 | Melanoma | Van Allen et al. 2015 | A2402,A3101,B0702, B0702,C0702,C0202 | A24,A03,B07, B27,UNK,UNK | 0 | 0 |
| Pat128 | 3.7150671 | 1 | CTLA-4 | M1c | Stage 4 | 29 | M | 76 | Melanoma | Van Allen et al. 2015 | A2601,A2601,B5501, B5501,C0303,C0303 | A01,A01,B07, B07,UNK,UNK | 1 | 0 |
| Pat129 | 17.7205413 | 0 | CTLA-4 | M1c | Stage 4 | 18 | M | 107 | Melanoma | Van Allen et al. 2015 | A1101,A2902,B5101, B4403,C1502,C1602 | A03,A01,A24,B07, B44,UNK,UNK | 0 | 0 |
| Pat130 | 1.4794515 | 1 | CTLA-4 | M1b | Stage 4 | 76 | M | 197 | Melanoma | Van Allen et al. 2015 | A0201,A0201,B4002, B1501,C0201,C0304 | A02,A02,B44, B62,UNK,UNK | 1 | 0 |
| Pat131 | 8.4493119 | 1 | CTLA-4 | M1c | Stage 4 | 32 | M | 102 | Melanoma | Van Allen et al. 2015 | A0101,A6601,B0801, B1801,C0701,C0701 | A01,A03,B08, B44,UNK,UNK | 1 | 0 |
| Pat132 | 22.2246492 | 0 | CTLA-4 | M1c | Stage 4 | 81 | M | 1862 | Melanoma | Van Allen et al. 2015 | A0101,A2301,B4403, B0801,C0701,C0401 | A01,A24,B44, B08,UNK,UNK | 0 | 1 |
| Pat133 | 17.8191714 | 1 | CTLA-4 | M1b | Stage 4 | 76 | M | 228 | Melanoma | Van Allen et al. 2015 | A1101,A2402,B0702, B4402,C0702,C0202 | A03,A24,B07, B44,UNK,UNK | 0 | 1 |
| Pat135 | 2.6630127 | 1 | CTLA-4 | M1c | Stage 4 | 29 | F | 238 | Melanoma | Van Allen et al. 2015 | A0301,A0201,B0801, B0702,C0702,C0701 | A03,A02,B08, B07,UNK,UNK | 0 | 0 |
| Pat138 | 48.5917626 | 1 | CTLA-4 | M1c | Stage 4 | 39 | F | 5120 | Melanoma | Van Allen et al. 2015 | A6801,A3201,B1402, B4402,C0501,C0802 | A03,A01,B27, B44,UNK,UNK | 0 | 0 |

APPENDIX 1-continued

Cohort 1

| Sample | OS_Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| Pat139 | 3.2547933 | 1 | CTLA-4 | M1c | Stage 4 | 58 | M | 1429 | Melanoma | Van Allen et al. 2015 | A0201,A3201,B3901,B1501,C0304,C1203 | A02,A01,B27,B62,UNK,UNK | 0 | 1 |
| Pat14 | 5.3589021 | 1 | CTLA-4 | M1c | Stage 4 | 48 | F | 46 | Melanoma | Van Allen et al. 2015 | A3001,A6602,B5701,B5301,C0602,C0401 | A01,A03,A02,B58,B07,UNK,UNK | 0 | 0 |
| Pat140 | 16.1753364 | 1 | CTLA-4 | M1c | Stage 4 | 62 | M | 326 | Melanoma | Van Allen et al. 2015 | A0301,A0201,B1302,B4002,C0202,C0602 | A03,A02,UNK,B44,UNK,UNK | 0 | 0 |
| Pat143 | 5.0301351 | 1 | CTLA-4 | M1c | Stage 4 | 71 | M | 878 | Melanoma | Van Allen et al. 2015 | A6801,A0201,B1501,B1501,C0304,C0303 | A03,A02,B62,B62,UNK,UNK | 1 | 0 |
| Pat147 | 7.3643808 | 1 | CTLA-4 | M1a | Stage 4 | 63 | M | 542 | Melanoma | Van Allen et al. 2015 | A0101,A2402,B0801,B5502,C0701,C0102 | A01,A24,B08,B07,UNK,UNK | 0 | 1 |
| Pat148 | 2.7616428 | 1 | CTLA-4 | M1c | Stage 4 | 35 | F | 227 | Melanoma | Van Allen et al. 2015 | A0101,A0101,B0801,B1501,C0701,C0304 | A01,A01,B08,B62,UNK,UNK | 1 | 1 |
| Pat15 | 1.643855 | 1 | CTLA-4 | M1c | Stage 4 | 32 | M | 242 | Melanoma | Van Allen et al. 2015 | A2902,A3201,B1501,B4001,C0303,C0304 | A01,A24,A01,B62,B44,UNK,UNK | 0 | 0 |
| Pat151 | 6.7068468 | 1 | CTLA-4 | M1c | Stage 4 | 68 | M | 1754 | Melanoma | Van Allen et al. 2015 | A6801,A0201,B5101,B4403,C1601,C1502 | A03,A02,B07,B44,UNK,UNK | 0 | 0 |
| Pat157 | 2.8273962 | 1 | CTLA-4 | M1c | Stage 4 | 69 | F | 132 | Melanoma | Van Allen et al. 2015 | A0101,A0201,B0704,B0702,C0702,C0702 | A01,A02,B07,B07,UNK,UNK | 1 | 0 |
| Pat160 | 4.9972584 | 1 | CTLA-4 | M1c | Stage 4 | 79 | M | 54 | Melanoma | Van Allen et al. 2015 | A0201,A0201,B5101,B1501,C0401,C0303 | A02,A02,B07,B62,UNK,UNK | 1 | 0 |
| Pat162 | 6.9369837 | 1 | CTLA-4 | M1a | Stage 4 | 55 | F | 54 | Melanoma | Van Allen et al. 2015 | A0101,A0101,B0801,B0702,C0701,C0702 | A01,A01,B08,B07,UNK,UNK | 1 | 0 |
| Pat165 | 3.7808205 | 1 | CTLA-4 | M1c | Stage 4 | 50 | F | 69 | Melanoma | Van Allen et al. 2015 | A6801,A0201,B1501,B4402,C0303,C0501 | A03,A02,B62,B44,UNK,UNK | 0 | 0 |
| Pat166 | 2.5315059 | 1 | CTLA-4 | M1c | Stage 4 | 31 | M | 57 | Melanoma | Van Allen et al. 2015 | A0301,A0201,B0702,B4001,C0702,C0304 | A03,A02,B07,B44,UNK,UNK | 0 | 1 |
| Pat167 | 13.4136936 | 1 | CTLA-4 | M1c | Stage 4 | 50 | M | 33 | Melanoma | Van Allen et al. 2015 | A3001,A0201,B5801,B1302,C0302,C0602 | A01,A03,A02,B58,UNK,UNK,UNK | 0 | 1 |
| Pat168 | 2.02027389 | 1 | CTLA-4 | M1c | Stage 4 | 68 | M | 245 | Melanoma | Van Allen et al. 2015 | A0101,A0201,B0801,B1501,C0701,C0303 | A01,A02,B08,B62,UNK,UNK | 0 | 0 |
| Pat117 | 6.7397235 | 1 | CTLA-4 | M1c | Stage 4 | 44 | M | 219 | Melanoma | Van Allen et al. 2015 | A3303,A2601,B5801,B4402,C0704,C0302 | A03,A01,B56,B44,UNK,UNK | 0 | 0 |
| Pat170 | 3.5506836 | 1 | CTLA-4 | M1c | Stage 4 | 48 | M | 234 | Melanoma | Van Allen et al. 2015 | A1101,A0201,B5301,B4402,C0501,C0401 | A03,A02,B07,B44,UNK,UNK | 0 | 0 |
| Pat171 | 15.3205422 | 1 | CTLA-4 | M1a | Stage 4 | 66 | M | 99 | Melanoma | Van Allen et al. 2015 | A0301,A0101,B3501,B3508,C0401,C0401 | A03,A01,B07,B07,UNK,UNK | 1 | 0 |
| Pat174 | 22.6191696 | 0 | CTLA-4 | M1a | Stage 4 | 57 | F | 668 | Melanoma | Van Allen et al. 2015 | A0201,A2902,B5101,B4402,C0704,C0202 | A02,A01,A24,B07,B44,UNK,UNK | 0 | 0 |
| Pat175 | 2.958903 | 1 | CTLA-4 | M1a | Stage 4 | 67 | F | 89 | Melanoma | Van Allen et al. 2015 | A0101,A0201,B0801,B4002,C0701,C0202 | A01,A02,B08,B44,UNK,UNK | 0 | 1 |
| Pat19 | 5.7534225 | 1 | CTLA-4 | M1c | Stage 4 | 59 | M | 470 | Melanoma | Van Allen et al. 2015 | A0101,A2402,B5701,B1501,C0602,C0303 | A01,A24,B58,B62,UNK,UNK | 0 | 0 |
| Pat21 | 22.2246492 | 1 | CTLA-4 | M1c | Stage 4 | 81 | M | 1375 | Melanoma | Van Allen et al. 2015 | A0301,A0101,B0801,B0801,C0701,C0701 | A03,A01,B08,B08,UNK,UNK | 1 | 0 |
| Pat24 | 31.9232757 | 0 | CTLA-4 | M1b | Stage 4 | 74 | F | 33 | Melanoma | Van Allen et al. 2015 | A0101,A0201,B4201,B0702,C0702,C0701 | A01,A02,B07,B07,UNK,UNK | 0 | 0 |
| Pat25 | 10.6849275 | 1 | CTLA-4 | M1c | Stage 4 | 69 | M | 51 | Melanoma | Van Allen et al. 2015 | A2902,A6601,B4002,B4403,C1601,C0202 | A01,A24,A03,B44,B44,UNK,UNK | 0 | 0 |

APPENDIX 1-continued

Cohort 1

| Sample | OS_Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| Pat29 | 43.5945042 | 0 | CTLA-4 | M1c | Stage 4 | 82 | M | 37 | Melanoma | Van Allen et al. 2015 | A0301,A0201,B0702,B1801,C0702,C1203 | A03,A02,B07,B44,UNK,UNK | 0 | 0 |
| Pat32 | 4.8328749 | 1 | CTLA-4 | M1c | Stage 4 | 72 | M | 714 | Melanoma | Van Allen et al. 2015 | A0301,A0301,B3801,B3501,C1203,C0401 | A03,A03,B27,B07,UNK,UNK | 1 | 0 |
| Pat33 | 6.9369837 | 1 | CTLA-4 | M1c | Stage 4 | 65 | M | 15 | Melanoma | Van Allen et al. 2015 | A1101,A3004,B0702,B4201,C0702,C0702 | A03,A01,B07,B07,UNK,UNK | 1 | 0 |
| Pat36 | 1.7753418 | 1 | CTLA-4 | M1c | Stage 4 | 52 | F | 12 | Melanoma | Van Allen et al. 2015 | A0101,A0101,B2705,B4402,C0501,C0303 | A01,A01,B27,B44,UNK,UNK | 1 | 0 |
| Pat37 | 2.301369 | 1 | CTLA-4 | M1c | Stage 4 | 47 | F | 108 | Melanoma | Van Allen et al. 2015 | A0101,A6601,B0801,B1402,C0701,C0802 | A01,A03,B08,B27,UNK,UNK | 0 | 0 |
| Pat38 | 50.5972413 | 0 | CTLA-4 | M1c | Stage 4 | 45 | M | 2398 | Melanoma | Van Allen et al. 2015 | A0301,A0201,B4002,B1517,C0701,C0202 | A03,A02,B44,B58,UNK,UNK | 0 | 1 |
| Pat39 | 48.8876529 | 0 | CTLA-4 | M1b | Stage 4 | 67 | M | 75 | Melanoma | Van Allen et al. 2015 | A0101,A0201,B0801,B5101,C0701,C1502 | A01,A02,B08,B07,UNK,UNK | 0 | 0 |
| Pat40 | 1.1178078 | 1 | CTLA-4 | M1c | Stage 4 | 74 | M | 108 | Melanoma | Van Allen et al. 2015 | A0101,A0201,B0801,B4402,C0701,C0501 | A01,A02,B08,B44,UNK,UNK | 0 | 0 |
| Pat41 | 4.2082176 | 1 | CTLA-4 | M1c | Stage 4 | 64 | M | 345 | Melanoma | Van Allen et al. 2015 | A2301,A0201,B2705,B4901,C0701,C0102 | A24,A02,B27,UNK,UNK,UNK | 0 | 0 |
| Pat43 | 1.2164379 | 1 | CTLA-4 | M1c | Stage 4 | 75 | F | 168 | Melanoma | Van Allen et al. 2015 | A0101,A2902,B2705,B4403,C0220,C1601 | A01,A01,A24,B27,B44,UNK,UNK | 0 | 0 |
| Pat44 | 8.9095857 | 1 | CTLA-4 | M1c | Stage 4 | 57 | F | 32 | Melanoma | Van Allen et al. 2015 | A1101,A2601,B3501,B5201,C1202,C0401 | A03,A01,B07,B62,UNK,UNK | 0 | 0 |
| Pat45 | 2.9260263 | 1 | CTLA-4 | M1c | Stage 4 | 68 | M | 937 | Melanoma | Van Allen et al. 2015 | A2402,A0201,B5101,B4402,C0501,C1502 | A24,A02,B07,B44,UNK,UNK | 0 | 0 |
| Pat46 | 5.260272 | 1 | CTLA-4 | M1b | Stage 4 | 36 | F | 244 | Melanoma | Van Allen et al. 2015 | A0101,A2601,B3701,B2705,C0202,C0602 | A01,A01,B44,B27,UNK,UNK | 0 | 0 |
| Pat47 | 36.3616302 | 0 | CTLA-4 | M1c | Stage 4 | 78 | M | 137 | Melanoma | Van Allen et al. 2015 | A2301,A3201,B1501,B4403,C0401,C0303 | A24,A01,B62,B44,UNK,UNK | 0 | 0 |
| Pat49 | 33.9945078 | 0 | CTLA-4 | M1c | Stage 4 | 36 | M | 669 | Melanoma | Van Allen et al. 2015 | A0101,A1101,B3701,B5701,C0602,C0602 | A01,A03,B44,B58,UNK,UNK | 1 | 0 |
| Pat50 | 2.1369855 | 1 | CTLA-4 | M1c | Stage 4 | 77 | M | 444 | Melanoma | Van Allen et al. 2015 | A1101,A0201,B1801,B2703,C0704,C1203 | A03,A02,B44,B27,UNK,UNK | 0 | 0 |
| Pat54 | 6.8383536 | 1 | CTLA-4 | M1c | Stage 4 | 73 | M | 866 | Melanoma | Van Allen et al. 2015 | A0301,A0201,B4001,B3501,C0304,C0401 | A03,A02,B44,B07,UNK,UNK | 0 | 0 |
| Pat55 | 6.3452031 | 1 | CTLA-4 | M1c | Stage 4 | 71 | F | 484 | Melanoma | Van Allen et al. 2015 | A0301,A0201,B0702,B1501,C0702,C0401 | A03,A02,B07,B62,UNK,UNK | 0 | 0 |
| Pat56 | 7.7260245 | 1 | CTLA-4 | M1c | Stage 4 | 68 | M | 44 | Melanoma | Van Allen et al. 2015 | A2402,A0201,B0702,B5501,C0702,C0303 | A24,A02,B07,B07,UNK,UNK | 0 | 0 |
| Pat57 | 8.219175 | 1 | CTLA-4 | M0 | Stage 3 | 69 | M | 56 | Melanoma | Van Allen et al. 2015 | A0301,A0101,B0702,B5701,C0702,C0701 | A03,A01,B07,B58,UNK,UNK | 0 | 0 |
| Pat58 | 21.4356084 | 1 | CTLA-4 | M0 | Stage 3 | 59 | F | 1921 | Melanoma | Van Allen et al. 2015 | A0201,A2902,B3901,B4403,C1601,C1203 | A02,A01,A24,B27,B44,UNK,UNK | 0 | 0 |
| Pat59 | 7.3643808 | 1 | CTLA-4 | M1b | Stage 4 | 36 | M | 273 | Melanoma | Van Allen et al. 2015 | A0201,A0201,B5101,B1501,C1502,C0303 | A02,A02,B07,B62,UNK,UNK | 1 | 0 |
| Pat60 | 8.9424624 | 1 | CTLA-4 | M1c | Stage 4 | 86 | M | 738 | Melanoma | Van Allen et al. 2015 | A0101,A1101,B0801,B5502,C0701,C0102 | A01,A03,B08,B07,UNK,UNK | 0 | 0 |
| Pat62 | 19.7917734 | 1 | CTLA-4 | M1c | Stage 4 | 76 | M | 1379 | Melanoma | Van Allen et al. 2015 | A2402,A0201,B5101,C1402,B2705,C0102,C1402 | A24,A02,B07,B27,UNK,UNK | 0 | 1 |

APPENDIX 1-continued

Cohort 1

| Sample | OS Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| Pat63 | 34.1588913 | 0 | CTLA-4 | M0 | Stage 3 | 65 | M | 209 | Melanoma | Van Allen et al. 2015 | A0301,A0301,B4402,B4405,C0704,C0202 | A03,A03,B44,B44,UNK,UNK | 1 | 0 |
| Pat64 | 3.4849302 | 1 | CTLA-4 | M1c | Stage 4 | 83 | M | 659 | Melanoma | Van Allen et al. 2015 | A0101,A1101,B0801,B5101,C0701,C1502 | A01,A03,B08,B07,UNK,UNK | 0 | 0 |
| Pat66 | 21.4684851 | 0 | CTLA-4 | M0 | Stage 3 | 44 | F | 327 | Melanoma | Van Allen et al. 2015 | A0101,A2402,B5501,B5801,C0303,C0303 | A01,A24,B07,B58,UNK,UNK | 1 | 1 |
| Pat67 | 2.5972593 | 1 | CTLA-4 | M1c | Stage 4 | 39 | M | 27 | Melanoma | Van Allen et al. 2015 | A1101,A2601,B0702,B3503,C1602,C0401 | A03,A01,B07,B07,UNK,UNK | 0 | 0 |
| Pat70 | 17.4904044 | 1 | CTLA-4 | M1c | Stage 4 | 38 | M | 77 | Melanoma | Van Allen et al. 2015 | A0301,A2402,B0702,B2702,C0702,C0202 | A03,A24,B07,B07,UNK,UNK | 0 | 0 |
| Pat71 | 4.5041079 | 1 | CTLA-4 | M1c | Stage 4 | 63 | M | 722 | Melanoma | Van Allen et al. 2015 | A2601,A0201,B0702,B3801,C0702,C1203 | A01,A02,B07,B27,UNK,UNK | 0 | 0 |
| Pat73 | 14.5315014 | 1 | CTLA-4 | M1c | Stage 4 | 71 | M | 243 | Melanoma | Van Allen et al. 2015 | A2601,A3101,B3801,B5101,C1203,C1502 | A01,A03,B27,B07,UNK,UNK | 0 | 0 |
| Pat74 | 6.3452031 | 1 | CTLA-4 | M1c | Stage 4 | 73 | M | 509 | Melanoma | Van Allen et al. 2015 | A3001,A1101,B5201,B1302,C1203,C0602 | A01A03,A03,B62,UNK,UNK,UNK | 0 | 0 |
| Pat76 | 4.5698613 | 1 | CTLA-4 | M1c | Stage 4 | 74 | M | 188 | Melanoma | Van Allen et al. 2015 | A0101,A0101,B0801,B3501,C0701,C0404 | A01,A01,B08,B07,UNK,UNK | 1 | 0 |
| Pat77 | 33.8301243 | 0 | CTLA-4 | M0 | Stage 3 | 21 | M | 375 | Melanoma | Van Allen et al. 2015 | A2402,A2601,B5502,B3801,C0102,C1203 | A24,A01,B07,B27,UNK,UNK | 0 | 1 |
| Pat78 | 1.2493146 | 1 | CTLA-4 | M1c | Stage 4 | 71 | F | 154 | Melanoma | Van Allen et al. 2015 | A0301,A0101,B1402,B0801,C0701,C0802 | A03,A01,B27,B08,UNK,UNK | 0 | 1 |
| Pat79 | 26.3342367 | 1 | CTLA-4 | M1b | Stage 4 | 69 | M | 321 | Melanoma | Van Allen et al. 2015 | A2301,A0201,B1402,B2705,C0202,C0802 | A24,A02,B27,B27,UNK,UNK | 0 | 1 |
| Pat80 | 23.8027308 | 1 | CTLA-4 | M1c | Stage 4 | 48 | M | 193 | Melanoma | Van Allen et al. 2015 | A0301,A0201,B0702,B4001,C0702,C0304 | A03,A02,B07,B07,UNK,UNK | 0 | 0 |
| Pat81 | 20.6465676 | 1 | CTLA-4 | M1a | Stage 4 | 54 | F | 111 | Melanoma | Van Allen et al. 2015 | A0201,A2601,B5101,B5801,C0706,C1402 | A02,A01,B07,B58,UNK,UNK | 0 | 0 |
| Pat82 | 3.4191768 | 1 | CTLA-4 | M1c | Stage 4 | 54 | F | 408 | Melanoma | Van Allen et al. 2015 | A2602,A2902,B0702,B4403,C0702,C1601 | A01,A01,A24,B07,B44,UNK,UNK | 0 | 0 |
| Pat85 | 15.0575286 | 1 | CTLA-4 | M1c | Stage 4 | 83 | M | 408 | Melanoma | Van Allen et al. 2015 | A1101,A0201,B2705,B2702,C0202,C0202 | A03,A02,B27,B27,UNK,UNK | 1 | 1 |
| Pat86 | 9.6328731 | 1 | CTLA-4 | M1a | Stage 4 | 55 | M | 82 | Melanoma | Van Allen et al. 2015 | A3001,A6801,B1302,B3503,C0602,C0401 | A01,A03,A03,UNK,B07,UNK,UNK | 0 | 1 |
| Pat88 | 32.5150563 | 0 | CTLA-4 | M1c | Stage 4 | 60 | F | 1597 | Melanoma | Van Allen et al. 2015 | A0301,A2902,B1402,B4403,C1601,C0802 | A03,A01,A24,B27,B44,UNK,UNK | 0 | 0 |
| Pat90 | 33.0410835 | 0 | CTLA-4 | M1c | Stage 4 | 59 | M | 207 | Melanoma | Van Allen et al. 2015 | A2402,A2601,B4002,B1801,C0701,C0202 | A24,A01,B44,B44,UNK,UNK | 0 | 0 |
| Pat92 | 4.0438341 | 1 | CTLA-4 | M1c | Stage 4 | 49 | M | 39 | Melanoma | Van Allen et al. 2015 | A0301,A0101,B3701,B3501,C0602,C0401 | A03,A01,B44,B07,UNK,UNK | 0 | 0 |
| Pat98 | 4.602738 | 1 | CTLA-4 | M1c | Stage 4 | 57 | F | 33 | Melanoma | Van Allen et al. 2015 | A0301,A0101,B0801,B3503,C0701,C0401 | A03,A01,B08,B07,UNK,UNK | 0 | 0 |
| Pt10 | 8.4164362 | 1 | PD-1 | M1a | Stage 4 | 81 | F | 75 | Melanoma | Riaz et al. 2017 | A3002,A0201,B4402,B1801,C0501,C0501 | A01,A02,B44,B44,UNK,UNK | 1 | 0 |
| Pt100 | 27.616428 | 1 | PD-1 | M1c | Stage 4 | 64 | M | 6 | Melanoma | Riaz et al. 2017 | A2601,A6802,B1402,B2705,C0202,C0802 | A01,A02,B27,B27,UNK,UNK | 0 | 0 |
| Pt101 | 27.4191678 | 0 | PD-1 | M1a | Stage 4 | 47 | F | 10 | Melanoma | Riaz et al. 2017 | A0301,A0301,B0702,B0702,C0702,C0702 | A03,A03,B07,B07,UNK,UNK | 1 | 0 |

APPENDIX 1-continued

Cohort 1

| Sample | OS Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) Yes; 0 = No) | LOH (1 = Yes; 0 = No) Yes; 0 = No) |
|---|---|---|---|---|---|---|---|---|---|---|---|---|---|---|
| Pt102 | 20.9095812 | 0 | PD-1 | NA | NA | 62 | F | 393 | Melanoma | Riaz et al. 2017 | A3001,A0201,B1302, B1801,C0701,C0602 | A01,A03,A02,UNK, B44,UNK,UNK | 0 | 0 |
| Pt103 | 15.9123228 | 0 | PD-1 | M1b | Stage 4 | 52 | F | 21 | Melanoma | Riaz et al. 2017 | A1101,A1101,B4001, B1301,C0304,C0304 | A03,A03,B44, UNK,UNK,UNK | 1 | 0 |
| Pt104 | 26.8931406 | 0 | PD-1 | NA | NA | 64 | M | 5 | Melanoma | Riaz et al. 2017 | A1101,A3101,B4001, B4901,C0304,C1701 | A03,A03,B44, UNK,UNK,UNK | 0 | 0 |
| Pt106 | 2.9911797 | 1 | PD-1 | M1c | Stage 4 | 53 | M | 700 | Melanoma | Riaz et al. 2017 | A6801,A6801,B4402, B4402,C0704,C0704 | A03,A03,B44 B44,UNK,UNK | 1 | 0 |
| Pt108 | 30.0164271 | 0 | PD-1 | M1b | Stage 4 | 37 | F | 19 | Melanoma | Riaz et al. 2017 | A2601,A2902,B0801, B1302,C0701,C0602 | A01,A01,A24,B08, UNK,UNK,UNK | 0 | 0 |
| Pt11 | 27.5177979 | 0 | PD-1 | NA | NA | 61 | F | 106 | Melanoma | Riaz et al. 2017 | A0301,A0101,B0801, B0702,C0702,C0701 | A03,A01,B08, B07,UNK,UNK | 0 | 1 |
| Pt13 | 9.205476 | 0 | PD-1 | NA | NA | 67 | M | 171 | Melanoma | Riaz et al. 2017 | A0301,A0201,B5501, B3701,C0602,C0303 | A03,A02,B07, B44,UNK,UNK | 0 | 0 |
| Pt17 | 1.8739719 | 1 | PD-1 | M1c | Stage 4 | 48 | F | 20 | Melanoma | Riaz et al. 2017 | A0301,A2902,B0702, B4403,C0702,C1601 | A03,A01,A24,B07, B44,UNK,UNK | 0 | 1 |
| Pt18 | 35.2766991 | 0 | PD-1 | M1a | Stage 4 | 53 | M | 217 | Melanoma | Riaz et al. 2017 | A0101,A3101,B0801, B4001,C0701,C0304 | A01,A03,B08, B44,UNK,UNK | 0 | 0 |
| Pt23 | 1.7095884 | 1 | PD-1 | M1c | Stage 4 | 53 | F | 646 | Melanoma | Riaz et al. 2017 | A0301,A0201,B1501, B1801,C0701,C0304 | A03,A02,B62, B44,UNK,UNK | 0 | 1 |
| Pt24 | 4.8986283 | 0 | PD-1 | M1c | Stage 4 | 63 | M | 1 | Melanoma | Riaz et al. 2017 | A3001,A1101,B3501, B5101,C0401,C0401 | A01,A03,A03,B07, B07,UNK,UNK | 1 | 0 |
| Pt25 | 3.3205467 | 1 | PD-1 | M1c | Stage 4 | 52 | M | 96 | Melanoma | Riaz et al. 2017 | A3002,A0201,B0702, B4001,C0702,C0501 | A01,A02,B07, B44,UNK,UNK | 0 | 0 |
| Pt26 | 31.2986184 | 0 | PD-1 | M1b | Stage 4 | 22 | F | 125 | Melanoma | Riaz et al. 2017 | A0101,A6802,B0801, B1402,C0701,C0802 | A01,A02,B08, B27,UNK,UNK | 0 | 0 |
| Pt27 | 15.6164325 | 1 | PD-1 | M1c | Stage 4 | 65 | M | 183 | Melanoma | Riaz et al. 2017 | A2402,A6801,B4001, B3501,C0401,C0304 | A24,A03,B44, B07,UNK,UNK | 0 | 1 |
| Pt28 | 24.328758 | 1 | PD-1 | NA | NA | 79 | F | 42 | Melanoma | Riaz et al. 2017 | A2301,A6801,B4001, B4102,C1701,C0304 | A24,A03,B44, B44,UNK,UNK | 0 | 0 |
| Pt29 | 8.9753391 | 1 | PD-1 | M1c | Stage 4 | 57 | F | 412 | Melanoma | Riaz et al. 2017 | A0201,A2902,B0702, B4403,C0702,C1601 | A02,A01,A24,B07, B44,UNK,UNK | 0 | 0 |
| Pt3 | 37.6109448 | 0 | PD-1 | NA | NA | 52 | M | 182 | Melanoma | Riaz et al. 2017 | A0101,A2301,B3901, B4403,C1203,C0401 | A01,A24,B27, B44,UNK,UNK | 0 | 0 |
| Pt30 | 34.6191651 | 0 | PD-1 | M1a | Stage 4 | 89 | F | 66 | Melanoma | Riaz et al. 2017 | A0101,A2402,B0801, B0801,C0701,C0702 | A01,A24,B08, B08,UNK,UNK | 1 | 1 |
| Pt31 | 31.5945087 | 0 | PD-1 | M1a | Stage 4 | 56 | F | 450 | Melanoma | Riaz et al. 2017 | A0201,A0201,B0702, B1402,C0702,C0802 | A02,A02,B07, B27,UNK,UNK | 1 | 0 |
| Pt32 | 3.7479438 | 1 | PD-1 | M1c | Stage 4 | 34 | M | 112 | Melanoma | Riaz et al. 2017 | A1101,A2301,B3701, B4403,C0602,C0401 | A03,A24,B44, B44,UNK,UNK | 0 | 0 |
| Pt34 | 27.4191678 | 0 | PD-1 | M1b | Stage 4 | 71 | F | 212 | Melanoma | Riaz et al. 2017 | A1101,A3201,B5501, B3501,C0401,C0303 | A03,A01,B07, B07,UNK,UNK | 0 | 1 |
| Pt36 | 35.5397127 | 0 | PD-1 | M1c | Stage 4 | 58 | M | 2 | Melanoma | Riaz et al. 2017 | A3001,A0101,B1302, B1801,C0701,C0602 | A01,A03,A01,UNK, B44,UNK,UNK | 0 | 0 |
| Pt37 | 21.2383482 | 0 | PD-1 | M1a | Stage 4 | 63 | M | 29 | Melanoma | Riaz et al. 2017 | A0101,A2402,B0801, B4402,C0701,C0501 | A01,A24,B08, B44,UNK,UNK | 0 | 0 |
| Pt38 | 5.4904089 | 1 | PD-1 | M1c | Stage 4 | 54 | F | 449 | Melanoma | Riaz et al. 2017 | A0301,A2402,B3503, B5701,C0602,C0401 | A03,A24,B07, B58,UNK,UNK | 0 | 0 |

APPENDIX 1-continued

Cohort 1

| Sample | OS Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| Pt4 | 20.8109511 | 1 | PD-1 | M1b | Stage 4 | 62 | F | 285 | Melanoma | Riaz et al. 2017 | A2301,A2402,B4501, B4501,C0602,C0602 | A24,A24,B44, B44,UNK,UNK | 1 | 0 |
| Pt44 | 35.9342331 | 0 | PD-1 | NA | NA | 61 | M | 365 | Melanoma | Riaz et al. 2017 | A0201,A0201,B4402, B5701,C0501,C0602 | A02,A02,B44, B58,UNK,UNK | 1 | 0 |
| Pt46 | 7.4630109 | 1 | PD-1 | M1a | Stage 4 | 79 | M | 180 | Melanoma | Riaz et al. 2017 | A0101,A0101,B0702, B0702,C0102,C0102 | A01,A01,B07, B07,UNK,UNK | 1 | 0 |
| Pt47 | 23.6054706 | 0 | PD-1 | M1b | Stage 4 | 52 | M | 1005 | Melanoma | Riaz et al. 2017 | A1101,A2402,B4402, B5108,C0102,C0501 | A03,A24,B44, B07,UNK,UNK | 0 | 0 |
| Pt48 | 34.3890282 | 0 | PD-1 | M1c | Stage 4 | 44 | M | 99 | Melanoma | Riaz et al. 2017 | A0301,A0301,B0702, B3501,C0702,C0401 | A03,A03,B07, B07,UNK,UNK | 1 | 0 |
| Pt49 | 27.1890309 | 0 | PD-1 | NA | NA | 52 | F | 852 | Melanoma | Riaz et al. 2017 | A0101,A2402,B3503, B5101,C1402,C0401 | A01,A24,B07, B07,UNK,UNK | 0 | 0 |
| Pt5 | 7.2986274 | 1 | PD-1 | M1c | Stage 4 | 58 | F | 52 | Melanoma | Riaz et al. 2017 | A0201,A0201,B4403, B5101,C0202,C1601 | A02,A02,B44, B07,UNK,UNK | 1 | 0 |
| Pt51 | 1.8739719 | 0 | PD-1 | M1a | Stage 4 | 43 | M | 204 | Melanoma | Riaz et al. 2017 | A0301,A0301,B0702, B0702,C0702,C0702 | A03,A03,B07, B07,UNK,UNK | 1 | 0 |
| Pt52 | 15.6493092 | 1 | PD-1 | M1c | Stage 4 | 45 | F | 353 | Melanoma | Riaz et al. 2017 | A0101,A0201,B3901, B4402,C1203,C0501 | A01,A02,B27, B44,UNK,UNK | 0 | 0 |
| Pt53 | 14.2356111 | 1 | PD-1 | M1c | Stage 4 | 82 | M | 81 | Melanoma | Riaz et al. 2017 | A3301,A2402,B1402, B1402,C0802,C0802 | A03,A24,B27, B27,UNK,UNK | 1 | 1 |
| Pt54 | 28.4383455 | 0 | PD-1 | NA | NA | 59 | M | 7360 | Melanoma | Riaz et al. 2017 | A6801,A0201,B0801, B2705,C0701,C0304 | A03,A02,B08, B27,UNK,UNK | 0 | 0 |
| Pt58 | 16.4054733 | 1 | PD-1 | M1c | Stage 4 | 53 | F | 862 | Melanoma | Riaz et al. 2017 | A0301,A0301,B0702, B0801,C0702,C0701 | A03,A03,B07, B08,UNK,UNK | 1 | 1 |
| Pt59 | 23.2767036 | 1 | PD-1 | M1a | Stage 4 | 49 | F | 432 | Melanoma | Riaz et al. 2017 | A2402,A2601,B0702, B5201,C0702,C1202 | A24,A01,B07, B62,UNK,UNK | 0 | 1 |
| Pt60 | 24.2630046 | 0 | PD-1 | M1a | Stage 4 | 50 | M | 829 | Melanoma | Riaz et al. 2017 | A0201,A2601,B3801, B4402,C1203,C0501 | A02,A01,B27, B44,UNK,UNK | 0 | 0 |
| Pt65 | 22.7506764 | 0 | PD-1 | M1b | Stage 4 | 63 | F | 2619 | Melanoma | Riaz et al. 2017 | A0101,A0201,B0702, B0702,C0702,C0501 | A01,A02,B07, B07,UNK,UNK | 1 | 0 |
| Pt66 | 17.8191714 | 1 | PD-1 | NA | NA | 49 | F | 153 | Melanoma | Riaz et al. 2017 | A2301,A0205,B5001, B4403,C0602,C0401 | A24,A02,B44, B44,UNK,UNK | 0 | 0 |
| Pt67 | 33.9287544 | 0 | PD-1 | M1c | Stage 4 | 33 | F | 16 | Melanoma | Riaz et al. 2017 | A0101,A0201,B0702, B4001,C0702,C0304 | A01,A02,B07, B44,UNK,UNK | 0 | 0 |
| Pt68 | 27.6821814 | 0 | PD-1 | M1b | Stage 4 | 69 | M | 1012 | Melanoma | Riaz et al. 2017 | A0301,A0101,B0702, B0801,C0701,C0702 | A03,A01,B07, B08,UNK,UNK | 0 | 0 |
| Pt7 | 37.7753283 | 0 | PD-1 | M1a | Stage 4 | 55 | M | 1517 | Melanoma | Riaz et al. 2017 | A1101,A2604,B1401, B5101,C0501,C0802 | A03,A01,B27, B44,UNK,UNK | 0 | 0 |
| Pt70 | 10.2246537 | 1 | PD-1 | M1b | Stage 4 | 72 | M | 428 | Melanoma | Riaz et al. 2017 | A6801,A3101,B0801, B4001,C0701,C0304 | A03,A03,B08, B44,UNK,UNK | 0 | 0 |
| Pt71 | 8.0876682 | 0 | PD-1 | M1c | Stage 4 | 50 | F | 5 | Melanoma | Riaz et al. 2017 | A0101,A0201,B0801, B2705,C0701,C0102 | A01,A02,B08, B27,UNK,UNK | 0 | 0 |
| Pt72 | 25.315059 | 1 | PD-1 | M1b | Stage 4 | 43 | F | 437 | Melanoma | Riaz et al. 2017 | A0301,A0201,B0702, B4402,C0702,C0501 | A03,A02,B07, B44,UNK,UNK | 0 | 0 |
| Pt73 | 9.2383527 | 0 | PD-1 | M1c | Stage 4 | 60 | M | 14 | Melanoma | Riaz et al. 2017 | A0301,A3201,B0702, B3501,C0702,C0401 | A03,A01,B07, B07,UNK,UNK | 0 | 0 |
| Pt74 | 0.657534 | 1 | PD-1 | M1c | Stage 4 | 27 | M | 44 | Melanoma | Riaz et al. 2017 | A0101,A2402,B0801, B1501,C0701,C0303 | A01,A24,B08, B62,UNK,UNK | 0 | 0 |

APPENDIX 1-continued

Cohort 1

| Sample | OS Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| Pt76 | 0.328767 | 1 | PD-1 | M1c | Stage 4 | 60 | M | 224 | Melanoma | Riaz et al. 2017 | A0301,A2902,B0702,B0702,C0702,C1601 | A03,A01,A24,B07,B07,UNK,UNK | 1 | 0 |
| Pt77 | 15.4849257 | 1 | PD-1 | M1a | Stage 4 | 56 | F | 49 | Melanoma | Riaz et al. 2017 | A6801,A2402,B0702,B0702,C0702,C0704 | A03,A24,B07,B07,UNK,UNK | 1 | 1 |
| Pt79 | 7.1671206 | 1 | PD-1 | NA | NA | 64 | M | 544 | Melanoma | Riaz et al. 2017 | A0301,A0101,A2402,B0702,B0702,C0702,C1601 | A03,A01,A24,B07,B07,UNK,UNK | 0 | 0 |
| Pt8 | 8.5150653 | 1 | PD-1 | M0 | Stage 3 | 40 | M | 87 | Melanoma | Riaz et al. 2017 | A0201,A0201,B4001,B4402,C0501,C0304 | A02,A02,B44,B44,UNK,UNK | 1 | 0 |
| Pt82 | 14.1041043 | 0 | PD-1 | M1c | Stage 4 | 60 | F | 33 | Melanoma | Riaz et al. 2017 | A0201,A0201,B0702,B1501,C0702,C0304 | A02,A02,B07,B62,UNK,UNK | 1 | 0 |
| Pt83 | 15.1890354 | 1 | PD-1 | M1c | Stage 4 | 39 | F | 339 | Melanoma | Riaz et al. 2017 | A1101,A0201,B0801,B3501,C0701,C0401 | A03,A02,B08,B07,UNK,UNK | 0 | 0 |
| Pt84 | 4.9643817 | 0 | PD-1 | M1c | Stage 4 | 48 | F | 11 | Melanoma | Riaz et al. 2017 | A0301,A0101,B0801,B3501,C0701,C0401 | A03,A01,B06,B07,UNK,UNK | 0 | 0 |
| Pt85 | 29.7205368 | 1 | PD-1 | M1a | Stage 4 | 66 | M | 129 | Melanoma | Riaz et al. 2017 | A3201,A0201,B2705,B4402,C0202,C0501 | A01,A02,B27,B44,UNK,UNK | 0 | 0 |
| Pt86 | 8.9424624 | 0 | PD-1 | M1c | Stage 4 | 50 | F | 562 | Melanoma | Riaz et al. 2017 | A0101,A1101,B0801,B3501,C0701,C0401 | A01,A03,B08,B07,UNK,UNK | 0 | 0 |
| Pt87 | 32.0219058 | 0 | PD-1 | NA | NA | 68 | M | 677 | Melanoma | Riaz et al. 2017 | A0101,A0201,B5701,B1501,C0602,C0303 | A01,A02,B56,B62,UNK,UNK | 0 | 0 |
| Pt89 | 27.7479348 | 1 | PD-1 | M1a | Stage 4 | 56 | M | 214 | Melanoma | Riaz et al. 2017 | A3401,A0201,B4001,B1502,C0702,C0403 | UNK,A02,B44,B62,UNK,UNK | 0 | 0 |
| Pt9 | 3.0246564 | 1 | PD-1 | M1c | Stage 4 | 46 | M | 409 | Melanoma | Riaz et al. 2017 | A0101,A3201,B0801,B1801,C0701,C0202 | A01,A01,B08,B44,UNK,UNK | 0 | 0 |
| Pt90 | 5.7205458 | 1 | PD-1 | M1c | Stage 4 | 60 | F | 283 | Melanoma | Riaz et al. 2017 | A6601,A0201,B4102,B4402,C1701,C0501 | A03,A02,B44,B44,UNK,UNK | 0 | 0 |
| Pt92 | 10.9479411 | 1 | PD-1 | NA | NA | 58 | M | 642 | Melanoma | Riaz et al. 2017 | A0101,A2402,B3801,B4901,C0701,C1203 | A01,A24,B27,UNK,UNK,UNK | 0 | 0 |
| Pt93 | 27.9123183 | 0 | PD-1 | M1c | Stage 4 | 52 | M | 7 | Melanoma | Riaz et al. 2017 | A0301,A0101,B2705,B5201,C1202,C0102 | A03,A01,B27,B62,UNK,UNK | 0 | 0 |
| Pt94 | 32.2520427 | 0 | PD-1 | M1c | Stage 4 | 41 | M | 405 | Melanoma | Riaz et al. 2017 | A0301,A2402,B1401,B1501,C0303,C0802 | A03,A24,B27,B62,UNK,UNK | 0 | 0 |
| Pt98 | 24.5588949 | 1 | PD-1 | M1c | Stage 4 | 74 | M | 20 | Melanoma | Riaz et al. 2017 | A1101,A2601,B3801,B5201,C1202,C1203 | A03,A01,B27,UNK,UNK,UNK | 0 | 0 |
| LAPT1 | 19.9561569 | 1 | PD-1 | M1c | Stage 4 | 66 | F | 1638 | Melanoma | Hugo et al. 2016 | A0101,A0201,B4001,B4402,C0304,C0501 | A01,A02,B44,B44,UNK,UNK | 0 | 0 |
| LAPT10 | 12.7232829 | 0 | PD-1 | M1a | Stage 4 | 60 | M | 225 | Melanoma | Hugo et al. 2016 | A0201,A0201,B4001,B4001,C0304,C0304 | A02,A02,B44,B44,UNK,UNK | 1 | 0 |
| LAPT11 | 15.3534189 | 1 | PD-1 | M1c | Stage 4 | 37 | M | 259 | Melanoma | Hugo et al. 2016 | A0101,A0301,B1601,B5701,C0602,C0501 | A01,A03,B44,B58,UNK,UNK | 0 | 0 |
| LAPT12 | 10.7506809 | 1 | PD-1 | M1c | Stage 4 | 59 | M | 50 | Melanoma | Hugo et al. 2016 | A0101,A2402,B5201,B3508,C0401,C1202 | A01,A24,B62,B07,UNK,UNK | 0 | 0 |
| LAPT13 | 30.1479339 | 0 | PD-1 | M1c | Stage 4 | 53 | F | 528 | Melanoma | Hugo et al. 2016 | A2501,A3101,B4001,B3901,C1203,C0304 | A01,A03,B44,UNK,UNK,UNK | 1 | 1 |
| LAPT14 | 1.7753418 | 0 | PD-1 | M1c | Stage 4 | 27 | F | 1457 | Melanoma | Hugo et al. 2016 | A0301,A0101,B3501,B0801,C0701,C0401 | B27,UNK,UNK,A03,A01,B07 | 0 | 0 |
| LAPT15 | 32.219166 | 1 | PD-1 | M1b | Stage 4 | 70 | M | 514 | Melanoma | Hugo et al. 2016 | A0201,A2402,B5101,B5801,C0102,C0302 | A02,A24,B07,B08,UNK,UNK,B58,UNK,UNK | 0 | 0 |

APPENDIX 1-continued

Cohort 1

| Sample | OS Months | OS Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| LAPT16 | 6.1150662 | 1 | PD-1 | M1b | Stage 4 | 19 | M | 519 | Melanoma | Hugo et al. 2016 | A0201,A0201,B4901, B5101,C1504,C1502 | A02,A02,UNK, B07,UNK,UNK | 1 | 0 |
| LAPT17 | 31.3314951 | 1 | PD-1 | M1a | Stage 4 | 67 | M | 846 | Melanoma | Hugo et al. 2016 | A0101,A2402,B0801, B4405,C0202,C0701 | A01,A24,B08, B44,UNK,UNK | 0 | 0 |
| LAPT18 | 35.5397127 | 0 | PD-1 | M1c | Stage 4 | 64 | M | 297 | Melanoma | Hugo et al. 2016 | A2402,A0201,B4001, B4402,C0304,C0501 | A24,A02,B44, B44,UNK,UNK | 0 | 0 |
| LAPT19 | 34.849302 | 0 | PD-1 | M1c | Stage 4 | 45 | M | 618 | Melanoma | Hugo et al. 2016 | A0201,A0301,B0702, B5101,C0702,C0202 | A02,A03,B07, B07,UNK,UNK | 0 | 0 |
| LAPT2 | 30.4670009 | 0 | PD-1 | M1c | Stage 4 | 55 | M | 1868 | Melanoma | Hugo et al. 2016 | A3101,A0301,B0702, B1801,C0701,C0702 | A03,A03,B07, B44,UNK,UNK | 0 | 0 |
| LAPT20 | 11.0794479 | 1 | PD-1 | M1c | Stage 4 | 63 | F | 542 | Melanoma | Hugo et al. 2016 | A2501,A0301,B801, B1302,C0701,C0602 | A01,A03,B06, UNK,UNK,UNK | 0 | 0 |
| LAPT21 | 31.0684815 | 0 | PD-1 | M1b | Stage 4 | 60 | M | 237 | Melanoma | Hugo et al. 2016 | A2902,A0301,B3503, B1801,C0701,C0401 | A01A24,A03,B07, B44,UNK,UNK | 0 | 0 |
| LAPT22 | 5.9835594 | 1 | PD-1 | M1c | Stage 4 | 55 | M | 68 | Melanoma | Hugo et al. 2016 | A0101,A0201,B3701, B2705,C0202,C0602 | A01,A02,B44, B27,UNK,UNK | 0 | 0 |
| LAPT23 | 3.3863001 | 1 | PD-1 | M1c | Stage 4 | 63 | M | 233 | Melanoma | Hugo et al. 2016 | A1101,A0201,B4402, B4402,C0501,C0501 | A03,A02,B44, B44,UNK,UNK | 1 | 0 |
| LAPT24 | 32.0219058 | 1 | PD-1 | M1c | Stage 4 | 70 | M | 385 | Melanoma | Hugo et al. 2016 | A2902,A2601,B4001, B2704,C0304,C1502 | A01A24,A01,B44, B27,UNK,UNK | 0 | 0 |
| LAPT25 | 8.6136954 | 1 | PD-1 | M1c | Stage 4 | 74 | M | 110 | Melanoma | Hugo et al. 2016 | A2501,A2601,B3801, B1801,C1203,C1203 | A01,A01,B27, B44,UNK,UNK | 1 | 0 |
| LAPT26 | 43.9232712 | 0 | PD-1 | M1c | Stage 4 | 71 | M | 1079 | Melanoma | Hugo et al. 2016 | A0301,A3201,B3501, B3801,C1203,C0401 | A03,A01,B07, B27,UNK,UNK | 0 | 0 |
| LAPT27 | 18.0164316 | 0 | PD-1 | M1c | Stage 4 | 83 | M | 2297 | Melanoma | Hugo et al. 2016 | A1101,A0301,B5601, B4402,C0102,C0501 | A03,A03,B07, B44,UNK,UNK | 0 | 0 |
| LAPT28 | 14.4328713 | 1 | PD-1 | M1c | Stage 4 | 82 | M | 465 | Melanoma | Hugo et al. 2016 | A3301,A0101,B1402, B5701,C0802,C0602 | A03,A01,B27, B58,UNK,UNK | 0 | 0 |
| LAPT29 | 8.8438323 | 1 | PD-1 | M1c | Stage 4 | 84 | M | 225 | Melanoma | Hugo et al. 2016 | A0201,A0201,B5701, B4402,C0501,C0602 | A02,A02,B56, B44,UNK,UNK | 1 | 0 |
| LAPT3 | 22.7177997 | 1 | PD-1 | M1c | Stage 4 | 58 | M | 1144 | Melanoma | Hugo et al. 2016 | A2901,A6801,B0705, B2705,C0202,C1505 | A01A24,A03,B07, B27,UNK,UNK | 0 | 1 |
| LAPT30 | 3.28767 | 1 | PD-1 | M1c | Stage 4 | 80 | F | 559 | Melanoma | Hugo et al. 2016 | A0301,A0301,B0702, B3501,C0702,C0401 | A03,A03,B07, B07,UNK,UNK | 1 | 0 |
| LAPT31 | 23.451968 | 0 | PD-1 | M1c | Stage 4 | 47 | M | 594 | Melanoma | Hugo et al. 2016 | A0301,A0101,B0801, B4402,C0701,C0501 | A03,A01,B06, B44,UNK,UNK | 0 | 0 |
| LAPT32 | 5.6219157 | 1 | PD-1 | M1c | Stage 4 | 47 | M | 259 | Melanoma | Hugo et al. 2016 | A1101,A6801,B3501, B1803,C0701,C0401 | A03,A03,B07, B44,UNK,UNK | 0 | 0 |
| LAPT33 | 71.5725759 | 0 | PD-1 | M1c | Stage 4 | 60 | F | 663 | Melanoma | Hugo et al. 2016 | A6802,A2301,B4901, B1402,C0701,C0802 | A02,A24,UNK, B27,UNK,UNK | 0 | 0 |
| LAPT34 | 13.7424606 | 0 | PD-1 | M1a | Stage 4 | 42 | M | 89 | Melanoma | Hugo et al. 2016 | A3004,A0301,B3503, B4403,C0706,C0401 | A01,A03,B07, B44,UNK,UNK | 0 | 1 |
| LAPT35 | 14.0383509 | 0 | PD-1 | M1c | Stage 4 | 65 | F | 313 | Melanoma | Hugo et al. 2016 | A0301,A0201,B0702, B4402,C0702,C0501 | A03,A02,B07, B44,UNK,UNK | 0 | 0 |
| LAPT36 | 27.5177979 | 1 | PD-1 | M1a | Stage 4 | 61 | F | 72 | Melanoma | Hugo et al. 2016 | A0301,A0101,B0702, B0801,C0702,C0701 | A03,A01,B07, B08,UNK,UNK | 0 | 0 |
| LAPT37 | 11.9671188 | 0 | PD-1 | M1c | Stage 4 | 70 | F | 553 | Melanoma | Hugo et al. 2016 | A0201,A2403,B3503, B3501,C0401,C0401 | A02,A24,B07, B07,UNK,UNK | 1 | 0 |

APPENDIX 1-continued

Cohort 1

| Sample | OS Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| LAPT38 | 14.7287616 | 0 | PD-1 | M1c | Stage 4 | 57 | F | 78 | Melanoma | Hugo et al. 2016 | A0201,A0201,B5101, B5101,C1402,C1502 | A02,A02,B07, B07,UNK,UNK | 1 | 0 |
| LAPT4 | 31.1671116 | 0 | PD-1 | M1c | Stage 4 | 62 | M | 3727 | Melanoma | Hugo et al. 2016 | A2301,A0201,B4002, B4402,C0202,C0501 | A24,A02,B44, B44,UNK,UNK | 0 | 0 |
| LAPT5 | 14.4326713 | 0 | PD-1 | M1c | Stage 4 | 61 | M | 312 | Melanoma | Hugo et al. 2016 | A0201,A6801,B1507, B4402,C0303,C0704 | A02,A03,B62, B44,UNK,UNK | 0 | 0 |
| LAPT6 | 28.9972494 | 0 | PD-1 | M1c | Stage 4 | 51 | M | 207 | Melanoma | Hugo et al. 2016 | A2402,A3201,B3501, B3501,C0401,C0401 | A24,A01,B07, B07,UNK,UNK | 1 | 1 |
| LAPT7 | 21.7643754 | 1 | PD-1 | M1a | Stage 4 | 55 | F | 1184 | Melanoma | Hugo et al. 2016 | A0201,A0201,B3503, B3801,C0401,C1203 | A02,A02,B07, B27,UNK,UNK | 1 | 1 |
| LAPT8 | NA | NA | PD-1 | M0 | Stage 3 | 69 | M | 805 | Melanoma | Hugo et al. 2016 | A1101,A0201,B5501, B4402,C0303,C0501 | A03,A02,B07, B44,UNK,UNK | 0 | NA |
| LAPT9 | 34.6520418 | 0 | PD-1 | M1c | Stage 4 | 68 | M | 474 | Melanoma | Hugo et al. 2016 | A0302,A0301,B5301, B5101,C0401,C1502 | A03,A03,B07, B07,UNK,UNK | 0 | 0 |
| AL4602 | 40.3 | 0 | PD-1 | M1c | Stage 4 | 59 | M | 146 | Non-Small Cell Lu | Rizvi et al. 2015 | A0301,A3201,B0801, B5101,C0702,C1502 | A03,A01,B08, B07,UNK,UNK | 0 | 0 |
| AU5884 | 2.4 | 1 | PD-1 | M1c | Stage 4 | 64 | M | 68 | Non-Small Cell Lu | Rizvi et al. 2015 | A2402,A0201,B5101, B1302,C0602,C1502 | A24,A02,B07, B07,UNK,UNK | 0 | 1 |
| BL3403 | 13.36666667 | 1 | PD-1 | M1c | Stage 4 | 73 | F | 36 | Non-Small Cell Lu | Rizvi et al. 2015 | A0201,A2601,B3501, B4402,C0501,C0401 | A02,A01,B07, B44,UNK,UNK | 0 | 0 |
| CA9903 | 49.53333333 | 0 | PD-1 | M1c | Stage 4 | 57 | M | 329 | Non-Small Cell Lu | Rizvi et al. 2015 | A1101,A0201,B1801, B5108,C0701,C1602 | A03,A02,B44, B07,UNK,UNK | 0 | 0 |
| CU9061 | 15.56666667 | 1 | PD-1 | M1c | Stage 4 | 57 | M | 324 | Non-Small Cell Lu | Rizvi et al. 2015 | A0101,A2902,B3801, B4403,C1601,C1203 | A01,A01,A24,B27, B44,UNK,UNK | 0 | 1 |
| DI6359 | 29.1 | 1 | PD-1 | M1c | Stage 4 | 61 | F | 237 | Non-Small Cell Lu | Rizvi et al. 2015 | A0301,A1101,B5101, B1801,C1203,C1504 | A03,A03,B07, B44,UNK,UNK | 0 | 0 |
| DM123062 | 2.9 | 1 | PD-1 | M1c | Stage 4 | 50 | M | 85 | Non-Small Cell Lu | Rizvi et al. 2015 | A0301,A0201,B1801, B4002,C0501,C0202 | A03,A02,B44, B44,UNK,UNK | 0 | 0 |
| FR9547 | 25.9 | 1 | PD-1 | M1c | Stage 4 | 65 | F | 265 | Non-Small Cell Lu | Rizvi et al. 2015 | A2402,A0201,B0801, B1801,C0701,C0701 | A24,A02,B08, B44,UNK,UNK | 0 | 1 |
| GR0134 | 34.16666667 | 0 | PD-1 | M1c | Stage 4 | 80 | M | 32 | Non-Small Cell Lu | Rizvi et al. 2015 | A0201,A3301,B1402, B1302,C0602,C0802 | A02,A03,B27, UNK,UNK,UNK | 0 | 0 |
| GR4788 | 2.766666667 | 1 | PD-1 | M1c | Stage 4 | 59 | M | 75 | Non-Small Cell Lu | Rizvi et al. 2015 | A0101,A2601,B3501, B3701,C0602,C0401 | A01,A01,B07, B44,UNK,UNK | 0 | 0 |
| HE3202 | 46.4 | 0 | PD-1 | M1c | Stage 4 | 63 | F | 681 | Non-Small Cell Lu | Rizvi et al. 2015 | A2403,A3201,B3801, B4101,C1203,C1701 | A24,A01,B27, B44,UNK,UNK | 0 | 0 |
| JB112852 | 15.86666667 | 0 | PD-1 | M1c | Stage 4 | 60 | M | 60 | Non-Small Cell Lu | Rizvi et al. 2015 | A1101,A1101,B4402, B3502,C0704,C0401 | A03,A03,B44, B07,UNK,UNK | 1 | 0 |
| KA3947 | 25.66666667 | 1 | PD-1 | M1c | Stage 4 | 64 | F | 302 | Non-Small Cell Lu | Rizvi et al. 2015 | A2301,A2402,B4101, B4901,C0701,C1701 | A24,A24,B44, UNK,UNK,UNK | 0 | 0 |
| LO3793 | 11.46666667 | 0 | PD-1 | M1c | Stage 4 | 62 | F | 75 | Non-Small Cell Lu | Rizvi et al. 2015 | A0301,A0201,B2705, B4901,C0701,C0102 | A03,A02,B27, UNK,UNK,UNK | 0 | 0 |
| LO5004 | 22.73333333 | 1 | PD-1 | M1c | Stage 4 | 56 | F | 31 | Non-Small Cell Lu | Rizvi et al. 2015 | A2601,A0201,B5501, B3801,C1203,C0303 | A01,A02,B07, B27,UNK,UNK | 0 | 0 |
| M4945 | 46.6 | 0 | PD-1 | M1c | Stage 4 | 66 | M | 250 | Non-Small Cell Lu | Rizvi et al. 2015 | A3001,A0201,B1302, B4403,C1602,C0602 | A01,A03,A02,UNK, B44,UNK,UNK | 0 | 0 |
| MA7027 | 2.766666667 | 1 | PD-1 | M1c | Stage 4 | 56 | M | 204 | Non-Small Cell Lu | Rizvi et al. 2015 | A2402,A2402,B0702, B5108,C0702,C1602 | A24,A24,B07, B07,UNK,UNK | 1 | 0 |

APPENDIX 1-continued

Cohort 1

| Sample | OS Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| NI9507 | 32.56666667 | 1 | PD-1 | M1c | Stage 4 | 41 | F | 62 | Non-Small Cell Lu | Rizvi et al. 2015 | A0301,A0201,B0702,B0702,C0702,C0702 | A03,A02,B07,B07,UNK,UNK | 1 | 1 |
| R7495 | 2.1 | 1 | PD-1 | M1c | Stage 4 | 63 | M | 80 | Non-Small Cell Lu | Rizvi et al. 2015 | A1101,A1101,B3801,B3501,C1203,C0401 | A03,A03,B27,B07,UNK,UNK | 1 | 0 |
| RH090935 | 11.13333333 | 0 | PD-1 | M1c | Stage 4 | 78 | F | 114 | Non-Small Cell Lu | Rizvi et al. 2015 | A2601,A3201,B3501,B3801,C1203,C0401 | A01,A01,B07,B27,UNK,UNK | 0 | 0 |
| RI1933 | 46.7 | 0 | PD-1 | M1c | Stage 4 | 60 | F | 441 | Non-Small Cell Lu | Rizvi et al. 2015 | A3101,A2601,B5701,B1302,C0602,C0602 | A03,A01,B58,UNK,UNK,UNK | 1 | 0 |
| RO3338 | 3.866666667 | 1 | PD-1 | M1c | Stage 4 | 71 | M | 54 | Non-Small Cell Lu | Rizvi et al. 2015 | A3002,A0201,B3801,B0801,C0701,C1203 | A01,A02,B27,B08,UNK,UNK | 0 | 0 |
| SA9755 | 40.1 | 0 | PD-1 | M1c | Stage 4 | 63 | F | 1109 | Non-Small Cell Lu | Rizvi et al. 2015 | A1101,A0101,B0801,B3501,C0701,C0401 | A03,A01,B08,B07,UNK,UNK | 0 | 1 |
| SB010944 | 27.56666667 | 0 | PD-1 | M1c | Stage 4 | 68 | M | 190 | Non-Small Cell Lu | Rizvi et al. 2015 | A0301,A0101,B0702,B0801,C0702,C0701 | A03,A01,B07,B08,UNK,UNK | 0 | 0 |
| SC0899 | 44.33333333 | 0 | PD-1 | M1c | Stage 4 | 64 | F | 364 | Non-Small Cell Lu | Rizvi et al. 2015 | A2402,A2601,B3801,B3502,C1203,C0401 | A24,A01,B27,B07,UNK,UNK | 0 | 0 |
| SC6470 | 36.83333333 | 0 | PD-1 | M1c | Stage 4 | 59 | M | 194 | Non-Small Cell Lu | Rizvi et al. 2015 | A3002,A3101,B3502,B1801,C0501,C0401 | A01,A03,B07,B44,UNK,UNK | 0 | 0 |
| SR070761 | 15.13333333 | 1 | PD-1 | M1c | Stage 4 | 51 | F | 138 | Non-Small Cell Lu | Rizvi et al. 2015 | A0101,A6801,B3502,B5502,C0102,C0401 | A01,A03,B07,B07,UNK,UNK | 0 | 1 |
| TU0428 | 3.666666667 | 1 | PD-1 | M1c | Stage 4 | 66 | M | 1167 | Non-Small Cell Lu | Rizvi et al. 2015 | A0301,A0101,B0702,B3501,C0702,C0401 | A03,A01,B07,B07,UNK,UNK | 0 | 0 |
| VA1330 | 23.36666667 | 1 | PD-1 | M1c | Stage 4 | 71 | F | 7 | Non-Small Cell Lu | Rizvi et al. 2015 | A0301,A2601,B3502,B4403,C0401,C0401 | A03,A01,B07,B44,UNK,UNK | 1 | 0 |
| VA7859 | 17.23333333 | 1 | PD-1 | M1c | Stage 4 | 57 | F | 3 | Non-Small Cell Lu | Rizvi et al. 2015 | A2301,A2902,B4901,B4403,C0701,C1601 | A24,A01,A24,UNK,B44,UNK,UNK | 0 | 0 |
| WA7899 | 18.73333333 | 1 | PD-1 | M1c | Stage 4 | 49 | M | 70 | Non-Small Cell Lu | Rizvi et al. 2015 | A0301,A2402,B3502,B3501,C0401,C0401 | A03,A24,B07,B07,UNK,UNK | 1 | 0 |
| Y2087 | 14.86666667 | 1 | PD-1 | M1c | Stage 4 | 68 | F | 170 | Non-Small Cell Lu | Rizvi et al. 2015 | A1101,A3101,B1302,B3501,C0602,C0401 | A03,A03,UNK,B07,UNK,UNK | 0 | 0 |
| ZA6505 | 25.76666667 | 1 | PD-1 | M1c | Stage 4 | 76 | F | 711 | Non-Small Cell Lu | Rizvi et al. 2015 | A2901,A2601,B0705,B1801,C1505,C1203 | A01,A24,A01,B07,B44,UNK,UNK | 0 | 0 |
| ZA6965 | 21.43333333 | 0 | PD-1 | M1c | Stage 4 | 57 | F | 60 | Non-Small Cell Lu | Rizvi et al. 2015 | A0201,A3201,B4001,B4501,C0602,C0304 | A02,A01,B44,B44,UNK,UNK | 0 | 0 |
| PT300 | 2.9260263 | 1 | PD-L1 + CTLA | M1c | Stage 4 | 52.3 | M | NA | Non-Small Cell Lu | Rizvi_CUMC | A3101,C0602,C0304 B4001,C0602,C0304 | A03,A03,B44,UNK,UNK | 1 | NA |
| PT301 | 14.3342412 | 0 | PD-1 | M1c | Stage 4 | 53.4 | M | NA | Non-Small Cell Lu | Rizvi_CUMC | A1101,A2301,B0702,B4403,C0401,C1502 | A03,A24,B07,B44,UNK,UNK | 0 | NA |
| PT302 | 13.2164334 | 0 | PD-1 | M1c | Stage 4 | 62.8 | M | NA | Non-Small Cell Lu | Rizvi_CUMC | A0101,A2901,B0705,B0801,C0701,C1505 | A01,A01,A24,B07,B08,UNK,UNK | 0 | NA |
| PT303 | 6.6739701 | 1 | PD-1 | M1c | Stage 4 | 64.4 | F | NA | Non-Small Cell Lu | Rizvi_CUMC | A0101,A0201,B5101,B5801,C0701,C1402 | A01,A02,B07,B58,UNK,UNK | 0 | NA |
| PT304 | 15.2547888 | 0 | PD-1 | M1c | Stage 4 | 76.4 | F | NA | Non-Small Cell Lu | Rizvi_CUMC | A0301,A3201,B0702,B5301,C0401,C0702 | A03,A01,B07,B07,UNK,UNK | 0 | NA |
| PT305 | 5.5561623 | 1 | PD-1 | M1c | Stage 4 | 61.9 | M | NA | Non-Small Cell Lu | Rizvi_CUMC | A3002,A6602,B1503,B5801,C0210,C1701 | A01,A03,B27,B58,UNK,UNK | 0 | NA |
| PT306 | 10.3561605 | 0 | PD-1 | M1c | Stage 4 | 74.7 | M | NA | Non-Small Cell Lu | Rizvi_CUMC | A0201,A2402,B0702,B2705,C0102,C0702 | A02,A24,B07,B27,UNK,UNK | 0 | NA |

APPENDIX 1-continued

Cohort 1

| Sample | OS Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| PT307 | 7.1342439 | 0 | PD-1 | M1c | Stage 4 | 71.6 | M | NA | Non-Small Cell Lu | Rizvi_CUMC | A0101,A0101,B2705, B5701,C0202,C0602 | A01,B27,B58, UNK,UNK | 1 | NA |
| PT308 | 17.0301306 | 0 | PD-1 | M1c | Stage 4 | 63.6 | F | NA | Non-Small Cell Lu | Rizvi_CUMC | A0201,A2301,B0702, B3924,C0701,C0702 | A02,A24,B07, B27,UNK,UNK | 0 | NA |
| PT309 | 12.493146 | 0 | PD-1 | M1c | Stage 4 | 54.6 | F | NA | Non-Small Cell Lu | Rizvi_CUMC | A0101,A0201,B5101, B5701,C0602,C1402 | A01,A02,B07, B58,UNK,UNK | 0 | NA |
| PT310 | 7.5945177 | 0 | PD-1 | M1c | Stage 4 | 77.1 | F | NA | Non-Small Cell Lu | Rizvi_CUMC | A0201,A0301,B5001, B5701,C0602,C0602 | A02,A03,B44, B58,UNK,UNK | 1 | NA |
| PT311 | 7.232874 | 1 | PD-1 | M1c | Stage 4 | 80.8 | M | NA | Non-Small Cell Lu | Rizvi_CUMC | A0305,A3002,B0702, B0801,C0702,C0702 | A03,A01,B07, B08,UNK,UNK | 0 | NA |
| PT312 | 13.3479402 | 0 | PD-1 | M1c | Stage 4 | 63.7 | M | NA | Non-Small Cell Lu | Rizvi_CUMC | A2402,A3010,B4101, B4403,C0401,C0602 | A24,UNK,B44, B44,UNK,UNK | 0 | NA |
| PT313 | 10.8164343 | 1 | PD-1 | M1c | Stage 4 | 69.2 | F | NA | Non-Small Cell Lu | Rizvi_CUMC | A1101,A2421,B5101, B5101,C0702,C1502 | A03,A24,B07, UNK,UNK,UNK | 1 | NA |
| PT314 | 3.945204 | 1 | PD-1 | M1c | Stage 4 | 78.6 | F | NA | Non-Small Cell Lu | Rizvi_CUMC | A6802,A6810,B5301, B5702,C0401,C1801 | A02,A03,B07, B58,UNK,UNK | 0 | NA |
| PT315 | 21.5342385 | 0 | PD-1 | M1c | Stage 4 | 69.6 | M | NA | Non-Small Cell Lu | Rizvi_CUMC | A0201,A0201,B1508, B5101,C0102,C1402 | A02,B07,B07, UNK,UNK,UNK | 1 | NA |
| PT316 | 11.9999955 | 0 | PD-1 | M1c | Stage 4 | 70.3 | F | NA | Non-Small Cell Lu | Rizvi_CUMC | A0201,A0201,B1503, B4501,C0210,C1601 | A02,B27,B44, UNK,UNK,UNK | 1 | NA |
| PT317 | 10.3890372 | 0 | PD-1 | M1c | Stage 4 | 51.3 | F | NA | Non-Small Cell Lu | Rizvi_CUMC | A0301,A3303,B0702, B3502,C0401,C0702 | A03,A03,B07, B07,UNK,UNK | 0 | NA |
| PT318 | 11.0465712 | 0 | PD-1 | M1c | Stage 4 | 76.1 | M | NA | Non-Small Cell Lu | Rizvi_CUMC | A0101,A6801,B3501, B5701,C0401,C0602 | A01,A03,B07, B58,UNK,UNK | 0 | NA |
| PT319 | 6.246573 | 1 | PD-1 | M1c | Stage 4 | 70.1 | F | NA | Non-Small Cell Lu | Rizvi_CUMC | A0101,A0301,B0702, B5701,C0602,C0702 | A01,A03,B07, B58,UNK,UNK | 0 | NA |
| PT320 | 2.6958894 | 1 | CTLA-4 + PD-1 | M1c | Stage 4 | 75.6 | F | NA | Non-Small Cell Lu | Rizvi_CUMC | A0201,A6801,B4001, B5701,C0304,C0602 | A02,A03,B44, B58,UNK,UNK | 0 | NA |
| PT321 | 17.424651 | 0 | PD-1 | M1c | Stage 4 | 70.4 | F | NA | Non-Small Cell Lu | Rizvi_CUMC | A2402,A6802,B1402, B1517,C0701,C0802 | A24,A02,B27, B58,UNK,UNK | 0 | NA |
| PT322 | 2.2684923 | 1 | PD-1 | M1c | Stage 4 | 67.2 | M | NA | Non-Small Cell Lu | Rizvi_CUMC | A0101,A1101,B3501, B5701,C0401,C0602 | A01,A03,B07, B58,UNK,UNK | 0 | NA |
| PT323 | 14.2027344 | 0 | PD-L1 + CTLA | M1c | Stage 4 | 63.9 | F | NA | Non-Small Cell Lu | Rizvi_CUMC | A2426,A2601,B1801, B3801,C1203,C1203 | A24,A01,B44, B27,UNK,UNK | 1 | NA |
| PT324 | 16.2082131 | 0 | PD-1 | M1c | Stage 4 | 75.7 | F | NA | Non-Small Cell Lu | Rizvi_CUMC | A3002,A6601,B4201, B5301,C0401,C1701 | A01,A03,B07, B07,UNK,UNK | 0 | NA |
| PT325 | 27.7808115 | 0 | PD-1 | M1c | Stage 4 | 52.3 | M | NA | Non-Small Cell Lu | Rizvi_CUMC | A0101,A3002,B1510, B4402,C0304,C0501 | A01,A01,B27, B44,UNK,UNK | 0 | NA |
| PT326 | 12.7232829 | 0 | PD-1 | M1c | Stage 4 | 69.6 | F | NA | Non-Small Cell Lu | Rizvi_CUMC | A0201,A2601,B0801, B1401,C0701,C0802 | A02,A01,B08, B27,UNK,UNK | 0 | NA |
| PT327 | 21.0082113 | 0 | PD-1 | M1c | Stage 4 | 51.4 | F | NA | Non-Small Cell Lu | Rizvi_CUMC | A0101,A2601,B0801, B3801,C0701,C1203 | A01,A01,B08, B27,UNK,UNK | 0 | NA |
| PT328 | 10.3561605 | 0 | PD-1 | M1c | Stage 4 | 70.7 | F | NA | Non-Small Cell Lu | Rizvi_CUMC | A0101,A2402,B1302, B3502,C0401,C0602 | A01,A24,UNK, B07,UNK,UNK | 0 | NA |
| PT329 | 17.2273908 | 1 | PD-1 | M1c | Stage 4 | 62.2 | M | NA | Non-Small Cell Lu | Rizvi_CUMC | A0101,A0207,B3701, B4601,C0102,C0602 | A01,A02,B44, B62,UNK,UNK | 0 | NA |
| PT330 | 8.7123255 | 0 | PD-1 | M1c | Stage 4 | 70.2 | M | NA | Non-Small Cell Lu | Rizvi_CUMC | A1101,A6802,B5201, B5301,C0401,C1202 | A03,A02,B62, B07,UNK,UNK | 0 | NA |

APPENDIX 1-continued

Cohort 1

| Sample | OS Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| PT331 | 6.6410934 | 1 | PD-L1 + CTLA | M1c | Stage 4 | 73.3 | F | NA | Non-Small Cell Lu | Rizvi_CUMC | A0301,A2902,B0702, B1402,C0702,C0802 | A03,A01,A24,B07, B27,UNK,UNK | 0 | NA |
| PT332 | 6.1150662 | 1 | PD-1 | M1c | Stage 4 | 59 | F | NA | Non-Small Cell Lu | Rizvi_CUMC | A2301,A2301,B0702, B5703,C0702,C1801 | A24,B07,B58, UNK,UNK | 1 | NA |
| PT333 | 9.3041061 | 1 | PD-1 | M1c | Stage 4 | 43.8 | M | NA | Non-Small Cell Lu | Rizvi_CUMC | A0205,A2601,B3801, B5801,C0701,C1203 | A02,A01,B27, B58,UNK,UNK | 0 | NA |
| PT334 | 1.0520544 | 1 | PD-1 | M1c | Stage 4 | 70.8 | M | NA | Non-Small Cell Lu | Rizvi_CUMC | A0301,A3001,B0702, B1302,C0602,C0702 | A03,A01,A03,B07, UNK,UNK,UNK | 0 | NA |
| PT335 | 2.2684923 | 1 | PD-1 | M1c | Stage 4 | 78.1 | M | NA | Non-Small Cell Lu | Rizvi_CUMC | A0201,A1101,B0702, B4002,C0202,C0702 | A02,A03,B07, B44,UNK,UNK | 0 | NA |
| PT336 | 38.136972 | 0 | PD-1 | M1c | Stage 4 | 80.5 | M | NA | Non-Small Cell Lu | Rizvi_CUMC | A0201,A3301,B1402, B1302,C0602,C0802 | A02,A03,B27, UNK,UNK,UNK | 0 | NA |
| PT337 | 16.2082131 | 1 | PD-1 | M1c | Stage 4 | 58.8 | F | NA | Non-Small Cell Lu | Rizvi_CUMC | A6802,A7401,B0702, B1503,C0210,C1505 | A02,A03,B07, B27,UNK,UNK | 0 | NA |
| PT338 | 8.4621886 | 1 | PD-1 | M1c | Stage 4 | 64.8 | F | NA | Non-Small Cell Lu | Rizvi_CUMC | A0201,A2601,B0702, B1501,C1203,C0401 | A02,A01,B07, B62,UNK,UNK | 0 | NA |
| PT339 | 7.1013672 | 0 | PD-1 | M1c | Stage 4 | 47.8 | M | NA | Non-Small Cell Lu | Rizvi_CUMC | A0207,A2601,B4001, B4601,C0102,C0304 | A02,A01,B44, B62,UNK,UNK | 0 | NA |
| PT340 | 6.2136963 | 0 | PD-1 | M1c | Stage 4 | 76 | M | NA | Non-Small Cell Lu | Rizvi_CUMC | A0201,A0301,B0702, B4402,C0501,C0702 | A02,A03,B07, B44,UNK,UNK | 0 | NA |
| PT341 | 5.4904089 | 0 | PD-1 | M1c | Stage 4 | 58.3 | F | NA | Non-Small Cell Lu | Rizvi_CUMC | A2601,A3301,B1401, B4403,C0202,C0802 | A01,A03,B27, B44,UNK,UNK | 0 | NA |
| PT342 | 4.3068477 | 0 | PD-1 | M1c | Stage 4 | 53.1 | F | NA | Non-Small Cell Lu | Rizvi_CUMC | A2902,A3101,B0702, B4002,C0305,C0702 | A01,A24,A03,B07, B44,UNK,UNK | 0 | NA |
| PT343 | 6.4438332 | 0 | PD-L1 + CTLA | M1c | Stage 4 | 50.6 | F | NA | Non-Small Cell Lu | Rizvi_CUMC | A2902,A3201,B4402, B4403,C0501,C1601 | A01,A24,A01,B44, B44,UNK,UNK | 0 | NA |
| PT344 | 1.3808214 | 0 | PD-1 | M1c | Stage 4 | 60.8 | F | NA | Non-Small Cell Lu | Rizvi_CUMC | A0301,A0301,B1801, B4402,C0501,C0701 | A03,B44,B44, UNK,UNK | 1 | NA |
| PT345 | 8.9753391 | 0 | PD-1 | M1c | Stage 4 | 70.6 | M | NA | Non-Small Cell Lu | Rizvi_CUMC | A0201,A0301,B1801, B4403,C0401,C0501 | A02,A03,B44, UNK,UNK,UNK | 0 | NA |
| PT346 | 17.6219112 | 0 | PD-1 | M1c | Stage 4 | 66.2 | F | NA | Non-Small Cell Lu | Rizvi_CUMC | A0201,A3001,B0702, B1503,C0210,C1203 | A02,A01,A03,B07, B27,UNK,UNK | 0 | NA |
| PT347 | 5.917806 | 0 | PD-1 | M1c | Stage 4 | 85.6 | M | NA | Non-Small Cell Lu | Rizvi_CUMC | A0201,A2501,B1302, B4402,C0501,C0602 | A02,A01,UNK, B44,UNK,UNK | 0 | NA |
| PT348 | 5.589039 | 0 | PD-1 | M1c | Stage 4 | 64.9 | M | NA | Non-Small Cell Lu | Rizvi_CUMC | A0101,A0101,B1801, B5101,C0501,C1203 | A01,B44,B07, UNK,UNK | 1 | NA |
| PT349 | 0.7232874 | 1 | PD-1 | M1c | Stage 4 | 86.8 | F | NA | Non-Small Cell Lu | Rizvi_CUMC | A0301,A3001,B1302, B4701,C0602,C0602 | A03,A01,A03, UNK,UNK,UNK | 1 | NA |
| PT350 | 10.0931469 | 0 | PD-1 | M1c | Stage 4 | 66.1 | F | NA | Non-Small Cell Lu | Rizvi_CUMC | A3201,A6801,B1801, B4001,C0304,C0701 | A01,A03,B44, B44,UNK,UNK | 0 | NA |
| PT351 | 1.8410952 | 0 | PD-1 | M1c | Stage 4 | 81.9 | M | NA | Non-Small Cell Lu | Rizvi_CUMC | A0201,A2902,B0702, B4402,C0501,C0702 | A02,A01,A24,B07, B44,UNK,UNK | 0 | NA |
| PT352 | 16.6504103 | 0 | PD-1 | M1c | Stage 4 | 64.4 | F | NA | Non-Small Cell Lu | Rizvi_CUMC | A0203,A1101,B4601, B4601,C0102,C0102 | A02,A03,B62, UNK | 1 | NA |
| PT353 | 5.0630118 | 0 | PD-1 | M1c | Stage 4 | 64.7 | F | NA | Non-Small Cell Lu | Rizvi_CUMC | A1101,A2403,B0702, B3501,C0401,C0702 | A03,A24,B07, B07,UNK,UNK | 0 | NA |
| PT354 | 3.3863001 | 0 | PD-1 | M1c | Stage 4 | 76.2 | F | NA | Non-Small Cell Lu | Rizvi_CUMC | A0101,A2403,B1517, B5801,C0701,C0701 | A01,A24,B58, B58,UNK,UNK | 1 | NA |

APPENDIX 1-continued

Cohort 1

| Sample | OS_Months | OS_Event | Drug Class | Stage M | Stage | Age | Gender | MutCnt | Cancer Type | Reference | HLA Class I Alleles | HLA Class I Supertypes | Homozygous (1 = Yes; 0 = No) | LOH (1 = Yes; 0 = No) |
|---|---|---|---|---|---|---|---|---|---|---|---|---|---|---|
| PT355 | 2.2356156 | 0 | PD-1 | M1c | Stage 4 | 55.5 | F | NA | Non-Small Cell Lu | Rizvi_CUMC | A0201,A6802,B4403, B5101,C0401,C1601 | A02,A02,B44, B07,UNK,UNK | 0 | NA |
| PT356 | 4.7671215 | 0 | PD-1 | M1c | Stage 4 | 70.9 | M | NA | Non-Small Cell Lu | Rizvi_CUMC | A0101,A3001,B0801, B1302,C0602,C0701 | A01,A01,A03,B08, UNK,UNK,UNK | 0 | NA |
| PT357 | 17.9506782 | 0 | PD-1 | M1c | Stage 4 | 78.6 | F | NA | Non-Small Cell Lu | Rizvi_CUMC | A0301,A6801,B1402, B5701,C0701,C0802 | A03,A03,B27, B58,UNK,UNK | 0 | NA |
| PT358 | 2.6958894 | 0 | PD-1 | M1c | Stage 4 | 76.5 | M | NA | Non-Small Cell Lu | Rizvi_CUMC | A2402,A3402,B3501, B5201,C0401,C1502 | A24,A03,B07, B62,UNK,UNK | 0 | NA |
| PT359 | 2.301369 | 0 | PD-1 | M1c | Stage 4 | 60.6 | M | NA | Non-Small Cell Lu | Rizvi_CUMC | A0301,A3301,B3501, B3501,C0401,C0401 | A03,A03,B07, UNK | 1 | NA |
| PT360 | 1.972602 | 0 | PD-1 | M1c | Stage 4 | 49.6 | M | NA | Non-Small Cell Lu | Rizvi_CUMC | A0202,A0202,B5001, B5703,C0602,C0701 | A02,B44,B58, UNK,UNK | 1 | NA |
| PT361 | 2.2027389 | 0 | CTLA-4 + PD-1 | M1c | Stage 4 | 76.6 | M | NA | Non-Small Cell Lu | Rizvi_CUMC | A0302,A2601,B1501, B3501,C0401,C0704 | A03,A01,B62, B07,UNK,UNK | 0 | NA |
| PT362 | 8.1862983 | 0 | PD-1 | M1c | Stage 4 | 74.1 | M | NA | Non-Small Cell Lu | Rizvi_CUMC | A1101,A2902,B3501, B5801,C0401,C0701 | A03,A01,A24,B07, B58,UNK,UNK | 0 | NA |
| PT363 | 5.5232856 | 0 | PD-1 | M1c | Stage 4 | 79.3 | M | NA | Non-Small Cell Lu | Rizvi_CUMC | A0201,A2901,B3503, B5801,C0401,C0701 | A02,A01,A24,B07, B58,UNK,UNK | 0 | NA |
| PT364 | 2.9917797 | 0 | PD-1 | M1c | Stage 4 | 88 | F | NA | Non-Small Cell Lu | Rizvi_CUMC | A0205,A0301,B4101, B5001,C0602,C1701 | A02,A03,B44, B44,UNK,UNK | 0 | NA |
| PT365 | 4.8986283 | 0 | CTLA-4 + PD-1 | M1c | Stage 4 | 75.1 | M | NA | Non-Small Cell Lu | Rizvi_CUMC | A0201,A1101,B1301, B4001,C0304,C0702 | A02,A03,UNK, B44,UNK,UNK | 0 | NA |
| PT366 | NA | 1 | PD-1 | M1c | Stage 4 | 60.9 | F | NA | Non-Small Cell Lu | Rizvi_CUMC | NA | UNK | NA | NA |

APPENDIX 1

| | | | | | | | | | | Homozygous (1 = Yes; 0 = No) |
|---|---|---|---|---|---|---|---|---|---|---|
| Sample | Age Group | OS_Months | OS_Event | IMPACT-MutCnt | Drug Class | Cancer Type | Reference | HLA Class I Alleles | HLA Class I Super-types | |
| OB042257 | 31-50 | 1 | 0 | 7.9 | PD-1/PDL-1 | Non-Small Cell Lung Cancer | MSK-IMPACT | A3001,A3301,B1402,B1302,C0802,C0602 | A01A03,A03,B27,UNK,UNK,UNK | 0 |
| EB372668 | <30 | 0 | 0 | 4.39 | PD-1/PDL-1 | Melanoma | MSK-IMPACT | A3201,A0201,B0702,B1517,C0701,C0702 | A01,A02,B07,B58,UNK,UNK | 0 |
| BV379195 | >71 | 3 | 1 | 1.76 | PD-1/PDL-1 | Bladder Cancer | MSK-IMPACT | A1101,A3303,B5201,B5801,C0302,C1202 | A03,A03,B62,B58,UNK,UNK | 0 |
| NB536456 | 31-50 | 2 | 0 | 20.19 | PD-1/PDL-1 | Non-Small Cell Lung Cancer | MSK-IMPACT | A3401,A3303,B1525,B5801,C0302,C0403 | UNK,A03,B62,B58,UNK,UNK | 0 |
| RX904694 | 31-50 | 2 | 0 | 60.56 | PD-1/PDL-1 | Melanoma | MSK-IMPACT | A2402,A0201,B5501,B3501,C0102,C0401 | A24,A02,B07,B07,UNK,UNK | 0 |
| AN293177 | 61-70 | 1 | 0 | 1.76 | PD-1/PDL-1 | Glioma | MSK-IMPACT | A0101,A3101,B0702,B3901,C1203,C0702 | A01,A03,B07,B27,UNK,UNK | 0 |
| NA303088 | 31-50 | 4 | 0 | 7.02 | PD-1/PDL-1 | Renal Cell Carcinoma | MSK-IMPACT | A3101,A2601,B4001,B5801,C0304,C0706 | A03,A01,B44,B58,UNK,UNK | 0 |
| NC668467 | 50-60 | 1 | 0 | 10.53 | PD-1/PDL-1 | Head and Neck Cancer | MSK-IMPACT | A2402,A0201,B0702,B3906,C0702,C0702 | A24,A02,B07,B27,UNK,UNK | 1 |
| KW787528 | >71 | 2 | 0 | 2.63 | PD-1/PDL-1 | Glioma | MSK-IMPACT | A2601,A6901,B6701,B5501,C0102,C1203 | A01,A02,B07,B07,UNK,UNK | 0 |
| AW882070 | <30 | 2 | 0 | 2.63 | PD-1/PDL-1 | Non-Small Cell Lung Cancer | MSK-IMPACT | A0206,A0205,B4801,B5001,C0803,C0602 | A02,A02,B27,B44,UNK,UNK | 0 |
| NE179096 | 61-70 | 2 | 0 | 4.39 | PD-1/PDL-1 | Glioma | MSK-IMPACT | A2402,A2402,B3801,B1517,C1203,C0701 | A24,A24,B27,B58,UNK,UNK | 1 |
| HK537369 | 50-60 | 6 | 1 | 8.78 | Combo | Esophagogastric Cancer | MSK-IMPACT | A1101,A0101,B0801,B5501,C0303,C0701 | A03,A01,B08,B07,UNK,UNK | 0 |
| WL084588 | 50-60 | 5 | 0 | 2.63 | PD-1/PDL-1 | Renal Cell Carcinoma | MSK-IMPACT | A3002,A6801,B1001,B4402,C0304,C0401 | A01,A03,B44,B44,UNK,UNK | 0 |
| WV248294 | 31-50 | 6 | 0 | 0.88 | PD-1/PDL-1 | Non-Small Cell Lung Cancer | MSK-IMPACT | A0301,A2902,B0702,B4403,C1501,C0702 | A03,A01A24,B07,B44,UNK,UNK | 0 |
| QT721351 | 31-50 | 0 | 0 | 44.76 | PD-1/PDL-1 | Soft Tissue Sarcoma | MSK-IMPACT | A0301,A0201,B0702,B5601,C0102,C0702 | A03,A02,B07,B07,UNK,UNK | 0 |
| WE615011 | 61-70 | 2 | 0 | 7.02 | PD-1/PDL-1 | Non-Small Cell Lung Cancer | MSK-IMPACT | A1101,A0201,B0702,B0702,C0702,C0702 | A03,A02,B07,B07,UNK,UNK | 1 |
| RL562554 | 50-60 | 9 | 0 | 8.78 | PD-1/PDL-1 | Gastrointestinal Neuroendocrine Tumor | MSK-IMPACT | A1101,A2402,B3501,B5101,C1502,C0401 | A03,A24,B07,B07,UNK,UNK | 0 |
| GL866200 | >71 | 5 | 0 | 4.39 | PD-1/PDL-1 | Glioma | MSK-IMPACT | A0205,A3301,B1402,B5801,C0802,C0706 | A02,A03,B27,B58,UNK,UNK | 0 |
| DC990051 | 31-50 | 6 | 0 | 2.63 | PD-1/PDL-1 | Mesothelioma | MSK-IMPACT | A0301,A2601,B0702,B6701,C1203,C0702 | A03,A01,B07,B07,UNK,UNK | 0 |
| AO750281 | 31-50 | 2 | 0 | 7.9 | PD-1/PDL-1 | Non-Small Cell Lung Cancer | MSK-IMPACT | A3201,A0201,B3901,B1401,C0802,C1203 | A01,A02,B27,B27,UNK,UNK | 0 |
| RU065936 | 31-50 | 7 | 0 | 35.99 | PD-1/PDL-1 | Melanoma | MSK-IMPACT | A0301,A0201,B3501,B4901,C0401,C0701 | A03,A02,B07,UNK,UNK,UNK | 0 |
| PW329375 | 31-50 | 5 | 0 | 0 | PD-1/PDL-1 | Skin Cancer; Non-Melanoma | MSK-IMPACT | A0101,A3303,B0801,B1801,C1203,C0701 | A01,A03,B08,B44,UNK,UNK | 0 |
| BP983860 | 50-60 | 46 | 0 | 7.9 | PD-1/PDL-1 | Melanoma | MSK-IMPACT | A0301,A0201,B0702,B1501,C0401,C0702 | A03,A02,B07,B62,UNK,UNK | 0 |
| ZK434939 | >71 | 6 | 0 | 7.02 | PD-1/PDL-1 | Melanoma | MSK-IMPACT | A6801,A0201,B1501,B4402,C0303,C0501 | A03,A02,B62,B44,UNK,UNK | 0 |
| RJ401736 | 31-50 | 3 | 0 | 3.51 | PD-1/PDL-1 | Melanoma | MSK-IMPACT | A2403,A2402,B3502,B1801,C1203,C0401 | A24,A24,B07,B44,UNK,UNK | 0 |
| ZL338926 | 61-70 | 3 | 1 | 0 | PD-1/PDL-1 | Skin Cancer; Non-Melanoma | MSK-IMPACT | A3201,A0201,B0702,B3501,C0401,C0401 | A01,A02,B07,B07,UNK,UNK | 1 |
| PT088136 | 50-60 | 0 | 0 | 3.51 | PD-1/PDL-1 | Cancer of Unknown Primary | MSK-IMPACT | A2402,A0201,B1501,B4102,C0304,C1701 | A24,A02,B62,B44,UNK,UNK | 0 |
| VI665293 | 31-50 | 3 | 0 | 0.88 | PD-1/PDL-1 | Melanoma | MSK-IMPACT | A2402,A6801,B1501,B3503,C0303,C0401 | A24,A03,B62,B07,UNK,UNK | 0 |
| PZ793599 | 31-50 | 53 | 0 | 66.71 | PD-1/PDL-1 | Colorectal Cancer | MSK-IMPACT | A0101,A0201,B0702,B5701,C0602,C0702 | A01,A02,B07,B58,UNK,UNK | 0 |
| OS197548 | 31-50 | 2 | 0 | 10.53 | PD-1/PDL-1 | Non-Small Cell Lung Cancer | MSK-IMPACT | A3002,A6901,B5501,B1801,C0102,C0501 | A01,A02,B07,B44,UNK,UNK | 0 |
| LR136554 | 61-70 | 3 | 0 | 2.63 | PD-1/PDL-1 | Glioma | MSK-IMPACT | A1101,A0207,B4601,B1527,C0102,C0401 | A03,A02,B62,UNK,UNK,UNK | 0 |
| WH928128 | 31-50 | 2 | 0 | 7.02 | PD-1/PDL-1 | Non-Small Cell Lung Cancer | MSK-IMPACT | A0101,A0201,B0702,B0801,C0701,C0702 | A01,A02,B07,B08,UNK,UNK | 0 |
| KB960411 | 50-60 | 1 | 0 | 52.66 | PD-1/PDL-1 | Glioma | MSK-IMPACT | A0101,A2902,B3701,B5801,C0602,C0706 | A01,A01A24,B44,B58,UNK,UNK | 0 |
| IH002321 | 50-60 | 2 | 0 | 10.53 | PD-1/PDL-1 | Non-Small Cell Lung Cancer | MSK-IMPACT | A7401,A2301,B1503,B4501,C0210,C0602 | A03,A24,B27,B44,UNK,UNK | 0 |
| HT275463 | 50-60 | 5 | 0 | 2.63 | PD-1/PDL-1 | Renal Cell Carcinoma | MSK-IMPACT | A2402,A2402,B0702,B5701,C0602,C0702 | A24,A24,B07,B58,UNK,UNK | 1 |

APPENDIX 1-continued

Cohort 2

| Sample | Age Group | OS_ Months | OS_ Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| AQ286794 | 31-50 | 1 | 0 | 7.02 | PD-1/PDL-1 | Non-Small Cell Lung Cancer | MSK-IMPACT | A0301,A0201,B0702, B3501,C0401,C0702 | A03,A02,B07, B07,UNK,UNK | 0 |
| VK425379 | 31-50 | 0 | 0 | 1.76 | PD-1/PDL-1 | Melanoma | MSK-IMPACT | A1101,A0201,B0702, B4402,C0501,C0702 | A03,A02,B07, B44,UNK,UNK | 0 |
| FH814563 | 31-50 | 2 | 0 | 69.34 | Combo | Melanoma | MSK-IMPACT | A0101,A2402,B5501, B5801,C0102,C0706 | A01,A24,B07, B58,UNK,UNK | 0 |
| DS020834 | 31-50 | 0 | 0 | 12.29 | PD-1/PDL-1 | Cancer of Unknown Primary | MSK-IMPACT | A2301,A6901,B3502, B5801,C0401,C0706 | A24,A02,B07, B58,UNK,UNK | 0 |
| QI713515 | 50-60 | 4 | 0 | 5.27 | PD-1/PDL-1 | Glioma | MSK-IMPACT | A3201,A0201,B4402, B5201,C1202,C0501 | A01,A02,B44, B62,UNK,UNK | 0 |
| IK662613 | >71 | 4 | 0 | 0 | PD-1/PDL-1 | Melanoma | MSK-IMPACT | A0101,A0201,B0702, B1302,C0602,C0702 | A01,A02,B07, UNK,UNK,UNK | 0 |
| CD689551 | 50-60 | 1 | 0 | 20.19 | PD-1/PDL-1 | Non-Small Cell Lung Cancer | MSK-IMPACT | A0101,A3303,B0702, B1801,C1505,C1203 | A01,A03,B07, B44,UNK,UNK | 0 |
| OD111817 | 50-60 | 0 | 0 | 11.41 | PD-1/PDL-1 | Bladder Cancer | MSK-IMPACT | A1101,A0101,B5701, B3701,C0602,C0602 | A03,A01,B58, B44,UNK,UNK | 1 |
| LS167399 | >71 | 1 | 0 | 8.78 | PD-1/PDL-1 | Head and Neck Cancer | MSK-IMPACT | A0301,A2601,B0702, B0702,C0702,C0702 | A03,A01,B07, B07,UNK,UNK | 1 |
| EL499261 | 50-60 | 0 | 1 | 4.39 | Combo | Non-Small Cell Lung Cancer | MSK-IMPACT | A1101,A1101,B5502, B3503,C0102,C1203 | A03,A03,B07, B07,UNK,UNK | 1 |
| BD241560 | 31-50 | 1 | 0 | 36.86 | Combo | Cancer of Unknown Primary | MSK-IMPACT | A2301,A6801,B5501, B4403,C0303,C0401 | A24,A03,B07, B44,UNK,UNK | 0 |
| WJ952117 | 31-50 | 1 | 0 | 8.78 | PD-1/PDL-1 | Bladder Cancer | MSK-IMPACT | A2902,A6802,B1402, B1402,C0802,C0802 | A01A24,A02,B27, B27,UNK,UNK | 1 |
| YR990519 | 50-60 | 0 | 0 | 21.94 | PD-1/PDL-1 | Non-Small Cell Lung Cancer | MSK-IMPACT | A0201,A0205,B1501, B4901,C0303,C0701 | A02,A02,B62, UNK,UNK,UNK | 0 |
| JL090305 | >71 | 4 | 0 | 2.63 | Combo | Melanoma | MSK-IMPACT | A0101,A0201,B4001, B3701,C0304,C0602 | A01,A02,B44, B44,UNK,UNK | 0 |
| VK851705 | 50-60 | 13 | 0 | 3.51 | Combo | Bladder Cancer | MSK-IMPACT | A1101,A0201,B1509, B3501,C0401,C0704 | A03,A02,B27, B07,UNK,UNK | 0 |
| WE602111 | 31-50 | 2 | 0 | 28.09 | PD-1/PDL-1 | Melanoma | MSK-IMPACT | A0101,A6802,B0801, B1402,C0802,C0701 | A01,A02,B08, B27,UNK,UNK | 0 |
| DL240387 | 50-60 | 2 | 0 | 57.93 | PD-1/PDL-1 | Bladder Cancer | MSK-IMPACT | A0101,A2402,B0801, B3501,C0401,C0701 | A01,A24,B08, B07,UNK,UNK | 0 |
| SE949393 | 50-60 | 3 | 0 | 22.82 | PD-1/PDL-1 | Non-Small Cell Lung Cancer | MSK-IMPACT | A0201,A0201,B1501, B4402,C0304,C0501 | A02,A02,B62, B44,UNK,UNK | 1 |
| VK102917 | 31-50 | 1 | 1 | 8.78 | PD-1/PDL-1 | Non-Small Cell Lung Cancer | MSK-IMPACT | A0101,A2902,B0801, B4403,C1601,C0701 | A01,A01A24,B08, B44,UNK,UNK | 0 |
| EX315834 | 31-50 | 9 | 0 | 0 | PD-1/PDL-1 | Skin Cancer; Non-Melanoma | MSK-IMPACT | A2301,A6802,B1402, B4901,C0701,C0802 | A24,A02,B27, UNK,UNK,UNK | 0 |
| GD961875 | 31-50 | 7 | 0 | 6.14 | PD-1/PDL-1 | Bladder Cancer | MSK-IMPACT | A0101,A0201,B0801, B3501,C0401,C0701 | A01,A02,B08, B07,UNK,UNK | 0 |
| GJ549646 | 31-50 | 22 | 0 | 5.27 | Combo | Bladder Cancer | MSK-IMPACT | A6601,A2601,B3801, B3508,C0401,C1203 | A03,A01,B27, B07,UNK,UNK | 0 |
| YL846622 | 61-70 | 0 | 0 | 1.76 | PD-1/PDL-1 | Hepatobiliary Cancer | MSK-IMPACT | A2402,A0201,B3501, B1302,C1402,C0602 | A24,A02,B07, UNK,UNK,UNK | 0 |
| TJ956009 | 31-50 | 0 | 0 | 9.65 | PD-1/PDL-1 | Non-Small Cell Lung Cancer | MSK-IMPACT | A1101,A0101,B3801, B3801,C1203,C1203 | A03,A01,B27, B27,UNK,UNK | 1 |
| PL020321 | 31-50 | 1 | 0 | 17.55 | PD-1/PDL-1 | Bladder Cancer | MSK-IMPACT | A0201,A0201,B1501, B5801,C0303,C0706 | A02,A02,B62, B58,UNK,UNK | 1 |
| OP960829 | 61-70 | 5 | 0 | 1.76 | Combo | Melanoma | MSK-IMPACT | A1101,A3101,B3801, B3501,C1203,C0401 | A03,A03,B27, B07,UNK,UNK | 0 |
| IN807029 | 31-50 | 1 | 0 | 6.14 | PD-1/PDL-1 | Melanoma | MSK-IMPACT | A2901,A2601,B0705, B3801,C1505,C1203 | A01A24,A01,B07, B27,UNK,UNK | 0 |
| ZV102948 | 31-50 | 3 | 0 | 1.76 | CTLA4 | Melanoma | MSK-IMPACT | A0103,A6501,B7301, B3501,C1505,C0401 | A01,A03,B27, B07,UNK,UNK | 0 |
| HV623240 | 31-50 | 4 | 0 | 6.14 | PD-1/PDL-1 | Melanoma | MSK-IMPACT | A2402,A2301,B1501, B4901,C0303,C0701 | A24,A24,B62, UNK,UNK,UNK | 0 |
| IB174035 | 50-60 | 10 | 0 | 5.27 | PD-1/PDL-1 | Renal Cell Carcinoma | MSK-IMPACT | A2402,A2601,B1801, B4102,C1203,C1701 | A24,A01,B44, B44,UNK,UNK | 0 |
| NA945383 | 31-50 | 16 | 0 | 4.39 | PD-1/PDL-1 | Non-Small Cell Lung Cancer | MSK-IMPACT | A2601,A2601,B3801, B3801,C1203,C1203 | A01,A01,B27, B27,UNK,UNK | 1 |
| AE200159 | >71 | 5 | 0 | 2.63 | PD-1/PDL-1 | Glioma | MSK-IMPACT | A0301,A3002,B4101, B5101,C0202,C0602 | A03,A01,B44, B07,UNK,UNK | 0 |
| HG070027 | 31-50 | 3 | 0 | 14.92 | PD-1/PDL-1 | Non-Small Cell Lung Cancer | MSK-IMPACT | A0301,A0201,B0702, B4402,C0501,C0702 | A03,A02,B07, B44,UNK,UNK | 0 |
| PH640297 | 50-60 | 4 | 0 | 14.92 | PD-1/PDL-1 | Non-Small Cell Lung Cancer | MSK-IMPACT | A3303,A3402,B1510, B5101,C0804,C1601 | A03,A03,B27, B07,UNK,UNK | 0 |
| FD411530 | 31-50 | 12 | 0 | 7.9 | PD-1/PDL-1 | Non-Small Cell Lung Cancer | MSK-IMPACT | A0301,A2901,B0705, B5601,C0102,C1505 | A03,A01A24,B07, B07,UNK,UNK | 0 |

APPENDIX 1-continued

| | | | | | | Cohort 2 | | | | |
|---|---|---|---|---|---|---|---|---|---|---|
| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
| RI929197 | 50-60 | 5 | 0 | 2.63 | PD-1/PDL-1 | Renal Cell Carcinoma | MSK-IMPACT | A1101,A2902,B5001, B5201,C1202,C0602 | A03,A01A24,B44, B62,UNK,UNK | 0 |
| GS234640 | 31-50 | 0 | 0 | 14.04 | PD-1/PDL-1 | Non-Small Cell Lung Cancer | MSK-IMPACT | A1101,A3303,B4601, B4403,C0103,C0706 | A03,A03,B62, B44,UNK,UNK | 0 |
| TZ388736 | 61-70 | 3 | 0 | 11.41 | PD-1/PDL-1 | Melanoma | MSK-IMPACT | A0101,A0201,B3906, B5701,C0602,C0702 | A01,A02,B27, B58,UNK,UNK | 0 |
| HR904519 | 31-50 | 3 | 0 | 17.55 | PD-1/PDL-1 | Melanoma | MSK-IMPACT | A0301,A0201,B0702, B5201,C1202,C0702 | A03,A02,B07, B62,UNK,UNK | 0 |
| MQ748114 | 61-70 | 3 | 0 | 1.76 | PD-1/PDL-1 | Melanoma | MSK-IMPACT | A0301,A0201,B0702, B4402,C0501,C0702 | A03,A02,B07, B44,UNK,UNK | 0 |
| YD623028 | 31-50 | 6 | 0 | 2.63 | PD-1/PDL-1 | Bladder Cancer | MSK-IMPACT | A3002,A0201,B1801, B4901,C0501,C0701 | A01,A02,B44, UNK,UNK,UNK | 0 |
| QV517854 | 61-70 | 4 | 0 | 1.76 | PD-1/PDL-1 | Renal Cell Carcinoma | MSK-IMPACT | A0301,A0201,B0702, B4402,C0501,C1202 | A03,A02,B07, B44,UNK,UNK | 0 |
| OM156383 | 31-50 | 14 | 0 | 9.65 | Combo | Bladder Cancer | MSK-IMPACT | A0201,A3301,B1402, B1801,C0802,C1203 | A02,A03,B07, B44,UNK,UNK | 0 |
| DO395401 | 31-50 | 2 | 0 | 1.76 | Combo | Melanoma | MSK-IMPACT | A6601,A2601,B3801, B3801,C1203,C1203 | A03,A01,B27, B27,UNK,UNK | 1 |
| ED236873 | 31-50 | 1 | 1 | 14.92 | PD-1/PDL-1 | Non-Small Cell Lung Cancer | MSK-IMPACT | A0301,A0101,B0801, B1402,C0802,C0701 | A03,A01,B08, B27,UNK,UNK | 0 |
| LQ491699 | 31-50 | 3 | 0 | 10.53 | Combo | Small Cell Lung Cancer | MSK-IMPACT | A2601,A0201,B0801, B1801,C0702,C0701 | A01,A02,B08, B44,UNK,UNK | 0 |
| RH138187 | 31-50 | 0 | 0 | 24.58 | PD-1/PDL-1 | Non-Small Cell Lung Cancer | MSK-IMPACT | A2403,A0201,B3801, B1518,C1203,C0704 | A24,A02,B27, B27,UNK,UNK | 0 |
| JE984424 | 50-60 | 4 | 0 | 5.27 | PD-1/PDL-1 | Renal Cell Carcinoma | MSK-IMPACT | A0101,A2301,B3801, B5301,C0602,C0401 | A01,A24,B27, B07,UNK,UNK | 0 |
| HN039410 | 61-70 | 1 | 0 | 4.39 | PD-1/PDL-1 | Breast Cancer | MSK-IMPACT | A1101,A0201,B0702, B0801,C0701,C0702 | A03,A02,B07, B08,UNK,UNK | 0 |
| LR229562 | 31-50 | 3 | 0 | 7.02 | Combo | Cancer of Unknown Primary | MSK-IMPACT | A2402,A3301,B1402, B3502,C0802,C0401 | A24,A03,B27, B07,UNK,UNK | 0 |
| WA186194 | 31-50 | 6 | 0 | 2.63 | PD-1/PDL-1 | Adrenocortical Carcinoma | MSK-IMPACT | A2301,A2901,B0705, B4403,C1505,C0401 | A24,A01A24,B07, B44,UNK,UNK | 0 |
| ES387661 | 31-50 | 1 | 0 | 29.84 | PD-1/PDL-1 | Non-Small Cell Lung Cancer | MSK-IMPACT | A2601,A0205,B5101, B5801,C0102,C0706 | A01,A02,B07, B58,UNK,UNK | 0 |
| AE162231 | >71 | 4 | 0 | 30.72 | PD-1/PDL-1 | Melanoma | MSK-IMPACT | A0301,A0101,B0702, B1501,C0304,C0702 | A03,A01,B07, B62,UNK,UNK | 0 |
| AH329297 | 31-50 | 1 | 0 | 23.7 | PD-1/PDL-1 | Bladder Cancer | MSK-IMPACT | A2402,A2402,B3901, B1801,C0501,C1203 | A24,A24,B27, B44,UNK,UNK | 1 |
| VB175191 | 31-50 | 3 | 0 | 12.29 | PD-1/PDL-1 | Non-Small Cell Lung Cancer | MSK-IMPACT | A3001,A0101,B0801, B1302,C0602,C0701 | A01A24,A01,B08, UNK,UNK,UNK | 0 |
| YX309246 | <30 | 0 | 0 | 3.51 | PD-1/PDL-1 | Cancer of Unknown Primary | MSK-IMPACT | A0101,A0101,B4002, B5701,C0202,C0602 | A01,A01,B44, B58,UNK,UNK | 1 |
| RC276819 | >71 | 4 | 0 | 30.72 | Combo | Melanoma | MSK-IMPACT | A3201,A3201,B1501, B3501,C0303,C0401 | A01,A01,B62, B07,UNK,UNK | 1 |
| DT499956 | 61-70 | 4 | 0 | 6.14 | PD-1/PDL-1 | Melanoma | MSK-IMPACT | A0301,A0301,B0702, B3501,C0401,C0702 | A03,A03,B07, B07,UNK,UNK | 1 |
| GS256044 | 50-60 | 0 | 1 | 23.7 | PD-1/PDL-1 | Adrenocortical Carcinoma | MSK-IMPACT | A0201,A0201,B5701, B3501,C0602,C0401 | A02,A02,B58, B07,UNK,UNK | 1 |
| TO930220 | 31-50 | 3 | 0 | 6.14 | PD-1/PDL-1 | Bladder Cancer | MSK-IMPACT | A0301,A3301,B1402, B2702,C0802,C0202 | A03,A03,B27, B27,UNK,UNK | 0 |
| YF920516 | 31-50 | 4 | 1 | 8.78 | PD-1/PDL-1 | Non-Small Cell Lung Cancer | MSK-IMPACT | A0301,A3001,B5701, B1801,C0602,C0701 | A03,A01A03,B58, B44,UNK,UNK | 0 |
| IN573123 | 31-50 | 4 | 0 | 28.96 | PD-1/PDL-1 | Non-Small Cell Lung Cancer | MSK-IMPACT | A0101,A2601,B3801, B5801,C1203,C0706 | A01,A01,B27, B58,UNK,UNK | 0 |
| TG765862 | 31-50 | 3 | 0 | 0.88 | PD-1/PDL-1 | Adrenocortical Carcinoma | MSK-IMPACT | A0101,A0201,B0801, B0702,C0303,C0701 | A01,A02,B08, B07,UNK,UNK | 0 |
| OV436909 | 61-70 | 0 | 0 | 8.78 | PD-1/PDL-1 | Cancer of Unknown Primary | MSK-IMPACT | A6602,A3303,B5801, B5301,C0404,C0706 | A03,A03,B58, B07,UNK,UNK | 0 |
| UA206372 | 61-70 | 3 | 0 | 24.58 | Combo | Melanoma | MSK-IMPACT | A0301,A0201,B0801, B4402,C0501,C0701 | A03,A02,B08, B44,UNK,UNK | 0 |
| OX953757 | 31-50 | 0 | 0 | 5.27 | PD-1/PDL-1 | Renal Cell Carcinoma | MSK-IMPACT | A3201,A0201,B5501, B5101,C0102,C1402 | A01,A02,B07, B07,UNK,UNK | 0 |
| PJ953909 | 50-60 | 0 | 0 | 11.41 | PD-1/PDL-1 | Non-Small Cell Lung Cancer | MSK-IMPACT | A0301,A1101,B3501, B5101,C1502,C0401 | A03,A03,B07, B07,UNK,UNK | 0 |
| XA307833 | 50-60 | 0 | 0 | 2.63 | PD-1/PDL-1 | Adrenocortical Carcinoma | MSK-IMPACT | A0205,A2601,B3501, B5001,C0602,C0401 | A02,A01,B07, B44,UNK,UNK | 0 |
| JX834810 | >71 | 1 | 0 | 0.88 | PD-1/PDL-1 | Breast Cancer | MSK-IMPACT | A0301,A0201,B5703, B5801,C0706,C1801 | A03,A02,B58, B58,UNK,UNK | 0 |
| YQ490591 | 31-50 | 2 | 0 | 5.27 | PD-1/PDL-1 | Melanoma | MSK-IMPACT | A0301,A3201,B3801, B3501,C1203,C0401 | A03,A01,B27, B07,UNK,UNK | 0 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| QZ553792 | 31-50 | 0 | 0 | 19.31 | PD-1/PDL-1 | Non-Small Cell Lung Cancer | MSK-IMPACT | A3001,A2402,B3501, B1302,C0602,C0401 | A01A03,A24,B07, UNK,UNK,UNK | 0 |
| MF150507 | 31-50 | 2 | 0 | 10.53 | PD-1/PDL-1 | Melanoma | MSK-IMPACT | A0301,A0101,B0702, B0702,C0702,C0702 | A03,A01,B07, B07,UNK,UNK | 1 |
| PG599368 | 31-50 | 6 | 0 | 4.39 | PD-1/PDL-1 | Non-Small Cell Lung Cancer | MSK-IMPACT | A0101,A0201,B0801, B1516,C1402,C0701 | A01,A02,B08, B58,UNK,UNK | 0 |
| LE993613 | 61-70 | 9 | 0 | 3.51 | CTLA4 | Breast Cancer | MSK-IMPACT | A1101,A0201,B1803, B3503,C0401,C0701 | A03,A02,B44, B07,UNK,UNK | 0 |
| LS244934 | 31-50 | 0 | 0 | 6.14 | PD-1/PDL-1 | Non-Small Cell Lung Cancer | MSK-IMPACT | A0201,A0201,B4402, B1501,C0401,C0501 | A02,A02,B44, B62,UNK,UNK | 1 |
| EW664244 | 31-50 | 9 | 0 | 14.04 | PD-1/PDL-1 | Non-Small Cell Lung Cancer | MSK-IMPACT | A0201,A3101,B0702, B1801,C0701,C0702 | A02,A03,B07, B44,UNK,UNK | 0 |
| NK732633 | 50-60 | 2 | 0 | 21.07 | Combo | Melanoma | MSK-IMPACT | A0301,A3002,B5604, B3501,C0102,C0401 | A03,A01,B07, B07,UNK,UNK | 0 |
| HP971166 | 31-50 | 0 | 0 | 2.63 | PD-1/PDL-1 | Melanoma | MSK-IMPACT | A0301,A2402,B4002, B3501,C0202,C0401 | A03,A24,B44, B07,UNK,UNK | 0 |
| WD007754 | 31-50 | 9 | 0 | 3.51 | PD-1/PDL-1 | Bladder Cancer | MSK-IMPACT | A1101,A0201,B4402, B5101,C1502,C0501 | A03,A02,B44, B07,UNK,UNK | 0 |
| OE782061 | 31-50 | 1 | 0 | 13.17 | PD-1/PDL-1 | Non-Small Cell Lung Cancer | MSK-IMPACT | A0101,A2601,B0801, B2705,C0202,C0701 | A01,A01,B08, B27,UNK,UNK | 0 |
| DD060789 | 61-70 | 9 | 0 | 13.17 | PD-1/PDL-1 | Colorectal Cancer | MSK-IMPACT | A2402,A3101,B0702, B3501,C0401,C0702 | A24,A03,B07, B07,UNK,UNK | 0 |
| RA911363 | 50-60 | 0 | 0 | 1.76 | PD-1/PDL-1 | Cancer of Unknown Primary | MSK-IMPACT | A0301,A1101,B5701, B5301,C0401,C0602 | A03,A03,B58, B07,UNK,UNK | 0 |
| CV324207 | >71 | 1 | 0 | 0.88 | PD-1/PDL-1 | Breast Cancer | MSK-IMPACT | A0301,A0101,B0702, B5701,C0602,C0702 | A03,A01,B07, B58,UNK,UNK | 0 |
| RV653854 | 31-50 | 2 | 0 | 51.79 | PD-1/PDL-1 | Melanoma | MSK-IMPACT | A0101,A2402,B0801, B1801,C1203,C0701 | A01,A24,B08, B44,UNK,UNK | 0 |
| MM502191 | 50-60 | 2 | 1 | 2.63 | PD-1/PDL-1 | Breast Cancer | MSK-IMPACT | A0101,A0101,B0801, B0801,C0701,C0701 | A01,A01,B08, B08,UNK,UNK | 1 |
| TY080273 | 61-70 | 0 | 0 | 6.14 | PD-1/PDL-1 | Colorectal Cancer | MSK-IMPACT | A2301,A3301,B4201, B7801,C1601,C1701 | A24,A03,B07, B07,UNK,UNK | 0 |
| CF668249 | >71 | 0 | 0 | 3.51 | PD-1/PDL-1 | Melanoma | MSK-IMPACT | A0301,A1101,B0702, B3501,C0401,C0702 | A03,A03,B07, B07,UNK,UNK | 0 |
| HI514659 | 31-50 | 3 | 0 | 1.76 | Combo | Melanoma | MSK-IMPACT | A2402,A3201,B5701, B5101,C1402,C0602 | A24,A01,B58, B07,UNK,UNK | 0 |
| RY826164 | 31-50 | 1 | 0 | 2.63 | PD-1/PDL-1 | Non-Small Cell Lung Cancer | MSK-IMPACT | A0201,A0201,B1801, B5502,C0102,C1203 | A02,A02,B44, B07,UNK,UNK | 1 |
| GK989158 | 31-50 | 5 | 1 | 24.58 | PD-1/PDL-1 | Non-Small Cell Lung Cancer | MSK-IMPACT | A0301,A0101,B0801, B1501,C0303,C0701 | A03,A01,B08, B62,UNK,UNK | 0 |
| RF088631 | 61-70 | 4 | 0 | 4.39 | PD-1/PDL-1 | Glioma | MSK-IMPACT | A0301,A0101,B0702, B0801,C0701,C0702 | A03,A01,B07, B08,UNK,UNK | 0 |
| BX552244 | 31-50 | 2 | 0 | 23.7 | PD-1/PDL-1 | Bladder Cancer | MSK-IMPACT | A2402,A0201,B4002, B1501,C0303,C0202 | A24,A02,B44, B62,UNK,UNK | 0 |
| HT859944 | 31-50 | 4 | 0 | 5.27 | PD-1/PDL-1 | Non-Small Cell Lung Cancer | MSK-IMPACT | A0201,A6901,B4402, B5101,C1502,C0501 | A02,A02,B44, B07,UNK,UNK | 0 |
| OF320000 | 31-50 | 0 | 0 | 8.78 | PD-1/PDL-1 | Bladder Cancer | MSK-IMPACT | A2301,A2402,B4101, B4901,C0701,C1701 | A24,A24,B44, UNK,UNK,UNK | 0 |
| UC505968 | >71 | 3 | 0 | 7.9 | PD-1/PDL-1 | Head and Neck Cancer | MSK-IMPACT | A3001,A0201,B4201, B3501,C1601,C1701 | A01A03,A02,B07, B07,UNK,UNK | 0 |
| SV274110 | 31-50 | 7 | 0 | 0.88 | PD-1/PDL-1 | Non-Small Cell Lung Cancer | MSK-IMPACT | A0301,A2402,B2705, B5101,C0102,C0202 | A03,A24,B27, B07,UNK,UNK | 0 |
| XE015183 | >71 | 0 | 0 | 16.68 | Combo | Cancer of Unknown Primary | MSK-IMPACT | A2402,A0201,B4001, B4001,C0304,C0304 | A24,A02,B44, B44,UNK,UNK | 1 |
| IY101457 | 50-60 | 5 | 0 | 0 | PD-1/PDL-1 | Head and Neck Cancer | MSK-IMPACT | A0205,A3301,B1402, B5001,C0802,C0602 | A02,A03,B27, B44,UNK,UNK | 0 |
| OA243943 | 31-50 | 14 | 0 | 46.52 | Combo | Breast Cancer | MSK-IMPACT | A0301,A0101,B0801, B0801,C0701,C0701 | A03,A01,B08, B08,UNK,UNK | 1 |
| GV237003 | 31-50 | 1 | 0 | 23.7 | PD-1/PDL-1 | Head and Neck Cancer | MSK-IMPACT | A0101,A2601,B0801, B1503,C1203,C0701 | A01,A01,B08, B27,UNK,UNK | 0 |
| QM933384 | 31-50 | 2 | 0 | 18.43 | PD-1/PDL-1 | Melanoma | MSK-IMPACT | A2402,A3301,B1401, B1517,C0802,C0701 | A24,A03,B27, B58,UNK,UNK | 0 |
| BF819843 | 31-50 | 1 | 0 | 5.27 | PD-1/PDL-1 | Head and Neck Cancer | MSK-IMPACT | A6807,A3201,B2702, B4402,C0202,C0501 | A02,A01,B27, B44,UNK,UNK | 0 |
| KV679102 | 50-60 | 6 | 0 | 35.11 | Combo | Melanoma | MSK-IMPACT | A0302,A0201,B0801, B0801,C0701,C0701 | A03,A02,B08, B08,UNK,UNK | 1 |
| WW331877 | 31-50 | 7 | 0 | 14.04 | PD-1/PDL-1 | Bladder Cancer | MSK-IMPACT | A1101,A0201,B1801, B3501,C0401,C0701 | A03,A02,B44, B07,UNK,UNK | 0 |
| HI004568 | 31-50 | 4 | 0 | 42.13 | PD-1/PDL-1 | Bladder Cancer | MSK-IMPACT | A0201,A0201,B4403, B3503,C1601,C0401 | A02,A02,B44, B07,UNK,UNK | 1 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| OW961409 | <30 | 0 | 0 | 1.76 | PD-1/PDL-1 | Melanoma | MSK-IMPACT | A0101,A0201,B0801,B4402,C0501,C0701 | A01,A02,B08,B44,UNK,UNK | 0 |
| UB602657 | 50-60 | 0 | 1 | 7.9 | PD-1/PDL-1 | Non-Small Cell Lung Cancer | MSK-IMPACT | A0205,A0201,B4006,B5001,C1502,C0602 | A02,A02,B44,B44,UNK,UNK | 0 |
| ND701493 | 50-60 | 4 | 0 | 26.33 | Combo | Melanoma | MSK-IMPACT | A0301,A0101,B5501,B1402,C0303,C0802 | A03,A01,B07,B27,UNK,UNK | 0 |
| ND919429 | 61-70 | 5 | 0 | 6.14 | PD-1/PDL-1 | Non-Small Cell Lung Cancer | MSK-IMPACT | A0101,A0201,B4002,B4402,C0202,C0704 | A01,A02,B44,B44,UNK,UNK | 0 |
| LH998687 | 50-60 | 2 | 0 | 79.87 | Combo | Melanoma | MSK-IMPACT | A3201,A0201,B4402,B4402,C0501,C0704 | A01,A02,B44,B44,UNK,UNK | 1 |
| MX747377 | 50-60 | 3 | 0 | 21.07 | PD-1/PDL-1 | Non-Small Cell Lung Cancer | MSK-IMPACT | A0301,A2402,B3801,B3502,C1203,C0401 | A03,A24,B27,B07,UNK,UNK | 0 |
| EJ342170 | 31-50 | 1 | 0 | 4.39 | PD-1/PDL-1 | Head and Neck Cancer | MSK-IMPACT | A1101,A2402,B3501,B4402,C0401,C0501 | A03,A24,B07,B44,UNK,UNK | 0 |
| RR251424 | 50-60 | 1 | 1 | 5.27 | PD-1/PDL-1 | Non-Small Cell Lung Cancer | MSK-IMPACT | A7401,A0201,B1801,B1801,C0202,C0701 | A03,A02,B44,B44,UNK,UNK | 1 |
| AY135758 | 50-60 | 2 | 0 | 8.78 | PD-1/PDL-1 | Cancer of Unknown Primary | MSK-IMPACT | A0201,A0201,B0702,B0702,C0304,C0702 | A02,A02,B07,B07,UNK,UNK | 1 |
| YD425234 | 61-70 | 1 | 0 | 4.39 | PD-1/PDL-1 | Non-Small Cell Lung Cancer | MSK-IMPACT | A6802,A3201,B1503,B7801,C0304,C1601 | A02,A01,B27,B07,UNK,UNK | 0 |
| TO095715 | <30 | 2 | 0 | 5.27 | PD-1/PDL-1 | Non-Small Cell Lung Cancer | MSK-IMPACT | A0101,A2402,B0801,B2702,C0202,C0701 | A01,A24,B08,B27,UNK,UNK | 0 |
| NE782263 | 61-70 | 2 | 0 | 19.31 | PD-1/PDL-1 | Melanoma | MSK-IMPACT | A0301,A2902,B1402,B1501,C0304,C0802 | A03,A01A24,B27,B62,UNK,UNK | 0 |
| KN798898 | 50-60 | 3 | 0 | 0.88 | PD-1/PDL-1 | Mesothelioma | MSK-IMPACT | A2901,A2601,B3801,B5701,C1203,C0701 | A01A24,A01,B27,B58,UNK,UNK | 0 |
| IR692253 | 50-60 | 3 | 0 | 9.65 | PD-1/PDL-1 | Non-Small Cell Lung Cancer | MSK-IMPACT | A0101,A0101,B3502,B5703,C0401,C0602 | A01,A01,B07,B58,UNK,UNK | 1 |
| YH996041 | 31-50 | 24 | 0 | 31.6 | PD-1/PDL-1 | Bladder Cancer | MSK-IMPACT | A1101,A2601,B0702,B4402,C0501,C0702 | A03,A01,B07,B44,UNK,UNK | 0 |
| VT397227 | 31-50 | 3 | 1 | 6.14 | PD-1/PDL-1 | Bladder Cancer | MSK-IMPACT | A0301,A6801,B0801,B4402,C0501,C0701 | A03,A03,B08,B44,UNK,UNK | 0 |
| JI889906 | 31-50 | 6 | 0 | 15.8 | PD-1/PDL-1 | Bladder Cancer | MSK-IMPACT | A2601,A6801,B3801,B5701,C1203,C0701 | A01,A03,B27,B58,UNK,UNK | 0 |
| OR646732 | 31-50 | 3 | 0 | 15.8 | PD-1/PDL-1 | Non-Hodgkin Lymphoma | MSK-IMPACT | A2601,A2601,B2705,B1801,C0202,C1203 | A01,A01,B27,B44,UNK,UNK | 1 |
| UD537460 | 61-70 | 2 | 0 | 5.27 | PD-1/PDL-1 | Non-Small Cell Lung Cancer | MSK-IMPACT | A0301,A0101,B1501,B3501,C0303,C0401 | A03,A01,B62,B07,UNK,UNK | 0 |
| LM227756 | 50-60 | 0 | 0 | 4.39 | PD-1/PDL-1 | Glioma | MSK-IMPACT | A0201,A0205,B4101,B1501,C0304,C0701 | A02,A02,B44,B62,UNK,UNK | 0 |
| VW330608 | <30 | 1 | 0 | 5.27 | PD-1/PDL-1 | Non-Small Cell Lung Cancer | MSK-IMPACT | A0101,A2601,B0801,B3801,C1203,C0701 | A01,A01,B08,B27,UNK,UNK | 0 |
| MC345007 | 61-70 | 4 | 0 | 5.27 | Combo | Melanoma | MSK-IMPACT | A2901,A2601,B0705,B3801,C1505,C1203 | A01A24,A01,B07,B27,UNK,UNK | 0 |
| BC681957 | 50-60 | 4 | 0 | 2.63 | PD-1/PDL-1 | Renal Cell Carcinoma | MSK-IMPACT | A0201,A0201,B0702,B4402,C0501,C0702 | A02,A02,B07,B44,UNK,UNK | 1 |
| MS303882 | 61-70 | 9 | 0 | 3.51 | PD-1/PDL-1 | Esophagogastric Cancer | MSK-IMPACT | A0201,A0201,B0702,B4402,C0501,C0501 | A02,A02,B07,B44,UNK,UNK | 1 |
| ZY851796 | 50-60 | 7 | 1 | 5.27 | PD-1/PDL-1 | Bladder Cancer | MSK-IMPACT | A2601,A0201,B2705,B4403,C0102,C0401 | A01,A02,B27,B44,UNK,UNK | 0 |
| DE743683 | 31-50 | 0 | 0 | 2.63 | PD-1/PDL-1 | Non-Small Cell Lung Cancer | MSK-IMPACT | A1101,A0207,B2705,B5801,C0102,C0302 | A03,A02,B27,B58,UNK,UNK | 0 |
| XC690073 | 50-60 | 1 | 0 | 7.9 | PD-1/PDL-1 | Non-Small Cell Lung Cancer | MSK-IMPACT | A1101,A0201,B5501,B4405,C0303,C0202 | A03,A02,B07,B44,UNK,UNK | 0 |
| LI926221 | 31-50 | 1 | 0 | 5.27 | PD-1/PDL-1 | Bladder Cancer | MSK-IMPACT | A0201,A0201,B4102,B4405,C0202,C1701 | A02,A02,B44,B44,UNK,UNK | 1 |
| SK041077 | 31-50 | 2 | 0 | 4.39 | PD-1/PDL-1 | Non-Small Cell Lung Cancer | MSK-IMPACT | A0201,A0201,B4101,B1801,C0701,C1701 | A02,A02,B44,B44,UNK,UNK | 1 |
| BU012611 | 31-50 | 3 | 0 | 3.51 | PD-1/PDL-1 | Bladder Cancer | MSK-IMPACT | A3201,A0201,B1401,B5201,C1202,C0802 | A01,A02,B27,B62,UNK,UNK | 0 |
| JK338812 | 50-60 | 10 | 0 | 2.63 | PD-1/PDL-1 | Glioma | MSK-IMPACT | A3001,A3201,B3502,B1302,C0602,C0401 | A01A03,A01,B07,UNK,UNK,UNK | 0 |
| LM615085 | 31-50 | 3 | 0 | 21.07 | PD-1/PDL-1 | Bladder Cancer | MSK-IMPACT | A0301,A0201,B4403,B5108,C0501,C0706 | A03,A02,B44,B07,UNK,UNK | 0 |
| GG838274 | 31-50 | 0 | 0 | 6.14 | PD-1/PDL-1 | Head and Neck Cancer | MSK-IMPACT | A0101,A0201,B5701,B3503,C0602,C0401 | A01,A02,B58,B07,UNK,UNK | 0 |
| CK759649 | >71 | 1 | 0 | 13.17 | Combo | Melanoma | MSK-IMPACT | A0201,A3303,B3501,B5101,C1502,C0401 | A02,A03,B07,B07,UNK,UNK | 0 |
| PR346356 | 61-70 | 5 | 1 | 14.04 | PD-1/PDL-1 | Bladder Cancer | MSK-IMPACT | A0302,A0201,B2705,B4402,C1604,C0202 | A03,A02,B27,B44,UNK,UNK | 0 |
| TG872084 | 31-50 | 0 | 0 | 1.76 | PD-1/PDL-1 | Melanoma | MSK-IMPACT | A0301,A0201,B1801,B4501,C0501,C1701 | A03,A02,B44,B44,UNK,UNK | 0 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| WB544363 | 31-50 | 1 | 0 | 0.87 | PD-1/PDL-1 | Melanoma | MSK-IMPACT | A0101,A0101,B0801,B0801,C0701,C0701 | A01,A01,B08,B08,UNK,UNK | 1 |
| HU011383 | 31-50 | 0 | 0 | 0.88 | PD-1/PDL-1 | Renal Cell Carcinoma | MSK-IMPACT | A0101,A0201,B1501,B5201,C1202,C0202 | A01,A02,B62,B62,UNK,UNK | 0 |
| OZ964185 | 50-60 | 0 | 0 | 1.76 | PD-1/PDL-1 | Glioma | MSK-IMPACT | A0201,A0201,B4001,B1501,C0304,C0401 | A02,A02,B44,B62,UNK,UNK | 1 |
| BX967817 | 31-50 | 2 | 0 | 100.06 | PD-1/PDL-1 | Melanoma | MSK-IMPACT | A3004,A0201,B1501,B3502,C0303,C0401 | A01,A02,B62,B07,UNK,UNK | 0 |
| KZ583833 | 61-70 | 11 | 1 | 1.97 | Combo | Bladder Cancer | MSK-IMPACT | A0206,A3303,B4801,B4801,C0302,C0401 | A02,A03,B27,B58,UNK,UNK | 0 |
| GB398563 | 31-50 | 12 | 0 | 26.56 | PD-1/PDL-1 | Melanoma | MSK-IMPACT | A2402,A2601,B3502,B3801,C0401,C1203 | A24,A01,B07,B27,UNK,UNK | 0 |
| WW668436 | 61-70 | 6 | 1 | 1.97 | PD-1/PDL-1 | Cancer of Unknown Primary | MSK-IMPACT | A2402,A2601,B0702,B3801,C1203,C0702 | A24,A01,B07,B27,UNK,UNK | 0 |
| VK845635 | 50-60 | 2 | 1 | 1.97 | PD-1/PDL-1 | Pancreatic Cancer | MSK-IMPACT | A3004,A2301,B3701,B4101,C0602,C1701 | A01,A24,B44,B44,UNK,UNK | 0 |
| KS136792 | 50-60 | 18 | 0 | 2.95 | CTLA4 | Melanoma | MSK-IMPACT | A2402,A3303,B5701,B3503,C0302,C0701 | A24,A03,B58,B07,UNK,UNK | 0 |
| RT578755 | 50-60 | 9 | 0 | 3.94 | CTLA4 | Breast Cancer | MSK-IMPACT | A2402,A6802,B0702,B5201,C1202,C0702 | A24,A02,B07,B62,UNK,UNK | 0 |
| AI716687 | 50-60 | 34 | 1 | 0 | PD-1/PDL-1 | Head and Neck Cancer | MSK-IMPACT | A1101,A3201,B4001,B5201,C0304,C1202 | A03,A01,B44,B62,UNK,UNK | 0 |
| EP826889 | 31-50 | 7 | 0 | 25.58 | PD-1/PDL-1 | Melanoma | MSK-IMPACT | A0301,A1101,B0702,B4403,C0401,C0702 | A03,A03,B07,B44,UNK,UNK | 0 |
| DE217723 | 31-50 | 9 | 0 | 1.97 | PD-1/PDL-1 | Bladder Cancer | MSK-IMPACT | A0101,A6801,B5701,B4001,C0304,C0602 | A01,A03,B58,B44,UNK,UNK | 0 |
| EM140795 | 61-70 | 13 | 1 | 4.92 | PD-1/PDL-1 | Colorectal Cancer | MSK-IMPACT | A2601,A0201,B3801,B5001,C1203,C1203 | A01,A02,B27,B44,UNK,UNK | 1 |
| FE593501 | >71 | 9 | 0 | 3.94 | Combo | Colorectal Cancer | MSK-IMPACT | A0301,A0101,B0702,B5701,C0602,C0702 | A03,A01,B07,B58,UNK,UNK | 0 |
| FJ722993 | 31-50 | 10 | 0 | 5.9 | PD-1/PDL-1 | Small Cell Lung Cancer | MSK-IMPACT | A3002,A0201,B3501,B5301,C0401,C0401 | A01,A02,B07,B07,UNK,UNK | 1 |
| FL700026 | 31-50 | 5 | 0 | 9.84 | PD-1/PDL-1 | Head and Neck Cancer | MSK-IMPACT | A2902,A3101,B5703,B4403,C1601,C0706 | A01A24,A03,B58,B44,UNK,UNK | 0 |
| NT293292 | 50-60 | 2 | 1 | 2.95 | Combo | Pancreatic Cancer | MSK-IMPACT | A0301,A2601,B3801,B1801,C1203,C1203 | A03,A01,B27,B44,UNK,UNK | 1 |
| GW362077 | 61-70 | 4 | 0 | 2.95 | PD-1/PDL-1 | Gastrointestinal Stromal Tumor | MSK-IMPACT | A0101,A0101,B0801,B0801,C0701,C0701 | A01,A01,B08,B08,UNK,UNK | 1 |
| QS331947 | <30 | 0 | 0 | 5.9 | PD-1/PDL-1 | Non-Small Cell Lung Cancer | MSK-IMPACT | A3002,A3002,B3801,B5801,C0302,C1203 | A01,A01,B27,B08,UNK,UNK | 1 |
| AH761070 | 31-50 | 9 | 1 | 9.84 | PD-1/PDL-1 | Bladder Cancer | MSK-IMPACT | A1101,A0101,B0702,B0801,C0701,C0702 | A03,A01,B07,B08,UNK,UNK | 0 |
| FB523718 | 50-60 | 3 | 0 | 0 | PD-1/PDL-1 | Melanoma | MSK-IMPACT | A0201,A0201,B1501,B5101,C0303,C0501 | A02,A02,B62,B07,UNK,UNK | 1 |
| NJ637519 | 31-50 | 2 | 0 | 43.29 | PD-1/PDL-1 | Colorectal Cancer | MSK-IMPACT | A0101,A3201,B4901,B5201,C1202,C0701 | A01,A01,UNK,B62,UNK,UNK | 0 |
| TP649659 | 50-60 | 7 | 0 | 15.74 | CTLA4 | Soft Tissue Sarcoma | MSK-IMPACT | A0301,A0201,B0702,B5201,C1202,C0702 | A03,A02,B07,B62,UNK,UNK | 0 |
| BF585566 | 31-50 | 3 | 0 | 8.85 | PD-1/PDL-1 | Bladder Cancer | MSK-IMPACT | A6802,A2601,B1402,B3801,C0802,C1203 | A02,A01,B27,B27,UNK,UNK | 0 |
| IK895715 | 31-50 | 22 | 0 | 7.87 | PD-1/PDL-1 | Head and Neck Cancer | MSK-IMPACT | A2601,A0201,B0705,B6701,C1505,C1203 | A01,A02,B07,B07,UNK,UNK | 0 |
| EI131873 | 50-60 | 15 | 1 | 9.84 | PD-1/PDL-1 | Small Cell Lung Cancer | MSK-IMPACT | A1101,A0101,B1517,B5101,C1502,C0701 | A03,A01,B58,B07,UNK,UNK | 0 |
| FW803759 | 50-60 | 54 | 0 | 19.68 | CTLA4 | Melanoma | MSK-IMPACT | A0101,A2402,B0702,B5501,C0303,C0702 | A01,A24,B07,B07,UNK,UNK | 0 |
| GW946602 | 31-50 | 6 | 0 | 7.87 | PD-1/PDL-1 | Melanoma | MSK-IMPACT | A0101,A0201,B1517,B1801,C0501,C0701 | A01,A02,B58,B44,UNK,UNK | 0 |
| PZ923250 | 31-50 | 3 | 0 | 3.94 | PD-1/PDL-1 | Glioma | MSK-IMPACT | A0301,A3101,B0702,B3508,C0401,C0702 | A03,A03,B07,B07,UNK,UNK | 0 |
| ZJ847611 | 31-50 | 9 | 0 | 0 | PD-1/PDL-1 | Non-Hodgkin Lymphoma | MSK-IMPACT | A0101,A2601,B5701,B3801,C1203,C0602 | A01,A01,B58,B27,UNK,UNK | 0 |
| BW398128 | 31-50 | 2 | 1 | 9.84 | PD-1/PDL-1 | Non-Small Cell Lung Cancer | MSK-IMPACT | A3201,A0201,B0702,B4002,C0202,C0702 | A01,A02,B07,B44,UNK,UNK | 0 |
| FG408326 | 31-50 | 5 | 1 | 6.89 | PD-1/PDL-1 | Hepatobiliary Cancer | MSK-IMPACT | A3001,A0101,B0801,B1801,C0701,C0701 | A01A03,A01,B08,B44,UNK,UNK | 1 |
| PD448224 | 50-60 | 2 | 1 | 2.95 | PD-1/PDL-1 | Adrenocortical Carcinoma | MSK-IMPACT | A0301,A0301,B0702,B1501,C0304,C0702 | A03,A03,B07,B62,UNK,UNK | 1 |
| IS872618 | 50-60 | 7 | 0 | 4.92 | PD-1/PDL-1 | Renal Cell Carcinoma | MSK-IMPACT | A0101,A0101,B5501,B1517,C0102,C0701 | A01,A01,B07,B68,UNK,UNK | 1 |
| LR744370 | 50-60 | 19 | 0 | 8.85 | Combo | Melanoma | MSK-IMPACT | A3002,A2402,B1402,B1508,C0102,C0802 | A01,A24,B27,B07,UNK,UNK | 0 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| PW748829 | 61-70 | 54 | 0 | 4.92 | CTLA4 | Melanoma | MSK-IMPACT | A6801,A0201,B5701,B4402,C0501,C0602 | A03,A02,B58,B44,UNK,UNK | 0 |
| JW229525 | 31-50 | 41 | 0 | 2.95 | Combo | Non-Small Cell Lung Cancer | MSK-IMPACT | A0301,A0201,B1501,B5802,C0303,C0602 | A03,A02,B62,B58,UNK,UNK | 0 |
| NR471516 | 31-50 | 12 | 1 | 8.85 | PD-1/PDL-1 | Melanoma | MSK-IMPACT | A0301,A0201,B0702,B6701,C1203,C0702 | A03,A02,B07,B07,UNK,UNK | 0 |
| XM766857 | 31-50 | 8 | 0 | 5.9 | PD-1/PDL-1 | Renal Cell Carcinoma | MSK-IMPACT | A0201,A0201,B2705,B3801,C0102,C1203 | A02,A02,B27,B27,UNK,UNK | 1 |
| YV996814 | 50-60 | 17 | 0 | 6.89 | PD-1/PDL-1 | Colorectal Cancer | MSK-IMPACT | A2402,A3301,B1402,B0801,C0802,C0718 | A24,A03,B27,B08,UNK,UNK | 0 |
| QR822407 | 50-60 | 17 | 0 | 18.69 | Combo | Melanoma | MSK-IMPACT | A1101,A0201,B0702,B1801,C0702,C0701 | A03,A02,B07,B44,UNK,UNK | 0 |
| RF041334 | 50-60 | 30 | 0 | 2.95 | PD-1/PDL-1 | Renal Cell Carcinoma | MSK-IMPACT | A0201,A2601,B0801,B1801,C0701,C0701 | A02,A01,B08,B44,UNK,UNK | 1 |
| SP588250 | 31-50 | 6 | 0 | 6.89 | PD-1/PDL-1 | Non-Small Cell Lung Cancer | MSK-IMPACT | A2402,A3303,B4001,B5801,C0302,C0702 | A24,A03,B44,B58,UNK,UNK | 0 |
| SS128035 | 31-50 | 4 | 0 | 8.85 | PD-1/PDL-1 | Head and Neck Cancer | MSK-IMPACT | A2402,A2601,B1501,B3801,C0303,C1203 | A24,A01,B62,B27,UNK,UNK | 0 |
| WN367297 | 31-50 | 15 | 0 | 3.94 | PD-1/PDL-1 | Non-Small Cell Lung Cancer | MSK-IMPACT | A3101,A3301,B1402,B3801,C0802,C1203 | A03,A03,B27,B27,UNK,UNK | 0 |
| YG152378 | 50-60 | 3 | 0 | 11.81 | PD-1/PDL-1 | Non-Hodgkin Lymphoma | MSK-IMPACT | A0301,A2601,B0702,B1801,C1203,C0702 | A03,A01,B07,B44,UNK,UNK | 0 |
| NY093664 | 61-70 | 2 | 1 | 10.82 | PD-1/PDL-1 | Non-Small Cell Lung Cancer | MSK-IMPACT | A0101,A0201,B1501,B3501,C0401,C0401 | A01,A02,B62,B07,UNK,UNK | 1 |
| BC811776 | 61-70 | 2 | 0 | 22.63 | PD-1/PDL-1 | Non-Small Cell Lung Cancer | MSK-IMPACT | A0101,A6801,B3701,B4402,C0602,C0704 | A01,A03,B44,B44,UNK,UNK | 0 |
| CB764271 | 31-50 | 5 | 1 | 0 | PD-1/PDL-1 | Hepatobiliary Cancer | MSK-IMPACT | A0101,A2402,B3502,B5501,C0303,C0401 | A01,A24,B07,B07,UNK,UNK | 0 |
| DB559032 | 50-60 | 4 | 0 | 7.87 | Combo | Melanoma | MSK-IMPACT | A0301,A2402,B0702,B3508,C0401,C0702 | A03,A24,B07,B07,UNK,UNK | 0 |
| HC203191 | 31-50 | 11 | 0 | 7.87 | PD-1/PDL-1 | Non-Small Cell Lung Cancer | MSK-IMPACT | A0301,A3303,B4901,B3501,C0802,C0701 | A03,A03,UNK,B07,UNK,UNK | 0 |
| OS427829 | 61-70 | 7 | 0 | 2.95 | CTLA4 | Prostate Cancer | MSK-IMPACT | A0101,A0101,B0801,B0801,C0701,C0701 | A01,A01,B08,B08,UNK,UNK | 1 |
| VR485557 | 31-50 | 19 | 0 | 4.92 | PD-1/PDL-1 | Bladder Cancer | MSK-IMPACT | A0201,A0201,B0801,B3508,C0401,C0701 | A02,A02,B08,B07,UNK,UNK | 1 |
| XU013435 | 50-60 | 6 | 0 | 23.61 | PD-1/PDL-1 | Non-Small Cell Lung Cancer | MSK-IMPACT | A3001,A2402,B1801,B1302,C0602,C0701 | A01A03,A24,B44,UNK,UNK,UNK | 0 |
| YA270966 | 31-50 | 40 | 0 | 6.89 | Combo | Melanoma | MSK-IMPACT | A0301,A0206,B0702,B4801,C0803,C0702 | A03,A02,B07,B27,UNK,UNK | 0 |
| KQ222690 | 50-60 | 15 | 0 | 4.92 | PD-1/PDL-1 | Renal Cell Carcinoma | MSK-IMPACT | A2402,A2301,B3801,B4901,C1203,C0701 | A24,A24,B27,UNK,UNK,UNK | 0 |
| RR191649 | 31-50 | 3 | 1 | 5.9 | PD-1/PDL-1 | Cancer of Unknown Primary | MSK-IMPACT | A3001,A3201,B5501,B1302,C0304,C0602 | A01A03,A01,B07,UNK,UNK,UNK | 0 |
| ZJ250921 | 50-60 | 1 | 1 | 10.82 | PD-1/PDL-1 | Non-Small Cell Lung Cancer | MSK-IMPACT | A0301,A3001,B5601,B5101,C0102,C0401 | A03,A01A03,B07,B07,UNK,UNK | 0 |
| DE029388 | 61-70 | 1 | 1 | 6.89 | PD-1/PDL-1 | Bladder Cancer | MSK-IMPACT | A0201,A0201,B4405,B1302,C0202,C0602 | A02,A02,B44,UNK,UNK,UNK | 1 |
| GS420214 | 31-50 | 36 | 0 | 3.94 | Combo | Non-Small Cell Lung Cancer | MSK-IMPACT | A0301,A0201,B2705,B3801,C0102,C1203 | A03,A02,B27,B27,UNK,UNK | 0 |
| IL444062 | 31-50 | 0 | 1 | 2.95 | PD-1/PDL-1 | Thyroid Cancer | MSK-IMPACT | A0301,A2402,B0702,B4001,C0304,C0702 | A03,A24,B07,B44,UNK,UNK | 0 |
| RA263407 | 61-70 | 5 | 0 | 24.59 | PD-1/PDL-1 | Adrenocortical Carcinoma | MSK-IMPACT | A6801,A6601,B4001,B4005,C0304,C0202 | A03,A03,B44,B44,UNK,UNK | 0 |
| RP070224 | >71 | 5 | 0 | 2.95 | PD-1/PDL-1 | Colorectal Cancer | MSK-IMPACT | A2902,A2402,B4402,B4403,C1601,C0501 | A01A24,A02,B44,B44,UNK,UNK | 0 |
| TF488143 | 50-60 | 3 | 1 | 2.95 | PD-1/PDL-1 | Renal Cell Carcinoma | MSK-IMPACT | A0301,A0201,B0702,B0702,C0702,C0702 | A03,A02,B07,B07,UNK,UNK | 1 |
| TF785669 | 31-50 | 42 | 0 | 5.9 | PD-1/PDL-1 | Non-Small Cell Lung Cancer | MSK-IMPACT | A3001,A0201,B4403,B1302,C0602,C1602 | A01A03,A02,B44,UNK,UNK,UNK | 0 |
| UK971155 | 31-50 | 2 | 0 | 20.66 | PD-1/PDL-1 | Non-Small Cell Lung Cancer | MSK-IMPACT | A0101,A0201,B0801,B5701,C0602,C0701 | A01,A02,B08,B58,UNK,UNK | 0 |
| WQ120057 | <30 | 26 | 0 | 48.21 | CTLA4 | Skin Cancer; Non-Melanoma | MSK-IMPACT | A0201,A2601,B3701,B1501,C0602,C0704 | A02,A01,B44,B62,UNK,UNK | 0 |
| BR374139 | 50-60 | 0 | 1 | 19.68 | PD-1/PDL-1 | Non-Hodgkin Lymphoma | MSK-IMPACT | A0101,A6801,B4001,B1801,C0304,C1203 | A01,A03,B44,B44,UNK,UNK | 0 |
| DD361465 | >71 | 2 | 0 | 1.97 | Combo | Cancer of Unknown Primary | MSK-IMPACT | A2902,A6802,B4901,B5802,C0602,C0701 | A01A24,A02,UNK,B58,UNK,UNK | 0 |
| GZ425566 | 50-60 | 3 | 1 | 2.95 | PD-1/PDL-1 | Non-Small Cell Lung Cancer | MSK-IMPACT | A0101,A2402,B0702,B1801,C0102,C0702 | A01,A24,B07,B44,UNK,UNK | 0 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| HO127075 | 31-50 | 1 | 1 | 14.76 | Combo | Small Cell Lung Cancer | MSK-IMPACT | A0101,A0201,B0801, B4402,C0501,C0701 | A01,A02,B08, B44,UNK,UNK | 0 |
| OT254694 | 50-60 | 11 | 0 | 2.95 | PD-1/PDL-1 | Renal Cell Carcinoma | MSK-IMPACT | A2402,A6802,B3503, B3501,C0401,C0401 | A24,A02,B07, B07,UNK,UNK | 1 |
| QV527200 | 31-50 | 7 | 0 | 10.82 | CTLA4 | Melanoma | MSK-IMPACT | A3002,A3301,B1402, B3801,C0802,C1203 | A01,A03,B27, B27,UNK,UNK | 0 |
| TH564442 | >71 | 11 | 1 | 3.94 | PD-1/PDL-1 | Bone Cancer | MSK-IMPACT | A0101,A2402,B0801, B0801,C0701,C0701 | A01,A24,B08, B08,UNK,UNK | 1 |
| ZP620505 | 31-50 | 18 | 1 | 25.58 | PD-1/PDL-1 | Non-Small Cell Lung Cancer | MSK-IMPACT | A0301,A2902,B5101, B4403,C1502,C1601 | A03,A01A24,B07, B44,UNK,UNK | 0 |
| IN021880 | <30 | 4 | 0 | 4.92 | PD-1/PDL-1 | Cancer of Unknown Primary | MSK-IMPACT | A0301,A0201,B0702, B3906,C0702,C0702 | A03,A02,B07, B27,UNK,UNK | 1 |
| JP245287 | 31-50 | 11 | 0 | 3.94 | PD-1/PDL-1 | Renal Cell Carcinoma | MSK-IMPACT | A0301,A0101,B0702, B0801,C0702,C0701 | A03,A01,B07, B08,UNK,UNK | 0 |
| JX534724 | >71 | 8 | 1 | 6.89 | PD-1/PDL-1 | Bone Cancer | MSK-IMPACT | A0301,A0301,B0702, B4901,C0701,C0702 | A03,A03,B07, UNK,UNK,UNK | 1 |
| MF335699 | 31-50 | 6 | 0 | 8.85 | PD-1/PDL-1 | Bladder Cancer | MSK-IMPACT | A0201,A0201,B0801, B3901,C0701,C0702 | A02,A02,B08, B27,UNK,UNK | 1 |
| NK472415 | 31-50 | 18 | 0 | 10.82 | Combo | Melanoma | MSK-IMPACT | A3001,A0206,B2705, B3508,C0303,C0401 | A01A03,A02,B27, B07,UNK,UNK | 0 |
| OE799834 | 50-60 | 5 | 1 | 1.97 | PD-1/PDL-1 | Glioma | MSK-IMPACT | A0301,A0301,B1501, B3801,C1203,C0303 | A03,A03,B62, B27,UNK,UNK | 1 |
| OM501087 | 31-50 | 2 | 1 | 7.87 | PD-1/PDL-1 | Non-Small Cell Lung Cancer | MSK-IMPACT | A1101,A2402,B1402, B5801,C0802,C0706 | A03,A24,B27, B58,UNK,UNK | 0 |
| XX353415 | >71 | 3 | 0 | 5.9 | PD-1/PDL-1 | Melanoma | MSK-IMPACT | A0101,A0201,B0801, B1402,C0802,C0701 | A01,A02,B08, B27,UNK,UNK | 0 |
| HK376614 | 50-60 | 4 | 0 | 13.77 | PD-1/PDL-1 | Melanoma | MSK-IMPACT | A0101,A2402,B3701, B1501,C0304,C0602 | A01,A24,B44, B62,UNK,UNK | 0 |
| IF324640 | >71 | 21 | 1 | 4.92 | Combo | Renal Cell Carcinoma | MSK-IMPACT | A0301,A3101,B0702, B5101,C1402,C0702 | A03,A03,B07, B07,UNK,UNK | 0 |
| KB724373 | 50-60 | 0 | 1 | 0.98 | PD-1/PDL-1 | Skin Cancer; Non-Melanoma | MSK-IMPACT | A1101,A3201,B5501, B3501,C0303,C0202 | A03,A01,B07, B07,UNK,UNK | 0 |
| OJ108820 | 61-70 | 3 | 1 | 65.42 | Combo | Non-Small Cell Lung Cancer | MSK-IMPACT | A1101,A2402,B5701, B5101,C0303,C0602 | A03,A24,B58, B07,UNK,UNK | 0 |
| RT756250 | <30 | 15 | 0 | 0.98 | PD-1/PDL-1 | Non-Small Cell Lung Cancer | MSK-IMPACT | A3101,A3303,B4403, B4006,C0801,C0706 | A03,A03,B44, B44,UNK,UNK | 0 |
| TX830700 | 61-70 | 2 | 1 | 0.98 | PD-1/PDL-1 | Bladder Cancer | MSK-IMPACT | A0302,A6801,B0801, B3503,C0401,C0701 | A03,A03,B08, B07,UNK,UNK | 0 |
| WI841389 | 50-60 | 12 | 0 | 44.27 | Combo | Melanoma | MSK-IMPACT | A0301,A3101,B0702, B4001,C0304,C0702 | A03,A03,B07, B44,UNK,UNK | 0 |
| ZP418201 | 50-60 | 7 | 0 | 1.97 | PD-1/PDL-1 | Renal Cell Carcinoma | MSK-IMPACT | A3001,A1101,B1302, B5101,C0102,C0602 | A01A03,A03,UNK, B07,UNK,UNK | 0 |
| ZU021130 | >71 | 2 | 1 | 4.92 | Combo | Small Cell Lung Cancer | MSK-IMPACT | A1101,A0201,B0705, B4402,C0401,C0501 | A03,A02,B07, B44,UNK,UNK | 0 |
| DA179245 | 50-60 | 8 | 0 | 8.85 | PD-1/PDL-1 | Renal Cell Carcinoma | MSK-IMPACT | A0101,A0201,B4901, B5701,C0602,C0701 | A01,A02,UNK, B58,UNK,UNK | 0 |
| EZ592112 | <30 | 1 | 1 | 1.97 | PD-1/PDL-1 | Mesothelioma | MSK-IMPACT | A0302,A0201,B1517, B1801,C0701,C0701 | A03,A02,B58, B44,UNK,UNK | 1 |
| KT781325 | <30 | 1 | 1 | 3.94 | PD-1/PDL-1 | Melanoma | MSK-IMPACT | A0201,A0201,B5601, B1801,C0102,C0501 | A02,A02,B07, B44,UNK,UNK | 1 |
| NU094987 | 50-60 | 3 | 1 | 3.94 | PD-1/PDL-1 | Glioma | MSK-IMPACT | A0301,A3201,B5701, B3501,C0401,C0602 | A03,A01,B58, B07,UNK,UNK | 0 |
| RE682184 | 31-50 | 0 | 0 | 3.94 | PD-1/PDL-1 | Hepatobiliary Cancer | MSK-IMPACT | A0201,A0201,B0702, B4002,C0202,C0702 | A02,A02,B07, B44,UNK,UNK | 1 |
| TX092727 | 50-60 | 3 | 0 | 4.92 | PD-1/PDL-1 | Colorectal Cancer | MSK-IMPACT | A2402,A2301,B4001, B4101,C0304,C1701 | A24,A24,B44, B44,UNK,UNK | 0 |
| UB564651 | 31-50 | 11 | 0 | 6.89 | PD-1/PDL-1 | Renal Cell Carcinoma | MSK-IMPACT | A0101,A2402,B0801, B1801,C0303,C0701 | A01,A24,B08, B44,UNK,UNK | 0 |
| VW357743 | 61-70 | 1 | 0 | 4.92 | PD-1/PDL-1 | Non-Small Cell Lung Cancer | MSK-IMPACT | A1104,A0207,B4601, B1502,C0102,C0801 | A03,A02,B62, B62,UNK,UNK | 0 |
| YA688084 | 61-70 | 16 | 0 | 36.4 | Combo | Melanoma | MSK-IMPACT | A3004,A2902,B0702, B5001,C0602,C0702 | A01,A01A24,B07, B44,UNK,UNK | 0 |
| CC632903 | 31-50 | 2 | 0 | 7.87 | PD-1/PDL-1 | Bladder Cancer | MSK-IMPACT | A0201,A6802,B1402, B1302,C0802,C0602 | A02,A02,B27, UNK,UNK,UNK | 0 |
| GV583013 | >71 | 7 | 1 | 3.94 | Combo | Melanoma | MSK-IMPACT | A0301,A2902,B0702, B4403,C1601,C0702 | A03,A01A24,B07, B44,UNK,UNK | 0 |
| HX366182 | >71 | 2 | 1 | 2.95 | PD-1/PDL-1 | Glioma | MSK-IMPACT | A2402,A2601,B4901, B5301,C0401,C0701 | A24,A01,UNK, B07,UNK,UNK | 0 |
| JJ949081 | 31-50 | 7 | 0 | 7.87 | PD-1/PDL-1 | Renal Cell Carcinoma | MSK-IMPACT | A0101,A2402,B0801, B1501,C0303,C0701 | A01,A24,B08, B62,UNK,UNK | 0 |
| OR856491 | 31-50 | 6 | 1 | 5.9 | PD-1/PDL-1 | Non-Small Cell Lung Cancer | MSK-IMPACT | A0101,A7401,B0801, B5601,C0102,C0706 | A01,A03,B08, B07,UNK,UNK | 0 |

APPENDIX 1-continued

| | | | | | | | | | Homozygous |
| Sample | Age Group | OS_Months | OS_Event | IMPACT-MutCnt | Drug Class | Cancer Type | Reference | HLA Class I Alleles | HLA Class I Super-types | (1 = Yes; 0 = No) |
|---|---|---|---|---|---|---|---|---|---|---|
| RV811068 | >71 | 12 | 1 | 3.94 | Combo | Melanoma | MSK-IMPACT | A0301,A0206,B1501,B4402,C0303,C0501 | A03,A02,B62,B44,UNK,UNK | 0 |
| TW125733 | 50-60 | 7 | 0 | 1.97 | PD-1/PDL-1 | Glioma | MSK-IMPACT | A0101,A2402,B3906,B4403,C0602,C0702 | A01,A24,B27,B44,UNK,UNK | 0 |
| AZ957907 | 50-60 | 6 | 0 | 47.22 | PD-1/PDL-1 | Bladder Cancer | MSK-IMPACT | A0301,A2601,B3801,B4002,C0202,C1203 | A03,A01,B27,B44,UNK,UNK | 0 |
| FF392752 | 61-70 | 3 | 0 | 4.92 | CTLA4 | Breast Cancer | MSK-IMPACT | A1101,A0201,B3503,B3501,C0401,C0401 | A03,A02,B07,B07,UNK,UNK | 1 |
| FO996647 | >71 | 9 | 0 | 13.77 | Combo | Melanoma | MSK-IMPACT | A0301,A2402,B5101,B5101,C0102,C0102 | A03,A24,B07,B07,UNK,UNK | 1 |
| TS839271 | 61-70 | 55 | 0 | 15.74 | CTLA4 | Melanoma | MSK-IMPACT | A0301,A0101,B0702,B4402,C0501,C0702 | A03,A01,B07,B44,UNK,UNK | 0 |
| UK533610 | 31-50 | 7 | 1 | 1.97 | PD-1/PDL-1 | Cancer of Unknown Primary | MSK-IMPACT | A0301,A3301,B0702,B1402,C0802,C0702 | A03,A03,B07,B27,UNK,UNK | 0 |
| UQ148407 | 31-50 | 1 | 0 | 0 | PD-1/PDL-1 | Head and Neck Cancer | MSK-IMPACT | A0101,A0101,B0801,B0801,C0701,C0701 | A01,A01,B08,B08,UNK,UNK | 1 |
| ZP246475 | 50-60 | 35 | 1 | 4.92 | PD-1/PDL-1 | Renal Cell Carcinoma | MSK-IMPACT | A1101,A2402,B3502,B5201,C1202,C0401 | A03,A24,B07,B62,UNK,UNK | 0 |
| KR586940 | 50-60 | 6 | 1 | 7.87 | PD-1/PDL-1 | Non-Small Cell Lung Cancer | MSK-IMPACT | A0101,A2403,B0801,B3502,C0401,C0701 | A01,A24,B08,B07,UNK,UNK | 0 |
| LS271625 | 50-60 | 7 | 0 | 6.89 | PD-1/PDL-1 | Hepatobiliary Cancer | MSK-IMPACT | A2402,A3303,B4001,B5801,C0302,C0702 | A24,A03,B44,B58,UNK,UNK | 0 |
| NI627069 | 61-70 | 5 | 0 | 1.97 | PD-1/PDL-1 | Hodgkin Lymphoma | MSK-IMPACT | A0207,A3303,B4002,B5801,C0303,C0302 | A02,A03,B44,B58,UNK,UNK | 0 |
| PD519263 | 31-50 | 4 | 0 | 48.21 | Combo | Melanoma | MSK-IMPACT | A2902,A0201,B0702,B5101,C1601,C0702 | A01A24,A02,B07,B07,UNK,UNK | 0 |
| RK555724 | 31-50 | 2 | 1 | 22.63 | PD-1/PDL-1 | Bladder Cancer | MSK-IMPACT | A2402,A3101,B4001,B1801,C0304,C0701 | A24,A03,B44,B44,UNK,UNK | 0 |
| UQ753932 | 50-60 | 34 | 0 | 9.84 | PD-1/PDL-1 | Non-Small Cell Lung Cancer | MSK-IMPACT | A0301,A3201,B0801,B5101,C1502,C0702 | A03,A01,B08,B07,UNK,UNK | 0 |
| YI876909 | 31-50 | 3 | 1 | 0.98 | PD-1/PDL-1 | Renal Cell Carcinoma | MSK-IMPACT | A0301,A2902,B1402,B5101,C1402,C0802 | A03,A01A24,B27,B07,UNK,UNK | 0 |
| EH052498 | 61-70 | 5 | 0 | 34.43 | PD-1/PDL-1 | Non-Small Cell Lung Cancer | MSK-IMPACT | A0101,A0101,B0801,B5701,C0602,C0701 | A01,A01,B08,B58,UNK,UNK | 1 |
| HB171494 | >71 | 58 | 1 | 12.79 | CTLA4 | Melanoma | MSK-IMPACT | A0101,A2402,B3502,B1302,C0502,C0401 | A01,A24,B07,UNK,UNK,UNK | 0 |
| HY420730 | 31-50 | 1 | 1 | 1.97 | PD-1/PDL-1 | Mesothelioma | MSK-IMPACT | A0101,A1101,B2705,B1508,C0102,C0102 | A01,A03,B27,B07,UNK,UNK | 1 |
| SM106076 | >71 | 18 | 0 | 5.9 | Combo | Melanoma | MSK-IMPACT | A0201,A0201,B4403,B1801,C0706,C0701 | A02,A02,B44,B44,UNK,UNK | 1 |
| XJ302031 | >71 | 4 | 1 | 0.98 | PD-1/PDL-1 | Hepatobiliary Cancer | MSK-IMPACT | A2902,A6802,B5201,B1302,C1604,C1202 | A01A24,A02,B62,UNK,UNK,UNK | 0 |
| XJ364453 | 61-70 | 10 | 0 | 1.97 | Combo | Non-Small Cell Lung Cancer | MSK-IMPACT | A2301,A0201,B3801,B5001,C0401,C1203 | A24,A02,B27,B44,UNK,UNK | 0 |
| BL021996 | 31-50 | 1 | 1 | 29.51 | Combo | Melanoma | MSK-IMPACT | A2902,A0201,B1801,B5108,C1203,C1602 | A01A24,A02,B44,B07,UNK,UNK | 0 |
| CN050789 | 61-70 | 22 | 0 | 5.9 | Combo | Renal Cell Carcinoma | MSK-IMPACT | A0101,A0101,B0702,B0801,C0701,C0702 | A01,A01,B07,B08,UNK,UNK | 1 |
| EO236447 | 31-50 | 7 | 0 | 8.85 | PD-1/PDL-1 | Small Cell Lung Cancer | MSK-IMPACT | A0101,A0201,B4201,B0702,C0701,C0702 | A01,A02,B07,B07,UNK,UNK | 0 |
| ME175230 | 31-50 | 1 | 1 | 4.92 | PD-1/PDL-1 | Prostate Cancer | MSK-IMPACT | A0301,A0201,B1801,B3503,C0401,C0701 | A03,A02,B44,B07,UNK,UNK | 0 |
| MX600877 | 61-70 | 13 | 0 | 5.9 | PD-1/PDL-1 | Non-Small Cell Lung Cancer | MSK-IMPACT | A2402,A2601,B4101,B3801,C1203,C1701 | A24,A01,B44,B27,UNK,UNK | 0 |
| TO021548 | >71 | 17 | 0 | 7.87 | Combo | Melanoma | MSK-IMPACT | A1101,A0101,B0801,B4403,C1601,C0701 | A03,A01,B08,B44,UNK,UNK | 0 |
| VC243698 | >71 | 8 | 0 | 2.95 | CTLA4 | Melanoma | MSK-IMPACT | A1101,A1101,B5502,B5101,C0102,C1402 | A03,A03,B07,B07,UNK,UNK | 1 |
| YD777623 | 31-50 | 2 | 0 | 5.9 | PD-1/PDL-1 | Renal Cell Carcinoma | MSK-IMPACT | A0201,A0201,B4006,B1501,C0102,C0304 | A02,A02,B44,B62,UNK,UNK | 1 |
| YT816084 | 50-60 | 2 | 1 | 7.87 | PD-1/PDL-1 | Head and Neck Cancer | MSK-IMPACT | A0101,A0201,B1402,B1501,C0304,C0802 | A01,A02,B27,B62,UNK,UNK | 0 |
| ZK930604 | 31-50 | 11 | 0 | 3.94 | PD-1/PDL-1 | Non-Small Cell Lung Cancer | MSK-IMPACT | A1101,A3101,B1401,B4901,C0802,C0701 | A03,A03,B27,UNK,UNK,UNK | 0 |
| ZM436268 | >71 | 4 | 0 | 0 | PD-1/PDL-1 | Pancreatic Cancer | MSK-IMPACT | A0201,A0201,B0801,B5102,C0401,C0701 | A02,A02,B08,B07,UNK,UNK | 1 |
| ZN659436 | 50-60 | 12 | 1 | 0 | Combo | Anal Cancer | MSK-IMPACT | A0201,A0201,B4402,B4402,C0501,C0501 | A02,A02,B44,B44,UNK,UNK | 1 |
| AK398732 | 31-50 | 3 | 1 | 6.89 | PD-1/PDL-1 | Non-Small Cell Lung Cancer | MSK-IMPACT | A0101,A2601,B3901,B3502,C1203,C0602 | A01,A01,B27,B07,UNK,UNK | 0 |
| DM247664 | >71 | 7 | 0 | 0.98 | PD-1/PDL-1 | Melanoma | MSK-IMPACT | A0301,A0101,B0702,B0801,C0701,C0702 | A03,A01,B07,B08,UNK,UNK | 0 |

APPENDIX 1-continued

| | | | | | | | | | | Homozygous (1 = Yes; 0 = No) |
|---|---|---|---|---|---|---|---|---|---|---|
| Sample | Age Group | OS_Months | OS_Event | IMPACT-MutCnt | Drug Class | Cancer Type | Reference | HLA Class I Alleles | HLA Class I Super-types | |
| GB961648 | 61-70 | 1 | 0 | 0 | PD-1/PDL-1 | Hepatobiliary Cancer | MSK-IMPACT | A1101,A2402,B4006,B3901,C0801,C0702 | A03,A24,B44,B27,UNK,UNK | 0 |
| LH544200 | >71 | 2 | 1 | 30.5 | PD-1/PDL-1 | Glioma | MSK-IMPACT | A0101,A3201,B5701,B4402,C0501,C0602 | A01,A01,B58,B44,UNK,UNK | 0 |
| LQ635575 | 31-50 | 10 | 0 | 1.97 | Combo | Melanoma | MSK-IMPACT | A1101,A0101,B1501,B5701,C0303,C0602 | A03,A01,B62,B58,UNK,UNK | 0 |
| PV718637 | >71 | 0 | 0 | 0 | PD-1/PDL-1 | Hepatobiliary Cancer | MSK-IMPACT | A0301,A0301,B4002,B5101,C1502,C0401 | A03,A03,B44,B07,UNK,UNK | 1 |
| QC207302 | 31-50 | 11 | 0 | 15.74 | PD-1/PDL-1 | Non-Small Cell Lung Cancer | MSK-IMPACT | A3001,A0201,B4101,B1302,C0602,C1701 | A01A03,A02,B44,UNK,UNK,UNK | 0 |
| SH764427 | >71 | 4 | 1 | 5.9 | PD-1/PDL-1 | Non-Small Cell Lung Cancer | MSK-IMPACT | A0101,A2402,B3906,B4402,C1604,C0702 | A01,A24,B27,B44,UNK,UNK | 0 |
| ZG143121 | >71 | 7 | 1 | 8.85 | PD-1/PDL-1 | Non-Small Cell Lung Cancer | MSK-IMPACT | A2402,A3201,B0702,B1401,C0802,C0702 | A24,A01,B07,B27,UNK,UNK | 0 |
| BZ683679 | 50-60 | 24 | 0 | 2.95 | PD-1/PDL-1 | Renal Cell Carcinoma | MSK-IMPACT | A0101,A3201,B0801,B4101,C0701,C1701 | A01,A01,B08,B44,UNK,UNK | 0 |
| DO813858 | >71 | 3 | 0 | 3.94 | PD-1/PDL-1 | Glioma | MSK-IMPACT | A0101,A3201,B1501,B5701,C0304,C0602 | A01,A01,B62,B58,UNK,UNK | 0 |
| GJ373999 | 31-50 | 32 | 1 | 5.9 | Combo | Melanoma | MSK-IMPACT | A1101,A1101,B5101,B3501,C0401,C0401 | A03,A03,B07,B07,UNK,UNK | 1 |
| GX055672 | >71 | 67 | 0 | 47.22 | CTLA4 | Melanoma | MSK-IMPACT | A1101,A0101,B0801,B1801,C0701,C0701 | A03,A01,B08,B44,UNK,UNK | 1 |
| IW603773 | 50-60 | 6 | 0 | 7.87 | PD-1/PDL-1 | Non-Small Cell Lung Cancer | MSK-IMPACT | A0201,A2601,B2705,B5101,C0202,C1602 | A02,A01,B27,B07,UNK,UNK | 0 |
| MW215777 | 61-70 | 1 | 1 | 5.9 | PD-1/PDL-1 | Anal Cancer | MSK-IMPACT | A3004,A3001,B8101,B5801,C0302,C0401 | A01,A01A03,B07,B58,UNK,UNK | 0 |
| SM334656 | 31-50 | 5 | 0 | 9.84 | PD-1/PDL-1 | Melanoma | MSK-IMPACT | A0301,A0101,B0801,B4001,C0304,C0701 | A03,A01,B08,B44,UNK,UNK | 0 |
| TP561311 | 50-60 | 8 | 1 | 3.94 | PD-1/PDL-1 | Renal Cell Carcinoma | MSK-IMPACT | A0201,A2601,B3801,B4402,C1203,C0501 | A02,A01,B27,B44,UNK,UNK | 0 |
| VX282680 | 61-70 | 1 | 0 | 0 | PD-1/PDL-1 | Melanoma | MSK-IMPACT | A0217,A3201,B5101,B5101,C1502,C1502 | A02,A01,B07,B07,UNK,UNK | 1 |
| VZ379970 | >71 | 18 | 0 | 6.89 | PD-1/PDL-1 | Glioma | MSK-IMPACT | A3001,A0101,B3502,B1302,C0401,C0602 | A01A03,A01,B07,UNK,UNK,UNK | 0 |
| AQ234293 | 31-50 | 3 | 0 | 6.89 | PD-1/PDL-1 | Non-Small Cell Lung Cancer | MSK-IMPACT | A1101,A3201,B4002,B3501,C0202,C0401 | A03,A01,B44,B07,UNK,UNK | 0 |
| BR404154 | 50-60 | 0 | 0 | 9.84 | PD-1/PDL-1 | Non-Small Cell Lung Cancer | MSK-IMPACT | A2902,A6802,B1510,B4403,C0304,C1601 | A01A24,A02,B27,B44,UNK,UNK | 0 |
| DU521291 | 61-70 | 9 | 0 | 0.98 | PD-1/PDL-1 | Renal Cell Carcinoma | MSK-IMPACT | A0301,A3201,B6701,B5601,C0102,C1203 | A03,A01,B07,B07,UNK,UNK | 0 |
| EZ372884 | >71 | 7 | 1 | 0 | PD-1/PDL-1 | Renal Cell Carcinoma | MSK-IMPACT | A0301,A3201,B3901,B4002,C0202,C1203 | A03,A01,B27,B44,UNK,UNK | 0 |
| HO314880 | 31-50 | 1 | 1 | 10.82 | Combo | Melanoma | MSK-IMPACT | A1101,A0201,B1501,B4001,C0303,C0304 | A03,A02,B62,B44,UNK,UNK | 0 |
| JC025622 | 31-50 | 17 | 0 | 45.25 | Combo | Melanoma | MSK-IMPACT | A0301,A1101,B0702,B4403,C1601,C0702 | A03,A03,B07,B44,UNK,UNK | 0 |
| NE722159 | <30 | 0 | 0 | 163.31 | PD-1/PDL-1 | Melanoma | MSK-IMPACT | A2902,A2601,B4403,B1801,C1601,C1203 | A01A24,A01,B44,B44,UNK,UNK | 0 |
| OU097839 | 31-50 | 25 | 0 | 2.95 | CTLA4 | Prostate Cancer | MSK-IMPACT | A0202,A0202,B1501,B4001,C0304,C0401 | A02,A02,B62,B44,UNK,UNK | 1 |
| TF774146 | 61-70 | 9 | 0 | 53.12 | PD-1/PDL-1 | Melanoma | MSK-IMPACT | A2402,A0201,B3508,B1801,C0401,C1203 | A24,A02,B07,B44,UNK,UNK | 0 |
| VE454857 | 50-60 | 2 | 0 | 40.34 | PD-1/PDL-1 | Bladder Cancer | MSK-IMPACT | A2301,A3101,B4402,B4901,C0501,C0701 | A24,A03,B44,UNK,UNK,UNK | 0 |
| XE884868 | 31-50 | 20 | 0 | 0 | Combo | Renal Cell Carcinoma | MSK-IMPACT | A0101,A2601,B3801,B5701,C1203,C0602 | A01,A01,B27,B58,UNK,UNK | 0 |
| ZE129370 | 31-50 | 7 | 0 | 12.79 | PD-1/PDL-1 | Pancreatic Cancer | MSK-IMPACT | A0101,A0205,B3801,B3502,C0401,C1203 | A01,A02,B27,B07,UNK,UNK | 0 |
| ZE213131 | >71 | 3 | 0 | 3.94 | Combo | Bone Cancer | MSK-IMPACT | A1101,A0203,B1512,B1301,C0304,C0403 | A03,A02,B62,UNK,UNK,UNK | 0 |
| DB788312 | 61-70 | 11 | 0 | 60.01 | PD-1/PDL-1 | Bladder Cancer | MSK-IMPACT | A2402,A3201,B0702,B4001,C0304,C0702 | A24,A01,B07,B44,UNK,UNK | 0 |
| NL327469 | 50-60 | 3 | 0 | 4.92 | PD-1/PDL-1 | Bladder Cancer | MSK-IMPACT | A2301,A0201,B0702,B5801,C0718,C0702 | A24,A02,B07,B58,UNK,UNK | 0 |
| NW860530 | 50-60 | 13 | 0 | 1.97 | CTLA4 | Gastrointestinal Stromal Tumor | MSK-IMPACT | A0301,A0201,B1501,B1801,C0303,C0501 | A03,A02,B52,B44,UNK,UNK | 0 |
| OW683720 | 50-60 | 8 | 0 | 3.94 | PD-1/PDL-1 | Renal Cell Carcinoma | MSK-IMPACT | A3001,A6801,B1302,B3501,C0401,C0602 | A01A03,A03,UNK,B07,UNK,UNK | 0 |
| PX347610 | 31-50 | 9 | 1 | 4.92 | PD-1/PDL-1 | Head and Neck Cancer | MSK-IMPACT | A0301,A3002,B0702,B4403,C1601,C0702 | A03,A01,B07,B44,UNK,UNK | 0 |
| QH692221 | 31-50 | 0 | 1 | 8.85 | PD-1/PDL-1 | Renal Cell Carcinoma | MSK-IMPACT | A2403,A0201,B5601,B4601,C0102,C0102 | A24,A02,B07,B62,UNK,UNK | 1 |

APPENDIX 1-continued

| | | | | | | | | | | Homozygous |
|---|---|---|---|---|---|---|---|---|---|---|
| Sample | Age Group | OS_Months | OS_Event | IMPACT-MutCnt | Drug Class | Cancer Type | Reference | HLA Class I Alleles | HLA Class I Super-types | (1 = Yes; 0 = No) |
| UE728227 | >71 | 20 | 0 | 6.89 | Combo | Renal Cell Carcinoma | MSK-IMPACT | A3201,A2601,B1801, B5101,C1502,C1203 | A01,A01,B44, B07,UNK,UNK | 0 |
| UW595893 | 61-70 | 1 | 0 | 5.9 | PD-1/PDL-1 | Glioma | MSK-IMPACT | A2301,A2901,B4403, B4901,C1601,C0701 | A24,A01A24,B44, UNK,UNK,UNK | 0 |
| XK080812 | 50-60 | 5 | 0 | 0.98 | CTLA4 | Melanoma | MSK-IMPACT | A0101,A6802,B1402, B3701,C0802,C0602 | A01,A02,B27, B44,UNK,UNK | 0 |
| CW049799 | 50-60 | 37 | 0 | 2.95 | Combo | Non-Small Cell Lung Cancer | MSK-IMPACT | A1101,A2402,B4001, B1501,C0401,C0702 | A03,A24,B44, B62,UNK,UNK | 0 |
| DR673373 | 50-60 | 20 | 0 | 14.76 | Combo | Melanoma | MSK-IMPACT | A2402,A2402,B3502, B4901,C0401,C0701 | A24,A24,B07, UNK,UNK,UNK | 1 |
| NI498165 | 31-50 | 6 | 0 | 0.98 | PD-1/PDL-1 | Head and Neck Cancer | MSK-IMPACT | A0101,A0201,B0802, B0802,C0701,C0701 | A01,A02,B08, B08,UNK,UNK | 1 |
| NU583295 | 61-70 | 5 | 0 | 53.12 | PD-1/PDL-1 | Colorectal Cancer | MSK-IMPACT | A1101,A2402,B1505, B3501,C0303,C0401 | A03,A24,B62, B07,UNK,UNK | 0 |
| PJ173593 | >71 | 12 | 0 | 2.95 | PD-1/PDL-1 | Melanoma | MSK-IMPACT | A2402,A0201,B5201, B1501,C0303,C1202 | A24,A02,B62, B62,UNK,UNK | 0 |
| PV847859 | 50-60 | 0 | 0 | 17.71 | PD-1/PDL-1 | Cancer of Unknown Primary | MSK-IMPACT | A0301,A2601,B3801, B3801,C1203,C1203 | A03,A01,B27, B27,UNK,UNK | 1 |
| PX688045 | 50-60 | 6 | 0 | 1.97 | PD-1/PDL-1 | Renal Cell Carcinoma | MSK-IMPACT | A0301,A3001,B1302, B5101,C1402,C0602 | A03,A01A03,UNK, B07,UNK,UNK | 0 |
| RC915805 | >71 | 17 | 0 | 3.94 | PD-1/PDL-1 | Bone Cancer | MSK-IMPACT | A0201,A0201,B4901, B1501,C0303,C0701 | A02,A02,UNK, B62,UNK,UNK | 1 |
| SG503340 | 31-50 | 4 | 1 | 11.81 | PD-1/PDL-1 | Non-Small Cell Lung Cancer | MSK-IMPACT | A2403,A2402,B1801, B1801,C1203,C0701 | A24,A24,B44, B44,UNK,UNK | 1 |
| TH039944 | >71 | 2 | 0 | 0.98 | PD-1/PDL-1 | Bone Cancer | MSK-IMPACT | A3002,A0201,B8101, B4501,C1601,C0804 | A01,A02,B07, B44,UNK,UNK | 0 |
| TP130607 | 50-60 | 1 | 0 | 0.98 | PD-1/PDL-1 | Adrenocortical Carcinoma | MSK-IMPACT | A0101,A0101,B0801, B3501,C0401,C0701 | A01,A01,B08, B07,UNK,UNK | 1 |
| VO020126 | 31-50 | 12 | 1 | 21.64 | Combo | Melanoma | MSK-IMPACT | A0301,A0101,B0702, B0801,C0701,C0702 | A03,A01,B07, B08,UNK,UNK | 0 |
| WK971939 | >71 | 11 | 0 | 0.98 | PD-1/PDL-1 | Hodgkin Lymphoma | MSK-IMPACT | A0101,A0101,B0801, B0801,C0701,C0701 | A01,A01,B08, B08,UNK,UNK | 1 |
| YV503688 | 50-60 | 19 | 0 | 1.97 | PD-1/PDL-1 | Glioma | MSK-IMPACT | A0301,A0302,B2705, B4402,C0102,C0704 | A03,A03,B27, B44,UNK,UNK | 0 |
| BA636244 | 31-50 | 26 | 0 | 3.94 | Combo | Renal Cell Carcinoma | MSK-IMPACT | A2402,A0201,B1517, B3503,C0401,C0701 | A24,A02,B58, B07,UNK,UNK | 0 |
| BM256386 | 31-50 | 13 | 1 | 6.89 | PD-1/PDL-1 | Non-Small Cell Lung Cancer | MSK-IMPACT | A2301,A2301,B4101, B5001,C0602,C1701 | A24,A24,B44, B44,UNK,UNK | 1 |
| BT364903 | 50-60 | 15 | 0 | 1.97 | Combo | Melanoma | MSK-IMPACT | A3002,A0205,B3701, B1801,C0501,C0602 | A01,A02,B44, B44,UNK,UNK | 0 |
| CQ365110 | 61-70 | 5 | 0 | 1.97 | PD-1/PDL-1 | Glioma | MSK-IMPACT | A0201,A3201,B0702, B5701,C0602,C0702 | A02,A01,B07, B58,UNK,UNK | 0 |
| DU909576 | 50-60 | 1 | 1 | 10.82 | PD-1/PDL-1 | Non-Small Cell Lung Cancer | MSK-IMPACT | A0101,A2601,B1517, B3502,C0401,C0701 | A01,A01,B58, B07,UNK,UNK | 0 |
| EK320634 | 61-70 | 10 | 1 | 10.82 | PD-1/PDL-1 | Non-Small Cell Lung Cancer | MSK-IMPACT | A2601,A0201,B0702, B4801,C0801,C0702 | A01,A02,B07, B27,UNK,UNK | 0 |
| EV854604 | 61-70 | 5 | 1 | 3.94 | PD-1/PDL-1 | Bladder Cancer | MSK-IMPACT | A0301,A0101,B0702, B0801,C0701,C0702 | A03,A01,B07, B08,UNK,UNK | 0 |
| GX642946 | 31-50 | 5 | 0 | 7.87 | PD-1/PDL-1 | Melanoma | MSK-IMPACT | A0301,A2402,B1501, B5101,C1502,C0304 | A03,A24,B62, B07,UNK,UNK | 0 |
| KH191548 | 61-70 | 11 | 1 | 4.92 | Combo | Head and Neck Cancer | MSK-IMPACT | A2402,A2902,B4403, B5701,C1601,C0602 | A24,A01A24,B44, B58,UNK,UNK | 0 |
| KX950195 | 31-50 | 0 | 0 | 11.8 | PD-1/PDL-1 | Melanoma | MSK-IMPACT | A1101,A0201,B0801, B1402,C0802,C0701 | A03,A02,B08, B27,UNK,UNK | 0 |
| OQ394665 | 61-70 | 56 | 0 | 18.69 | CTLA4 | Melanoma | MSK-IMPACT | A0101,A2402,B0801, B1801,C1203,C0701 | A01,A24,B08, B44,UNK,UNK | 0 |
| PD027960 | 61-70 | 1 | 0 | 5.9 | PD-1/PDL-1 | Glioma | MSK-IMPACT | A0201,A0205,B5001, B1801,C0602,C0501 | A02,A02,B44, B44,UNK,UNK | 0 |
| PX578748 | 50-60 | 5 | 0 | 7.87 | PD-1/PDL-1 | Renal Cell Carcinoma | MSK-IMPACT | A2402,A3201,B0702, B0801,C0701,C0702 | A24,A01,B07, B08,UNK,UNK | 0 |
| RG945840 | 31-50 | 4 | 0 | 7.87 | PD-1/PDL-1 | Non-Small Cell Lung Cancer | MSK-IMPACT | A0301,A3201,B3801, B4901,C1203,C0701 | A03,A01,B27, UNK,UNK,UNK | 0 |
| SP021117 | 61-70 | 16 | 0 | 0.98 | Combo | Renal Cell Carcinoma | MSK-IMPACT | A0301,A3002,B5701, B1801,C0501,C0602 | A03,A01,B58, B44,UNK,UNK | 0 |
| TE855191 | 50-60 | 10 | 0 | 10.82 | PD-1/PDL-1 | Esophagogastric Cancer | MSK-IMPACT | A0301,A2902,B0702, B4403,C1601,C0702 | A03,A01A24,B07, B44,UNK,UNK | 0 |
| VZ661197 | 50-60 | 26 | 0 | 3.94 | PD-1/PDL-1 | Renal Cell Carcinoma | MSK-IMPACT | A2402,A3201,B4001, B3501,C0303,C0304 | A24,A01,B44, B07,UNK,UNK | 0 |
| XV950799 | 31-50 | 6 | 0 | 6.89 | PD-1/PDL-1 | Bladder Cancer | MSK-IMPACT | A0201,A2601,B4402, B3801,C0501,C1203 | A02,A01,B44, B27,UNK,UNK | 0 |
| ZE182555 | 31-50 | 21 | 0 | 17.71 | CTLA4 | Melanoma | MSK-IMPACT | A1101,A0201,B5101, B4402,C1402,C1502 | A03,A02,B07, B44,UNK,UNK | 0 |

APPENDIX 1-continued

| | | | | | | | | | | Homozygous |
|---|---|---|---|---|---|---|---|---|---|---|
| Sample | Age Group | OS_Months | OS_Event | IMPACT-MutCnt | Drug Class | Cancer Type | Reference | HLA Class I Alleles | HLA Class I Super-types | (1 = Yes; 0 = No) |
| | | | | | Cohort 2 | | | | | |
| AR843502 | 31-50 | 2 | 1 | 5.9 | PD-1/PDL-1 | Non-Small Cell Lung Cancer | MSK-IMPACT | A0101,A0201,B0801,B1501,C0304,C0701 | A01,A02,B08,B62,UNK,UNK | 0 |
| DY577205 | 50-60 | 4 | 0 | 57.06 | PD-1/PDL-1 | Glioma | MSK-IMPACT | A0201,A0201,B1302,B5101,C0401,C0602 | A02,A02,UNK,B07,UNK,UNK | 1 |
| FL158584 | 50-60 | 18 | 0 | 0.98 | Combo | Melanoma | MSK-IMPACT | A2601,A2601,B3801,B3801,C1203,C1203 | A01,A01,B27,B27,UNK,UNK | 1 |
| GA026392 | 31-50 | 11 | 0 | 19.68 | PD-1/PDL-1 | Melanoma | MSK-IMPACT | A3001,A0201,B1302,B5102,C0401,C0602 | A01A03,A02,UNK,B07,UNK,UNK | 0 |
| HV618060 | >71 | 0 | 1 | 2.95 | PD-1/PDL-1 | Hepatobiliary Cancer | MSK-IMPACT | A0301,A0201,B1402,B1501,C0303,C0802 | A03,A02,B27,B62,UNK,UNK | 0 |
| IG053882 | 31-50 | 6 | 0 | 95.43 | PD-1/PDL-1 | Melanoma | MSK-IMPACT | A0301,A2402,B0702,B5101,C1502,C0702 | A03,A24,B07,B07,UNK,UNK | 0 |
| KZ373856 | 31-50 | 6 | 0 | 1.97 | PD-1/PDL-1 | Hepatobiliary Cancer | MSK-IMPACT | A2402,A0206,B0705,B6701,C0702,C0702 | A24,A02,B07,B07,UNK,UNK | 1 |
| OF215282 | 61-70 | 2 | 0 | 2.95 | PD-1/PDL-1 | Colorectal Cancer | MSK-IMPACT | A1101,A2902,B2705,B4501,C0202,C0602 | A03,A01A24,B27,B44,UNK,UNK | 0 |
| OG884951 | >71 | 15 | 0 | 18.69 | Combo | Melanoma | MSK-IMPACT | A2402,A3201,B0702,B2705,C0602,C0702 | A24,A01,B07,B27,UNK,UNK | 0 |
| PN375315 | 31-50 | 11 | 0 | 2.95 | PD-1/PDL-1 | Renal Cell Carcinoma | MSK-IMPACT | A6801,A3101,B4001,B4402,C0304,C0704 | A03,A03,B44,B44,UNK,UNK | 0 |
| PV753450 | 50-60 | 0 | 0 | 4.92 | PD-1/PDL-1 | Cancer of Unknown Primary | MSK-IMPACT | A3001,A0301,B4201,B5802,C1701,C0602 | A01A03,A03,B07,B58,UNK,UNK | 0 |
| SC680835 | 31-50 | 11 | 0 | 2.95 | PD-1/PDL-1 | Mesothelioma | MSK-IMPACT | A1101,A0207,B4601,B1502,C0102,C0801 | A03,A02,B62,B62,UNK,UNK | 0 |
| SC857468 | 61-70 | 7 | 0 | 0 | PD-1/PDL-1 | Cancer of Unknown Primary | MSK-IMPACT | A0301,A6801,B0702,B4402,C0704,C0702 | A03,A03,B07,B44,UNK,UNK | 0 |
| TD169754 | 50-60 | 8 | 0 | 22.63 | PD-1/PDL-1 | Non-Small Cell Lung Cancer | MSK-IMPACT | A0101,A0201,B3701,B1801,C1203,C0602 | A01,A02,B44,B44,UNK,UNK | 0 |
| UR220432 | >71 | 6 | 0 | 5.9 | Combo | Breast Cancer | MSK-IMPACT | A0201,A0201,B0702,B5101,C0303,C0701 | A02,A02,B07,B62,UNK,UNK | 1 |
| VS987443 | 61-70 | 0 | 1 | 0.98 | Combo | Prostate Cancer | MSK-IMPACT | A0301,A0301,B5801,B3501,C0302,C0401 | A03,A03,B58,B07,UNK,UNK | 1 |
| YZ765266 | >71 | 6 | 0 | 2.95 | PD-1/PDL-1 | Renal Cell Carcinoma | MSK-IMPACT | A0101,A3101,B3901,B5701,C1203,C0602 | A01,A03,B27,B58,UNK,UNK | 0 |
| ZC277272 | >71 | 4 | 1 | 8.85 | CTLA4 | Colorectal Cancer | MSK-IMPACT | A1102,A2402,B4001,B3505,C0401,C0702 | A03,A24,B44,B07,UNK,UNK | 0 |
| AI419880 | 31-50 | 1 | 1 | 7.87 | PD-1/PDL-1 | Non-Hodgkin Lymphoma | MSK-IMPACT | A0301,A6801,B2705,B5101,C0102,C0702 | A03,A03,B27,B07,UNK,UNK | 0 |
| EQ427020 | >71 | 3 | 1 | 1.97 | Combo | Melanoma | MSK-IMPACT | A2402,A0201,B2705,B1801,C1502,C0701 | A24,A02,B27,B44,UNK,UNK | 0 |
| FE789562 | 31-50 | 2 | 0 | 9.84 | PD-1/PDL-1 | Glioma | MSK-IMPACT | A2301,A2601,B1501,B4102,C0704,C1701 | A24,A01,B62,B44,UNK,UNK | 0 |
| GY753639 | 61-70 | 7 | 0 | 14.76 | PD-1/PDL-1 | Small Cell Lung Cancer | MSK-IMPACT | A2902,A3201,B4403,B5108,C1602,C1601 | A01A24,A01,B44,B07,UNK,UNK | 0 |
| IK672558 | >71 | 31 | 0 | 1.97 | PD-1/PDL-1 | Thyroid Cancer | MSK-IMPACT | A3001,A0101,B2702,B5101,C1502,C0202 | A01A03,A01,B27,B07,UNK,UNK | 0 |
| IV940855 | 61-70 | 11 | 0 | 0 | PD-1/PDL-1 | Non-Small Cell Lung Cancer | MSK-IMPACT | A0301,A0101,B5501,B0702,C0303,C0702 | A03,A01,B07,B07,UNK,UNK | 0 |
| KH410745 | 31-50 | 0 | 1 | 8.85 | PD-1/PDL-1 | Non-Small Cell Lung Cancer | MSK-IMPACT | A3001,A0101,B5701,B1302,C0602,C0602 | A01A03,A01,B58,UNK,UNK,UNK | 1 |
| MT645316 | 31-50 | 16 | 0 | 18.69 | PD-1/PDL-1 | Melanoma | MSK-IMPACT | A0101,A2601,B0702,B0801,C0701,C0702 | A01,A01,B07,B08,UNK,UNK | 0 |
| OS835316 | 31-50 | 15 | 0 | 27.55 | PD-1/PDL-1 | Bladder Cancer | MSK-IMPACT | A2601,A6601,B2705,B4102,C0102,C1701 | A01,A03,B27,B44,UNK,UNK | 0 |
| PH153703 | 31-50 | 5 | 0 | 5.9 | PD-1/PDL-1 | Melanoma | MSK-IMPACT | A2301,A0201,B1801,B4901,C0701,C0701 | A24,A02,B44,UNK,UNK,UNK | 1 |
| SU802799 | 50-60 | 8 | 0 | 38.37 | PD-1/PDL-1 | Melanoma | MSK-IMPACT | A0301,A0201,B0702,B1302,C0602,C0702 | A03,A02,B07,UNK,UNK,UNK | 0 |
| TW199824 | 31-50 | 23 | 0 | 0 | CTLA4 | Prostate Cancer | MSK-IMPACT | A1101,A2402,B5201,B3508,C1202,C0401 | A03,A24,B62,B07,UNK,UNK | 0 |
| UH905646 | 31-50 | 2 | 0 | 0.98 | PD-1/PDL-1 | Soft Tissue Sarcoma | MSK-IMPACT | A2402,A6801,B3906,B1302,C0602,C0702 | A24,A03,B27,UNK,UNK,UNK | 0 |
| WH068307 | 61-70 | 3 | 0 | 4.92 | PD-1/PDL-1 | Glioma | MSK-IMPACT | A0101,A3201,B0801,B4001,C0304,C0701 | A01,A01,B08,B44,UNK,UNK | 0 |
| XQ654957 | 31-50 | 1 | 0 | 3.94 | PD-1/PDL-1 | Glioma | MSK-IMPACT | A1101,A2402,B3802,B3802,C0702,C0702 | A03,A24,UNK,UNK,UNK,UNK | 1 |
| YC912629 | 31-50 | 13 | 0 | 3.94 | CTLA4 | Breast Cancer | MSK-IMPACT | A2402,A0201,B4006,B3503,C1502,C0401 | A24,A02,B44,B07,UNK,UNK | 0 |
| ZI588054 | 31-50 | 0 | 0 | 5.9 | PD-1/PDL-1 | Renal Cell Carcinoma | MSK-IMPACT | A3001,A1101,B5501,B1302,C0303,C0602 | A01A03,A03,B07,UNK,UNK,UNK | 0 |

APPENDIX 1-continued

| | | | | | | | | | | Homozygous (1 = Yes; 0 = No) |
|---|---|---|---|---|---|---|---|---|---|---|
| Sample | Age Group | OS_Months | OS_Event | IMPACT-MutCnt | Drug Class | Cancer Type | Reference | HLA Class I Alleles | HLA Class I Super-types | |
| ZX742344 | 31-50 | 1 | 1 | 4.92 | PD-1/PDL-1 | Esophagogastric Cancer | MSK-IMPACT | A0301,A2601,B3801, B1801,C1203,C1203 | A03,A01,B27, B44,UNK,UNK | 1 |
| BP367380 | 31-50 | 5 | 1 | 5.9 | PD-1/PDL-1 | Non-Small Cell Lung Cancer | MSK-IMPACT | A6802,A6601,B1402, B1801,C0802,C1203 | A02,A03,B27, B44,UNK,UNK | 0 |
| DZ958878 | 50-60 | 18 | 0 | 3.94 | PD-1/PDL-1 | Glioma | MSK-IMPACT | A1101,A3101,B0702, B3901,C1203,C0702 | A03,A03,B07, B27,UNK,UNK | 0 |
| GR856721 | 31-50 | 11 | 0 | 21.64 | PD-1/PDL-1 | Bladder Cancer | MSK-IMPACT | A0101,A0101,B5701, B3508,C0401,C0602 | A01,A01,B58, B07,UNK,UNK | 1 |
| HH642834 | 61-70 | 5 | 0 | 100.35 | PD-1/PDL-1 | Glioma | MSK-IMPACT | A2402,A3101,B1801, B5701,C0602,C0701 | A24,A03,B44, B58,UNK,UNK | 0 |
| JW331281 | 31-50 | 16 | 0 | 5.9 | PD-1/PDL-1 | Melanoma | MSK-IMPACT | A2601,A2601,B1501, B3801,C0303,C1203 | A01,A01,B62, B27,UNK,UNK | 1 |
| LD541574 | 31-50 | 15 | 0 | 2.95 | PD-1/PDL-1 | Renal Cell Carcinoma | MSK-IMPACT | A2402,A0201,B0801, B5101,C0202,C0701 | A24,A02,B08, B07,UNK,UNK | 0 |
| MD017290 | 61-70 | 5 | 1 | 6.89 | PD-1/PDL-1 | Head and Neck Cancer | MSK-IMPACT | A0101,A2402,B0801, B5701,C0602,C0701 | A01,A24,B08, B58,UNK,UNK | 0 |
| MW651937 | 50-60 | 0 | 1 | 16.72 | PD-1/PDL-1 | Bladder Cancer | MSK-IMPACT | A2402,A0201,B1501, B4402,C0303,C0501 | A24,A02,B62, B44,UNK,UNK | 0 |
| OZ442015 | 61-70 | 11 | 0 | 6.89 | PD-1/PDL-1 | Glioma | MSK-IMPACT | A0201,A2601,B3901, B4002,C1502,C1203 | A02,A01,B27, B44,UNK,UNK | 0 |
| RU189416 | 61-70 | 18 | 0 | 1.97 | PD-1/PDL-1 | Glioma | MSK-IMPACT | A1101,A1101,B1801, B3501,C0401,C0701 | A03,A03,B44, B07,UNK,UNK | 1 |
| TS854723 | 50-60 | 0 | 0 | 20.66 | PD-1/PDL-1 | Non-Small Cell Lung Cancer | MSK-IMPACT | A6601,A3101,B0801, B1509,C0701,C0704 | A03,A03,B08, B27,UNK,UNK | 0 |
| UJ633658 | 50-60 | 7 | 1 | 7.87 | Combo | Melanoma | MSK-IMPACT | A0201,A0201,B1801, B5101,C1502,C0701 | A02,A02,B44, B07,UNK,UNK | 1 |
| UL388657 | 31-50 | 1 | 1 | 4.92 | CTLA4 | Pancreatic Cancer | MSK-IMPACT | A3002,A0101,B1801, B5001,C0602,C0501 | A01,A01,B44, B44,UNK,UNK | 0 |
| WG479585 | >71 | 20 | 0 | 4.92 | PD-1/PDL-1 | Glioma | MSK-IMPACT | A0201,A0201,B5702, B5001,C0602,C1801 | A02,A02,B58, B44,UNK,UNK | 1 |
| AH954476 | 61-70 | 11 | 0 | 3.94 | PD-1/PDL-1 | Cancer of Unknown Primary | MSK-IMPACT | A0101,A2902,B0702, B3503,C0401,C0702 | A01,A01A24,B07, B07,UNK,UNK | 0 |
| CW247724 | 31-50 | 15 | 0 | 19.68 | Combo | Non-Small Cell Lung Cancer | MSK-IMPACT | A2402,A3101,B2705, B0801,C0102,C0701 | A24,A03,B27, B08,UNK,UNK | 0 |
| DT197689 | 31-50 | 0 | 0 | 0.98 | PD-1/PDL-1 | Hepatobiliary Cancer | MSK-IMPACT | A0301,A0301,B0702, B1402,C0802,C0702 | A03,A03,B07, B27,UNK,UNK | 1 |
| EO439129 | 31-50 | 5 | 0 | 0.98 | Combo | Melanoma | MSK-IMPACT | A3002,A2301,B0702, B1302,C0804,C0702 | A01,A24,B07, UNK,UNK,UNK | 0 |
| GB346707 | 31-50 | 2 | 1 | 8.85 | PD-1/PDL-1 | Non-Small Cell Lung Cancer | MSK-IMPACT | A2402,A2601,B3801, B3508,C1203,C0401 | A24,A01,B27, B07,UNK,UNK | 0 |
| IN703823 | 50-60 | 6 | 0 | 3.94 | Combo | Melanoma | MSK-IMPACT | A1101,A0217,B5501, B4002,C0303,C0304 | A03,A02,B07, B44,UNK,UNK | 0 |
| MV401545 | 50-60 | 2 | 0 | 3.94 | PD-1/PDL-1 | Glioma | MSK-IMPACT | A2402,A3201,B4001, B1302,C0304,C0602 | A24,A01,B44, UNK,UNK,UNK | 0 |
| PE291148 | 31-50 | 4 | 0 | 7.87 | PD-1/PDL-1 | Non-Small Cell Lung Cancer | MSK-IMPACT | A3201,A2601,B3508, B1302,C0401,C0602 | A01,A01,B07, UNK,UNK,UNK | 0 |
| PM383343 | 50-60 | 10 | 1 | 10.82 | PD-1/PDL-1 | Non-Small Cell Lung Cancer | MSK-IMPACT | A1101,A2601,B0801, B4001,C0701,C0702 | A03,A01,B08, B44,UNK,UNK | 0 |
| TR249275 | 50-60 | 11 | 0 | 6.89 | PD-1/PDL-1 | Renal Cell Carcinoma | MSK-IMPACT | A0101,A0201,B4001, B5001,C0304,C0602 | A01,A02,B44, B44,UNK,UNK | 0 |
| WC440856 | 31-50 | 6 | 1 | 3.94 | PD-1/PDL-1 | Non-Small Cell Lung Cancer | MSK-IMPACT | A2902,A2901,B1402, B5701,C0602,C0802 | A01A24,A01A24,B27, B58,UNK,UNK | 0 |
| WX598960 | 31-50 | 39 | 0 | 2.95 | CTLA4 | Melanoma | MSK-IMPACT | A6801,A0201,B1402, B2702,C0202,C0802 | A03,A02,B27, B27,UNK,UNK | 0 |
| YE912753 | 50-60 | 3 | 0 | 2.95 | PD-1/PDL-1 | Anal Cancer | MSK-IMPACT | A3201,A0201,B2705, B4402,C0202,C0501 | A01,A02,B27, B44,UNK,UNK | 0 |
| YU883868 | 50-60 | 7 | 0 | 4.92 | PD-1/PDL-1 | Non-Hodgkin Lymphoma | MSK-IMPACT | A0101,A7401,B1402, B5802,C0802,C0802 | A01,A03,B27, B58,UNK,UNK | 0 |
| YY988865 | 31-50 | 3 | 0 | 96.41 | PD-1/PDL-1 | Skin Cancer; Non-Melanoma | MSK-IMPACT | A2301,A0201,B0702, B1801,C0501,C0702 | A24,A02,B07, B44,UNK,UNK | 0 |
| YZ113825 | 31-50 | 7 | 1 | 3.94 | PD-1/PDL-1 | Non-Small Cell Lung Cancer | MSK-IMPACT | A0301,A2601,B0702, B3501,C0702,C0401 | A03,A01,B07, B07,UNK,UNK | 0 |
| ZE100444 | 31-50 | 12 | 0 | 0 | PD-1/PDL-1 | Soft Tissue Sarcoma | MSK-IMPACT | A0201,A0201,B1501, B5101,C0303,C1602 | A02,A02,B62, B07,UNK,UNK | 1 |
| ZT370662 | 31-50 | 2 | 1 | 0 | Combo | Melanoma | MSK-IMPACT | A0301,A0201,B4001, B3501,C0304,C0401 | A03,A02,B44, B07,UNK,UNK | 0 |
| CU577679 | 50-60 | 5 | 0 | 1.97 | PD-1/PDL-1 | Soft Tissue Sarcoma | MSK-IMPACT | A2301,A3201,B1801, B4901,C0701,C0701 | A24,A01,B44, UNK,UNK,UNK | 1 |
| JJ451223 | >71 | 5 | 0 | 2.95 | PD-1/PDL-1 | Pancreatic Cancer | MSK-IMPACT | A0301,A0201,B0702, B0705,C1505,C0702 | A03,A02,B07, B07,UNK,UNK | 0 |
| LL341780 | 31-50 | 5 | 0 | 36.4 | PD-1/PDL-1 | Non-Small Cell Lung Cancer | MSK-IMPACT | A3201,A0201,B4701, B1801,C0401,C0602 | A01,A02,UNK, B44,UNK,UNK | 0 |

APPENDIX 1-continued

Cohort 2

| Sample | Age Group | OS_ Months | OS_ Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| MM334107 | 31-50 | 13 | 1 | 3.94 | PD-1/PDL-1 | Non-Small Cell Lung Cancer | MSK-IMPACT | A1101,A0203,B4001, B5102,C0102,C0304 | A03,A02,B44, B07,UNK,UNK | 0 |
| MT926683 | 31-50 | 11 | 0 | 4.92 | PD-1/PDL-1 | Renal Cell Carcinoma | MSK-IMPACT | A0201,A0201,B4101, B1801,C1701,C0701 | A02,A02,B44, B44,UNK,UNK | 1 |
| PA328028 | 61-70 | 0 | 1 | 0 | PD-1/PDL-1 | Non-Small Cell Lung Cancer | MSK-IMPACT | A0101,A3301,B1402, B3502,C0802,C0401 | A01,A03,B27, B07,UNK,UNK | 0 |
| PW579192 | 31-50 | 1 | 0 | 2.95 | PD-1/PDL-1 | Hepatobiliary Cancer | MSK-IMPACT | A0101,A2402,B3801, B5701,C1203,C0602 | A01,A24,B27, B58,UNK,UNK | 0 |
| RF326353 | 61-70 | 4 | 0 | 4.92 | PD-1/PDL-1 | Renal Cell Carcinoma | MSK-IMPACT | A2902,A0206,B4403, B3902,C1601,C0702 | A01A24,A02,B44, B27,UNK,UNK | 0 |
| SL233608 | 31-50 | 10 | 0 | 0.98 | PD-1/PDL-1 | Melanoma | MSK-IMPACT | A3004,A2402,B0702, B5001,C0602,C0702 | A01,A24,B07, B44,UNK,UNK | 0 |
| SM717841 | 61-70 | 12 | 0 | 52.14 | PD-1/PDL-1 | Melanoma | MSK-IMPACT | A0101,A0201,B0702, B5701,C0602,C0702 | A01,A02,B07, B58,UNK,UNK | 0 |
| TA620796 | 50-60 | 4 | 0 | 1.97 | PD-1/PDL-1 | Sex Cord Stromal Tumor | MSK-IMPACT | A0101,A3101,B0801, B4001,C0304,C0701 | A01,A03,B08, B44,UNK,UNK | 0 |
| VY234263 | 50-60 | 41 | 0 | 7.87 | PD-1/PDL-1 | Renal Cell Carcinoma | MSK-IMPACT | A1101,A0101,B0801, B3501,C0401,C0701 | A03,A01,B08, B07,UNK,UNK | 0 |
| WG852822 | 50-60 | 0 | 1 | 2.95 | PD-1/PDL-1 | Non-Small Cell Lung Cancer | MSK-IMPACT | A0301,A0201,B1402, B1801,C0802,C0701 | A03,A02,B27, B44,UNK,UNK | 0 |
| YV942117 | 31-50 | 17 | 0 | 8.85 | PD-1/PDL-1 | Melanoma | MSK-IMPACT | A1101,A0101,B5701, B5201,C1202,C0602 | A03,A01,B58, B62,UNK,UNK | 0 |
| ZJ820780 | 31-50 | 4 | 1 | 14.76 | PD-1/PDL-1 | Bladder Cancer | MSK-IMPACT | A0101,A0201,B3901, B3501,C0401,C0401 | A01,A02,B27, B07,UNK,UNK | 1 |
| AI663614 | 31-50 | 8 | 0 | 10.82 | PD-1/PDL-1 | Non-Small Cell Lung Cancer | MSK-IMPACT | A1101,A3201,B1501, B5801,C0303,C0302 | A03,A01,B62, B58,UNK,UNK | 0 |
| CD455638 | 61-70 | 32 | 0 | 14.76 | CTLA4 | Melanoma | MSK-IMPACT | A2402,A0201,B1501, B4403,C0303,C1601 | A24,A02,B62, B44,UNK,UNK | 0 |
| CG203297 | 31-50 | 1 | 0 | 5.9 | PD-1/PDL-1 | Breast Cancer | MSK-IMPACT | A2402,A0201,B1402, B4405,C0802,C0202 | A24,A02,B27, B44,UNK,UNK | 0 |
| DM486141 | 50-60 | 0 | 1 | 10.82 | PD-1/PDL-1 | Non-Small Cell Lung Cancer | MSK-IMPACT | A2402,A3303,B0702, B4403,C0706,C0702 | A24,A03,B07, B44,UNK,UNK | 0 |
| EK931793 | 31-50 | 10 | 1 | 2.95 | PD-1/PDL-1 | Bladder Cancer | MSK-IMPACT | A1101,A2402,B0801, B1801,C1203,C0702 | A03,A24,B08, B44,UNK,UNK | 0 |
| HC293273 | 50-60 | 31 | 0 | 1.97 | Combo | Renal Cell Carcinoma | MSK-IMPACT | A3004,A0101,B4101, B1517,C1701,C0701 | A01,A01,B44, B58,UNK,UNK | 0 |
| IB756171 | 31-50 | 11 | 0 | 2.95 | PD-1/PDL-1 | Head and Neck Cancer | MSK-IMPACT | A2402,A0201,B4403, B1501,C0303,C1601 | A24,A02,B44, B62,UNK,UNK | 0 |
| KD258411 | 31-50 | 10 | 0 | 3.94 | PD-1/PDL-1 | Pancreatic Cancer | MSK-IMPACT | A1101,A2601,B5501, B1402,C0102,C0802 | A03,A01,B07, B27,UNK,UNK | 0 |
| OC866849 | >71 | 13 | 0 | 8.85 | Combo | Non-Small Cell Lung Cancer | MSK-IMPACT | A0101,A2402,B5701, B3502,C0602,C0401 | A01,A24,B58, B07,UNK,UNK | 0 |
| RL299291 | 31-50 | 13 | 0 | 6.89 | PD-1/PDL-1 | Non-Small Cell Lung Cancer | MSK-IMPACT | A6801,A3201,B2705, B4001,C0102,C0304 | A03,A01,B27, B44,UNK,UNK | 0 |
| YB400702 | 61-70 | 0 | 0 | 2.95 | PD-1/PDL-1 | Glioma | MSK-IMPACT | A2301,A6802,B4403, B4402,C0401,C0401 | A24,A02,B44, B44,UNK,UNK | 1 |
| YB599485 | >71 | 3 | 1 | 4.92 | PD-1/PDL-1 | Glioma | MSK-IMPACT | A1102,A6802,B3802, B5301,C0401,C0702 | A03,A02,UNK, B07,UNK,UNK | 0 |
| YD008671 | 50-60 | 1 | 1 | 27.55 | PD-1/PDL-1 | Bladder Cancer | MSK-IMPACT | A3201,A2601,B0702, B4402,C0501,C0702 | A01,A01,B07, B44,UNK,UNK | 0 |
| YN251276 | >71 | 0 | 0 | 6.89 | PD-1/PDL-1 | Breast Cancer | MSK-IMPACT | A0101,A0201,B0801, B1501,C0303,C0701 | A01,A02,B08, B62,UNK,UNK | 0 |
| AD875088 | 50-60 | 0 | 1 | 24.59 | PD-1/PDL-1 | Bladder Cancer | MSK-IMPACT | A2301,A2402,B4403, B3502,C0401,C0401 | A24,A24,B44, B07,UNK,UNK | 1 |
| BG455363 | 61-70 | 5 | 0 | 18.69 | PD-1/PDL-1 | Prostate Cancer | MSK-IMPACT | A0101,A2301,B5701, B4901,C0602,C0701 | A01,A24,B58, UNK,UNK,UNK | 0 |
| BX707409 | 50-60 | 9 | 0 | 3.94 | PD-1/PDL-1 | Non-Small Cell Lung Cancer | MSK-IMPACT | A0201,A3101,B1501, B5701,C0303,C0602 | A02,A03,B62, B58,UNK,UNK | 0 |
| BY656262 | 50-60 | 28 | 1 | 4.92 | PD-1/PDL-1 | Head and Neck Cancer | MSK-IMPACT | A2301,A6801,B4901, B5101,C1502,C0701 | A24,A03,UNK, B07,UNK,UNK | 0 |
| CU241212 | 50-60 | 7 | 0 | 11.81 | PD-1/PDL-1 | Cancer of Unknown Primary | MSK-IMPACT | A1101,A3301,B1402, B4402,C0501,C0802 | A03,A03,B27, B44,UNK,UNK | 0 |
| DC116501 | 31-50 | 1 | 1 | 1.97 | PD-1/PDL-1 | Renal Cell Carcinoma | MSK-IMPACT | A2601,A2601,B0702, B3501,C0401,C0702 | A01,A01,B07, B07,UNK,UNK | 1 |
| FN036373 | 61-70 | 16 | 1 | 12.79 | PD-1/PDL-1 | Bladder Cancer | MSK-IMPACT | A0201,A0201,B4001, B4001,C0304,C0304 | A02,A02,B44, B44,UNK,UNK | 1 |
| FQ591029 | 31-50 | 12 | 0 | 0.98 | PD-1/PDL-1 | Thyroid Cancer | MSK-IMPACT | A0101,A2402,B0801, B4403,C1601,C0701 | A01,A01A24,B08, B44,UNK,UNK | 0 |
| GX642098 | 31-50 | 4 | 1 | 10.82 | PD-1/PDL-1 | Non-Small Cell Lung Cancer | MSK-IMPACT | A0201,A2601,B1801, B1801,C1203,C0701 | A02,A01,B44, B44,UNK,UNK | 1 |
| JQ503820 | 31-50 | 5 | 0 | 11.81 | PD-1/PDL-1 | Non-Small Cell Lung Cancer | MSK-IMPACT | A0101,A2902,B4402, B5801,C0501,C0706 | A01,A01A24,B44, B58,UNK,UNK | 0 |

APPENDIX 1-continued

| | | | | | | | | | | Homozygous |
|---|---|---|---|---|---|---|---|---|---|---|
| | | | | | | | | | | (1 = Yes; |
| Sample | Age Group | OS_Months | OS_Event | IMPACT-MutCnt | Drug Class | Cancer Type | Reference | HLA Class I Alleles | HLA Class I Super-types | 0 = No) |
| KT271657 | 31-50 | 7 | 0 | 11.81 | PD-1/PDL-1 | Head and Neck Cancer | MSK-IMPACT | A3004,A0201,B1801, B4403,C0706,C0701 | A01,A02,B44, B44,UNK,UNK | 0 |
| LE923094 | >71 | 9 | 0 | 13.77 | PD-1/PDL-1 | Adrenocortical Carcinoma | MSK-IMPACT | A3002,A2301,B1402, B4403,C0802,C0401 | A01,A24,B27, B44,UNK,UNK | 0 |
| OZ370159 | 61-70 | 1 | 0 | 2.95 | PD-1/PDL-1 | Non-Small Cell Lung Cancer | MSK-IMPACT | A0301,A0101,B3503, B3501,C0401,C0401 | A03,A01,B07, B07,UNK,UNK | 1 |
| PW995997 | 31-50 | 7 | 1 | 1.97 | PD-1/PDL-1 | Renal Cell Carcinoma | MSK-IMPACT | A3001,A6901,B5501, B5801,C0102,C0706 | A01A03,A02,B07, B58,UNK,UNK | 0 |
| QK851300 | 50-60 | 3 | 0 | 6.89 | PD-1/PDL-1 | Non-Small Cell Lung Cancer | MSK-IMPACT | A3002,A0201,B2702, B1801,C0202,C0501 | A01,A02,B27, B44,UNK,UNK | 0 |
| ZK094596 | >71 | 9 | 1 | 0.98 | PD-1/PDL-1 | Glioma | MSK-IMPACT | A0101,A0201,B1402, B5701,C0802,C0602 | A01,A02,B27, B58,UNK,UNK | 0 |
| CC702072 | 31-50 | 4 | 0 | 20.66 | PD-1/PDL-1 | Cancer of Unknown Primary | MSK-IMPACT | A1101,A0201,B3501, B3501,C0303,C0401 | A03,A02,B07, B07,UNK,UNK | 1 |
| CH796273 | 31-50 | 3 | 1 | 6.89 | PD-1/PDL-1 | Pancreatic Cancer | MSK-IMPACT | A0101,A0201,B1801, B1302,C0602,C0701 | A01,A02,B44, UNK,UNK,UNK | 0 |
| EL247113 | 31-50 | 4 | 0 | 5.9 | PD-1/PDL-1 | Melanoma | MSK-IMPACT | A0301,A0201,B4001, B3501,C0304,C0401 | A03,A02,B44, B07,UNK,UNK | 0 |
| EP440324 | 61-70 | 10 | 0 | 1.97 | PD-1/PDL-1 | Adrenocortical Carcinoma | MSK-IMPACT | A0201,A0201,B1501, B5101,C1502,C0304 | A02,A02,B62, B07,UNK,UNK | 1 |
| FU946944 | 31-50 | 0 | 1 | 12.79 | PD-1/PDL-1 | Non-Small Cell Lung Cancer | MSK-IMPACT | A1101,A2402,B5701, B3508,C1203,C0602 | A03,A24,B58, B07,UNK,UNK | 0 |
| FY552297 | 31-50 | 30 | 0 | 17.71 | PD-1/PDL-1 | Renal Cell Carcinoma | MSK-IMPACT | A1101,A0101,B1801, B5801,C0701,C0706 | A03,A01,B44, B58,UNK,UNK | 0 |
| HE368595 | >71 | 3 | 0 | 4.92 | PD-1/PDL-1 | Colorectal Cancer | MSK-IMPACT | A0201,A0205,B4402, B1517,C0501,C0701 | A02,A02,B44, B58,UNK,UNK | 0 |
| HJ778699 | >71 | 1 | 1 | 1.97 | Combo | Esophagogastric Cancer | MSK-IMPACT | A0101,A0201,B0702, B1501,C0304,C0702 | A01,A02,B07, B62,UNK,UNK | 0 |
| HM524670 | 31-50 | 11 | 0 | 0 | PD-1/PDL-1 | Skin Cancer; Non-Melanoma | MSK-IMPACT | A0301,A2301,B3502, B3503,C0602,C0401 | A03,A24,B07, B07,UNK,UNK | 0 |
| IQ442756 | 31-50 | 7 | 0 | 20.66 | PD-1/PDL-1 | Skin Cancer; Non-Melanoma | MSK-IMPACT | A0201,A0205,B0702, B2705,C1502,C0702 | A02,A02,B07, B27,UNK,UNK | 0 |
| JD423803 | 31-50 | 4 | 0 | 15.74 | PD-1/PDL-1 | Melanoma | MSK-IMPACT | A1101,A2601,B3801, B4001,C0304,C1203 | A03,A01,B27, B44,UNK,UNK | 0 |
| JI639707 | 61-70 | 10 | 0 | 0 | PD-1/PDL-1 | Renal Cell Carcinoma | MSK-IMPACT | A3001,A0201,B1801, B1302,C0602,C0701 | A01A03,A02,B44, UNK,UNK,UNK | 0 |
| KG964615 | 50-60 | 26 | 1 | 0.98 | Combo | Melanoma | MSK-IMPACT | A0101,A0201,B0801, B1801,C0701,C0701 | A01,A02,B08, B44,UNK,UNK | 1 |
| KT138482 | 31-50 | 1 | 0 | 3.94 | Combo | Soft Tissue Sarcoma | MSK-IMPACT | A0101,A0201,B1402, B1302,C0602,C0706 | A01,A02,B27, UNK,UNK,UNK | 0 |
| KZ477043 | 31-50 | 19 | 0 | 9.84 | Combo | Renal Cell Carcinoma | MSK-IMPACT | A2902,A2601,B1402, B1802,C1203,C0802 | A01A24,A01,B27, B44,UNK,UNK | 0 |
| NP845180 | 61-70 | 17 | 0 | 3.94 | Combo | Renal Cell Carcinoma | MSK-IMPACT | A0301,A0101,B0702, B3701,C0602,C0702 | A03,A01,B07, B44,UNK,UNK | 0 |
| NS410554 | 50-60 | 33 | 0 | 5.9 | PD-1/PDL-1 | Renal Cell Carcinoma | MSK-IMPACT | A2601,A6801,B3701, B3503,C0401,C0602 | A01,A03,B44, B07,UNK,UNK | 0 |
| OW705404 | 50-60 | 30 | 0 | 13.77 | CTLA4 | Melanoma | MSK-IMPACT | A0301,A2402,B3501, B3508,C0401,C0401 | A03,A24,B07, B07,UNK,UNK | 1 |
| PB770726 | 31-50 | 40 | 0 | 33.45 | PD-1/PDL-1 | Melanoma | MSK-IMPACT | A0301,A0201,B1501, B3503,C0304,C0401 | A03,A02,B62, B07,UNK,UNK | 0 |
| TV538691 | >71 | 15 | 0 | 2.95 | Combo | Cancer of Unknown Primary | MSK-IMPACT | A2901,A0205,B0705, B5001,C1505,C0602 | A01A24,A02,B07, B44,UNK,UNK | 0 |
| UZ818372 | 31-50 | 0 | 1 | 1.97 | PD-1/PDL-1 | Non-Small Cell Lung Cancer | MSK-IMPACT | A0217,A0201,B4402, B5101,C0501,C1502 | A02,A02,B44, B07,UNK,UNK | 0 |
| WX037861 | 31-50 | 25 | 0 | 0 | PD-1/PDL-1 | Renal Cell Carcinoma | MSK-IMPACT | A2402,A0201,B0801, B1501,C0303,C0701 | A24,A02,B08, B62,UNK,UNK | 0 |
| XS233951 | 31-50 | 0 | 0 | 5.9 | PD-1/PDL-1 | Non-Small Cell Lung Cancer | MSK-IMPACT | A6801,A0201,B1503, B1518,C0210,C0704 | A03,A02,B27, B27,UNK,UNK | 0 |
| YI335108 | 31-50 | 2 | 1 | 12.79 | PD-1/PDL-1 | Non-Small Cell Lung Cancer | MSK-IMPACT | A0201,A2601,B0702, B3501,C1602,C0702 | A02,A01,B07, B07,UNK,UNK | 0 |
| ZG039934 | 50-60 | 6 | 0 | 7.87 | PD-1/PDL-1 | Non-Small Cell Lung Cancer | MSK-IMPACT | A0301,A0201,B0702, B1801,C0501,C0702 | A03,A02,B07, B44,UNK,UNK | 0 |
| DJ241021 | 61-70 | 7 | 1 | 3.94 | PD-1/PDL-1 | Renal Cell Carcinoma | MSK-IMPACT | A0301,A0301,B0702, B3701,C0602,C0702 | A03,A03,B07, B44,UNK,UNK | 1 |
| DL894556 | 61-70 | 2 | 0 | 13.77 | PD-1/PDL-1 | Salivary Gland Cancer | MSK-IMPACT | A2402,A0201,B0801, B3906,C0702,C0701 | A24,A02,B08, B27,UNK,UNK | 0 |
| EF262650 | 31-50 | 17 | 0 | 89.52 | PD-1/PDL-1 | Colorectal Cancer | MSK-IMPACT | A0302,A2402,B4601, B3501,C0102,C0401 | A03,A24,B62, B07,UNK,UNK | 0 |
| FJ315360 | 31-50 | 6 | 0 | 3.94 | PD-1/PDL-1 | Head and Neck Cancer | MSK-IMPACT | A0101,A3301,B1402, B3502,C0401,C0802 | A01,A03,B27, B07,UNK,UNK | 0 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| FR397048 | 31-50 | 1 | 1 | 8.85 | PD-1/PDL-1 | Non-Small Cell Lung Cancer | MSK-IMPACT | A3002,A1101,B5101, B3501,C0401,C1602 | A01,A03,B07, B07,UNK,UNK | 0 |
| GK275052 | 50-60 | 39 | 1 | 6.89 | CTLA4 | Melanoma | MSK-IMPACT | A0101,A0201,B2705, B5701,C0102,C0602 | A01,A02,B27, B58,UNK,UNK | 0 |
| HG173625 | 31-50 | 3 | 1 | 1.97 | PD-1/PDL-1 | Pancreatic Cancer | MSK-IMPACT | A0301,A2402,B5701, B3501,C0602,C0401 | A03,A24,B58, B07,UNK,UNK | 0 |
| HH607905 | 31-50 | 11 | 0 | 3.94 | PD-1/PDL-1 | Non-Small Cell Lung Cancer | MSK-IMPACT | A0301,A0101,B3801, B3502,C1203,C0401 | A03,A01,B27, B07,UNK,UNK | 0 |
| IB028541 | 31-50 | 20 | 1 | 3.94 | PD-1/PDL-1 | Renal Cell Carcinoma | MSK-IMPACT | A6801,A0201,B2705, B3501,C0102,C0401 | A03,A02,B27, B07,UNK,UNK | 0 |
| IK737288 | 61-70 | 1 | 0 | 4.92 | PD-1/PDL-1 | Colorectal Cancer | MSK-IMPACT | A0301,A0101,B0702, B0801,C0701,C0702 | A03,A01,B07, B08,UNK,UNK | 0 |
| IZ882356 | 31-50 | 20 | 1 | 3.94 | PD-1/PDL-1 | Renal Cell Carcinoma | MSK-IMPACT | A0301,A0101,B0702, B0702,C0702,C0702 | A03,A01,B07, B07,UNK,UNK | 1 |
| JM917596 | 50-60 | 5 | 0 | 3.94 | Combo | Melanoma | MSK-IMPACT | A2601,A0205,B4101, B3801,C1203,C0701 | A01,A02,B44, B27,UNK,UNK | 0 |
| KC683122 | 61-70 | 6 | 0 | 6.89 | PD-1/PDL-1 | Thyroid Cancer | MSK-IMPACT | A2402,A2402,B1302, B5101,C0102,C0602 | A24,A24,UNK, B07,UNK,UNK | 1 |
| KG865106 | 31-50 | 37 | 0 | 2.95 | CTLA4 | Melanoma | MSK-IMPACT | A3401,A0207,B4601, B4002,C0102,C1502 | UNK,A02,B62, B44,UNK,UNK | 0 |
| LI329268 | 31-50 | 3 | 0 | 5.9 | PD-1/PDL-1 | Glioma | MSK-IMPACT | A0101,A0201,B0801, B1501,C0303,C0701 | A01,A02,B08, B62,UNK,UNK | 0 |
| MP310830 | 31-50 | 4 | 0 | 5.9 | PD-1/PDL-1 | Glioma | MSK-IMPACT | A1101,A0201,B5501, B1801,C0303,C0701 | A03,A02,B07, B44,UNK,UNK | 0 |
| MW707685 | >71 | 0 | 1 | 0.98 | PD-1/PDL-1 | Esophagogastric Cancer | MSK-IMPACT | A1101,A2403,B0702, B3502,C0401,C0702 | A03,A24,B07, B07,UNK,UNK | 0 |
| MY935343 | 31-50 | 2 | 1 | 3.94 | PD-1/PDL-1 | Small Cell Lung Cancer | MSK-IMPACT | A2601,A6901,B6701, B5501,C0303,C1203 | A01,A02,B07, B07,UNK,UNK | 0 |
| RH600784 | 61-70 | 2 | 0 | 3.94 | PD-1/PDL-1 | Non-Small Cell Lung Cancer | MSK-IMPACT | A3201,A6901,B4002, B3801,C0202,C1203 | A01,A02,B44, B27,UNK,UNK | 0 |
| RK158581 | 31-50 | 9 | 1 | 8.85 | Combo | Melanoma | MSK-IMPACT | A0301,A2402,B3508, B5101,C0102,C0401 | A03,A24,B07, B07,UNK,UNK | 0 |
| SI657615 | 50-60 | 4 | 1 | 19.68 | PD-1/PDL-1 | Non-Small Cell Lung Cancer | MSK-IMPACT | A3001,A2402,B1801, B1302,C0602,C0718 | A01A03,A24,B44, UNK,UNK,UNK | 0 |
| UJ858608 | 31-50 | 14 | 0 | 3.94 | PD-1/PDL-1 | Non-Small Cell Lung Cancer | MSK-IMPACT | A2601,A0201,B1401, B0801,C1203,C0701 | A01,A02,B27, B08,UNK,UNK | 0 |
| UT194883 | 61-70 | 25 | 0 | 2.95 | PD-1/PDL-1 | Renal Cell Carcinoma | MSK-IMPACT | A0201,A0201,B1801, B1801,C0701,C0701 | A02,A02,B44, B44,UNK,UNK | 1 |
| VU236547 | 31-50 | 6 | 0 | 1.97 | PD-1/PDL-1 | Non-Small Cell Lung Cancer | MSK-IMPACT | A3601,A0201,B3901, B3501,C0401,C0304 | A01,A02,B27, B07,UNK,UNK | 0 |
| YB335119 | 50-60 | 7 | 0 | 1.97 | PD-1/PDL-1 | Renal Cell Carcinoma | MSK-IMPACT | A0201,A0201,B0801, B0801,C0701,C0701 | A02,A02,B08, B08,UNK,UNK | 1 |
| ZT695305 | >71 | 35 | 0 | 14.76 | PD-1/PDL-1 | Esophagogastric Cancer | MSK-IMPACT | A0201,A2601,B2702, B3801,C0202,C1203 | A02,A01,B27, B27,UNK,UNK | 0 |
| BG557112 | 61-70 | 9 | 0 | 3.94 | PD-1/PDL-1 | Renal Cell Carcinoma | MSK-IMPACT | A7401,A3303,B1503, B1503,C0210,C0210 | A03,A03,B27, B27,UNK,UNK | 1 |
| CB360697 | 31-50 | 9 | 0 | 2.95 | PD-1/PDL-1 | Glioma | MSK-IMPACT | A0101,A6901,B4402, B5801,C0302,C0501 | A01,A02,B44, B58,UNK,UNK | 0 |
| DY566456 | 31-50 | 11 | 1 | 1.97 | PD-1/PDL-1 | Melanoma | MSK-IMPACT | A0301,A7401,B3910, B4403,C1505,C0401 | A03,A03,B07, B44,UNK,UNK | 0 |
| FD268208 | 50-60 | 18 | 0 | 3.94 | PD-1/PDL-1 | Head and Neck Cancer | MSK-IMPACT | A0101,A0201,B3501, B1302,C0401,C0602 | A01,A02,B07, UNK,UNK,UNK | 0 |
| GD049509 | 61-70 | 3 | 1 | 3.94 | PD-1/PDL-1 | Non-Small Cell Lung Cancer | MSK-IMPACT | A2402,A0201,B4402, B4405,C0501,C0202 | A24,A02,B44, B44,UNK,UNK | 0 |
| IV980629 | 61-70 | 3 | 1 | 0.98 | PD-1/PDL-1 | Bladder Cancer | MSK-IMPACT | A6801,A0201,B4002, B4402,C0304,C0501 | A03,A02,B44, B44,UNK,UNK | 0 |
| KF271493 | 50-60 | 10 | 0 | 3.94 | PD-1/PDL-1 | Renal Cell Carcinoma | MSK-IMPACT | A2402,A2402,B5501, B3502,C0102,C0401 | A24,A24,B07, B07,UNK,UNK | 1 |
| LK714581 | >71 | 13 | 0 | 1.97 | PD-1/PDL-1 | Renal Cell Carcinoma | MSK-IMPACT | A1101,A0101,B2705, B1501,C0303,C0202 | A03,A01,B27, B62,UNK,UNK | 0 |
| MT578443 | 31-50 | 2 | 0 | 0.98 | PD-1/PDL-1 | Non-Small Cell Lung Cancer | MSK-IMPACT | A0101,A6801,B3701, B5101,C1402,C0602 | A01,A03,B44, B07,UNK,UNK | 0 |
| MT610848 | 31-50 | 4 | 1 | 15.74 | PD-1/PDL-1 | Non-Small Cell Lung Cancer | MSK-IMPACT | A0301,A0101,B0801, B3701,C0602,C0701 | A03,A01,B08, B44,UNK,UNK | 0 |
| NP594656 | 61-70 | 8 | 0 | 17.71 | PD-1/PDL-1 | Non-Small Cell Lung Cancer | MSK-IMPACT | A1101,A2601,B3801, B5201,C1203,C1202 | A03,A01,B27, B62,UNK,UNK | 0 |
| NY608269 | 31-50 | 7 | 0 | 0.98 | PD-1/PDL-1 | Melanoma | MSK-IMPACT | A2402,A0201,B4403, B4901,C1601,C0701 | A24,A02,B44, UNK,UNK,UNK | 0 |
| OE704083 | >71 | 8 | 0 | 0 | PD-1/PDL-1 | Hepatobiliary Cancer | MSK-IMPACT | A0101,A0201,B3902, B0801,C0702,C0701 | A01,A02,B27, B08,UNK,UNK | 0 |
| ON459466 | 31-50 | 22 | 0 | 5.9 | PD-1/PDL-1 | Hepatobiliary Cancer | MSK-IMPACT | A0201,A0201,B5701, B1801,C0602,C0202 | A02,A02,B58, B44,UNK,UNK | 1 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| PL375255 | 50-60 | 4 | 0 | 3.94 | PD-1/PDL-1 | Renal Cell Carcinoma | MSK-IMPACT | A0101,A2402,B0702, B5701,C0602,C0702 | A01,A24,B07, B58,UNK,UNK | 0 |
| QF486379 | 61-70 | 3 | 1 | 3.94 | PD-1/PDL-1 | Breast Cancer | MSK-IMPACT | A2402,A0201,B2705, B3501,C1601,C0202 | A24,A02,B27, B07,UNK,UNK | 0 |
| QO131046 | 50-60 | 0 | 0 | 64.93 | PD-1/PDL-1 | Melanoma | MSK-IMPACT | A0101,A0201,B0801, B4901,C0701,C0701 | A01,A02,B08, UNK,UNK,UNK | 1 |
| QZ214610 | 31-50 | 6 | 1 | 19.68 | PD-1/PDL-1 | Bladder Cancer | MSK-IMPACT | A0301,A2301,B3701, B4403,C0401,C0602 | A03,A24,B44, B44,UNK,UNK | 0 |
| RS498156 | 50-60 | 7 | 0 | 1.97 | PD-1/PDL-1 | Non-Small Cell Lung Cancer | MSK-IMPACT | A3101,A0201,B1301, B5102,C1502,C0801 | A03,A02,UNK, B07,UNK,UNK | 0 |
| TY648092 | 31-50 | 0 | 0 | 8.85 | PD-1/PDL-1 | Non-Small Cell Lung Cancer | MSK-IMPACT | A1101,A2601,B1801, B4403,C1601,C1203 | A03,A01,B44, B44,UNK,UNK | 0 |
| UW635468 | 31-50 | 0 | 1 | 8.85 | PD-1/PDL-1 | Bladder Cancer | MSK-IMPACT | A0201,A0205,B4001, B5001,C0304,C0602 | A02,A02,B44, B44,UNK,UNK | 0 |
| VT365111 | 31-50 | 13 | 0 | 0.98 | PD-1/PDL-1 | Esophagogastric Cancer | MSK-IMPACT | A0201,A6802,B1402, B4402,C0802,C0501 | A02,A02,B27, B44,UNK,UNK | 0 |
| WB570014 | 50-60 | 6 | 0 | 4.92 | PD-1/PDL-1 | Bladder Cancer | MSK-IMPACT | A3002,A3201,B4101, B1801,C0501,C1701 | A01,A01,B44, B44,UNK,UNK | 0 |
| WM142326 | 31-50 | 7 | 0 | 4.92 | PD-1/PDL-1 | Non-Small Cell Lung Cancer | MSK-IMPACT | A0301,A2403,B3801, B3501,C0401,C1203 | A03,A24,B27, B07,UNK,UNK | 0 |
| XC744092 | 31-50 | 9 | 1 | 16.72 | PD-1/PDL-1 | Non-Hodgkin Lymphoma | MSK-IMPACT | A0301,A0201,B1402, B4402,C0501,C0802 | A03,A02,B27, B44,UNK,UNK | 0 |
| YA003885 | 31-50 | 15 | 1 | 5.9 | PD-1/PDL-1 | Glioma | MSK-IMPACT | A0301,A2601,B2705, B4403,C0401,C0202 | A03,A01,B27, B44,UNK,UNK | 0 |
| ZH374437 | 61-70 | 11 | 0 | 3.94 | PD-1/PDL-1 | Renal Cell Carcinoma | MSK-IMPACT | A0301,A2403,B3508, B5101,C0102,C0401 | A03,A24,B07, B07,UNK,UNK | 0 |
| AJ588466 | 61-70 | 11 | 0 | 1.97 | Combo | Melanoma | MSK-IMPACT | A0101,A2402,B0801, B1801,C0704,C0701 | A01,A24,B08, B44,UNK,UNK | 0 |
| CJ942524 | >71 | 7 | 0 | 26.56 | Combo | Melanoma | MSK-IMPACT | A3201,A0201,B5501, B5001,C0602,C0602 | A01,A02,B07, B44,UNK,UNK | 1 |
| DR880178 | 31-50 | 8 | 1 | 3.94 | PD-1/PDL-1 | Head and Neck Cancer | MSK-IMPACT | A2301,A0201,B4403, B3501,C0401,C0401 | A24,A02,B44, B07,UNK,UNK | 1 |
| EI492052 | 61-70 | 11 | 0 | 1.97 | PD-1/PDL-1 | Renal Cell Carcinoma | MSK-IMPACT | A0205,A6802,B1801, B5802,C0501,C0602 | A02,A02,B44, B58,UNK,UNK | 0 |
| FA457711 | 61-70 | 6 | 1 | 0 | PD-1/PDL-1 | Mesothelioma | MSK-IMPACT | A0201,A2601,B1801, B4402,C1203,C0501 | A02,A01,B44, B44,UNK,UNK | 0 |
| FV068094 | 31-50 | 7 | 0 | 4.92 | PD-1/PDL-1 | Melanoma | MSK-IMPACT | A2402,A6801,B1402, B4403,C0802,C0401 | A24,A03,B27, B44,UNK,UNK | 0 |
| GY675187 | 50-60 | 6 | 0 | 1.97 | PD-1/PDL-1 | Non-Small Cell Lung Cancer | MSK-IMPACT | A3001,A3303,B4201, B4403,C1701,C0706 | A01A03,A03,B07, B44,UNK,UNK | 0 |
| HD432932 | 50-60 | 10 | 0 | 2.95 | PD-1/PDL-1 | Melanoma | MSK-IMPACT | A2402,A0201,B0702, B4402,C0501,C0702 | A24,A02,B07, B44,UNK,UNK | 0 |
| MR283895 | 50-60 | 15 | 0 | 5.9 | PD-1/PDL-1 | Non-Small Cell Lung Cancer | MSK-IMPACT | A2402,A0201,B4402, B5101,C1402,C0501 | A24,A02,B44, B07,UNK,UNK | 0 |
| NH936650 | 50-60 | 1 | 1 | 80.67 | PD-1/PDL-1 | Colorectal Cancer | MSK-IMPACT | A2402,A2301,B4403, B1302,C0401,C0602 | A24,A24,B44, UNK,UNK,UNK | 0 |
| PS172901 | 50-60 | 3 | 1 | 2.95 | PD-1/PDL-1 | Renal Cell Carcinoma | MSK-IMPACT | A0301,A0201,B4101, B4002,C0202,C1701 | A03,A02,B44, B44,UNK,UNK | 0 |
| QZ305528 | >71 | 15 | 0 | 3.94 | CTLA4 | Breast Cancer | MSK-IMPACT | A2301,A3402,B1503, B1302,C0804,C0210 | A24,A03,B27, UNK,UNK,UNK | 0 |
| RM606755 | 50-60 | 2 | 0 | 9.84 | PD-1/PDL-1 | Head and Neck Cancer | MSK-IMPACT | A3101,A0206,B5201, B3503,C1202,C0401 | A03,A02,B62, B07,UNK,UNK | 0 |
| SF663454 | 50-60 | 5 | 0 | 4.92 | PD-1/PDL-1 | Glioma | MSK-IMPACT | A0301,A0101,B3502, B4402,C0401,C0704 | A03,A01,B07, B44,UNK,UNK | 0 |
| SL376792 | 31-50 | 0 | 0 | 7.87 | PD-1/PDL-1 | Non-Small Cell Lung Cancer | MSK-IMPACT | A0301,A0201,B4001, B4402,C0304,C0501 | A03,A02,B44, B44,UNK,UNK | 0 |
| TP431425 | 61-70 | 2 | 0 | 3.94 | PD-1/PDL-1 | Colorectal Cancer | MSK-IMPACT | A0101,A0201,B0801, B1801,C0701,C0701 | A01,A02,B08, B44,UNK,UNK | 1 |
| TU246190 | >71 | 2 | 1 | 4.92 | PD-1/PDL-1 | Head and Neck Cancer | MSK-IMPACT | A0205,A2402,B3701, B5001,C0602,C0602 | A02,A24,B44, B44,UNK,UNK | 1 |
| WL781475 | 50-60 | 9 | 0 | 12.79 | PD-1/PDL-1 | Head and Neck Cancer | MSK-IMPACT | A2402,A0201,B5501, B4901,C0102,C0701 | A24,A02,B07, UNK,UNK,UNK | 0 |
| WM370639 | 61-70 | 7 | 0 | 32.47 | PD-1/PDL-1 | Non-Small Cell Lung Cancer | MSK-IMPACT | A0101,A2301,B0702, B5601,C0102,C0702 | A01,A24,B07, B07,UNK,UNK | 0 |
| WQ553952 | 61-70 | 16 | 0 | 0.98 | PD-1/PDL-1 | Renal Cell Carcinoma | MSK-IMPACT | A0101,A0201,B0702, B2705,C0202,C0702 | A01,A02,B07, B27,UNK,UNK | 0 |
| XH115119 | 31-50 | 5 | 0 | 25.58 | CTLA4 | Melanoma | MSK-IMPACT | A3301,A2601,B1402, B3901,C0802,C1203 | A03,A01,B27, B07,UNK,UNK | 0 |
| YO621057 | 31-50 | 6 | 0 | 0.98 | Combo | Melanoma | MSK-IMPACT | A1101,A2301,B4403, B4901,C1601,C0701 | A03,A24,B44, UNK,UNK,UNK | 0 |
| AN056765 | 31-50 | 11 | 0 | 209.55 | PD-1/PDL-1 | Bladder Cancer | MSK-IMPACT | A2902,A0201,B4403, B4501,C1601,C1601 | A01A24,A02,B44, B44,UNK,UNK | 1 |

APPENDIX 1-continued

| | | | | | | | | | | Homozygous (1 = Yes; 0 = No) |
|---|---|---|---|---|---|---|---|---|---|---|
| Sample | Age Group | OS_ Months | OS_ Event | IMPACT-MutCnt | Drug Class | Cancer Type | Reference | HLA Class I Alleles | HLA Class I Super-types | |
| colspan=11 | Cohort 2 |
| AO895857 | 31-50 | 3 | 0 | 2.95 | PD-1/PDL-1 | Bladder Cancer | MSK-IMPACT | A3001,A0201,B4402,B1302,C0602,C0501 | A01A03,A02,B44,UNK,UNK,UNK | 0 |
| BA321062 | 50-60 | 9 | 0 | 0.98 | PD-1/PDL-1 | Melanoma | MSK-IMPACT | A0101,A3101,B3502,B1801,C0401,C0701 | A01,A03,B07,B44,UNK,UNK | 0 |
| BD574032 | 31-50 | 13 | 0 | 2.95 | PD-1/PDL-1 | Non-Small Cell Lung Cancer | MSK-IMPACT | A0101,A2601,B0801,B1302,C0701,C0701 | A01,A01,B08,UNK,UNK,UNK | 1 |
| BZ275325 | 50-60 | 7 | 0 | 5.9 | PD-1/PDL-1 | Bladder Cancer | MSK-IMPACT | A0201,A0201,B0702,B1401,C0802,C0702 | A02,A02,B07,B27,UNK,UNK | 1 |
| CR081968 | 61-70 | 0 | 0 | 4.92 | PD-1/PDL-1 | Breast Cancer | MSK-IMPACT | A0101,A0101,B3701,B0801,C0602,C0701 | A01,A01,B44,B08,UNK,UNK | 1 |
| EX155661 | 31-50 | 10 | 0 | 8.85 | PD-1/PDL-1 | Non-Small Cell Lung Cancer | MSK-IMPACT | A0301,A0201,B5101,B3501,C0102,C0401 | A03,A02,B07,B07,UNK,UNK | 0 |
| GP968505 | 31-50 | 4 | 1 | 1.97 | CTLA4 | Breast Cancer | MSK-IMPACT | A0301,A0201,B1402,B3501,C0401,C0802 | A03,A02,B27,B07,UNK,UNK | 0 |
| IP840936 | <30 | 13 | 0 | 16.72 | PD-1/PDL-1 | Melanoma | MSK-IMPACT | A2301,A6802,B1801,B3501,C0401,C0701 | A24,A02,B44,B07,UNK,UNK | 0 |
| NE560956 | 61-70 | 0 | 0 | 4.92 | PD-1/PDL-1 | Glioma | MSK-IMPACT | A0101,A0101,B1402,B1801,C1203,C0802 | A01,A01,B27,B44,UNK,UNK | 1 |
| NF005757 | >71 | 5 | 1 | 1.97 | CTLA4 | Breast Cancer | MSK-IMPACT | A0301,A0101,B0801,B1501,C0704,C0701 | A03,A01,B08,B62,UNK,UNK | 0 |
| OL416633 | 50-60 | 0 | 0 | 4.92 | PD-1/PDL-1 | Non-Small Cell Lung Cancer | MSK-IMPACT | A0301,A6601,B1402,B1302,C0802,C0602 | A03,A03,B27,UNK,UNK,UNK | 0 |
| OP518972 | >71 | 3 | 0 | 6.89 | PD-1/PDL-1 | Melanoma | MSK-IMPACT | A2402,A3101,B2705,B3502,C0102,C0401 | A24,A03,B27,B07,UNK,UNK | 0 |
| OR099414 | 31-50 | 2 | 0 | 7.87 | PD-1/PDL-1 | Non-Small Cell Lung Cancer | MSK-IMPACT | A0301,A0201,B3501,B5101,C0401,C0202 | A03,A02,B07,B07,UNK,UNK | 0 |
| OS252841 | 50-60 | 10 | 1 | 6.89 | Combo | Melanoma | MSK-IMPACT | A3004,A2301,B4403,B5801,C0706,C0706 | A01,A24,B44,B58,UNK,UNK | 1 |
| OW781235 | 31-50 | 15 | 0 | 1.97 | PD-1/PDL-1 | Non-Small Cell Lung Cancer | MSK-IMPACT | A0301,A0101,B0702,B0801,C0701,C0702 | A03,A01,B07,B08,UNK,UNK | 0 |
| PN231718 | >71 | 7 | 0 | 2.95 | PD-1/PDL-1 | NA | MSK-IMPACT | A3001,A0207,B4601,B1302,C0102,C0602 | A01A03,A02,B62,UNK,UNK,UNK | 0 |
| SZ972064 | 50-60 | 2 | 0 | 11.81 | PD-1/PDL-1 | Non-Small Cell Lung Cancer | MSK-IMPACT | A0301,A3101,B0702,B0702,C0702,C0702 | A03,A03,B07,B07,UNK,UNK | 1 |
| TH038973 | 61-70 | 1 | 1 | 4.92 | PD-1/PDL-1 | Gastrointestinal Neuroendocrine Tumor | MSK-IMPACT | A0101,A2601,B4002,B5101,C1502,C0202 | A01,A01,B44,B07,UNK,UNK | 0 |
| VK243562 | >71 | 14 | 0 | 11.71 | PD-1/PDL-1 | Head and Neck Cancer | MSK-IMPACT | A3201,A0201,B2705,B3901,C1203,C0202 | A01,A02,B27,B27,UNK,UNK | 0 |
| XM411141 | 31-50 | 4 | 0 | 17.71 | PD-1/PDL-1 | Non-Small Cell Lung Cancer | MSK-IMPACT | A2601,A2501,B1801,B1801,C1203,C1203 | A01,A01,B44,B44,UNK,UNK | 1 |
| XQ918599 | 61-70 | 3 | 0 | 6.89 | PD-1/PDL-1 | Melanoma | MSK-IMPACT | A2402,A2402,B3906,B3502,C0401,C0702 | A24,A24,B27,B07,UNK,UNK | 1 |
| XS919703 | 61-70 | 2 | 1 | 0 | PD-1/PDL-1 | Mesothelioma | MSK-IMPACT | A2402,A3401,B1502,B1501,C0801,C0702 | A24,UNK,B62,B62,UNK,UNK | 0 |
| XT149820 | 50-60 | 12 | 0 | 8.85 | PD-1/PDL-1 | Renal Cell Carcinoma | MSK-IMPACT | A0101,A0101,B1402,B5701,C0802,C0602 | A01,A01,B27,B58,UNK,UNK | 1 |
| XV738523 | 61-70 | 1 | 0 | 0 | PD-1/PDL-1 | Hodgkin Lymphoma | MSK-IMPACT | A0301,A0101,B0702,B3701,C0602,C0702 | A03,A01,B07,B44,UNK,UNK | 0 |
| YI008527 | 31-50 | 22 | 0 | 66.9 | PD-1/PDL-1 | Colorectal Cancer | MSK-IMPACT | A0101,A2608,B0702,B1801,C0701,C0702 | A01,A01,B07,B44,UNK,UNK | 0 |
| YM026555 | 31-50 | 2 | 1 | 17.71 | PD-1/PDL-1 | Non-Small Cell Lung Cancer | MSK-IMPACT | A2901,A0201,B0702,B1517,C0701,C0702 | A01A24,A02,B07,B58,UNK,UNK | 0 |
| YQ511961 | 31-50 | 2 | 1 | 13.77 | PD-1/PDL-1 | Non-Small Cell Lung Cancer | MSK-IMPACT | A6801,A6601,B2702,B1801,C0202,C1203 | A03,A03,B27,B44,UNK,UNK | 0 |
| ZY339428 | 50-60 | 32 | 0 | 7.87 | CTLA4 | Melanoma | MSK-IMPACT | A1101,A2901,B0705,B4001,C1505,C0702 | A01,A01A24,A02,B07,B44,UNK,UNK | 0 |
| EN312634 | 31-50 | 12 | 0 | 40.34 | Combo | Melanoma | MSK-IMPACT | A3201,A0201,B4402,B5801,C0501,C0706 | A01,A02,B44,B58,UNK,UNK | 0 |
| FN198586 | 61-70 | 14 | 1 | 4.92 | PD-1/PDL-1 | Colorectal Cancer | MSK-IMPACT | A3201,A0201,B0702,B1501,C0303,C0702 | A01,A02,B07,B62,UNK,UNK | 0 |
| HH259934 | 50-60 | 0 | 0 | 6.89 | PD-1/PDL-1 | Esophagogastric Cancer | MSK-IMPACT | A0101,A0201,B0801,B4402,C0704,C0701 | A01,A02,B08,B44,UNK,UNK | 0 |
| IC506084 | 31-50 | 10 | 0 | 3.94 | PD-1/PDL-1 | Melanoma | MSK-IMPACT | A0301,A0201,B1402,B4101,C1701,C0802 | A03,A02,B27,B44,UNK,UNK | 0 |
| LB442555 | 50-60 | 1 | 0 | 2.95 | PD-1/PDL-1 | Anal Cancer | MSK-IMPACT | A1101,A3301,B1402,B3701,C0602,C0802 | A03,A03,B27,B44,UNK,UNK | 0 |
| LF922776 | 50-60 | 5 | 0 | 2.95 | PD-1/PDL-1 | Melanoma | MSK-IMPACT | A0201,A3101,B1501,B4402,C0102,C0501 | A02,A03,B62,B44,UNK,UNK | 0 |
| LI730809 | 31-50 | 5 | 1 | 11.81 | Combo | Non-Small Cell Lung Cancer | MSK-IMPACT | A0101,A6801,B0801,B4402,C0704,C0701 | A01,A03,B08,B44,UNK,UNK | 0 |
| MA289096 | >71 | 4 | 1 | 9.84 | PD-1/PDL-1 | Colorectal Cancer | MSK-IMPACT | A0201,A0201,B5001,B3501,C0401,C0602 | A02,A02,B44,B07,UNK,UNK | 1 |

APPENDIX 1-continued

| | | | | | | | | | | Homozygous (1 = Yes; 0 = No) |
|---|---|---|---|---|---|---|---|---|---|---|
| Sample | Age Group | OS_Months | OS_Event | IMPACT-MutCnt | Drug Class | Cancer Type | Reference | HLA Class I Alleles | HLA Class I Super-types | |

Cohort 2

| Sample | Age Group | OS_Months | OS_Event | IMPACT-MutCnt | Drug Class | Cancer Type | Reference | HLA Class I Alleles | HLA Class I Super-types | Homozygous |
|---|---|---|---|---|---|---|---|---|---|---|
| ME718412 | <30 | 10 | 0 | 35.42 | PD-1/PDL-1 | Melanoma | MSK-IMPACT | A0201,A0201,B1401,B4402,C0802,C0501 | A02,A02,B27,B44,UNK,UNK | 1 |
| MN756477 | >71 | 6 | 0 | 7.87 | PD-1/PDL-1 | Breast Cancer | MSK-IMPACT | A6601,A0205,B4403,B4102,C1601,C1701 | A03,A02,B44,B44,UNK,UNK | 0 |
| NY665367 | 31-50 | 14 | 0 | 24.59 | Combo | Bladder Cancer | MSK-IMPACT | A0101,A2402,B0801,B4403,C1601,C0701 | A01,A24,B08,B44,UNK,UNK | 0 |
| OP481847 | 61-70 | 6 | 0 | 3.94 | PD-1/PDL-1 | Glioma | MSK-IMPACT | A2402,A2902,B1501,B3501,C0303,C0303 | A24,A01A24,B62,B07,UNK,UNK | 1 |
| TQ390536 | <30 | 10 | 0 | 61.98 | PD-1/PDL-1 | Esophagogastric Cancer | MSK-IMPACT | A2402,A6801,B4901,B3508,C0401,C0701 | A24,A03,UNK,B07,UNK,UNK | 0 |
| UG182832 | 31-50 | 6 | 0 | 6.89 | PD-1/PDL-1 | Esophagogastric Cancer | MSK-IMPACT | A3101,A2601,B3801,B1302,C1203,C0602 | A03,A01,B27,UNK,UNK,UNK | 0 |
| UU047700 | >71 | 1 | 1 | 15.74 | Combo | Melanoma | MSK-IMPACT | A0301,A0101,B4001,B4402,C0304,C0501 | A03,A01,B44,B44,UNK,UNK | 0 |
| UW067254 | >71 | 9 | 1 | 3.94 | PD-1/PDL-1 | Glioma | MSK-IMPACT | A0101,A0205,B4403,B5001,C0602,C0706 | A01,A02,B44,B44,UNK,UNK | 0 |
| VF477197 | 31-50 | 16 | 0 | 8.85 | PD-1/PDL-1 | Renal Cell Carcinoma | MSK-IMPACT | A0101,A0206,B4801,B3502,C0401,C0803 | A01,A02,B27,B07,UNK,UNK | 0 |
| VL999909 | 50-60 | 1 | 1 | 1.97 | PD-1/PDL-1 | Head and Neck Cancer | MSK-IMPACT | A0101,A0101,B0801,B2703,C0202,C0701 | A01,A01,B08,B27,UNK,UNK | 1 |
| VP308482 | 31-50 | 2 | 1 | 7.87 | PD-1/PDL-1 | Non-Small Cell Lung Cancer | MSK-IMPACT | A0101,A3201,B2705,B5701,C0102,C0602 | A01,A01,B27,B58,UNK,UNK | 0 |
| WF233416 | 61-70 | 16 | 0 | 1.97 | Combo | Renal Cell Carcinoma | MSK-IMPACT | A0201,A3402,B0801,B5701,C0602,C0701 | A02,A03,B08,B58,UNK,UNK | 0 |
| XB162513 | 31-50 | 4 | 1 | 9.84 | PD-1/PDL-1 | Non-Small Cell Lung Cancer | MSK-IMPACT | A2601,A2601,B2705,B3801,C0102,C1203 | A01,A01,B27,B27,UNK,UNK | 1 |
| XK727574 | 31-50 | 5 | 0 | 47.22 | PD-1/PDL-1 | Melanoma | MSK-IMPACT | A0101,A0201,B0801,B4402,C0501,C0701 | A01,A02,B08,B44,UNK,UNK | 0 |
| XW686398 | 50-60 | 3 | 0 | 59.03 | PD-1/PDL-1 | Melanoma | MSK-IMPACT | A1101,A0202,B4101,B3501,C0401,C1701 | A03,A02,B44,B07,UNK,UNK | 0 |
| ZL119793 | 50-60 | 11 | 0 | 12.79 | Combo | Bladder Cancer | MSK-IMPACT | A0101,A6601,B3801,B5201,C1203,C1202 | A01,A03,B27,B62,UNK,UNK | 0 |
| ZV563438 | 31-50 | 5 | 1 | 7.87 | PD-1/PDL-1 | Pancreatic Cancer | MSK-IMPACT | A6802,A0201,B3906,B1402,C0802,C0702 | A02,A02,B27,B27,UNK,UNK | 0 |
| BJ473490 | 31-50 | 4 | 1 | 13.77 | PD-1/PDL-1 | Non-Small Cell Lung Cancer | MSK-IMPACT | A0301,A0301,B0702,B3801,C1203,C0702 | A03,A03,B07,B27,UNK,UNK | 1 |
| BY950416 | 50-60 | 0 | 1 | 23.61 | CTLA4 | Esophagogastric Cancer | MSK-IMPACT | A0101,A0101,B0801,B3508,C0401,C0718 | A01,A01,B08,B07,UNK,UNK | 1 |
| DW018325 | 31-50 | 18 | 0 | 17.71 | Combo | Melanoma | MSK-IMPACT | A0201,A0201,B0702,B5101,C1402,C0702 | A02,A02,B07,B07,UNK,UNK | 1 |
| DW879977 | <30 | 0 | 0 | 0 | PD-1/PDL-1 | Non-Small Cell Lung Cancer | MSK-IMPACT | A0201,A0201,B0702,B4402,C0501,C0702 | A02,A02,B07,B44,UNK,UNK | 1 |
| EH539523 | 50-60 | 3 | 0 | 0 | PD-1/PDL-1 | Soft Tissue Sarcoma | MSK-IMPACT | A2901,A3303,B4403,B2705,C1502,C0706 | A01A24,A03,B44,B27,UNK,UNK | 0 |
| FW831458 | 31-50 | 2 | 0 | 18.69 | PD-1/PDL-1 | Non-Small Cell Lung Cancer | MSK-IMPACT | A1101,A6901,B4402,B3801,C0501,C1203 | A03,A02,B44,B27,UNK,UNK | 0 |
| HA119880 | 61-70 | 7 | 1 | 5.9 | PD-1/PDL-1 | Glioma | MSK-IMPACT | A0301,A0201,B2702,B1801,C0202,C1203 | A03,A02,B27,B44,UNK,UNK | 0 |
| NG419064 | 50-60 | 5 | 0 | 11.81 | PD-1/PDL-1 | Melanoma | MSK-IMPACT | A0101,A0201,B3502,B3805,C0401,C0602 | A01,A02,B07,B07,UNK,UNK | 0 |
| NP589780 | 61-70 | 12 | 0 | 14.76 | Combo | Melanoma | MSK-IMPACT | A0301,A3301,B1402,B1402,C0802,C0802 | A03,A03,B27,B27,UNK,UNK | 1 |
| OD510699 | 31-50 | 4 | 0 | 9.84 | PD-1/PDL-1 | Non-Small Cell Lung Cancer | MSK-IMPACT | A0101,A0101,B0801,B3502,C0401,C0701 | A01,A01,B08,B07,UNK,UNK | 1 |
| PG803905 | 50-60 | 28 | 1 | 2.95 | PD-1/PDL-1 | Renal Cell Carcinoma | MSK-IMPACT | A0101,A2902,B0702,B1402,C0802,C0702 | A01,A01A24,B07,B27,UNK,UNK | 0 |
| PS791389 | 31-50 | 6 | 0 | 4.92 | PD-1/PDL-1 | Glioma | MSK-IMPACT | A0301,A0201,B1402,B4402,C0501,C0802 | A03,A02,B27,B44,UNK,UNK | 0 |
| PT990489 | 50-60 | 13 | 0 | 34.43 | PD-1/PDL-1 | Non-Small Cell Lung Cancer | MSK-IMPACT | A3301,A3301,B1402,B1402,C0802,C0802 | A03,A03,B27,B27,UNK,UNK | 1 |
| QT113700 | 50-60 | 23 | 1 | 1.97 | PD-1/PDL-1 | Renal Cell Carcinoma | MSK-IMPACT | A0101,A2301,B0801,B4403,C0401,C0701 | A01,A24,B08,B44,UNK,UNK | 0 |
| QZ186262 | 31-50 | 39 | 0 | 92.48 | PD-1/PDL-1 | Melanoma | MSK-IMPACT | A0301,A2301,B0702,B4901,C0702,C0701 | A03,A24,B07,UNK,UNK,UNK | 0 |
| ST162140 | 50-60 | 6 | 0 | 7.87 | PD-1/PDL-1 | Colorectal Cancer | MSK-IMPACT | A0301,A0101,B0702,B0801,C0701,C0702 | A03,A01,B07,B08,UNK,UNK | 0 |
| TI731664 | 50-60 | 11 | 0 | 6.89 | PD-1/PDL-1 | Non-Small Cell Lung Cancer | MSK-IMPACT | A0301,A0201,B4402,B5101,C0102,C0501 | A03,A02,B44,B07,UNK,UNK | 0 |
| VB077802 | 61-70 | 42 | 0 | 3.94 | CTLA4 | Melanoma | MSK-IMPACT | A0301,A0201,B0702,B1801,C0702,C0701 | A03,A02,B07,B44,UNK,UNK | 0 |
| VS997541 | 50-60 | 15 | 0 | 4.92 | PD-1/PDL-1 | Melanoma | MSK-IMPACT | A0101,A0206,B4801,B0801,C0803,C0718 | A01,A02,B27,B08,UNK,UNK | 0 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| WJ196194 | 50-60 | 7 | 0 | 2.95 | PD-1/PDL-1 | Glioma | MSK-IMPACT | A1101,A6802,B1402,B5101,C0802,C0501 | A03,A02,B27,B07,UNK,UNK | 0 |
| WX378273 | 50-60 | 18 | 0 | 17.71 | Combo | Melanoma | MSK-IMPACT | A2301,A3201,B4402,B4901,C0501,C0701 | A24,A01,B44,UNK,UNK,UNK | 0 |
| XK162854 | 31-50 | 0 | 0 | 3.94 | PD-1/PDL-1 | Non-Small Cell Lung Cancer | MSK-IMPACT | A0301,A2902,B0702,B4403,C1601,C0702 | A03,A01A24,B07,B44,UNK,UNK | 0 |
| XY160168 | 31-50 | 12 | 0 | 21.64 | PD-1/PDL-1 | Non-Small Cell Lung Cancer | MSK-IMPACT | A3201,A6801,B2702,B4403,C0202,C0401 | A01,A03,B27,B44,UNK,UNK | 0 |
| AJ891505 | 31-50 | 6 | 1 | 11.81 | PD-1/PDL-1 | Non-Small Cell Lung Cancer | MSK-IMPACT | A0301,A0101,B0801,B1801,C0501,C0701 | A03,A01,B08,B44,UNK,UNK | 0 |
| AK052983 | 61-70 | 4 | 0 | 6.89 | PD-1/PDL-1 | Glioma | MSK-IMPACT | A3201,A0205,B5001,B3508,C0304,C0602 | A01,A02,B44,B07,UNK,UNK | 0 |
| BY277443 | 61-70 | 13 | 0 | 0.98 | PD-1/PDL-1 | Glioma | MSK-IMPACT | A1101,A0203,B5201,B1301,C0304,C1202 | A03,A02,B62,UNK,UNK,UNK | 0 |
| CU714354 | 50-60 | 20 | 0 | 1.97 | Combo | Bladder Cancer | MSK-IMPACT | A1101,A3303,B4403,B5601,C0102,C0706 | A03,A03,B44,B07,UNK,UNK | 0 |
| DC957706 | 31-50 | 1 | 1 | 1.97 | Combo | Soft Tissue Sarcoma | MSK-IMPACT | A0201,A3101,B3901,B3508,C0401,C0702 | A02,A03,B27,B07,UNK,UNK | 0 |
| DR074297 | 61-70 | 10 | 0 | 3.94 | PD-1/PDL-1 | Renal Cell Carcinoma | MSK-IMPACT | A0101,A0201,B5201,B3501,C1202,C0401 | A01,A02,B62,B07,UNK,UNK | 0 |
| FG902387 | 31-50 | 12 | 1 | 5.9 | PD-1/PDL-1 | Ampullary Carcinoma | MSK-IMPACT | A0201,A2601,B3701,B1801,C0602,C0701 | A02,A01,B44,B44,UNK,UNK | 0 |
| HE548457 | 31-50 | 2 | 0 | 7.87 | PD-1/PDL-1 | Glioma | MSK-IMPACT | A2301,A2601,B3801,B4901,C1203,C0701 | A24,A01,B27,UNK,UNK,UNK | 0 |
| IE505811 | 31-50 | 0 | 0 | 6.89 | PD-1/PDL-1 | Non-Small Cell Lung Cancer | MSK-IMPACT | A0101,A2601,B5701,B1801,C1203,C0701 | A01,A01,B58,B44,UNK,UNK | 0 |
| KD996653 | 61-70 | 11 | 0 | 15.74 | PD-1/PDL-1 | Non-Small Cell Lung Cancer | MSK-IMPACT | A2402,A6801,B1801,B5101,C1502,C0701 | A24,A03,B44,B07,UNK,UNK | 0 |
| LU243185 | 31-50 | 1 | 0 | 2.95 | PD-1/PDL-1 | Non-Small Cell Lung Cancer | MSK-IMPACT | A1101,A0201,B4402,B3501,C0401,C0501 | A03,A02,B44,B07,UNK,UNK | 0 |
| LW347198 | 61-70 | 10 | 1 | 2.95 | PD-1/PDL-1 | Melanoma | MSK-IMPACT | A3002,A2402,B1503,B4002,C0304,C0401 | A01,A24,B27,B44,UNK,UNK | 0 |
| MG883401 | 50-60 | 20 | 0 | 12.79 | Combo | Melanoma | MSK-IMPACT | A6801,A3301,B1402,B4402,C0802,C0704 | A03,A03,B27,B44,UNK,UNK | 0 |
| MQ099328 | 31-50 | 0 | 0 | 5.9 | PD-1/PDL-1 | Breast Cancer | MSK-IMPACT | A2902,A0201,B4403,B1801,C1601,C0701 | A01A24,A02,B44,B44,UNK,UNK | 0 |
| NR864503 | >71 | 16 | 0 | 7.87 | Combo | Melanoma | MSK-IMPACT | A2902,A2601,B4403,B4402,C1601,C0501 | A01A24,A01,B44,B44,UNK,UNK | 0 |
| OL048054 | 50-60 | 4 | 1 | 2.95 | PD-1/PDL-1 | Melanoma | MSK-IMPACT | A0301,A2301,B1402,B1510,C0304,C0802 | A03,A24,B27,B27,UNK,UNK | 0 |
| OO343430 | 50-60 | 0 | 0 | 3.94 | PD-1/PDL-1 | Renal Cell Carcinoma | MSK-IMPACT | A3201,A0201,B3701,B1501,C0401,C0602 | A01,A02,B44,B62,UNK,UNK | 0 |
| PX423160 | 50-60 | 1 | 1 | 19.68 | PD-1/PDL-1 | Melanoma | MSK-IMPACT | A3001,A0101,B2705,B2705,C0202,C0602 | A01A03,A01,B27,B27,UNK,UNK | 1 |
| RM264272 | 50-60 | 10 | 1 | 6.89 | PD-1/PDL-1 | Renal Cell Carcinoma | MSK-IMPACT | A0101,A0201,B4403,B3503,C0401,C0401 | A01,A02,B44,B07,UNK,UNK | 1 |
| SK499637 | 61-70 | 12 | 0 | 3.94 | PD-1/PDL-1 | Glioma | MSK-IMPACT | A0101,A0101,B5701,B5701,C0602,C0602 | A01,A01,B58,B58,UNK,UNK | 1 |
| SN378137 | 31-50 | 0 | 1 | 5.9 | PD-1/PDL-1 | Non-Small Cell Lung Cancer | MSK-IMPACT | A0301,A2601,B0702,B6701,C1203,C0702 | A03,A01,B07,B07,UNK,UNK | 0 |
| SQ358496 | 31-50 | 7 | 1 | 6.89 | PD-1/PDL-1 | Bladder Cancer | MSK-IMPACT | A6801,A0205,B0702,B1509,C0702,C0704 | A03,A02,B07,B27,UNK,UNK | 0 |
| TE370578 | 50-60 | 10 | 0 | 65.91 | Combo | Melanoma | MSK-IMPACT | A0301,A0101,B0801,B3501,C0401,C0701 | A03,A01,B08,B07,UNK,UNK | 0 |
| TO340081 | 31-50 | 3 | 0 | 1.97 | PD-1/PDL-1 | Head and Neck Cancer | MSK-IMPACT | A0301,A0201,B4402,B4402,C0501,C0704 | A03,A02,B44,B44,UNK,UNK | 1 |
| TO569127 | >71 | 5 | 0 | 2.95 | Combo | Melanoma | MSK-IMPACT | A2601,A0201,B0702,B3501,C0303,C0702 | A01,A02,B07,B07,UNK,UNK | 0 |
| UB931860 | 31-50 | 2 | 1 | 0.98 | PD-1/PDL-1 | Head and Neck Cancer | MSK-IMPACT | A2402,A0201,B0702,B1501,C0303,C0702 | A24,A02,B07,B62,UNK,UNK | 0 |
| VR847789 | 61-70 | 13 | 0 | 22.63 | PD-1/PDL-1 | Renal Cell Carcinoma | MSK-IMPACT | A0201,A3303,B4006,B5801,C0304,C0303 | A02,A03,B44,B58,UNK,UNK | 0 |
| VX079278 | 61-70 | 6 | 1 | 2.95 | PD-1/PDL-1 | Non-Small Cell Lung Cancer | MSK-IMPACT | A2402,A0207,B4601,B1302,C0102,C0602 | A24,A02,B62,UNK,UNK,UNK | 0 |
| WG606901 | 50-60 | 6 | 0 | 25.58 | PD-1/PDL-1 | Skin Cancer; Non-Melanoma | MSK-IMPACT | A0201,A2601,B0702,B3501,C0401,C0702 | A02,A01,B07,B07,UNK,UNK | 0 |
| XE626384 | 50-60 | 11 | 0 | 11.81 | PD-1/PDL-1 | Non-Small Cell Lung Cancer | MSK-IMPACT | A0101,A2601,B0801,B0702,C0701,C0702 | A01,A01,B08,B07,UNK,UNK | 0 |
| YR566743 | 31-50 | 0 | 1 | 3.94 | Combo | Pancreatic Cancer | MSK-IMPACT | A0301,A2402,B1402,B1402,C0802,C0802 | A03,A24,B27,B27,UNK,UNK | 1 |
| ZF792273 | 31-50 | 0 | 0 | 9.84 | PD-1/PDL-1 | Pancreatic Cancer | MSK-IMPACT | A2403,A0205,B5001,B3501,C0401,C0602 | A24,A02,B44,B07,UNK,UNK | 0 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| AA919263 | >71 | 3 | 0 | 0.98 | PD-1/PDL-1 | Head and Neck Cancer | MSK-IMPACT | A3001,A2402,B3503,B1516,C1601,C1203 | A01A03,A24,B07,B58,UNK,UNK | 0 |
| BB148083 | 61-70 | 2 | 0 | 1.97 | PD-1/PDL-1 | Renal Cell Carcinoma | MSK-IMPACT | A0301,A0101,B0801,B4402,C0501,C0701 | A03,A01,B08,B44,UNK,UNK | 0 |
| EI574944 | 31-50 | 3 | 1 | 0 | PD-1/PDL-1 | Head and Neck Cancer | MSK-IMPACT | A3201,A0201,B3801,B5101,C1402,C1203 | A01,A02,B27,B07,UNK,UNK | 0 |
| FM634739 | 50-60 | 17 | 0 | 6.89 | PD-1/PDL-1 | Colorectal Cancer | MSK-IMPACT | A2301,A0201,B4001,B4901,C0304,C0701 | A24,A02,B44,UNK,UNK,UNK | 0 |
| GH655330 | 50-60 | 28 | 1 | 1.97 | CTLA4 | Melanoma | MSK-IMPACT | A0201,A3301,B4201,B7801,C1701,C1601 | A02,A03,B07,B07,UNK,UNK | 0 |
| JM757194 | 61-70 | 3 | 1 | 11.81 | PD-1/PDL-1 | Melanoma | MSK-IMPACT | A2403,A0201,B1801,B5301,C0401,C1203 | A24,A02,B44,B07,UNK,UNK | 0 |
| JN174072 | 31-50 | 12 | 0 | 35.42 | Combo | Melanoma | MSK-IMPACT | A3002,A2601,B2705,B1801,C0102,C0501 | A01,A01,B27,B44,UNK,UNK | 0 |
| JR658183 | 50-60 | 1 | 1 | 1.97 | PD-1/PDL-1 | Non-Small Cell Lung Cancer | MSK-IMPACT | A0101,A0201,B0801,B4402,C0501,C0701 | A01,A02,B08,B44,UNK,UNK | 0 |
| JS285396 | 31-50 | 15 | 0 | 5.9 | PD-1/PDL-1 | Non-Small Cell Lung Cancer | MSK-IMPACT | A0101,A0201,B0801,B3501,C0401,C0701 | A01,A02,B08,B07,UNK,UNK | 0 |
| KI034546 | 50-60 | 0 | 0 | 48.21 | PD-1/PDL-1 | Melanoma | MSK-IMPACT | A2402,A0201,B4403,B5101,C0102,C0501 | A24,A02,B44,B07,UNK,UNK | 0 |
| KI279575 | >71 | 17 | 0 | 44.27 | PD-1/PDL-1 | Colorectal Cancer | MSK-IMPACT | A0301,A2402,B0702,B1801,C1203,C0702 | A03,A24,B07,B44,UNK,UNK | 0 |
| LZ739624 | 50-60 | 12 | 1 | 1.97 | CTLA4 | Melanoma | MSK-IMPACT | A0101,A2402,B5701,B3502,C0401,C0602 | A01,A24,B58,B07,UNK,UNK | 0 |
| MG245949 | 50-60 | 6 | 0 | 10.82 | Combo | Melanoma | MSK-IMPACT | A3001,A0201,B1801,B1302,C0602,C0701 | A01A03,A02,B44,UNK,UNK,UNK | 0 |
| MY236910 | 31-50 | 4 | 1 | 7.87 | Combo | Melanoma | MSK-IMPACT | A0101,A6802,B0801,B1402,C0802,C0701 | A01,A02,B08,B27,UNK,UNK | 0 |
| NP095956 | 31-50 | 5 | 0 | 31.48 | Combo | Melanoma | MSK-IMPACT | A0101,A0101,B0801,B5701,C0602,C0701 | A01,A01,B08,B58,UNK,UNK | 1 |
| OR826293 | 31-50 | 1 | 0 | 9.84 | Combo | Small Cell Lung Cancer | MSK-IMPACT | A0301,A2402,B0702,B3508,C0401,C0702 | A03,A24,B07,B07,UNK,UNK | 0 |
| OT894166 | 61-70 | 9 | 1 | 4.92 | PD-1/PDL-1 | Glioma | MSK-IMPACT | A1101,A1101,B1301,B5101,C0304,C1402 | A03,A03,UNK,B07,UNK,UNK | 1 |
| SF898078 | 31-50 | 37 | 0 | 3.94 | PD-1/PDL-1 | Renal Cell Carcinoma | MSK-IMPACT | A0301,A2601,B0702,B3701,C0602,C0702 | A03,A01,B07,B44,UNK,UNK | 0 |
| TS228316 | 31-50 | 39 | 0 | 48.21 | CTLA4 | Melanoma | MSK-IMPACT | A0101,A2402,B0801,B5701,C0602,C0701 | A01,A24,B08,B58,UNK,UNK | 0 |
| TX032049 | 31-50 | 14 | 0 | 1.97 | PD-1/PDL-1 | Glioma | MSK-IMPACT | A1101,A3201,B5201,B5201,C1202,C1202 | A03,A01,B62,B62,UNK,UNK | 1 |
| UN859698 | 50-60 | 0 | 0 | 2.95 | PD-1/PDL-1 | Non-Small Cell Lung Cancer | MSK-IMPACT | A3303,A0201,B0702,B1801,C1203,C0702 | A03,A02,B07,B44,UNK,UNK | 0 |
| VV775396 | >71 | 5 | 0 | 0 | PD-1/PDL-1 | Soft Tissue Sarcoma | MSK-IMPACT | A1101,A3101,B5201,B5101,C1502,C1202 | A03,A03,B62,B07,UNK,UNK | 0 |
| YH915303 | 31-50 | 5 | 0 | 5.9 | PD-1/PDL-1 | Thyroid Cancer | MSK-IMPACT | A2902,A6801,B1402,B2702,C0802,C0202 | A01A24,A03,B27,B27,UNK,UNK | 0 |
| ZZ383896 | 50-60 | 7 | 0 | 10.82 | PD-1/PDL-1 | Bladder Cancer | MSK-IMPACT | A3001,A3201,B3801,B1302,C0602,C1203 | A01A03,A01,B27,UNK,UNK,UNK | 0 |
| AI289139 | 61-70 | 29 | 1 | 2.95 | PD-1/PDL-1 | Renal Cell Carcinoma | MSK-IMPACT | A3001,A3101,B2705,B1501,C0102,C0303 | A01A03,A03,B27,B62,UNK,UNK | 0 |
| AZ436323 | 50-60 | 17 | 0 | 3.94 | PD-1/PDL-1 | Glioma | MSK-IMPACT | A2601,A3301,B0702,B1402,C0802,C0702 | A01,A03,B07,B27,UNK,UNK | 0 |
| CM374720 | 50-60 | 8 | 0 | 4.92 | PD-1/PDL-1 | Renal Cell Carcinoma | MSK-IMPACT | A0301,A0201,B0801,B4001,C0304,C0701 | A03,A02,B08,B44,UNK,UNK | 0 |
| CT849635 | 61-70 | 11 | 1 | 1.97 | PD-1/PDL-1 | Head and Neck Cancer | MSK-IMPACT | A0201,A0206,B2705,B1302,C0303,C0602 | A02,A02,B27,UNK,UNK,UNK | 0 |
| EN879707 | 31-50 | 7 | 0 | 10.82 | CTLA4 | Melanoma | MSK-IMPACT | A0101,A2402,B2705,B5101,C0102,C0202 | A01,A24,B27,B07,UNK,UNK | 0 |
| EZ883373 | 31-50 | 29 | 0 | 3.94 | PD-1/PDL-1 | Renal Cell Carcinoma | MSK-IMPACT | A2602,A0207,B1501,B1501,C0303,C0303 | A01,A02,B62,B62,UNK,UNK | 1 |
| FQ072342 | 31-50 | 2 | 0 | 3.94 | PD-1/PDL-1 | Bladder Cancer | MSK-IMPACT | A0101,A0201,B4001,B5701,C0304,C0602 | A01,A02,B44,B58,UNK,UNK | 0 |
| HP035557 | 50-60 | 14 | 0 | 1.97 | PD-1/PDL-1 | Bladder Cancer | MSK-IMPACT | A0301,A3303,B0702,B4901,C0701,C0702 | A03,A03,B07,UNK,UNK,UNK | 0 |
| IG343955 | >71 | 0 | 0 | 0.98 | Combo | Non-Small Cell Lung Cancer | MSK-IMPACT | A0101,A3303,B3701,B5101,C1602,C0602 | A01,A03,B44,B07,UNK,UNK | 0 |
| KB328348 | 61-70 | 4 | 0 | 7.87 | PD-1/PDL-1 | Head and Neck Cancer | MSK-IMPACT | A0205,A3303,B0702,B1516,C1402,C0702 | A02,A03,B07,B58,UNK,UNK | 0 |
| KK881118 | 50-60 | 5 | 0 | 2.95 | PD-1/PDL-1 | Glioma | MSK-IMPACT | A0101,A6802,B1402,B5801,C0802,C0706 | A01,A02,B27,B58,UNK,UNK | 0 |
| MI360504 | 50-60 | 9 | 0 | 6.89 | PD-1/PDL-1 | Non-Hodgkin Lymphoma | MSK-IMPACT | A0201,A0201,B3503,B3503,C0401,C0401 | A02,A02,B07,B07,UNK,UNK | 1 |

APPENDIX 1-continued

| | | | | | | | | | | Homozygous (1 = Yes; 0 = No) |
|---|---|---|---|---|---|---|---|---|---|---|
| Sample | Age Group | OS_Months | OS_Event | IMPACT-MutCnt | Drug Class | Cancer Type | Reference | HLA Class I Alleles | HLA Class I Super-types | |

Cohort 2

| Sample | Age Group | OS_Months | OS_Event | IMPACT-MutCnt | Drug Class | Cancer Type | Reference | HLA Class I Alleles | HLA Class I Super-types | Homozygous |
|---|---|---|---|---|---|---|---|---|---|---|
| MJ017310 | 50-60 | 2 | 0 | 3.94 | PD-1/PDL-1 | Glioma | MSK-IMPACT | A2402,A2601,B4101,B1801,C1701,C1203 | A24,A01,B44,B44,UNK,UNK | 0 |
| ND912084 | 31-50 | 7 | 0 | 0.98 | PD-1/PDL-1 | Skin Cancer; Non-Melanoma | MSK-IMPACT | A3001,A6801,B4001,B4001,C0304,C0304 | A01A03,A03,B44,B44,UNK,UNK | 1 |
| NH243829 | 50-60 | 7 | 0 | 11.81 | CTLA4 | Melanoma | MSK-IMPACT | A2601,A0201,B1402,B3801,C0802,C1203 | A01,A02,B27,B27,UNK,UNK | 0 |
| OW583283 | 31-50 | 4 | 0 | 36.4 | PD-1/PDL-1 | Melanoma | MSK-IMPACT | A3001,A6602,B4201,B1801,C0501,C1701 | A01A03,A03,B07,B44,UNK,UNK | 0 |
| QE052353 | 31-50 | 2 | 0 | 10.82 | PD-1/PDL-1 | Non-Small Cell Lung Cancer | MSK-IMPACT | A0301,A2601,B0702,B6701,C1203,C0702 | A03,A01,B07,B07,UNK,UNK | 0 |
| RT206143 | 31-50 | 6 | 0 | 7.87 | PD-1/PDL-1 | Cancer of Unknown Primary | MSK-IMPACT | A0201,A0201,B4402,B4402,C0501,C0704 | A02,A02,B44,B44,UNK,UNK | 1 |
| SB277970 | 50-60 | 10 | 0 | 13.77 | Combo | Melanoma | MSK-IMPACT | A1101,A2601,B3801,B3503,C0401,C1203 | A03,A01,B27,B07,UNK,UNK | 0 |
| UE671470 | 61-70 | 65 | 0 | 1.97 | PD-1/PDL-1 | Renal Cell Carcinoma | MSK-IMPACT | A0101,A2402,B0702,B4402,C0501,C0702 | A01,A24,B07,B44,UNK,UNK | 0 |
| VB628966 | 31-50 | 13 | 0 | 9.84 | Combo | Renal Cell Carcinoma | MSK-IMPACT | A1101,A2901,B0705,B1402,C0802,C1505 | A03,A01A24,B07,B27,UNK,UNK | 0 |
| VI875864 | >71 | 1 | 1 | 4.92 | PD-1/PDL-1 | Glioma | MSK-IMPACT | A0301,A2601,B4402,B4701,C1604,C0602 | A03,A01,B44,UNK,UNK,UNK | 0 |
| VS684136 | 50-60 | 9 | 1 | 3.94 | PD-1/PDL-1 | Bladder Cancer | MSK-IMPACT | A1101,A2402,B4901,B5201,C1202,C0701 | A03,A24,UNK,B62,UNK,UNK | 0 |
| WB258446 | 31-50 | 11 | 1 | 3.94 | PD-1/PDL-1 | Renal Cell Carcinoma | MSK-IMPACT | A0101,A2301,B4403,B3503,C0401,C0401 | A01,A24,B44,B07,UNK,UNK | 1 |
| WX194323 | 50-60 | 4 | 1 | 2.95 | PD-1/PDL-1 | Glioma | MSK-IMPACT | A6801,A0201,B0702,B3501,C0401,C0702 | A03,A02,B07,B07,UNK,UNK | 0 |
| YU641238 | 50-60 | 3 | 1 | 4.92 | PD-1/PDL-1 | Pancreatic Cancer | MSK-IMPACT | A2402,A0201,B3801,B4402,C1203,C0501 | A24,A02,B27,B44,UNK,UNK | 0 |
| AU586996 | 50-60 | 3 | 1 | 0.98 | PD-1/PDL-1 | Renal Cell Carcinoma | MSK-IMPACT | A2402,A0205,B4402,B3503,C0401,C0501 | A24,A02,B44,B07,UNK,UNK | 0 |
| DQ804796 | 31-50 | 8 | 0 | 5.9 | PD-1/PDL-1 | Non-Small Cell Lung Cancer | MSK-IMPACT | A0101,A2402,B0801,B3502,C0401,C0701 | A01,A24,B08,B07,UNK,UNK | 0 |
| EE822574 | 61-70 | 13 | 1 | 2.95 | CTLA4 | Melanoma | MSK-IMPACT | A0201,A0201,B3701,B3801,C1203,C0602 | A02,A02,B44,B27,UNK,UNK | 1 |
| EJ979278 | 61-70 | 9 | 0 | 1.97 | Combo | Melanoma | MSK-IMPACT | A0301,A2402,B2702,B1501,C0303,C0202 | A03,A24,B27,B62,UNK,UNK | 0 |
| GC769217 | 31-50 | 0 | 0 | 17.71 | PD-1/PDL-1 | Non-Small Cell Lung Cancer | MSK-IMPACT | A0101,A2902,B4403,B5601,C1601,C0701 | A01,A01A24,B44,B07,UNK,UNK | 0 |
| JQ416542 | >71 | 2 | 1 | 3.94 | PD-1/PDL-1 | Pancreatic Cancer | MSK-IMPACT | A1101,A0101,B0801,B5101,C1502,C0701 | A03,A01,B08,B07,UNK,UNK | 0 |
| KA699526 | 31-50 | 18 | 0 | 12.79 | Combo | Melanoma | MSK-IMPACT | A0302,A0201,B4402,B3502,C0501,C0401 | A03,A02,B44,B07,UNK,UNK | 0 |
| MA647036 | 31-50 | 8 | 0 | 14.76 | PD-1/PDL-1 | Non-Small Cell Lung Cancer | MSK-IMPACT | A3001,A0301,B1402,B1302,C0802,C0602 | A01A03,A03,B27,UNK,UNK,UNK | 0 |
| MX495884 | 50-60 | 1 | 1 | 4.92 | PD-1/PDL-1 | Esophagogastric Cancer | MSK-IMPACT | A1101,A6802,B4403,B5301,C0401,C0401 | A03,A02,B44,B07,UNK,UNK | 1 |
| OM805229 | 31-50 | 9 | 0 | 15.74 | PD-1/PDL-1 | Melanoma | MSK-IMPACT | A2402,A2601,B1801,B3508,C1203,C0401 | A24,A01,B44,B07,UNK,UNK | 0 |
| OQ415968 | >71 | 16 | 0 | 65.91 | PD-1/PDL-1 | Colorectal Cancer | MSK-IMPACT | A0101,A2902,B7301,B4403,C1601,C1505 | A01,A01A24,B27,B44,UNK,UNK | 0 |
| PF967643 | 31-50 | 2 | 0 | 12.79 | PD-1/PDL-1 | Non-Small Cell Lung Cancer | MSK-IMPACT | A0101,A6601,B1501,B4102,C1701,C0701 | A01,A03,B62,B44,UNK,UNK | 0 |
| RT169392 | 31-50 | 4 | 0 | 74.77 | PD-1/PDL-1 | Melanoma | MSK-IMPACT | A0101,A2601,B3701,B3801,C1203,C0602 | A01,A01,B44,B27,UNK,UNK | 0 |
| RX243136 | 50-60 | 13 | 0 | 11.81 | PD-1/PDL-1 | Non-Small Cell Lung Cancer | MSK-IMPACT | A0301,A2601,B0801,B5301,C0304,C0210 | A03,A01,B08,B07,UNK,UNK | 0 |
| SG417338 | 50-60 | 2 | 1 | 7.87 | PD-1/PDL-1 | Non-Hodgkin Lymphoma | MSK-IMPACT | A0301,A2402,B3501,B3508,C0401,C0401 | A03,A24,B07,B07,UNK,UNK | 1 |
| TJ094097 | 31-50 | 5 | 0 | 11.81 | PD-1/PDL-1 | Melanoma | MSK-IMPACT | A2402,A2601,B3801,B3801,C1203,C1203 | A24,A01,B27,B27,UNK,UNK | 1 |
| VM721100 | 31-50 | 7 | 0 | 20.66 | PD-1/PDL-1 | Melanoma | MSK-IMPACT | A0201,A0201,B0702,B1801,C0702,C0701 | A02,A02,B07,B44,UNK,UNK | 1 |
| WV623589 | 61-70 | 12 | 0 | 7.87 | PD-1/PDL-1 | Colorectal Cancer | MSK-IMPACT | A2902,A6801,B1518,B4403,C1601,C0704 | A01A24,A03,B44,B44,UNK,UNK | 0 |
| XC653229 | 31-50 | 2 | 1 | 13.77 | PD-1/PDL-1 | Non-Small Cell Lung Cancer | MSK-IMPACT | A2301,A0201,B2705,B4901,C0102,C0701 | A24,A02,B27,UNK,UNK,UNK | 0 |
| ZJ926402 | 61-70 | 9 | 0 | 4.92 | PD-1/PDL-1 | Non-Small Cell Lung Cancer | MSK-IMPACT | A2902,A3301,B1402,B4403,C0802,C1601 | A01A03,A03,B27,B44,UNK,UNK | 0 |
| AP548960 | 31-50 | 21 | 0 | 35.42 | PD-1/PDL-1 | Melanoma | MSK-IMPACT | A2402,A0201,B1501,B4402,C0303,C0501 | A24,A02,B62,B44,UNK,UNK | 0 |
| BD940228 | 50-60 | 14 | 0 | 7.87 | Combo | NA | MSK-IMPACT | A2402,A0201,B0702,B3901,C0702,C0702 | A24,A02,B07,B27,UNK,UNK | 1 |

APPENDIX 1-continued

| | | | | | | Cohort 2 | | | | |
|---|---|---|---|---|---|---|---|---|---|---|
| Sample | Age Group | OS_ Months | OS_ Event | IMPACT-MutCnt | Drug Class | Cancer Type | Reference | HLA Class I Alleles | HLA Class I Super-types | Homozygous (1 = Yes; 0 = No) |
| CS024658 | 50-60 | 1 | 0 | 3.94 | PD-1/PDL-1 | Glioma | MSK-IMPACT | A0201,A0201,B3801, B4402,C0501,C1203 | A02,A02,B27, B44,UNK,UNK | 1 |
| DK756867 | 61-70 | 5 | 0 | 4.92 | PD-1/PDL-1 | Breast Cancer | MSK-IMPACT | A0301,A0101,B0801, B3503,C0401,C0701 | A03,A01,B08, B07,UNK,UNK | 0 |
| EQ981337 | 31-50 | 4 | 1 | 3.94 | PD-1/PDL-1 | Renal Cell Carcinoma | MSK-IMPACT | A0101,A2902,B0801, B4403,C1601,C0701 | A01,A01A24,B08, B44,UNK,UNK | 0 |
| GO662209 | 31-50 | 0 | 0 | 10.82 | Combo | Small Cell Lung Cancer | MSK-IMPACT | A0301,A2601,B1801, B3503,C1203,C0701 | A03,A01,B44, B07,UNK,UNK | 0 |
| GU236132 | 50-60 | 1 | 1 | 3.94 | PD-1/PDL-1 | Anal Cancer | MSK-IMPACT | A0301,A6802,B3701, B5301,C0401,C0602 | A03,A02,B44, B07,UNK,UNK | 0 |
| KA118426 | 31-50 | 3 | 0 | 6.89 | PD-1/PDL-1 | Renal Cell Carcinoma | MSK-IMPACT | A2402,A0201,B1402, B4001,C0102,C0802 | A24,A02,B27, B44,UNK,UNK | 0 |
| MJ236116 | 31-50 | 22 | 1 | 5.9 | CTLA4 | Pancreatic Cancer | MSK-IMPACT | A0201,A0201,B0801, B1501,C0303,C0701 | A02,A02,B08, B62,UNK,UNK | 1 |
| PC349900 | 31-50 | 3 | 0 | 3.94 | PD-1/PDL-1 | Colorectal Cancer | MSK-IMPACT | A3001,A1101,B0702, B1302,C0602,C0702 | A01A03,A03,B07, UNK,UNK,UNK | 0 |
| PW868809 | 50-60 | 8 | 0 | 16.72 | PD-1/PDL-1 | Non-Small Cell Lung Cancer | MSK-IMPACT | A0101,A0201,B0801, B4403,C0401,C0701 | A01,A02,B08, B44,UNK,UNK | 0 |
| QZ994733 | 31-50 | 16 | 0 | 0 | PD-1/PDL-1 | Skin Cancer; Non-Melanoma | MSK-IMPACT | A0301,A2402,B6701, B5501,C0102,C1203 | A03,A24,B07, B07,UNK,UNK | 0 |
| SM492088 | 50-60 | 8 | 0 | 2.95 | PD-1/PDL-1 | Adrenocortical Carcinoma | MSK-IMPACT | A0101,A0201,B5701, B4001,C0304,C0602 | A01,A02,B58, B44,UNK,UNK | 0 |
| ST964388 | 31-50 | 12 | 1 | 150.52 | PD-1/PDL-1 | Melanoma | MSK-IMPACT | A0301,A0201,B0702, B1501,C0304,C0702 | A03,A02,B07, B62,UNK,UNK | 0 |
| TD080094 | 61-70 | 4 | 0 | 8.85 | PD-1/PDL-1 | Colorectal Cancer | MSK-IMPACT | A2402,A0201,B0705, B3701,C1505,C0802 | A24,A02,B07, B44,UNK,UNK | 0 |
| VF708164 | 31-50 | 11 | 0 | 8.85 | Combo | Non-Small Cell Lung Cancer | MSK-IMPACT | A2402,A6901,B5501, B3502,C0303,C0401 | A24,A02,B07, B07,UNK,UNK | 0 |
| XW509252 | 31-50 | 0 | 0 | 3.94 | PD-1/PDL-1 | Non-Small Cell Lung Cancer | MSK-IMPACT | A0101,A0201,B0801, B4101,C1701,C0701 | A01,A02,B08, B44,UNK,UNK | 0 |
| BL451101 | 31-50 | 3 | 1 | 1.97 | PD-1/PDL-1 | Esophagogastric Cancer | MSK-IMPACT | A3001,A0301,B0702, B5703,C0701,C0702 | A01A03,A03,B07, B58,UNK,UNK | 0 |
| CP437800 | 61-70 | 2 | 0 | 0.98 | PD-1/PDL-1 | Melanoma | MSK-IMPACT | A3001,A0201,B0801, B3801,C1203,C0701 | A01A03,A02,B08, B27,UNK,UNK | 0 |
| DH083727 | >71 | 1 | 1 | 12.79 | PD-1/PDL-1 | Non-Hodgkin Lymphoma | MSK-IMPACT | A0101,A0201,B5701, B5701,C0602,C0602 | A01,A02,B58, B58,UNK,UNK | 1 |
| EY617944 | >71 | 3 | 0 | 65.91 | PD-1/PDL-1 | NA | MSK-IMPACT | A0207,A3303,B4601, B5801,C0102,C0302 | A02,A03,B62, B58,UNK,UNK | 0 |
| FO818879 | >71 | 22 | 0 | 68.87 | PD-1/PDL-1 | Colorectal Cancer | MSK-IMPACT | A1101,A0201,B1302, B3501,C0401,C0602 | A03,A02,UNK, B07,UNK,UNK | 0 |
| FT888206 | 61-70 | 15 | 0 | 8.85 | Combo | Renal Cell Carcinoma | MSK-IMPACT | A1101,A6801,B1402, B3501,C0802,C0704 | A03,A03,B27, B07,UNK,UNK | 0 |
| GC414305 | 50-60 | 10 | 0 | 5.9 | PD-1/PDL-1 | Renal Cell Carcinoma | MSK-IMPACT | A0301,A2402,B4101, B4402,C1701,C1604 | A03,A24,B44, B44,UNK,UNK | 0 |
| JL036420 | 50-60 | 5 | 1 | 5.9 | PD-1/PDL-1 | Glioma | MSK-IMPACT | A3001,A0101,B0801, B5201,C1202,C0701 | A01A03,A01,B08, B62,UNK,UNK | 0 |
| KJ592597 | 50-60 | 14 | 0 | 4.92 | PD-1/PDL-1 | Melanoma | MSK-IMPACT | A0101,A0201,B0801, B4402,C0501,C0701 | A01,A02,B08, B44,UNK,UNK | 0 |
| LE083915 | >71 | 12 | 1 | 23.61 | Combo | Bladder Cancer | MSK-IMPACT | A2301,A2301,B4201, B1516,C1402,C1701 | A24,A24,B07, B58,UNK,UNK | 1 |
| MA086950 | 50-60 | 0 | 1 | 4.92 | PD-1/PDL-1 | Melanoma | MSK-IMPACT | A3001,A2402,B0801, B3502,C0401,C0701 | A01A03,A24,B08, B07,UNK,UNK | 0 |
| NL203214 | >71 | 9 | 0 | 10.82 | PD-1/PDL-1 | Head and Neck Cancer | MSK-IMPACT | A2402,A0201,B5701, B5101,C0102,C0605 | A24,A02,B58, B07,UNK,UNK | 0 |
| RE754398 | <30 | 11 | 0 | 22.63 | PD-1/PDL-1 | Melanoma | MSK-IMPACT | A0101,A3101,B0801, B4701,C0602,C0701 | A01,A03,B08, UNK,UNK,UNK | 0 |
| RY613181 | 50-60 | 12 | 0 | 5.9 | PD-1/PDL-1 | Bladder Cancer | MSK-IMPACT | A0201,A0201,B1401, B5101,C0802,C0202 | A02,A02,B27, B07,UNK,UNK | 1 |
| SD909203 | 31-50 | 0 | 1 | 2.95 | PD-1/PDL-1 | Non-Small Cell Lung Cancer | MSK-IMPACT | A0101,A6801,B0801, B3503,C0401,C0701 | A01,A03,B08, B07,UNK,UNK | 0 |
| SH271275 | 50-60 | 7 | 0 | 3.94 | PD-1/PDL-1 | Renal Cell Carcinoma | MSK-IMPACT | A1101,A6801,B0705, B5101,C1402,C0702 | A03,A03,B07, B07,UNK,UNK | 0 |
| TT770421 | 31-50 | 0 | 0 | 10.82 | PD-1/PDL-1 | Head and Neck Cancer | MSK-IMPACT | A2601,A0205,B0801, B5001,C0602,C0702 | A01,A02,B08, B44,UNK,UNK | 0 |
| TU904333 | 61-70 | 6 | 1 | 5.9 | PD-1/PDL-1 | Non-Hodgkin Lymphoma | MSK-IMPACT | A0101,A3301,B1402, B5701,C0802,C0602 | A01,A03,B27, B58,UNK,UNK | 0 |
| UP272365 | 31-50 | 6 | 0 | 16.72 | PD-1/PDL-1 | Non-Small Cell Lung Cancer | MSK-IMPACT | A0101,A0101,B0801, B3502,C0401,C0701 | A01,A01,B08, B07,UNK,UNK | 1 |
| WS993881 | 61-70 | 2 | 1 | 7.87 | PD-1/PDL-1 | Non-Small Cell Lung Cancer | MSK-IMPACT | A2402,A2601,B3801, B1801,C1203,C1203 | A24,A01,B27, B44,UNK,UNK | 1 |
| XK412876 | 61-70 | 11 | 0 | 3.94 | PD-1/PDL-1 | Renal Cell Carcinoma | MSK-IMPACT | A0101,A2902,B4403, B4402,C1601,C0501 | A01,A01A24,B44, B44,UNK,UNK | 0 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| YT686462 | 50-60 | 23 | 0 | 3.94 | PD-1/PDL-1 | Renal Cell Carcinoma | MSK-IMPACT | A2901,A0201,B4002,B5108,C0202,C1502 | A01A24,A02,B44,B07,UNK,UNK | 0 |
| YX193539 | <30 | 19 | 0 | 38.37 | PD-1/PDL-1 | Melanoma | MSK-IMPACT | A2402,A0205,B3801,B5201,C1202,C1203 | A24,A02,B27,B62,UNK,UNK | 0 |
| ZF254339 | 50-60 | 2 | 0 | 1.97 | PD-1/PDL-1 | Anal Cancer | MSK-IMPACT | A2402,A3303,B4402,B3503,C0501,C1203 | A24,A03,B44,B07,UNK,UNK | 0 |
| AN801016 | 50-60 | 26 | 1 | 4.92 | Combo | Renal Cell Carcinoma | MSK-IMPACT | A0201,A0201,B1801,B1801,C0701,C0701 | A02,A02,B44,B44,UNK,UNK | 1 |
| AP783434 | 31-50 | 6 | 0 | 3.94 | PD-1/PDL-1 | Colorectal Cancer | MSK-IMPACT | A0301,A0302,B0702,B5101,C1502,C0702 | A03,A03,B07,B07,UNK,UNK | 0 |
| BE099274 | 31-50 | 1 | 1 | 4.92 | PD-1/PDL-1 | Pancreatic Cancer | MSK-IMPACT | A3301,A3301,B1402,B1402,C0802,C0802 | A03,A03,B27,B27,UNK,UNK | 1 |
| CR195193 | 50-60 | 2 | 1 | 2.95 | PD-1/PDL-1 | Esophagogastric Cancer | MSK-IMPACT | A3001,A2601,B1801,B1302,C1203,C0602 | A01A03,A01,B44,UNK,UNK,UNK | 0 |
| GM551205 | 50-60 | 6 | 0 | 7.87 | PD-1/PDL-1 | Renal Cell Carcinoma | MSK-IMPACT | A0301,A2902,B1510,B1302,C0304,C0602 | A03,A01A24,B27,UNK,UNK,UNK | 0 |
| HO216759 | 61-70 | 26 | 0 | 1.97 | PD-1/PDL-1 | Renal Cell Carcinoma | MSK-IMPACT | A2402,A0201,B4403,B3503,C1203,C1601 | A24,A02,B44,B07,UNK,UNK | 0 |
| IO169657 | 50-60 | 3 | 1 | 5.9 | PD-1/PDL-1 | NA | MSK-IMPACT | A2301,A0201,B1503,B4403,C0210,C0706 | A24,A02,B27,B44,UNK,UNK | 0 |
| MD570774 | 50-60 | 8 | 1 | 7.87 | PD-1/PDL-1 | Non-Small Cell Lung Cancer | MSK-IMPACT | A2301,A0201,B1401,B4403,C0401,C0802 | A24,A02,B27,B44,UNK,UNK | 0 |
| PJ729478 | 31-50 | 8 | 0 | 43.29 | PD-1/PDL-1 | Esophagogastric Cancer | MSK-IMPACT | A6802,A0205,B5001,B5301,C0401,C0602 | A02,A02,B44,B07,UNK,UNK | 0 |
| XP870786 | 61-70 | 13 | 0 | 2.95 | Combo | Renal Cell Carcinoma | MSK-IMPACT | A0101,A6801,B3701,B4001,C0304,C0602 | A01,A03,B44,B44,UNK,UNK | 0 |
| YL892257 | 31-50 | 27 | 0 | 33.45 | CTLA4 | Melanoma | MSK-IMPACT | A6801,A0201,B4001,B4701,C0304,C0602 | A03,A02,B44,UNK,UNK,UNK | 0 |
| ZH585728 | 31-50 | 12 | 1 | 1.97 | PD-1/PDL-1 | Non-Small Cell Lung Cancer | MSK-IMPACT | A0301,A2601,B5101,B1302,C1402,C0602 | A03,A01,B07,UNK,UNK,UNK | 0 |
| ZW725633 | 31-50 | 3 | 1 | 6.89 | PD-1/PDL-1 | Non-Small Cell Lung Cancer | MSK-IMPACT | A3002,A3201,B1501,B1801,C0303,C0501 | A01,A01,B62,B44,UNK,UNK | 0 |
| BN163408 | 31-50 | 2 | 1 | 5.9 | PD-1/PDL-1 | Pancreatic Cancer | MSK-IMPACT | A1101,A1101,B4403,B5201,C1202,C1601 | A03,A03,B44,B62,UNK,UNK | 1 |
| BV652107 | 31-50 | 4 | 0 | 7.87 | PD-1/PDL-1 | Bladder Cancer | MSK-IMPACT | A0101,A0201,B0801,B2705,C0202,C0701 | A01,A02,B08,B27,UNK,UNK | 0 |
| EP826129 | 31-50 | 0 | 1 | 12.79 | PD-1/PDL-1 | Bladder Cancer | MSK-IMPACT | A3002,A3301,B1402,B3901,C0802,C1203 | A01,A03,B27,B27,UNK,UNK | 0 |
| HG877982 | 31-50 | 16 | 0 | 2.95 | Combo | Melanoma | MSK-IMPACT | A2402,A0203,B5502,B5601,C0102,C1203 | A24,A02,B07,B07,UNK,UNK | 0 |
| HI763616 | 61-70 | 0 | 1 | 1.97 | PD-1/PDL-1 | Head and Neck Cancer | MSK-IMPACT | A0301,A1101,B0702,B3502,C0401,C0702 | A03,A03,B07,B07,UNK,UNK | 0 |
| IN074031 | 50-60 | 3 | 1 | 0.98 | PD-1/PDL-1 | Melanoma | MSK-IMPACT | A2403,A6801,B3801,B4901,C1203,C0701 | A24,A03,B27,UNK,UNK,UNK | 0 |
| IV487195 | 61-70 | 9 | 0 | 0 | PD-1/PDL-1 | Melanoma | MSK-IMPACT | A0201,A3201,B5501,B4402,C0303,C0501 | A02,A01,B07,B44,UNK,UNK | 0 |
| IY406522 | 50-60 | 12 | 0 | 0.98 | PD-1/PDL-1 | Non-Small Cell Lung Cancer | MSK-IMPACT | A2301,A6601,B4102,B4901,C1701,C0701 | A24,A03,B44,UNK,UNK,UNK | 0 |
| JP389116 | 31-50 | 42 | 0 | 5.9 | PD-1/PDL-1 | Renal Cell Carcinoma | MSK-IMPACT | A0101,A2301,B0702,B5201,C0401,C1202 | A01,A24,B07,B62,UNK,UNK | 0 |
| KJ238343 | 50-60 | 10 | 0 | 8.85 | PD-1/PDL-1 | Melanoma | MSK-IMPACT | A2301,A0201,B4101,B5101,C1701,C1601 | A24,A02,B44,B07,UNK,UNK | 0 |
| MB990307 | 50-60 | 0 | 0 | 2.95 | PD-1/PDL-1 | Head and Neck Cancer | MSK-IMPACT | A2902,A0201,B0702,B4403,C0702,C1601 | A01A24,A02,B07,B44,UNK,UNK | 0 |
| MI013541 | 61-70 | 18 | 0 | 8.85 | Combo | Renal Cell Carcinoma | MSK-IMPACT | A0201,A0201,B0702,B3901,C1203,C0702 | A02,A02,B07,B27,UNK,UNK | 1 |
| QO539853 | 50-60 | 11 | 1 | 12.79 | PD-1/PDL-1 | Head and Neck Cancer | MSK-IMPACT | A0101,A0201,B4101,B5101,C1502,C1701 | A01,A02,B44,B07,UNK,UNK | 0 |
| RI645610 | 31-50 | 18 | 0 | 15.74 | PD-1/PDL-1 | Melanoma | MSK-IMPACT | A0101,A0201,B0801,B4001,C0304,C0701 | A01,A02,B08,B44,UNK,UNK | 0 |
| TF132355 | 31-50 | 3 | 1 | 1.97 | PD-1/PDL-1 | Esophagogastric Cancer | MSK-IMPACT | A1101,A3101,B3901,B4501,C1203,C0602 | A03,A03,B27,B44,UNK,UNK | 0 |
| WF098442 | 31-50 | 1 | 1 | 3.94 | PD-1/PDL-1 | Mesothelioma | MSK-IMPACT | A3002,A0201,B0702,B1801,C0501,C0702 | A01,A02,B07,B44,UNK,UNK | 0 |
| WW621794 | 31-50 | 12 | 0 | 5.9 | PD-1/PDL-1 | Melanoma | MSK-IMPACT | A6802,A0201,B4403,B1801,C0501,C0401 | A02,A02,B44,B44,UNK,UNK | 0 |
| CA664206 | 31-50 | 0 | 1 | 6.89 | PD-1/PDL-1 | Cancer of Unknown Primary | MSK-IMPACT | A6801,A0201,B4402,B5701,C0602,C0704 | A03,A02,B44,B58,UNK,UNK | 0 |
| DB719328 | 31-50 | 0 | 0 | 2.95 | PD-1/PDL-1 | Non-Small Cell Lung Cancer | MSK-IMPACT | A0101,A0201,B0801,B1510,C0304,C0701 | A01,A02,B08,B27,UNK,UNK | 0 |
| DT109230 | 31-50 | 0 | 1 | 10.82 | PD-1/PDL-1 | Non-Small Cell Lung Cancer | MSK-IMPACT | A1101,A3301,B2705,B1402,C0202,C0802 | A03,A03,B27,B27,UNK,UNK | 0 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| FV129897 | 31-50 | 9 | 0 | 19.68 | PD-1/PDL-1 | Non-Small Cell Lung Cancer | MSK-IMPACT | A3002,A0205,B3801, B1801,C0501,C1203 | A01,A02,B27, B44,UNK,UNK | 0 |
| GL764741 | 31-50 | 4 | 1 | 4.92 | PD-1/PDL-1 | Esophagogastric Cancer | MSK-IMPACT | A0301,A0201,B0702, B0702,C0702,C0702 | A03,A02,B07, B07,UNK,UNK | 1 |
| HR150352 | 50-60 | 13 | 0 | 3.94 | PD-1/PDL-1 | Non-Small Cell Lung Cancer | MSK-IMPACT | A0301,A2902,B1402, B4403,C0802,C1601 | A03,A01A24,B27, B44,UNK,UNK | 0 |
| IY582475 | 61-70 | 1 | 1 | 0 | PD-1/PDL-1 | Head and Neck Cancer | MSK-IMPACT | A0201,A3101,B5601, B5001,C0102,C0602 | A02,A03,B07, B44,UNK,UNK | 0 |
| LR544436 | 31-50 | 5 | 0 | 13.77 | PD-1/PDL-1 | Melanoma | MSK-IMPACT | A3001,A1101,B5201, B3501,C0401,C1202 | A01A03,A03,B62, B07,UNK,UNK | 0 |
| LZ556947 | 61-70 | 4 | 0 | 6.89 | PD-1/PDL-1 | Bladder Cancer | MSK-IMPACT | A0101,A0201,B3502, B5701,C0602,C0602 | A01,A02,B07, B58,UNK,UNK | 1 |
| NI555118 | 61-70 | 1 | 1 | 25.58 | PD-1/PDL-1 | Cancer of Unknown Primary | MSK-IMPACT | A0301,A0201,B1801, B5701,C0602,C0701 | A03,A02,B44, B58,UNK,UNK | 0 |
| NO558430 | 50-60 | 2 | 1 | 4.92 | PD-1/PDL-1 | Small Cell Lung Cancer | MSK-IMPACT | A0101,A0201,B4402, B4001,C0304,C1604 | A01,A02,B44, B44,UNK,UNK | 0 |
| PO599962 | >71 | 1 | 1 | 11.81 | PD-1/PDL-1 | Head and Neck Cancer | MSK-IMPACT | A0202,A0201,B3508, B1801,C1601,C0401 | A02,A02,B07, B44,UNK,UNK | 0 |
| QQ122966 | 31-50 | 2 | 1 | 1.97 | PD-1/PDL-1 | Non-Small Cell Lung Cancer | MSK-IMPACT | A0101,A1101,B3501, B4901,C0401,C0701 | A01,A03,B07, UNK,UNK,UNK | 0 |
| RA448371 | 31-50 | 7 | 1 | 24.59 | PD-1/PDL-1 | Head and Neck Cancer | MSK-IMPACT | A0201,A0201,B1507, B4402,C0303,C0501 | A02,A02,B62, B44,UNK,UNK | 1 |
| UR039273 | 31-50 | 14 | 0 | 6.89 | Combo | Head and Neck Cancer | MSK-IMPACT | A1101,A0101,B4402, B0801,C0501,C0701 | A03,A01,B44, B08,UNK,UNK | 0 |
| UU457916 | <30 | 24 | 1 | 7.87 | PD-1/PDL-1 | Non-Small Cell Lung Cancer | MSK-IMPACT | A3201,A0201,B3501, B5801,C0401,C0706 | A01,A02,B07, B58,UNK,UNK | 0 |
| VO447635 | 50-60 | 1 | 1 | 1.97 | PD-1/PDL-1 | Non-Small Cell Lung Cancer | MSK-IMPACT | A0101,A6802,B3502, B1801,C0501,C0401 | A01,A02,B07, B44,UNK,UNK | 0 |
| YI659458 | 31-50 | 9 | 0 | 5.9 | PD-1/PDL-1 | Glioma | MSK-IMPACT | A2402,A2601,B3801, B3502,C0401,C1203 | A24,A01,B27, B07,UNK,UNK | 0 |
| ZX303297 | 61-70 | 25 | 0 | 1.97 | Combo | Esophagogastric Cancer | MSK-IMPACT | A0201,A0201,B5101, B4501,C1502,C0602 | A02,A02,B07, B44,UNK,UNK | 1 |
| AF406418 | 61-70 | 11 | 0 | 3.94 | Combo | Melanoma | MSK-IMPACT | A2403,A0201,B0705, B3501,C1505,C0401 | A24,A02,B07, B07,UNK,UNK | 0 |
| AH216825 | 61-70 | 19 | 0 | 2.95 | Combo | Renal Cell Carcinoma | MSK-IMPACT | A1101,A0205,B5001, B3801,C0401,C0602 | A03,A02,B44, B07,UNK,UNK | 0 |
| CB980147 | 50-60 | 3 | 1 | 5.9 | CTLA4 | Breast Cancer | MSK-IMPACT | A1101,A2407,B3802, B3802,C0702,C0702 | A03,UNK,UNK, UNK,UNK,UNK | 1 |
| DB857913 | 31-50 | 8 | 0 | 3.94 | PD-1/PDL-1 | Renal Cell Carcinoma | MSK-IMPACT | A3401,A0201,B1502, B3505,C0401,C0801 | UNK,A02,B62, B07,UNK,UNK | 0 |
| FF987914 | >71 | 6 | 1 | 3.94 | PD-1/PDL-1 | Glioma | MSK-IMPACT | A0201,A2601,B3906, B3901,C1203,C1203 | A02,A01,B27, B27,UNK,UNK | 1 |
| GZ870894 | >71 | 11 | 0 | 9.84 | PD-1/PDL-1 | Non-Hodgkin Lymphoma | MSK-IMPACT | A1101,A3303,B0705, B5801,C0302,C0702 | A03,A03,B07, B58,UNK,UNK | 0 |
| IB207672 | 61-70 | 15 | 0 | 8.85 | PD-1/PDL-1 | Non-Hodgkin Lymphoma | MSK-IMPACT | A0101,A0201,B0704, B3502,C0401,C0702 | A01,A02,B07, B07,UNK,UNK | 0 |
| IK144116 | >71 | 0 | 0 | 1.97 | PD-1/PDL-1 | Pancreatic Cancer | MSK-IMPACT | A0301,A3001,B0702, B4201,C1701,C0702 | A03,A01A03,B07, B07,UNK,UNK | 0 |
| IL112662 | 31-50 | 0 | 1 | 0 | PD-1/PDL-1 | Non-Small Cell Lung Cancer | MSK-IMPACT | A0301,A3201,B5201, B5101,C0102,C1202 | A03,A01,B62, B07,UNK,UNK | 0 |
| KN168588 | >71 | 6 | 0 | 3.94 | PD-1/PDL-1 | Embryonal Tumor | MSK-IMPACT | A0201,A0205,B4101, B4002,C0202,C0701 | A02,A02,B44, B44,UNK,UNK | 0 |
| LD646751 | >71 | 35 | 0 | 4.92 | PD-1/PDL-1 | Renal Cell Carcinoma | MSK-IMPACT | A3201,A0201,B1801, B5101,C1402,C0701 | A01,A02,B44, B07,UNK,UNK | 0 |
| LJ213345 | 61-70 | 17 | 0 | 5.9 | PD-1/PDL-1 | Head and Neck Cancer | MSK-IMPACT | A0301,A2601,B4001, B4003,C1403,C0304 | A03,A01,B44, B44,UNK,UNK | 0 |
| LJ413431 | 50-60 | 12 | 0 | 5.9 | PD-1/PDL-1 | Non-Small Cell Lung Cancer | MSK-IMPACT | A1101,A0207,B6701, B5604,C0102,C0702 | A03,A02,B07, B07,UNK,UNK | 0 |
| LQ937165 | >71 | 9 | 0 | 47.22 | Combo | Colorectal Cancer | MSK-IMPACT | A0101,A3101,B4101, B4001,C0304,C1701 | A01,A03,B44, B44,UNK,UNK | 0 |
| LZ664850 | 50-60 | 1 | 1 | 7.87 | PD-1/PDL-1 | Esophagogastric Cancer | MSK-IMPACT | A3001,A2301,B4403, B1302,C0401,C0602 | A01A03,A24,B44, UNK,UNK,UNK | 0 |
| OZ912616 | 61-70 | 1 | 0 | 1.97 | PD-1/PDL-1 | Non-Small Cell Lung Cancer | MSK-IMPACT | A0207,A0207,B4601, B4601,C0102,C0102 | A02,A02,B62, B62,UNK,UNK | 1 |
| PG408469 | 61-70 | 6 | 1 | 11.81 | Combo | Melanoma | MSK-IMPACT | A2402,A3101,B4402, B3801,C1604,C1203 | A24,A03,B44, B27,UNK,UNK | 0 |
| PS726558 | 31-50 | 3 | 0 | 6.89 | PD-1/PDL-1 | Colorectal Cancer | MSK-IMPACT | A2301,A0201,B1801, B4901,C0701,C0701 | A24,A02,B44, UNK,UNK,UNK | 1 |
| RB741231 | 31-50 | 18 | 0 | 9.84 | PD-1/PDL-1 | Non-Small Cell Lung Cancer | MSK-IMPACT | A6801,A2901,B1518, B5001,C0602,C0704 | A03,A01A24,B27, B44,UNK,UNK | 0 |
| RD469703 | >71 | 5 | 1 | 51.16 | PD-1/PDL-1 | Glioma | MSK-IMPACT | A0101,A0201,B0702, B5801,C0702,C0706 | A01,A02,B07, B58,UNK,UNK | 0 |

APPENDIX 1-continued

Cohort 2

| Sample | Age Group | OS_ Months | OS_ Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| RV981815 | <30 | 11 | 1 | 24.59 | PD-1/PDL-1 | Melanoma | MSK-IMPACT | A0101,A0201,B0801,B5801,C0718,C0706 | A01,A02,B08,B58,UNK,UNK | 0 |
| RX295147 | 31-50 | 2 | 0 | 4.92 | CTLA4 | Prostate Cancer | MSK-IMPACT | A0301,A0201,B1501,B3501,C0303,C0702 | A03,A02,B62,B07,UNK,UNK | 0 |
| TW555037 | 31-50 | 7 | 1 | 1.97 | PD-1/PDL-1 | Head and Neck Cancer | MSK-IMPACT | A2901,A6801,B4101,B4402,C1701,C0704 | A01A24,A03,B44,B44,UNK,UNK | 0 |
| VR974691 | 50-60 | 3 | 0 | 4.92 | PD-1/PDL-1 | Colorectal Cancer | MSK-IMPACT | A2402,A2402,B1801,B1801,C0701,C0701 | A24,A24,B44,B44,UNK,UNK | 1 |
| VT439023 | 31-50 | 7 | 0 | 37.38 | CTLA4 | Melanoma | MSK-IMPACT | A0101,A2601,B0801,B3801,C1203,C0701 | A01,A01,B08,B27,UNK,UNK | 0 |
| YH901261 | 61-70 | 5 | 1 | 4.92 | Combo | Head and Neck Cancer | MSK-IMPACT | A3002,A1101,B4403,B5301,C0401,C0706 | A01,A03,B44,B07,UNK,UNK | 0 |
| ZK802313 | 31-50 | 3 | 1 | 2.95 | PD-1/PDL-1 | Head and Neck Cancer | MSK-IMPACT | A2402,A2902,B1801,B5801,C1203,C0706 | A24,A01A24,B44,B58,UNK,UNK | 0 |
| ZO158210 | 50-60 | 16 | 0 | 1.97 | PD-1/PDL-1 | Non-Small Cell Lung Cancer | MSK-IMPACT | A0205,A0206,B1501,B5801,C0303,C0706 | A02,A02,B62,B58,UNK,UNK | 0 |
| BF080539 | 31-50 | 15 | 0 | 19.68 | CTLA4 | Melanoma | MSK-IMPACT | A6601,A6901,B5501,B3502,C0303,C0401 | A03,A02,B07,B07,UNK,UNK | 0 |
| DG100147 | 31-50 | 6 | 0 | 23.61 | PD-1/PDL-1 | Non-Small Cell Lung Cancer | MSK-IMPACT | A3002,A2601,B4403,B5301,C1601,C0401 | A01,A01,B44,B07,UNK,UNK | 0 |
| DR570890 | 31-50 | 11 | 0 | 1.97 | PD-1/PDL-1 | Non-Hodgkin Lymphoma | MSK-IMPACT | A3101,A3303,B0702,B6701,C1203,C0702 | A03,A03,B07,B07,UNK,UNK | 0 |
| EO910001 | 50-60 | 5 | 0 | 4.92 | PD-1/PDL-1 | Non-Small Cell Lung Cancer | MSK-IMPACT | A2902,A0201,B4403,B4003,C0304,C1601 | A01A24,A02,B44,B44,UNK,UNK | 0 |
| EQ924504 | >71 | 0 | 1 | 8.85 | PD-1/PDL-1 | Glioma | MSK-IMPACT | A0101,A6801,B3701,B4001,C0304,C0602 | A01,A03,B44,B44,UNK,UNK | 0 |
| EY863064 | 61-70 | 1 | 1 | 1.97 | Combo | Melanoma | MSK-IMPACT | A0301,A3201,B0702,B4002,C0202,C0702 | A03,A01,B07,B44,UNK,UNK | 0 |
| FC067855 | 50-60 | 6 | 1 | 2.95 | Combo | Pancreatic Cancer | MSK-IMPACT | A0201,A0201,B1501,B3501,C0102,C0401 | A02,A02,B62,B07,UNK,UNK | 1 |
| GR143555 | 31-50 | 7 | 1 | 13.77 | PD-1/PDL-1 | Non-Small Cell Lung Cancer | MSK-IMPACT | A3002,A2402,B3502,B1801,C0401,C0501 | A01,A24,B07,B44,UNK,UNK | 0 |
| JD809822 | 50-60 | 0 | 1 | 6.89 | PD-1/PDL-1 | Non-Small Cell Lung Cancer | MSK-IMPACT | A3001,A3001,B1801,B1801,C0210,C0210 | A01A03,A01A03,B44,B44,UNK,UNK | 1 |
| JI866544 | 31-50 | 0 | 1 | 3.94 | PD-1/PDL-1 | Esophagogastric Cancer | MSK-IMPACT | A2301,A3303,B5301,B5301,C0401,C0602 | A24,A03,B07,B07,UNK,UNK | 1 |
| KM672291 | 61-70 | 32 | 0 | 8.85 | CTLA4 | Melanoma | MSK-IMPACT | A0201,A0201,B3801,B3503,C0401,C1203 | A02,A02,B27,B07,UNK,UNK | 1 |
| MP430689 | 31-50 | 5 | 0 | 20.66 | PD-1/PDL-1 | Non-Small Cell Lung Cancer | MSK-IMPACT | A0101,A0101,B4701,B5201,C1202,C0602 | A01,A01,UNK,B62,UNK,UNK | 1 |
| NE455314 | 31-50 | 9 | 1 | 2.95 | PD-1/PDL-1 | Esophagogastric Cancer | MSK-IMPACT | A0301,A0301,B0702,B0702,C0702,C0702 | A03,A03,B07,B07,UNK,UNK | 1 |
| NG601396 | >71 | 10 | 1 | 1.97 | Combo | Melanoma | MSK-IMPACT | A2402,A2601,B0702,B0702,C0202,C0702 | A24,A01,B07,B27,UNK,UNK | 0 |
| NN070436 | 61-70 | 12 | 1 | 4.92 | PD-1/PDL-1 | Glioma | MSK-IMPACT | A1101,A0206,B4601,B4001,C0102,C0304 | A03,A02,B62,B44,UNK,UNK | 0 |
| NV234451 | >71 | 0 | 1 | 6.89 | Combo | Melanoma | MSK-IMPACT | A0201,A2601,B2705,B4402,C0102,C0501 | A02,A01,B27,B44,UNK,UNK | 0 |
| OD563707 | 31-50 | 2 | 1 | 0 | PD-1/PDL-1 | Mesothelioma | MSK-IMPACT | A0301,A0201,B0702,B5101,C1502,C0702 | A03,A02,B07,B07,UNK,UNK | 0 |
| PQ019402 | 31-50 | 2 | 0 | 0.98 | PD-1/PDL-1 | Hepatobiliary Cancer | MSK-IMPACT | A0301,A0101,B1402,B5701,C0802,C0602 | A03,A01,B27,B58,UNK,UNK | 0 |
| QJ432676 | 50-60 | 15 | 0 | 2.95 | PD-1/PDL-1 | Glioma | MSK-IMPACT | A1101,A2402,B5501,B3502,C0303,C0401 | A03,A24,B07,B07,UNK,UNK | 0 |
| TE746331 | >71 | 18 | 0 | 8.85 | PD-1/PDL-1 | Esophagogastric Cancer | MSK-IMPACT | A2402,A2601,B1402,B5201,C0802,C1202 | A24,A01,B27,B62,UNK,UNK | 0 |
| YT556349 | 31-50 | 22 | 0 | 3.94 | Combo | Melanoma | MSK-IMPACT | A1101,A0101,B3801,B5701,C1203,C0602 | A03,A01,B27,B58,UNK,UNK | 0 |
| BF956201 | 31-50 | 13 | 0 | 5.9 | PD-1/PDL-1 | Non-Small Cell Lung Cancer | MSK-IMPACT | A0201,A2601,B1801,B4501,C1601,C1203 | A02,A01,B44,B44,UNK,UNK | 0 |
| BO691217 | 31-50 | 13 | 0 | 9.84 | PD-1/PDL-1 | Non-Small Cell Lung Cancer | MSK-IMPACT | A0201,A3101,B0801,B1801,C0701,C0701 | A02,A03,B08,B44,UNK,UNK | 1 |
| BW588321 | 50-60 | 11 | 0 | 4.92 | Combo | Melanoma | MSK-IMPACT | A2301,A2601,B3801,B4901,C1203,C0701 | A24,A01,B27,UNK,UNK,UNK | 0 |
| CM345531 | 31-50 | 9 | 0 | 0 | PD-1/PDL-1 | Non-Small Cell Lung Cancer | MSK-IMPACT | A0201,A3303,B4403,B3501,C0401,C0401 | A02,A03,B44,B07,UNK,UNK | 1 |
| CZ908459 | 31-50 | 11 | 0 | 3.94 | PD-1/PDL-1 | Glioma | MSK-IMPACT | A2601,A6801,B3801,B1302,C0602,C1203 | A01,A03,B27,UNK,UNK,UNK | 0 |
| DH345617 | >71 | 12 | 1 | 3.94 | Combo | Melanoma | MSK-IMPACT | A0201,A0201,B4402,B5101,C0102,C0501 | A02,A02,B44,B07,UNK,UNK | 1 |
| DP953249 | 61-70 | 5 | 0 | 23.61 | PD-1/PDL-1 | Non-Small Cell Lung Cancer | MSK-IMPACT | A2301,A3101,B4403,B3508,C0401,C0401 | A24,A03,B44,B07,UNK,UNK | 1 |

APPENDIX 1-continued

| | | | | | | | | | | Homozygous |
|---|---|---|---|---|---|---|---|---|---|---|
| Sample | Age Group | OS_ Months | OS_ Event | IMPACT-MutCnt | Drug Class | Cancer Type | Reference | HLA Class I Alleles | HLA Class I Super-types | (1 = Yes; 0 = No) |

Cohort 2

| Sample | Age Group | OS_ Months | OS_ Event | IMPACT-MutCnt | Drug Class | Cancer Type | Reference | HLA Class I Alleles | HLA Class I Super-types | Homozygous |
|---|---|---|---|---|---|---|---|---|---|---|
| EJ708176 | >71 | 3 | 1 | 0.98 | CTLA4 | Breast Cancer | MSK-IMPACT | A0301,A0201,B2705, B3503,C0102,C1203 | A03,A02,B27, B07,UNK,UNK | 0 |
| ER096137 | 31-50 | 3 | 1 | 9.84 | PD-1/PDL-1 | Esophagogastric Cancer | MSK-IMPACT | A0302,A0201,B5201, B1302,C0602,C1202 | A03,A02,B62, UNK,UNK,UNK | 0 |
| HD143613 | 31-50 | 3 | 1 | 11.81 | PD-1/PDL-1 | Bladder Cancer | MSK-IMPACT | A0301,A0201,B0702, B3503,C0401,C0702 | A03,A02,B07, B07,UNK,UNK | 0 |
| HV906622 | >71 | 0 | 1 | 33.45 | Combo | Melanoma | MSK-IMPACT | A0101,A3201,B1801, B3502,C0401,C0701 | A01,A01,B44, B07,UNK,UNK | 0 |
| IE795484 | 31-50 | 3 | 0 | 37.38 | PD-1/PDL-1 | Melanoma | MSK-IMPACT | A0301,A0101,B0801, B2705,C0202,C0701 | A03,A01,B08, B27,UNK,UNK | 0 |
| IJ433188 | 50-60 | 11 | 0 | 1.97 | PD-1/PDL-1 | Soft Tissue Sarcoma | MSK-IMPACT | A0201,A0201,B5501, B1501,C0304,C0303 | A02,A02,B07, B62,UNK,UNK | 1 |
| IM301482 | 50-60 | 6 | 0 | 5.9 | PD-1/PDL-1 | Renal Cell Carcinoma | MSK-IMPACT | A3002,A0201,B4402, B3501,C0501,C0401 | A01,A02,B44, B07,UNK,UNK | 0 |
| IM308572 | 61-70 | 1 | 1 | 9.84 | Combo | Melanoma | MSK-IMPACT | A1101,A3101,B3508, B5101,C0202,C0401 | A03,A03,B07, B07,UNK,UNK | 0 |
| IY740960 | 31-50 | 15 | 0 | 2.95 | Combo | Renal Cell Carcinoma | MSK-IMPACT | A2402,A6801,B2705, B1801,C1502,C0701 | A24,A03,B27, B44,UNK,UNK | 0 |
| LJ501075 | 61-70 | 11 | 0 | 3.94 | PD-1/PDL-1 | Renal Cell Carcinoma | MSK-IMPACT | A6801,A0201,B1402, B4402,C0501,C0802 | A03,A02,B27, B44,UNK,UNK | 0 |
| QA401796 | 31-50 | 15 | 0 | 2.95 | PD-1/PDL-1 | Non-Small Cell Lung Cancer | MSK-IMPACT | A0201,A0201,B0702, B4405,C0202,C0702 | A02,A02,B07, B44,UNK,UNK | 1 |
| SE569393 | 31-50 | 2 | 0 | 7.87 | PD-1/PDL-1 | Non-Small Cell Lung Cancer | MSK-IMPACT | A0301,A2301,B1402, B4901,C0802,C0701 | A03,A24,B27, UNK,UNK,UNK | 0 |
| TX408749 | 50-60 | 8 | 1 | 8.85 | PD-1/PDL-1 | Melanoma | MSK-IMPACT | A0301,A260,B1501, B4001,C0304,C0303 | A03,A01,B62, B44,UNK,UNK | 0 |
| UR037737 | 61-70 | 0 | 1 | 9.84 | PD-1/PDL-1 | Non-Small Cell Lung Cancer | MSK-IMPACT | A0301,A3101,B0801, B5101,C0701,C0701 | A03,A03,B08, B07,UNK,UNK | 1 |
| VU634626 | 31-50 | 10 | 0 | 1.97 | PD-1/PDL-1 | Melanoma | MSK-IMPACT | A0101,A0101,B0801, B0801,C0701,C0701 | A01,A01,B08, B08,UNK,UNK | 1 |
| WF523568 | 31-50 | 20 | 0 | 5.9 | PD-1/PDL-1 | Head and Neck Cancer | MSK-IMPACT | A2601,A2601,B3801, B5101,C1502,C1203 | A01,A01,B27, B07,UNK,UNK | 1 |
| XU469861 | >71 | 17 | 0 | 0.98 | PD-1/PDL-1 | Bone Cancer | MSK-IMPACT | A6601,A0201,B4102, B4402,C1701,C0704 | A03,A02,B44, B44,UNK,UNK | 0 |
| BR857502 | 31-50 | 12 | 1 | 2.95 | PD-1/PDL-1 | Non-Small Cell Lung Cancer | MSK-IMPACT | A1101,A2402,B4002, B3801,C0304,C1203 | A03,A24,B44, B27,UNK,UNK | 0 |
| DE430582 | 31-50 | 5 | 1 | 3.94 | PD-1/PDL-1 | Renal Cell Carcinoma | MSK-IMPACT | A3001,A3001,B5001, B4501,C1601,C0701 | A01A03,A01A03,B44, B44,UNK,UNK | 1 |
| DK753827 | 50-60 | 15 | 0 | 2.95 | Combo | Renal Cell Carcinoma | MSK-IMPACT | A1101,A2601,B2705, B1402,C0102,C0802 | A03,A01,B27, B27,UNK,UNK | 0 |
| EB388647 | <30 | 4 | 1 | 36.4 | PD-1/PDL-1 | Melanoma | MSK-IMPACT | A0101,A6801,B0801, B3701,C0602,C0701 | A01,A03,B08, B44,UNK,UNK | 0 |
| EU139890 | >71 | 4 | 0 | 1.97 | PD-1/PDL-1 | Non-Small Cell Lung Cancer | MSK-IMPACT | A3101,A3101,B1508, B1508,C0102,C0102 | A03,A03,B07, B07,UNK,UNK | 1 |
| HG213091 | 31-50 | 2 | 0 | 5.9 | PD-1/PDL-1 | Small Cell Lung Cancer | MSK-IMPACT | A6601,A0201,B3502, B4402,C0401,C1502 | A03,A02,B07, B44,UNK,UNK | 0 |
| HH230546 | 61-70 | 4 | 0 | 203.64 | PD-1/PDL-1 | Colorectal Cancer | MSK-IMPACT | A3001,A2402,B4002, B3501,C0303,C0304 | A01A03,A24,B44, B07,UNK,UNK | 0 |
| JF991036 | 31-50 | 1 | 0 | 50.17 | Combo | Non-Small Cell Lung Cancer | MSK-IMPACT | A2402,A0201,B4402, B4402,C0501,C1504 | A24,A02,B44, B44,UNK,UNK | 1 |
| KF580579 | 31-50 | 3 | 0 | 5.9 | CTLA4 | Pancreatic Cancer | MSK-IMPACT | A6801,A6802,B1402, B2702,C0802,C0202 | A03,A02,B27, B27,UNK,UNK | 0 |
| KO267493 | 61-70 | 7 | 0 | 14.76 | CTLA4 | Soft Tissue Sarcoma | MSK-IMPACT | A2601,A2601,B3801, B3801,C1203,C1203 | A01,A01,B27, B27,UNK,UNK | 1 |
| MB313563 | 50-60 | 0 | 0 | 5.9 | PD-1/PDL-1 | Cancer of Unknown Primary | MSK-IMPACT | A3004,A2301,B4901, B4901,C0701,C0701 | A01,A24,UNK, UNK,UNK,UNK | 1 |
| PY916704 | >71 | 0 | 0 | 7.87 | PD-1/PDL-1 | Glioma | MSK-IMPACT | A2301,A0201,B1402, B4402,C0802,C0501 | A03,A02,B27, B44,UNK,UNK | 0 |
| QM120917 | 31-50 | 2 | 1 | 0 | PD-1/PDL-1 | Renal Cell Carcinoma | MSK-IMPACT | A1101,A2402,B4402, B1801,C1604,C0701 | A03,A24,B44, B44,UNK,UNK | 0 |
| QP194424 | <30 | 5 | 1 | 62.96 | PD-1/PDL-1 | Skin Cancer; Non-Melanoma | MSK-IMPACT | A0201,A0201,B0702, B4402,C0501,C0702 | A02,A02,B07, B44,UNK,UNK | 1 |
| RD412780 | 31-50 | 11 | 0 | 5.9 | PD-1/PDL-1 | Renal Cell Carcinoma | MSK-IMPACT | A3201,A3303,B2705, B1801,C1203,C1502 | A01,A03,B27, B44,UNK,UNK | 0 |
| RN967996 | >71 | 15 | 0 | 1.97 | PD-1/PDL-1 | Colorectal Cancer | MSK-IMPACT | A1101,A2402,B3906, B4006,C1502,C0702 | A03,A24,B27, B44,UNK,UNK | 0 |
| TX586079 | 61-70 | 22 | 0 | 29.51 | PD-1/PDL-1 | Esophagogastric Cancer | MSK-IMPACT | A2301,A6802,B1510, B4901,C0304,C0701 | A24,A02,B27, UNK,UNK,UNK | 0 |
| UD586728 | 31-50 | 0 | 0 | 18.69 | PD-1/PDL-1 | Non-Small Cell Lung Cancer | MSK-IMPACT | A2301,A0201,B3901, B4102,C1203,C1701 | A24,A02,B27, B44,UNK,UNK | 0 |
| UW666903 | 50-60 | 18 | 1 | 7.87 | PD-1/PDL-1 | Non-Small Cell Lung Cancer | MSK-IMPACT | A0301,A0201,B5501, B5501,C0102,C0701 | A03,A02,B07, B07,UNK,UNK | 1 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| VE077996 | 61-70 | 0 | 0 | 4.92 | PD-1/PDL-1 | Non-Small Cell Lung Cancer | MSK-IMPACT | A1101,A0207,B0705, B4601,C0102,C1505 | A03,A02,B07, B62,UNK,UNK | 0 |
| VO581533 | 31-50 | 0 | 0 | 33.45 | PD-1/PDL-1 | Non-Small Cell Lung Cancer | MSK-IMPACT | A3004,A0102,B8101, B4403,C0804,C0706 | A01,UNK,B07, B44,UNK,UNK | 0 |
| XA334516 | 50-60 | 23 | 0 | 1.97 | Combo | Non-Small Cell Lung Cancer | MSK-IMPACT | A2601,A3301,B1402, B3801,C0802,C1203 | A01,A03,B27, B27,UNK,UNK | 0 |
| XF280080 | >71 | 3 | 1 | 0 | PD-1/PDL-1 | Adrenocortical Carcinoma | MSK-IMPACT | A0301,A2601,B4403, B5101,C0303,C1601 | A03,A01,B44, B07,UNK,UNK | 0 |
| YI633805 | 31-50 | 8 | 0 | 1.97 | PD-1/PDL-1 | Skin Cancer; Non-Melanoma | MSK-IMPACT | A2402,A3303,B4901, B3502,C0401,C0701 | A24,A03,UNK, B07,UNK,UNK | 0 |
| YR519762 | 31-50 | 16 | 0 | 3.94 | PD-1/PDL-1 | Non-Small Cell Lung Cancer | MSK-IMPACT | A0101,A3201,B0801, B2703,C0202,C0701 | A01,A01,B08, B27,UNK,UNK | 0 |
| ZK526534 | 31-50 | 13 | 0 | 6.89 | PD-1/PDL-1 | Bladder Cancer | MSK-IMPACT | A1101,A3201,B0702, B1801,C0501,C0702 | A03,A01,B07, B44,UNK,UNK | 0 |
| DK273036 | >71 | 8 | 0 | 2.95 | PD-1/PDL-1 | Glioma | MSK-IMPACT | A6801,A0201,B3901, B5101,C1504,C0702 | A03,A02,B27, B07,UNK,UNK | 0 |
| DM301970 | >71 | 2 | 0 | 2.95 | PD-1/PDL-1 | Colorectal Cancer | MSK-IMPACT | A0301,A1101,B0702, B3503,C0401,C0702 | A03,A03,B07, B07,UNK,UNK | 0 |
| GC996651 | 31-50 | 5 | 1 | 8.85 | Combo | Head and Neck Cancer | MSK-IMPACT | A0101,A2402,B0702, B5101,C1502,C0702 | A01,A24,B07, B07,UNK,UNK | 0 |
| IT581561 | 31-50 | 3 | 0 | 6.89 | PD-1/PDL-1 | Glioma | MSK-IMPACT | A0301,A0201,B0702, B4402,C0501,C0702 | A03,A02,B07, B44,UNK,UNK | 0 |
| IV185293 | 31-50 | 6 | 0 | 2.95 | PD-1/PDL-1 | Melanoma | MSK-IMPACT | A2402,A2902,B1517, B1402,C0802,C0701 | A24,A01A24,B58, B27,UNK,UNK | 0 |
| LJ345209 | 31-50 | 2 | 1 | 3.94 | PD-1/PDL-1 | Head and Neck Cancer | MSK-IMPACT | A3201,A3201,B4002, B4402,C0501,C0202 | A01,A01,B44, B44,UNK,UNK | 1 |
| LQ921060 | 31-50 | 0 | 1 | 16.72 | PD-1/PDL-1 | Non-Small Cell Lung Cancer | MSK-IMPACT | A0101,A2601,B0801, B1517,C0701,C0718 | A01,A01,B08, B58,UNK,UNK | 0 |
| NE921221 | 31-50 | 4 | 0 | 6.89 | PD-1/PDL-1 | Non-Small Cell Lung Cancer | MSK-IMPACT | A2402,A2402,B1801, B5101,C1402,C1203 | A24,A24,B44, B07,UNK,UNK | 1 |
| PS842981 | 31-50 | 9 | 1 | 3.94 | PD-1/PDL-1 | Bladder Cancer | MSK-IMPACT | A0101,A0205,B5001, B1801,C0602,C0602 | A01,A02,B44, B44,UNK,UNK | 1 |
| RA926807 | 61-70 | 6 | 0 | 7.87 | PD-1/PDL-1 | Non-Small Cell Lung Cancer | MSK-IMPACT | A1101,A2601,B0702, B5201,C1202,C0702 | A03,A01,B07, B62,UNK,UNK | 0 |
| WC205663 | 31-50 | 2 | 0 | 3.94 | Combo | Non-Small Cell Lung Cancer | MSK-IMPACT | A2402,A0201,B2705, B4001,C0304,C0202 | A24,A02,B27, B44,UNK,UNK | 0 |
| WL137245 | 61-70 | 47 | 0 | 11.81 | PD-1/PDL-1 | Melanoma | MSK-IMPACT | A0201,A0201,B4402, B4001,C0304,C0701 | A02,A02,B44, B44,UNK,UNK | 1 |
| WM306951 | 50-60 | 32 | 1 | 0 | PD-1/PDL-1 | Renal Cell Carcinoma | MSK-IMPACT | A2402,A3201,B3501, B3501,C0102,C0401 | A24,A01,B07, B07,UNK,UNK | 1 |
| WP072873 | 61-70 | 6 | 0 | 15.74 | Combo | Melanoma | MSK-IMPACT | A0301,A2601,B0702, B3501,C0401,C0702 | A03,A01,B07, B07,UNK,UNK | 0 |
| YK675744 | 50-60 | 4 | 0 | 14.76 | PD-1/PDL-1 | Bladder Cancer | MSK-IMPACT | A0301,A1101,B0702, B0702,C0702,C0702 | A03,A03,B07, B07,UNK,UNK | 1 |
| YU626285 | 50-60 | 8 | 0 | 19.68 | PD-1/PDL-1 | Melanoma | MSK-IMPACT | A1101,A0201,B5501, B1801,C0303,C0701 | A03,A02,B07, B44,UNK,UNK | 0 |
| ZK342685 | 31-50 | 7 | 1 | 8.85 | PD-1/PDL-1 | Melanoma | MSK-IMPACT | A2402,A0201,B3906, B3501,C0401,C0702 | A04,A02,B27, B07,UNK,UNK | 0 |
| DS616046 | 50-60 | 20 | 0 | 0 | PD-1/PDL-1 | Melanoma | MSK-IMPACT | A2402,A0201,B1501, B4001,C0303,C0304 | A24,A02,B62, B44,UNK,UNK | 0 |
| FI164601 | 50-60 | 15 | 0 | 49.49 | PD-1/PDL-1 | Non-Small Cell Lung Cancer | MSK-IMPACT | A0301,A1102,B2704, B4402,C1202,C0501 | A03,A03,B27, B44,UNK,UNK | 0 |
| GG613373 | 31-50 | 7 | 1 | 0 | PD-1/PDL-1 | Esophagogastric Cancer | MSK-IMPACT | A1101,A2301,B3503, B4901,C1203,C0718 | A03,A24,B07, UNK,UNK,UNK | 0 |
| GK892986 | >71 | 16 | 0 | 3.94 | PD-1/PDL-1 | Bone Cancer | MSK-IMPACT | A0101,A0201,B0801, B1502,C0801,C0702 | A01,A02,B08, B62,UNK,UNK | 0 |
| HA469182 | 31-50 | 25 | 0 | 46.24 | CTLA4 | Melanoma | MSK-IMPACT | A0301,A0206,B0702, B3501,C0303,C0702 | A03,A02,B07, B07,UNK,UNK | 0 |
| KU939300 | 61-70 | 10 | 0 | 21.64 | Combo | Melanoma | MSK-IMPACT | A3001,A3002,B1302, B3501,C0602,C0401 | A01A03,A01,UNK, B07,UNK,UNK | 0 |
| LM168179 | 50-60 | 1 | 0 | 3.94 | PD-1/PDL-1 | Non-Small Cell Lung Cancer | MSK-IMPACT | A2902,A3301,B1402, B4403,C0802,C1801 | A01A24,A03,B27, B44,UNK,UNK | 0 |
| OD052630 | >71 | 32 | 1 | 4.92 | PD-1/PDL-1 | Non-Small Cell Lung Cancer | MSK-IMPACT | A1101,A0201,B0702, B0702,C0702,C0702 | A03,A02,B07, B07,UNK,UNK | 1 |
| OE955832 | 50-60 | 9 | 1 | 10.82 | PD-1/PDL-1 | Non-Small Cell Lung Cancer | MSK-IMPACT | A3001,A3001,B1510, B1801,C0304,C0202 | A01A03,A01A03,B27, B44,UNK,UNK | 1 |
| OP247065 | 31-50 | 14 | 0 | 68.87 | PD-1/PDL-1 | Colorectal Cancer | MSK-IMPACT | A2402,A2402,B0702, B3503,C0401,C0702 | A24,A24,B07, B07,UNK,UNK | 1 |
| OZ621986 | 50-60 | 12 | 0 | 1.97 | Combo | Melanoma | MSK-IMPACT | A0301,A3002,B2705, B1801,C0102,C0501 | A03,A01,B27, B44,UNK,UNK | 0 |
| RW388101 | 50-60 | 2 | 1 | 5.9 | PD-1/PDL-1 | Non-Small Cell Lung Cancer | MSK-IMPACT | A0201,A0201,B4402, B0501,C0102,C0202 | A02,A02,B44, B44,UNK,UNK | 1 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| SD891023 | <30 | 17 | 0 | 3.94 | PD-1/PDL-1 | Non-Small Cell Lung Cancer | MSK-IMPACT | A0101,A3101,B3801,B3503,C0401,C1203 | A01,A03,B27,B07,UNK,UNK | 0 |
| WU141360 | 61-70 | 3 | 0 | 6.89 | Combo | Melanoma | MSK-IMPACT | A0201,A0201,B0801,B1501,C0303,C0701 | A02,A02,B08,B62,UNK,UNK | 1 |
| WY430099 | 50-60 | 3 | 0 | 2.95 | PD-1/PDL-1 | Non-Small Cell Lung Cancer | MSK-IMPACT | A0101,A2601,B1801,B3502,C1203,C0401 | A01,A01,B44,B07,UNK,UNK | 0 |
| XI023833 | 31-50 | 2 | 0 | 4.92 | PD-1/PDL-1 | Non-Small Cell Lung Cancer | MSK-IMPACT | A2402,A2402,B3502,B3501,C0401,C0401 | A24,A24,B07,B07,UNK,UNK | 1 |
| XK805958 | 61-70 | 5 | 1 | 10.82 | PD-1/PDL-1 | Non-Small Cell Lung Cancer | MSK-IMPACT | A1101,A2301,B1501,B1801,C0303,C0501 | A03,A24,B62,B44,UNK,UNK | 0 |
| YR534379 | >71 | 2 | 0 | 5.9 | PD-1/PDL-1 | Colorectal Cancer | MSK-IMPACT | A1101,A6801,B1801,B5201,C1601,C0701 | A03,A03,B44,B62,UNK,UNK | 0 |
| AY728758 | >71 | 20 | 0 | 9.84 | Combo | Melanoma | MSK-IMPACT | A0301,A3201,B4405,B5101,C0102,C0202 | A03,A01,B44,B07,UNK,UNK | 0 |
| CH836399 | 50-60 | 12 | 0 | 3.94 | CTLA4 | Breast Cancer | MSK-IMPACT | A2301,A0201,B4403,B4501,C0401,C1601 | A24,A02,B44,B44,UNK,UNK | 0 |
| DF482553 | 31-50 | 1 | 0 | 11.81 | PD-1/PDL-1 | Head and Neck Cancer | MSK-IMPACT | A0101,A0101,B0801,B0801,C0701,C0701 | A01,A01,B08,B08,UNK,UNK | 1 |
| DS424270 | 31-50 | 1 | 1 | 9.84 | PD-1/PDL-1 | Non-Small Cell Lung Cancer | MSK-IMPACT | A0301,A6601,B3801,B4102,C1203,C1701 | A03,A03,B27,B44,UNK,UNK | 0 |
| GZ954783 | 61-70 | 17 | 0 | 19.68 | PD-1/PDL-1 | Non-Small Cell Lung Cancer | MSK-IMPACT | A7401,A7401,B0702,B1503,C0210,C0702 | A03,A03,B07,B27,UNK,UNK | 1 |
| JC504331 | >71 | 7 | 0 | 4.92 | CTLA4 | Breast Cancer | MSK-IMPACT | A0101,A0201,B0801,B4402,C0704,C0701 | A01,A02,B08,B44,UNK,UNK | 0 |
| JD755987 | 50-60 | 5 | 0 | 4.92 | PD-1/PDL-1 | Renal Cell Carcinoma | MSK-IMPACT | A0101,A0101,B0801,B1302,C0602,C0701 | A01,A01,B08,UNK,UNK,UNK | 1 |
| KI514356 | 50-60 | 0 | 0 | 5.9 | PD-1/PDL-1 | Renal Cell Carcinoma | MSK-IMPACT | A3001,A2902,B3701,B1302,C0602,C0602 | A01A03,A01A24,B44,UNK,UNK,UNK | 1 |
| KL738755 | 50-60 | 14 | 0 | 14.76 | CTLA4 | Breast Cancer | MSK-IMPACT | A3601,A0201,B3501,B5301,C1601,C0401 | A01,A02,B07,B07,UNK,UNK | 0 |
| KN186707 | 31-50 | 2 | 0 | 3.94 | CTLA4 | Breast Cancer | MSK-IMPACT | A0201,A0201,B0702,B5101,C1502,C0702 | A02,A02,B07,B07,UNK,UNK | 1 |
| MT269010 | 50-60 | 3 | 1 | 7.87 | PD-1/PDL-1 | Non-Small Cell Lung Cancer | MSK-IMPACT | A0301,A1101,B1801,B5201,C1202,C0701 | A03,A03,B44,B62,UNK,UNK | 0 |
| NJ492568 | 50-60 | 33 | 0 | 4.92 | Combo | Renal Cell Carcinoma | MSK-IMPACT | A2402,A0201,B5501,B3701,C0303,C0602 | A24,A02,B07,B44,UNK,UNK | 0 |
| NL685509 | 61-70 | 8 | 1 | 1.97 | Combo | Esophagogastric Cancer | MSK-IMPACT | A0301,A0201,B4403,B4402,C0401,C0704 | A03,A02,B44,B44,UNK,UNK | 0 |
| OW338232 | 50-60 | 3 | 0 | 17.71 | PD-1/PDL-1 | Bladder Cancer | MSK-IMPACT | A0301,A3101,B3801,B3801,C1203,C1203 | A03,A03,B27,B27,UNK,UNK | 1 |
| PM135012 | 31-50 | 13 | 1 | 6.89 | PD-1/PDL-1 | Bladder Cancer | MSK-IMPACT | A0301,A0301,B0702,B0702,C0702,C0702 | A03,A03,B07,B07,UNK,UNK | 1 |
| PS208416 | 50-60 | 6 | 0 | 4.92 | PD-1/PDL-1 | Glioma | MSK-IMPACT | A0301,A1101,B0702,B1501,C0304,C0304 | A03,A03,B07,B62,UNK,UNK | 1 |
| PY486092 | 31-50 | 3 | 1 | 2.95 | PD-1/PDL-1 | Non-Small Cell Lung Cancer | MSK-IMPACT | A1101,A0201,B0801,B5701,C0602,C0701 | A03,A02,B08,B58,UNK,UNK | 0 |
| QD664127 | >71 | 58 | 0 | 11.81 | CTLA4 | Melanoma | MSK-IMPACT | A0101,A0201,B4403,B4402,C1601,C0501 | A01,A02,B44,B44,UNK,UNK | 0 |
| RI100586 | 50-60 | 1 | 0 | 1.97 | PD-1/PDL-1 | Glioma | MSK-IMPACT | A1101,A2902,B5501,B4403,C0303,C1601 | A03,A01A24,B07,B44,UNK,UNK | 0 |
| RW567050 | 31-50 | 11 | 0 | 102.31 | PD-1/PDL-1 | Melanoma | MSK-IMPACT | A0201,A6901,B0705,B5501,C1505,C0303 | A02,A02,B07,B07,UNK,UNK | 0 |
| SQ789755 | 31-50 | 0 | 1 | 0.98 | PD-1/PDL-1 | Non-Small Cell Lung Cancer | MSK-IMPACT | A0301,A0201,B3501,B5801,C0401,C076 | A03,A02,B07,B58,UNK,UNK | 0 |
| UD810304 | 50-60 | 2 | 0 | 2.95 | PD-1/PDL-1 | Non-Small Cell Lung Cancer | MSK-IMPACT | A1101,A0101,B2705,B3503,C0202,C0401 | A03,A01,B27,B07,UNK,UNK | 0 |
| UP639709 | 50-60 | 4 | 0 | 7.87 | PD-1/PDL-1 | Non-Small Cell Lung Cancer | MSK-IMPACT | A0201,A0201,B4402,B5101,C0501,C0202 | A02,A02,B44,B07,UNK,UNK | 1 |
| WG937133 | 31-50 | 4 | 0 | 13.77 | PD-1/PDL-1 | Colorectal Cancer | MSK-IMPACT | A2601,A0201,B0801,B1501,C0304,C0701 | A01,A02,B08,B62,UNK,UNK | 0 |
| WZ633302 | 31-50 | 1 | 1 | 3.94 | PD-1/PDL-1 | Cancer of Unknown Primary | MSK-IMPACT | A2402,A0201,B1501,B5701,C0303,C0602 | A24,A02,B62,B58,UNK,UNK | 0 |
| YG749643 | 50-60 | 29 | 0 | 3.94 | PD-1/PDL-1 | Renal Cell Carcinoma | MSK-IMPACT | A1101,A3101,B4101,B3503,C0401,C1701 | A03,A03,B44,B07,UNK,UNK | 0 |
| YQ266016 | 61-70 | 14 | 0 | 5.9 | PD-1/PDL-1 | Glioma | MSK-IMPACT | A0201,A2601,B1401,B1801,C0802,C1203 | A02,A01,B27,B44,UNK,UNK | 0 |
| YQ653157 | 61-70 | 2 | 0 | 2.95 | PD-1/PDL-1 | Non-Small Cell Lung Cancer | MSK-IMPACT | A1101,A0203,B1518,B1801,C0704,C0702 | A03,A02,B27,B44,UNK,UNK | 0 |
| ZO253625 | 31-50 | 22 | 1 | 2.95 | PD-1/PDL-1 | Bladder Cancer | MSK-IMPACT | A0101,A0201,B5101,B5101,C1402,C0202 | A01,A02,B07,B07,UNK,UNK | 1 |
| ZQ021549 | 50-60 | 51 | 0 | 19.68 | CTLA4 | Melanoma | MSK-IMPACT | A0301,A2601,B0702,B5101,C1402,C0702 | A03,A01,B07,B07,UNK,UNK | 0 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| CE919172 | 31-50 | 10 | 0 | 8.85 | PD-1/PDL-1 | Non-Small Cell Lung Cancer | MSK-IMPACT | A0301,A2402,B5801,B5101,C0202,C0706 | A03,A24,B58,B07,UNK,UNK | 0 |
| DD869488 | 61-70 | 5 | 1 | 6.89 | PD-1/PDL-1 | Head and Neck Cancer | MSK-IMPACT | A0101,A2402,B0702,B1517,C0701,C0702 | A01,A24,B07,B58,UNK,UNK | 0 |
| DN709186 | 50-60 | 13 | 0 | 2.95 | PD-1/PDL-1 | Non-Small Cell Lung Cancer | MSK-IMPACT | A0201,A0201,B4403,B4901,C1601,C0701 | A02,A02,B44,UNK,UNK,UNK | 1 |
| EB405485 | 31-50 | 1 | 1 | 5.9 | Combo | Melanoma | MSK-IMPACT | A0101,A0201,B3901,B1517,C1203,C0701 | A01,A02,B27,B58,UNK,UNK | 0 |
| HA424390 | 61-70 | 48 | 1 | 13.77 | Combo | Melanoma | MSK-IMPACT | A0301,A6601,B0702,B4201,C1701,C0702 | A03,A03,B07,B07,UNK,UNK | 0 |
| HU860149 | 50-60 | 1 | 0 | 6.89 | PD-1/PDL-1 | Colorectal Cancer | MSK-IMPACT | A0101,A0201,B4403,B5201,C0302,C1501 | A01,A02,B44,B62,UNK,UNK | 0 |
| HY288210 | 31-50 | 1 | 1 | 8.85 | PD-1/PDL-1 | Non-Small Cell Lung Cancer | MSK-IMPACT | A0201,A0201,B2705,B4402,C0202,C0704 | A02,A02,B27,B44,UNK,UNK | 1 |
| IJ267060 | 31-50 | 7 | 0 | 4.92 | PD-1/PDL-1 | Glioma | MSK-IMPACT | A0301,A0101,B5701,B3501,C0401,C0602 | A03,A01,B58,B07,UNK,UNK | 0 |
| IJ938694 | 50-60 | 6 | 0 | 1.97 | PD-1/PDL-1 | Melanoma | MSK-IMPACT | A3002,A0201,B1801,B5201,C0501,C1202 | A01,A02,B44,B62,UNK,UNK | 0 |
| IU057564 | 31-50 | 31 | 0 | 3.94 | Combo | Renal Cell Carcinoma | MSK-IMPACT | A0301,A0201,B0702,B4405,C0202,C0702 | A03,A02,B07,B44,UNK,UNK | 0 |
| KE694138 | >71 | 13 | 0 | 3.94 | PD-1/PDL-1 | Renal Cell Carcinoma | MSK-IMPACT | A1101,A0201,B5401,B4001,C0304,C1502 | A03,A02,B07,B44,UNK,UNK | 0 |
| LR648308 | 31-50 | 38 | 0 | 2.95 | Combo | Non-Small Cell Lung Cancer | MSK-IMPACT | A2601,A6802,B4201,B3801,C1701,C1203 | A01,A02,B07,B27,UNK,UNK | 0 |
| NN760931 | 61-70 | 1 | 1 | 5.9 | Combo | Head and Neck Cancer | MSK-IMPACT | A2402,A0201,B1402,B4001,C0304,C0802 | A24,A02,B27,B44,UNK,UNK | 0 |
| NV186145 | 61-70 | 1 | 0 | 1.97 | PD-1/PDL-1 | Breast Cancer | MSK-IMPACT | A0101,A2402,B1501,B3503,C0303,C0401 | A01,A24,B62,B07,UNK,UNK | 0 |
| NW458476 | <30 | 8 | 0 | 4.92 | PD-1/PDL-1 | Non-Small Cell Lung Cancer | MSK-IMPACT | A0301,A0302,B0801,B5601,C0102,C0701 | A03,A03,B08,B07,UNK,UNK | 0 |
| SQ342450 | 50-60 | 6 | 0 | 27.55 | PD-1/PDL-1 | Breast Cancer | MSK-IMPACT | A2301,A0201,B4402,B1801,C0501,C0501 | A24,A02,B44,B44,UNK,UNK | 1 |
| SY001440 | <30 | 3 | 1 | 7.87 | PD-1/PDL-1 | Non-Hodgkin Lymphoma | MSK-IMPACT | A0302,A3303,B4402,B5801,C1604,C0302 | A03,A03,B44,B58,UNK,UNK | 0 |
| WC509975 | 31-50 | 2 | 1 | 4.92 | PD-1/PDL-1 | Melanoma | MSK-IMPACT | A0101,A2601,B1517,B3801,C1203,C0701 | A01,A01,B58,B27,UNK,UNK | 0 |
| XB540163 | 31-50 | 10 | 0 | 2.95 | Combo | Melanoma | MSK-IMPACT | A3201,A0201,B4402,B3501,C0501,C0401 | A01,A02,B44,B07,UNK,UNK | 0 |
| ZK699203 | 61-70 | 14 | 0 | 2.95 | PD-1/PDL-1 | Glioma | MSK-IMPACT | A0101,A0201,B0702,B1801,C0702,C0701 | A01,A02,B07,B44,UNK,UNK | 0 |
| BU258265 | 50-60 | 9 | 1 | 14.76 | PD-1/PDL-1 | Non-Small Cell Lung Cancer | MSK-IMPACT | A0101,A2601,B3801,B5701,C1203,C1203 | A01,A01,B27,B58,UNK,UNK | 1 |
| CS636630 | 61-70 | 10 | 0 | 45.25 | PD-1/PDL-1 | Non-Small Cell Lung Cancer | MSK-IMPACT | A0201,A2601,B3801,B1801,C1203,C1203 | A02,A01,B27,B44,UNK,UNK | 1 |
| CY423132 | 31-50 | 7 | 0 | 0.98 | PD-1/PDL-1 | Soft Tissue Sarcoma | MSK-IMPACT | A2403,A0206,B1525,B1525,C0403,C0702 | A24,A02,B62,B62,UNK,UNK | 1 |
| FM860744 | 50-60 | 9 | 0 | 69.85 | Combo | Melanoma | MSK-IMPACT | A0201,A3101,B6701,B5601,C0102,C0702 | A02,A03,B07,B07,UNK,UNK | 0 |
| IS891001 | >71 | 0 | 0 | 0 | PD-1/PDL-1 | Esophagogastric Cancer | MSK-IMPACT | A0201,A2601,B4102,B1801,C1203,C1701 | A02,A01,B44,B44,UNK,UNK | 0 |
| JM263371 | 31-50 | 2 | 1 | 4.92 | PD-1/PDL-1 | Bladder Cancer | MSK-IMPACT | A3001,A3201,B1302,B1501,C0303,C0602 | A01A03,A01,UNK,B62,UNK,UNK | 0 |
| KM601311 | 61-70 | 11 | 0 | 50.17 | PD-1/PDL-1 | Pancreatic Cancer | MSK-IMPACT | A0301,A0101,B0801,B5101,C1502,C0701 | A03,A01,B08,B07,UNK,UNK | 0 |
| MM286349 | <30 | 1 | 1 | 8.85 | PD-1/PDL-1 | Non-Small Cell Lung Cancer | MSK-IMPACT | A0101,A6802,B1402,B3701,C0802,C0602 | A01,A02,B27,B44,UNK,UNK | 0 |
| OD704763 | 31-50 | 0 | 0 | 6.89 | PD-1/PDL-1 | Esophagogastric Cancer | MSK-IMPACT | A3303,A0205,B4403,B5201,C1202,C0706 | A03,A02,B44,B62,UNK,UNK | 0 |
| OU070759 | 61-70 | 0 | 1 | 2.95 | PD-1/PDL-1 | Thyroid Cancer | MSK-IMPACT | A2301,A6601,B1503,B1503,C0210,C0210 | A24,A03,B27,B27,UNK,UNK | 1 |
| QP957710 | >71 | 0 | 0 | 0 | PD-1/PDL-1 | Head and Neck Cancer | MSK-IMPACT | A0201,A2601,B3801,B3501,C0401,C1203 | A02,A01,B27,B07,UNK,UNK | 0 |
| RL045521 | 61-70 | 11 | 0 | 2.95 | PD-1/PDL-1 | Soft Tissue Sarcoma | MSK-IMPACT | A0302,A2601,B0801,B3801,C1203,C0701 | A03,A01,B08,B27,UNK,UNK | 0 |
| UX818012 | 50-60 | 22 | 0 | 2.95 | Combo | Melanoma | MSK-IMPACT | A0301,A0101,B5101,B5201,C1502,C1202 | A03,A01,B07,B62,UNK,UNK | 0 |
| WI153171 | >71 | 3 | 0 | 2.95 | PD-1/PDL-1 | Non-Small Cell Lung Cancer | MSK-IMPACT | A2601,A0205,B3801,B5001,C1203,C0602 | A01,A02,B27,B44,UNK,UNK | 0 |
| XD202834 | 50-60 | 8 | 0 | 1.97 | PD-1/PDL-1 | Renal Cell Carcinoma | MSK-IMPACT | A2402,A0201,B0702,B4402,C0501,C0702 | A24,A02,B07,B44,UNK,UNK | 0 |
| XJ239469 | 31-50 | 5 | 1 | 11.81 | PD-1/PDL-1 | Melanoma | MSK-IMPACT | A0301,A6901,B1402,B5501,C0102,C0802 | A03,A02,B27,B07,UNK,UNK | 0 |

APPENDIX 1-continued

| | | | | | | | | | | Homozygous (1 = Yes; 0 = No) |
|---|---|---|---|---|---|---|---|---|---|---|
| Sample | Age Group | OS_Months | OS_Event | IMPACT-MutCnt | Drug Class | Cancer Type | Reference | HLA Class I Alleles | HLA Class I Super-types | |
| XP592070 | 61-70 | 0 | 0 | 1.97 | PD-1/PDL-1 | Cancer of Unknown Primary | MSK-IMPACT | A1101,A2402,B0702, B3501,C0401,C0702 | A03,A24,B07, B07,UNK,UNK | 0 |
| CI009821 | 31-50 | 46 | 0 | 0.98 | PD-1/PDL-1 | Renal Cell Carcinoma | MSK-IMPACT | A2402,A3303,B3801, B1801,C1203,C1203 | A24,A03,B27, B44,UNK,UNK | 1 |
| CW956274 | 50-60 | 15 | 0 | 7.87 | PD-1/PDL-1 | Bladder Cancer | MSK-IMPACT | A3201,A6801,B2705, B1517,C0102,C0701 | A01,A03,B27, B58,UNK,UNK | 0 |
| FL718778 | 31-50 | 10 | 0 | 51.16 | PD-1/PDL-1 | Melanoma | MSK-IMPACT | A0101,A3101,B5701, B4001,C0304,C0602 | A01,A03,B58, B44,UNK,UNK | 0 |
| HJ341308 | 61-70 | 2 | 0 | 6.89 | PD-1/PDL-1 | Colorectal Cancer | MSK-IMPACT | A0301,A1101,B0801, B4901,C0701,C0701 | A03,A03,B08, UNK,UNK,UNK | 1 |
| IL793595 | 50-60 | 2 | 0 | 8.85 | PD-1/PDL-1 | Non-Small Cell Lung Cancer | MSK-IMPACT | A2301,A2301,B4901, B4901,C0701,C0701 | A24,A24,UNK, UNK,UNK,UNK | 1 |
| IO180287 | >71 | 6 | 1 | 0.98 | CTLA4 | Breast Cancer | MSK-IMPACT | A1101,A0207,B4601, B3801,C0102,C0702 | A03,A02,B62, UNK,UNK,UNK | 0 |
| IQ553381 | >71 | 8 | 0 | 2.95 | PD-1/PDL-1 | Glioma | MSK-IMPACT | A2902,A0201,B0801, B4501,C0602,C0701 | A01A24,A02,B08, B44,UNK,UNK | 0 |
| IT690202 | 31-50 | 24 | 0 | 25.58 | CTLA4 | Melanoma | MSK-IMPACT | A0201,A0201,B2705, B3501,C0102,C0401 | A02,A02,B27, B07,UNK,UNK | 1 |
| JD896803 | 31-50 | 4 | 0 | 8.85 | PD-1/PDL-1 | Head and Neck Cancer | MSK-IMPACT | A0301,A6802,B1516, B1402,C0802,C1601 | A03,A02,B58, B27,UNK,UNK | 0 |
| JN789460 | >71 | 5 | 0 | 3.94 | PD-1/PDL-1 | Colorectal Cancer | MSK-IMPACT | A0201,A0201,B4001, B4001,C0304,C0304 | A02,A02,B44, B44,UNK,UNK | 1 |
| ME751004 | 61-70 | 8 | 0 | 0.98 | Combo | Melanoma | MSK-IMPACT | A1101,A2402,B4801, B3802,C0801,C0702 | A03,A24,B27, UNK,UNK,UNK | 0 |
| RS929970 | 50-60 | 0 | 1 | 13.77 | PD-1/PDL-1 | Non-Small Cell Lung Cancer | MSK-IMPACT | A0301,A2402,B1402, B4901,C0802,C0701 | A03,A24,B27, UNK,UNK,UNK | 0 |
| YQ690189 | 31-50 | 1 | 1 | 56.08 | Combo | Melanoma | MSK-IMPACT | A0301,A2402,B0702, B5101,C1602,C0702 | A03,A24,B07, B07,UNK,UNK | 0 |
| ZM495295 | 50-60 | 21 | 0 | 49.19 | Combo | Melanoma | MSK-IMPACT | A0101,A0201,B0801, B2705,C0102,C0701 | A01,A02,B08, B27,UNK,UNK | 0 |
| AJ060934 | 31-50 | 6 | 0 | 1.97 | Combo | Melanoma | MSK-IMPACT | A0201,A0201,B4402, B3501,C0303,C0501 | A02,A02,B44, B07,UNK,UNK | 1 |
| DF384822 | 50-60 | 2 | 0 | 1.97 | PD-1/PDL-1 | Adrenocortical Carcinoma | MSK-IMPACT | A0301,A0101,B0801, B3501,C0401,C0701 | A03,A01,B08, B07,UNK,UNK | 0 |
| EG383799 | 50-60 | 3 | 1 | 17.71 | PD-1/PDL-1 | Bladder Cancer | MSK-IMPACT | A0301,A6601,B0702, B4102,C1701,C0702 | A03,A03,B07, B44,UNK,UNK | 0 |
| GF170625 | 31-50 | 0 | 0 | 11.81 | Combo | Melanoma | MSK-IMPACT | A1101,A0101,B4403, B3501,C0401,C0401 | A03,A01,B44, B07,UNK,UNK | 1 |
| GQ117672 | 61-70 | 19 | 0 | 1.97 | CTLA4 | Prostate Cancer | MSK-IMPACT | A0301,A3402,B4001, B4901,C0304,C0701 | A03,A03,B44, UNK,UNK,UNK | 0 |
| HM704600 | 50-60 | 5 | 0 | 2.95 | Combo | Renal Cell Carcinoma | MSK-IMPACT | A1101,A2402,B3502, B5201,C0401,C1202 | A03,A24,B07, B62,UNK,UNK | 0 |
| LB607333 | 31-50 | 1 | 1 | 9.84 | PD-1/PDL-1 | Non-Small Cell Lung Cancer | MSK-IMPACT | A0301,A3301,B4403, B1501,C0202,C0202 | A03,A03,B44, B62,UNK,UNK | 1 |
| NM969273 | 61-70 | 4 | 1 | 3.94 | PD-1/PDL-1 | Renal Cell Carcinoma | MSK-IMPACT | A0201,A0201,B4402, B1801,C0701,C0704 | A02,A02,B44, B44,UNK,UNK | 1 |
| OR743518 | 50-60 | 1 | 1 | 153.47 | PD-1/PDL-1 | Colorectal Cancer | MSK-IMPACT | A0301,A0301,B3501, B1801,C1203,C0401 | A03,A03,B07, B44,UNK,UNK | 1 |
| QK745450 | 61-70 | 0 | 1 | 0 | PD-1/PDL-1 | Prostate Cancer | MSK-IMPACT | A0303,A3101,B1402, B4001,C0304,C0802 | A03,A03,B27, B44,UNK,UNK | 0 |
| QP994107 | 50-60 | 7 | 0 | 2.95 | PD-1/PDL-1 | Bladder Cancer | MSK-IMPACT | A0301,A2402,B2705, B5601,C0102,C0102 | A03,A24,B27, B07,UNK,UNK | 1 |
| SN968302 | 31-50 | 0 | 0 | 10.82 | PD-1/PDL-1 | Non-Small Cell Lung Cancer | MSK-IMPACT | A3002,A2902,B1801, B3501,C0401,C0701 | A01,A01A24,B44, B07,UNK,UNK | 0 |
| WM051316 | 31-50 | 0 | 1 | 16.72 | PD-1/PDL-1 | Small Cell Lung Cancer | MSK-IMPACT | A1101,A3301,B1801, B3503,C0802,C1203 | A03,A03,B44, B07,UNK,UNK | 0 |
| XY337478 | 31-50 | 1 | 1 | 8.85 | PD-1/PDL-1 | Small Cell Lung Cancer | MSK-IMPACT | A2301,A0201,B0801, B5101,C1402,C0701 | A24,A02,B08, B07,UNK,UNK | 0 |
| YK193564 | 31-50 | 46 | 0 | 1.97 | CTLA4 | Prostate Cancer | MSK-IMPACT | A2402,A3101,B3502, B3502,C0401,C0401 | A24,A03,B07, B07,UNK,UNK | 1 |
| CG383415 | 31-50 | 1 | 0 | 9.84 | PD-1/PDL-1 | Non-Small Cell Lung Cancer | MSK-IMPACT | A6601,A0201,B4403, B1801,C0602,C0704 | A03,A02,B44, B44,UNK,UNK | 0 |
| CO637650 | 61-70 | 0 | 0 | 6.89 | PD-1/PDL-1 | Anal Cancer | MSK-IMPACT | A0301,A1101,B5501, B3501,C0303,C0401 | A03,A03,B07, B07,UNK,UNK | 0 |
| EB780441 | 31-50 | 3 | 0 | 5.9 | PD-1/PDL-1 | Non-Small Cell Lung Cancer | MSK-IMPACT | A2902,A3101,B4403, B3502,C1601,C0401 | A01A24,A03,B44, B07,UNK,UNK | 0 |
| ES720972 | 31-50 | 35 | 0 | 6.89 | PD-1/PDL-1 | Renal Cell Carcinoma | MSK-IMPACT | A2902,A0202,B4001, B4501,C0304,C0602 | A01A24,A02,B44, B44,UNK,UNK | 0 |
| FQ781658 | >71 | 21 | 0 | 5.9 | Combo | Melanoma | MSK-IMPACT | A2402,A3201,B4002, B5701,C0202,C0602 | A24,A01,B44, B58,UNK,UNK | 0 |
| JO533617 | 61-70 | 15 | 0 | 15.74 | Combo | Melanoma | MSK-IMPACT | A1101,A3303,B4402, B5801,C0302,C0501 | A03,A03,B44, B58,UNK,UNK | 0 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| KE061649 | 61-70 | 9 | 0 | 53.12 | CTLA4 | Melanoma | MSK-IMPACT | A0301,A2902,B4403,B1801,C1601,C0701 | A03,A01A24,B44,B44,UNK,UNK | 0 |
| LL204901 | 50-60 | 25 | 0 | 2.95 | Combo | Renal Cell Carcinoma | MSK-IMPACT | A2402,A6901,B5501,B5101,C0303,C1602 | A24,A02,B07,B07,UNK,UNK | 0 |
| MN398266 | 31-50 | 3 | 1 | 12.79 | PD-1/PDL-1 | Bladder Cancer | MSK-IMPACT | A6601,A6901,B5501,B1801,C0102,C1203 | A03,A02,B07,B44,UNK,UNK | 0 |
| MZ946567 | 31-50 | 22 | 0 | 15.74 | Combo | Melanoma | MSK-IMPACT | A2601,A0205,B3801,B5001,C1203,C0602 | A01,A02,B27,B44,UNK,UNK | 0 |
| NF584722 | 31-50 | 7 | 0 | 3.94 | PD-1/PDL-1 | Non-Small Cell Lung Cancer | MSK-IMPACT | A2402,A0201,B4101,B4006,C0304,C1701 | A24,A02,B44,B44,UNK,UNK | 0 |
| OY229666 | 31-50 | 3 | 1 | 5.9 | PD-1/PDL-1 | Bladder Cancer | MSK-IMPACT | A2402,A2601,B1801,B4402,C1604,C1203 | A24,A01,B44,B44,UNK,UNK | 0 |
| PA236764 | 31-50 | 5 | 1 | 5.9 | PD-1/PDL-1 | Non-Small Cell Lung Cancer | MSK-IMPACT | A0201,A2601,B4002,B4501,C1601,C0202 | A02,A01,B44,B44,UNK,UNK | 0 |
| PP274205 | 31-50 | 3 | 0 | 59.03 | PD-1/PDL-1 | Non-Small Cell Lung Cancer | MSK-IMPACT | A2402,A0201,B4402,B1501,C0303,C0501 | A24,A02,B44,B62,UNK,UNK | 0 |
| RH563185 | 31-50 | 1 | 1 | 3.94 | PD-1/PDL-1 | Non-Small Cell Lung Cancer | MSK-IMPACT | A3601,A3402,B5301,B5301,C0401,C0401 | A01,A03,B07,B07,UNK,UNK | 1 |
| SH122153 | 50-60 | 0 | 0 | 10.82 | PD-1/PDL-1 | Non-Small Cell Lung Cancer | MSK-IMPACT | A0301,A2402,B0801,B4403,C0602,C0702 | A03,A24,B08,B44,UNK,UNK | 0 |
| SP276688 | 31-50 | 10 | 1 | 7.87 | PD-1/PDL-1 | Glioma | MSK-IMPACT | A2902,A0201,B1501,B3501,C0304,C0401 | A01A24,A02,B62,B07,UNK,UNK | 0 |
| TA931155 | 50-60 | 3 | 0 | 2.95 | PD-1/PDL-1 | Non-Small Cell Lung Cancer | MSK-IMPACT | A0201,A2601,B1518,B2705,C0102,C0704 | A02,A01,B27,B27,UNK,UNK | 0 |

PG 416

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| AM575114 | 50-60 | 7 | 1 | 43.29 | PD-1/PDL-1 | Melanoma | MSK-IMPACT | A0301,A0301,B0702,B3906,C0702,C0702 | A03,A03,B07,B27,UNK,UNK | 1 |
| CC355649 | 50-60 | 7 | 1 | 3.94 | PD-1/PDL-1 | Pancreatic Cancer | MSK-IMPACT | A1101,A2402,B5401,B1501,C0303,C0102 | A03,A24,B07,B62,UNK,UNK | 0 |
| CF773926 | 31-50 | 0 | 1 | 7.87 | PD-1/PDL-1 | Non-Small Cell Lung Cancer | MSK-IMPACT | A0301,A1101,B1517,B3801,C1203,C0701 | A03,A03,B58,B27,UNK,UNK | 0 |
| IE285088 | 50-60 | 25 | 0 | 8.85 | Combo | Non-Small Cell Lung Cancer | MSK-IMPACT | A0101,A3101,B0801,B4001,C0304,C0701 | A01,A03,B08,B44,UNK,UNK | 0 |
| JU006201 | 50-60 | 20 | 0 | 3.94 | PD-1/PDL-1 | Renal Cell Carcinoma | MSK-IMPACT | A0301,A2402,B5501,B1501,C0303,C0303 | A03,A24,B07,B62,UNK,UNK | 1 |
| NE982910 | 31-50 | 7 | 0 | 30.5 | PD-1/PDL-1 | Non-Small Cell Lung Cancer | MSK-IMPACT | A0301,A0301,B0702,B0801,C0702,C0701 | A03,A03,B07,B08,UNK,UNK | 1 |
| OJ264581 | >71 | 23 | 1 | 0.98 | Combo | Non-Small Cell Lung Cancer | MSK-IMPACT | A0302,A1101,B4101,B3503,C0401,C1701 | A03,A03,B44,B07,UNK,UNK | 0 |
| ON455477 | 50-60 | 13 | 0 | 4.92 | PD-1/PDL-1 | Non-Small Cell Lung Cancer | MSK-IMPACT | A0101,A2301,B5701,B4901,C0602,C0701 | A01,A24,B58,UNK,UNK,UNK | 0 |
| RT030006 | 61-70 | 9 | 1 | 3.94 | PD-1/PDL-1 | Glioma | MSK-IMPACT | A1101,A2402,B1402,B5201,C0202,C1202 | A03,A24,B27,B62,UNK,UNK | 0 |
| SD028427 | 50-60 | 0 | 0 | 12.79 | Combo | Small Cell Lung Cancer | MSK-IMPACT | A2402,A3303,B4001,B3503,C1203,C0702 | A24,A03,B44,B07,UNK,UNK | 0 |
| SY259900 | 50-60 | 0 | 1 | 52.14 | PD-1/PDL-1 | Colorectal Cancer | MSK-IMPACT | A0205,A3301,B5101,B5101,C1502,C1502 | A02,A03,B07,B07,UNK,UNK | 1 |
| TA865919 | 50-60 | 3 | 0 | 2.95 | PD-1/PDL-1 | Renal Cell Carcinoma | MSK-IMPACT | A0301,A0101,B0801,B1801,C0701,C0701 | A03,A01,B08,B44,UNK,UNK | 1 |
| YW286579 | 31-50 | 5 | 0 | 25.58 | PD-1/PDL-1 | Melanoma | MSK-IMPACT | A0301,A0301,B0702,B0702,C0702,C0702 | A03,A03,B07,B07,UNK,UNK | 1 |
| ZU115700 | 31-50 | 11 | 0 | 66.9 | Combo | Melanoma | MSK-IMPACT | A0101,A2902,B0801,B4403,C0401,C0701 | A01,A01A24,B08,B44,UNK,UNK | 0 |
| ZU944390 | 31-50 | 2 | 1 | 0 | PD-1/PDL-1 | Bladder Cancer | MSK-IMPACT | A0201,A3101,B0705,B3502,C1505,C0401 | A02,A03,B07,B07,UNK,UNK | 0 |
| BB892688 | 31-50 | 28 | 0 | 55.09 | PD-1/PDL-1 | Non-Small Cell Lung Cancer | MSK-IMPACT | A0201,A0201,B0801,B1801,C0701,C0701 | A02,A02,B08,B44,UNK,UNK | 1 |
| CN518405 | 61-70 | 11 | 1 | 3.94 | PD-1/PDL-1 | Glioma | MSK-IMPACT | A0301,A0201,B4402,B5101,C0102,C0501 | A03,A02,B44,B07,UNK,UNK | 0 |
| CP570210 | 61-70 | 19 | 0 | 24.59 | Combo | Melanoma | MSK-IMPACT | A0101,A0101,B0801,B0801,C0718,C0718 | A01,A01,B08,B08,UNK,UNK | 1 |
| EA843645 | >71 | 4 | 1 | 0.98 | PD-1/PDL-1 | Glioma | MSK-IMPACT | A0202,A0206,B2705,B3501,C1601,C0202 | A02,A02,B27,B07,UNK,UNK | 0 |
| FC638791 | 31-50 | 25 | 0 | 1.97 | PD-1/PDL-1 | Renal Cell Carcinoma | MSK-IMPACT | A3001,A2301,B4102,B1302,C0602,C1701 | A01A03,A24,B44,UNK,UNK,UNK | 0 |
| HM265065 | 50-60 | 10 | 0 | 4.92 | PD-1/PDL-1 | Renal Cell Carcinoma | MSK-IMPACT | A0101,A0201,B4403,B1501,C0303,C1601 | A01,A02,B44,B62,UNK,UNK | 0 |
| IO630165 | 31-50 | 0 | 1 | 5.9 | PD-1/PDL-1 | Non-Small Cell Lung Cancer | MSK-IMPACT | A1101,A0101,B5701,B5101,C0401,C0602 | A03,A01,B58,B07,UNK,UNK | 0 |
| JP019086 | 50-60 | 12 | 0 | 4.92 | PD-1/PDL-1 | Non-Small Cell Lung Cancer | MSK-IMPACT | A3001,A0101,B0801,B4405,C0701,C0202 | A01A03,A01,B08,B44,UNK,UNK | 0 |

APPENDIX 1-continued

Cohort 2

| Sample | Age Group | OS_Months | OS_Event | IMPACT-MutCnt | Drug Class | Cancer Type | Reference | HLA Class I Alleles | HLA Class I Super-types | Homozygous (1 = Yes; 0 = No) |
|---|---|---|---|---|---|---|---|---|---|---|
| KA251902 | 31-50 | 20 | 0 | 23.61 | CTLA4 | Melanoma | MSK-IMPACT | A0201,A0201,B5301, B5101,C0102,C0401 | A02,A02,B07, B07,UNK,UNK | 1 |
| LU597217 | 61-70 | 2 | 0 | 11.81 | Combo | Melanoma | MSK-IMPACT | A0301,A2402,B3701, B3501,C0401,C0602 | A03,A24,B44, B07,UNK,UNK | 0 |
| NQ158708 | 31-50 | 13 | 0 | 43.29 | PD-1/PDL-1 | Melanoma | MSK-IMPACT | A2402,A2402,B3801, B3502,C0401,C1203 | A24,A24,B27, B07,UNK,UNK | 1 |
| TH671342 | 61-70 | 0 | 0 | 3.94 | PD-1/PDL-1 | Glioma | MSK-IMPACT | A0201,A0205,B0702, B5001,C0602,C0702 | A02,A02,B07, B44,UNK,UNK | 0 |
| VY563784 | 50-60 | 1 | 1 | 3.94 | PD-1/PDL-1 | Glioma | MSK-IMPACT | A0301,A0201,B0702, B1517,C0701,C0702 | A03,A02,B07, B58,UNK,UNK | 0 |
| XG294932 | 31-50 | 3 | 1 | 5.9 | Combo | Bladder Cancer | MSK-IMPACT | A0301,A0201,B1801, B3801,C1203,C0701 | A03,A02,B44, B27,UNK,UNK | 0 |
| AG183498 | 50-60 | 8 | 0 | 3.94 | PD-1/PDL-1 | Renal Cell Carcinoma | MSK-IMPACT | A0301,A0201,B1501, B3501,C0304,C0401 | A03,A02,B62, B07,UNK,UNK | 0 |
| CF802090 | 50-60 | 35 | 0 | 10.82 | PD-1/PDL-1 | Non-Small Cell Lung Cancer | MSK-IMPACT | A3002,A3101,B1801, B3502,C0401,C0501 | A01,A03,B44, B07,UNK,UNK | 0 |
| DX937247 | 31-50 | 7 | 1 | 4.92 | Combo | Bladder Cancer | MSK-IMPACT | A0301,A0301,B4701, B5101,C1502,C0602 | A03,A03,UNK, B07,UNK,UNK | 1 |
| EU725595 | <30 | 8 | 0 | 0 | PD-1/PDL-1 | Skin Cancer; Non-Melanoma | MSK-IMPACT | A0201,A6901,B3501, B4402,C0401,C0704 | A02,A02,B07, B44,UNK,UNK | 0 |
| EY684077 | >71 | 1 | 0 | 3.94 | PD-1/PDL-1 | Soft Tissue Sarcoma | MSK-IMPACT | A2402,A0201,B1402, B5001,C0802,C0602 | A24,A02,B27, B44,UNK,UNK | 0 |
| HR473373 | 31-50 | 0 | 1 | 7.87 | PD-1/PDL-1 | Non-Small Cell Lung Cancer | MSK-IMPACT | A2402,A0201,B0702, B4001,C0304,C0702 | A24,A02,B07, B44,UNK,UNK | 0 |
| KX293532 | 31-50 | 6 | 1 | 14.76 | PD-1/PDL-1 | Bladder Cancer | MSK-IMPACT | A2601,A0205,B5001, B4901,C0602,C0701 | A01,A02,B44, UNK,UNK,UNK | 0 |
| LJ970887 | 31-50 | 9 | 0 | 104.28 | PD-1/PDL-1 | Skin Cancer; Non-Melanoma | MSK-IMPACT | A0101,A2402,B0801, B1801,C0501,C0701 | A01,A24,B08, B44,UNK,UNK | 0 |
| NV509595 | >71 | 10 | 0 | 1.97 | PD-1/PDL-1 | Hepatobiliary Cancer | MSK-IMPACT | A0301,A1101,B0702, B4002,C0803,C0702 | A03,A03,B07, B44,UNK,UNK | 0 |
| PE010787 | 50-60 | 4 | 1 | 12.79 | PD-1/PDL-1 | Non-Small Cell Lung Cancer | MSK-IMPACT | A2402,A2402,B1508, B4601,C0102,C0102 | A24,A24,B07, B62,UNK,UNK | 1 |
| QD162536 | 31-50 | 8 | 0 | 5.9 | PD-1/PDL-1 | Non-Small Cell Lung Cancer | MSK-IMPACT | A0101,A3201,B0801, B5201,C1202,C0701 | A01,A01,B08, B62,UNK,UNK | 0 |
| UA949121 | >71 | 13 | 1 | 12.79 | PD-1/PDL-1 | Non-Hodgkin Lymphoma | MSK-IMPACT | A6801,A2601,B3502, B5101,C1602,C0401 | A03,A01,B07, B07,UNK,UNK | 0 |
| VV580731 | 61-70 | 26 | 0 | 3.94 | PD-1/PDL-1 | Renal Cell Carcinoma | MSK-IMPACT | A2402,A2601,B3801, B3502,C0401,C1203 | A24,A01,B27, B07,UNK,UNK | 0 |
| YO886748 | 50-60 | 6 | 1 | 10.82 | PD-1/PDL-1 | Colorectal Cancer | MSK-IMPACT | A0301,A2402,B5501, B4701,C0102,C0602 | A03,A24,B07, UNK,UNK,UNK | 0 |
| ZD030437 | 31-50 | 20 | 0 | 13.77 | PD-1/PDL-1 | Non-Small Cell Lung Cancer | MSK-IMPACT | A3002,A6802,B1402, B1503,C0210,C0802 | A01,A02,B27, B27,UNK,UNK | 0 |
| ZN003309 | >71 | 7 | 0 | 0.98 | PD-1/PDL-1 | Head and Neck Cancer | MSK-IMPACT | A2402,A6801,B3801, B5101,C0102,C1203 | A24,A03,B27, B07,UNK,UNK | 0 |

APPENDIX 2

| HLA Allele | PDB ID | Resolution | Bridge | A | Position A | B | Position B | C | Position C | Dep. Date | Rel. Date | Rev. Date | Exp. Method | Structure Title |
|---|---|---|---|---|---|---|---|---|---|---|---|---|---|---|
| B0702 | 5EO0 | 1.70 | Y | R | 62 | I | 66 | E | 163 | Nov. 10, 2015 | Feb. 24, 2015 | * Mar. 30, 2016 | X-RAY DIFFRACTION | Crystal Structure of HLA-B0702-RFLS |
| B0702 | 5EO1 | 1.85 | Y | R | 62 | I | 66 | E | 163 | Nov. 10, 2015 | Feb. 24, 2015 | * Apr. 20, 2016 | X-RAY DIFFRACTION | Crystal Structure of HLA-B0702-RL0 |
| B0801 | 1AGB | 2.20 | N | R | 62 | I | 66 | T | 163 | Mar. 24, 1997 | Jun. 16, 1997 | * Apr. 1, 2003 | X-RAY DIFFRACTION | ANTAGONIST HIV-1 GAG PEPTIDES INDUCE STRUCTURAL CHANGES IN HLA B8-HIV-1 GAG PEPTIDE (GGRKKYKL-3R MUTATION) |
| B0801 | 1AGC | 2.10 | N | R | 62 | I | 66 | T | 163 | Mar. 24, 1997 | Jun. 16, 1997 | * Feb. 24, 2009 | X-RAY DIFFRACTION | ANTAGONIST HIV-1 GAG PEPTIDES INDUCE STRUCTURAL CHANGES IN HLA B8-HIV-1 GAG PEPTIDE (GGKKKYQL-7Q MUTATION) |
| B0801 | 1AGD | 2.05 | N | R | 62 | I | 66 | T | 163 | Mar. 24, 1997 | Jun. 16, 1997 | * Apr. 1, 2003 | X-RAY DIFFRACTION | ANTAGONIST HIV-1 GAG PEPTIDES INDUCE STRUCTURAL CHANGES IN HLA B8-HIV-1 GAG PEPTIDE (GGKKKYKL-INDEX PEPTIDE) |
| B0801 | 1AGE | 2.30 | N | R | 62 | I | 66 | T | 163 | Mar. 24, 1997 | Jun. 16, 1997 | * Feb. 24, 2009 | X-RAY DIFFRACTION | ANTAGONIST HIV-1 GAG PEPTIDES INDUCE STRUCTURAL CHANGES IN HLA B8-HIV-1 GAG PEPTIDE (GGKKKYRL-7R MUTATION) |
| B0801 | 1AGF | 2.20 | N | R | 62 | I | 66 | T | 163 | Mar. 24, 1997 | Jun. 16, 1997 | * Apr. 1, 2003 | X-RAY DIFFRACTION | ANTAGONIST HIV-1 GAG PEPTIDES INDUCE STRUCTURAL CHANGES IN HLA B8-HIV-1 GAG PEPTIDE (GGKKKYKL-5R MUTATION) |
| B0801 | 1M05 | 1.00 | N | R | 62 | I | 66 | T | 163 | Jun. 11, 2002 | Sep. 2, 2003 | * Feb. 24, 2009 | X-RAY DIFFRACTION | HLA B8 in complex with an Epstein Barr Virus determinant |
| B0801 | 3X13 | 1.80 | N | R | 62 | I | 66 | T | 163 | Oct. 24, 2014 | Dec. 24, 2014 | * Apr. 8, 2015 | X-RAY DIFFRACTION | Crystal Structure of HLA-B*0801! |
| B0801 | 3X14 | 2.00 | N | R | 62 | I | 66 | T | 163 | Oct. 25, 2014 | Dec. 24, 2014 | * Apr. 8, 2015 | X-RAY DIFFRACTION | Crystal Structure of HLA-B*0801.N90!.N90!R82L.G83R |
| B0801 | 4QRP | 2.90 | N | R | 62 | I | 66 | T | 163 | Jul. 2, 2014 | Nov. 12, 2014 | * Dec. 24, 2014 | X-RAY DIFFRACTION | Crystal Structure of HLA-B*0801 in complex with HSKKKCOEL and DO31 TOR |
| B0801 | 4QRQ | 1.70 | N | R | 62 | I | 66 | T | 163 | Jul. 2, 2014 | Nov. 12, 2014 | * Dec. 24, 2014 | X-RAY DIFFRACTION | Crystal Structure of HLA-B*0801 in complex with HSKKKCDEL |
| B0801 | 4QRS | 1.40 | N | R | 62 | I | 66 | T | 163 | Jul. 2, 2014 | Dec. 10, 2014 | | X-RAY DIFFRACTION | Crystal Structure of HLA-B*0801 in complex with ELK_IYM ELKRKMYM |
| B0801 | 4QRT | 1.40 | N | R | 62 | I | 66 | T | 163 | Jul. 2, 2014 | Jul. 16, 2014 | | X-RAY DIFFRACTION | Crystal Structure of HLA-B*0801 in complex with ELN_YYM ELNRKMYM |
| B0801 | 4QRU | 1.60 | N | R | 62 | I | 66 | T | 163 | Jul. 2, 2014 | Feb. 4, 2015 | | X-RAY DIFFRACTION | Crystal Structure of HLA-B*0801 in complex with ELR_MYM ELRRKMYM |
| B1501 | 1XR8 | 2.30 | Y | R | 62 | I | 66 | L | 163 | Oct. 14, 2001 | Apr. 14, 2005 | * Mar. 18, 2008 | X-RAY DIFFRACTION | Crystal Structures of HLA-B*1501 in Complex with Peptides from Human UbcH6 and Epstein-Barr Virus EBNA 3 |
| B1501 | 1XR9 | 1.79 | Y | R | 62 | I | 66 | L | 163 | Oct. 14, 2001 | Apr. 14, 2005 | * Mar. 18, 2008 | X-RAY DIFFRACTION | Crystal Structures of HLA-B*1501 in Complex with Peptides from Human UbcH6 and Epstein-Barr Virus EBNA 3 |
| B1501 | 3G9N | 1.87 | Y | R | 62 | I | 66 | L | 163 | Feb. 18, 2008 | Feb. 26, 2009 | * May 6, 2008 | X-RAY DIFFRACTION | Crystal Structures of a SARS Corona Virus Dariveo Peptide Bound to the Human Major Histocompatibility Complex Class I molecule HLA-B*1501 |
| B0801 | 4JOV | 1.50 | N | R | 62 | I | 66 | T | 163 | Mar. 20, 2013 | Jun. 26, 2013 | * Jul. 17, 2013 | X-RAY DIFFRACTION | HLA-B*18:01 in complex with Epstein-Barr virus BZLF1-derived peptide (residues 173-120) |
| B0801 | 4XXO | 1.43 | N | R | 62 | I | 66 | T | 163 | Jan. 30, 2015 | Apr. 8, 2015 | * May 13, 2015 | X-RAY DIFFRACTION | HLA-B*1801 in complex with self-peptide, DELEIKAY |
| B2705 | 1HSA | 2.10 | Y | R | 62 | I | 66 | E | 163 | Jun. 11, 1992 | Oct. 15, 1992 | * Apr. 1, 2003 | X-RAY DIFFRACTION | THE THREE-DIMENSIONAL STRUCTURE OF HLA-B27 AT 2.1 ANGSTROMS RESOLUTION SUGGESTS A GENERAL MECHANISM FOR TIGHT PEPTIDE BINDING TO MHO |
| B2705 | 1JGE | 2.10 | N | R | 62 | I | 66 | E | 163 | Jun. 25, 2001 | Oct. 30, 2002 | * Dec. 23, 2002 | X-RAY DIFFRACTION | HLA-B*2705 bound to nona-peptide m9 |
| B2705 | 1OGT | 1.47 | Y | R | 62 | I | 66 | E | 163 | May 13, 2003 | Jan. 29, 2004 | * Aug. 12, 2009 | X-RAY DIFFRACTION | CRYSTAL STRUCTURE OF HLA-B*2705 COMPLEXED WITH THE VASOACTIVE INTESTINAL PEPTIDE TYPE 1 RECEPTOR (VIPR) |

APPENDIX 2-continued

| HLA Allele | PDB ID | Resolution | Bridge | A | Position A | B | Position B | C | Position C | Dep. Date | Rel. Date | Rev. Date | Exp. Method | Structure Title |
|---|---|---|---|---|---|---|---|---|---|---|---|---|---|---|
| B2705 | 1UXS | 1.55 | Y | R | 62 | I | 66 | E | 163 | Mar. 1, 2004 | Nov. 9, 2004 | *Jan. 27, 2005 | X-RAY DIFFRACTION | CRYSTAL STRUCTURE OF HLA-B*2705 COMPLEXED WITH THE LATENT MEMBRANE PROTEIN 2 PEPTIDE (LMP2)OF EPSTEIN-BARR VIRUS PEPTIDE (RESIDUES 400-400) |
| B2705 | 1W0V | 2.27 | Y | R | 62 | I | 66 | E | 163 | Jun. 14, 2004 | Mar. 7, 2005 | *Feb. 24, 2009 | X-RAY DIFFRACTION | CRYSTAL STRUCTURE OF HLA-B*2705 COMPLEXED WITH THE SELF-PEPTIDE TIS FROM EGF-RESPONSE FACTOR 1 |
| B2705 | 2A8B | 1.40 | N | R | 62 | I | 66 | E | 163 | Jul. 7, 2005 | Dec. 27, 2005 | *Nov. 21, 2006 | X-RAY DIFFRACTION | Crystal Structure of hla-b*2705 complexed with the glucagon receptor (gr) peptide (residues 412-420) |
| B2705 | 2BSR | 2.30 | Y | R | 62 | I | 66 | E | 163 | May 23, 2005 | May 24, 2005 | *Feb. 24, 2009 | X-RAY DIFFRACTION | CRYSTAL STRUCTURES AND KIR3DL1 RECOGNITION OF THREE IMMUNODOMINANT VIRAL PEPTIDES COMPLEXED TO HLA-B2705 |
| B2705 | 2BSS | 2.00 | N | R | 62 | I | 66 | E | 163 | May 23, 2005 | May 24, 2005 | *Feb. 24, 2009 | X-RAY DIFFRACTION | CRYSTAL STRUCTURES AND KIR3DL1 RECOGNITION OF THREE IMMUNODOMINANT VIRAL PEPTIDES COMPLEXED TO HLA-B2705 |
| B2705 | 2BST | 2.10 | N | R | 62 | I | 66 | E | 163 | May 23, 2005 | May 24, 2005 | *Feb. 24, 2009 | X-RAY DIFFRACTION | Crystal structures and KIR3DL1 recognition of three immunodominant viral peptides complexed to HLA-B2705 |
| B2705 | 3B8S | 1.80 | Y | R | 62 | I | 66 | E | 163 | Oct. 29, 2007 | Jul. 22, 2008 | *Oct. 14, 2006 | X-RAY DIFFRACTION | Crystal Structure of hla-b*2705 Complexed with the Citrullinated Vasoactive Intestinal Peptide Type 1 Receptor (vipr) Peptide (residues 400-400) |
| B2705 | 3BP4 | 1.85 | Y | R | 62 | I | 66 | E | 163 | Dec. 19, 2007 | Dec. 23, 2008 | *Aug. 18, 2009 | X-RAY DIFFRACTION | The high resolution crystal structure of HLA-B*2705 in complex with a Cathepsin A signal sequence peptide pCatA |
| B2705 | 3DTX | 2.10 | Y | R | 62 | I | 66 | E | 163 | Jul. 18, 2008 | May 5, 2009 | *Oct. 12, 2011 | X-RAY DIFFRACTION | Crystal Structure of HLA-B*2705 complexed with the double citrullinated vasoactive intestinal peptide type 1 receptor (VIPR) peptide (residues 400-408) |
| B2705 | 3LV3 | 1.94 | Y | R | 62 | I | 66 | E | 163 | Feb. 19, 2010 | Nov. 24, 2010 | *Dec. 1, 2010 | X-RAY DIFFRACTION | Crystal structure of HLA-B*2705 complexed with a peptide derived from the human voltage-dependent calcium channel alpha1 subunit (residues 513-521) |
| B2705 | 4G8G | 2.40 | Y | R | 62 | I | 66 | E | 163 | Jul. 23, 2012 | Mar. 20, 2013 | *Feb. 9, 2011 | X-RAY DIFFRACTION | Crystal Structure of C12C TCR-HA B2705-KK10 |
| B2705 | 4G8I | 1.60 | Y | R | 62 | I | 66 | E | 163 | Jul. 23, 2012 | Mar. 20, 2013 | *Apr. 10, 2013 | X-RAY DIFFRACTION | Crystal Structure of HLA B2705-KK10-L6M |
| B2705 | 4G9D | 1.60 | N | R | 62 | I | 66 | E | 163 | Jul. 23, 2012 | Mar. 20, 2013 | *Apr. 10, 2013 | X-RAY DIFFRACTION | Crystal Structure of HLA B2705-KK10 |
| B2705 | 4G9F | 1.90 | Y | R | 62 | I | 66 | E | 163 | Jul. 23, 2012 | Mar. 20, 2013 | *Apr. 10, 2013 | X-RAY DIFFRACTION | Crystal Structure of C12C TCR-HLAB2705 KK10-L6M |
| B3501 | 1A1N | 2.00 | N | R | 62 | I | 66 | L | 163 | Dec. 11, 1997 | Apr. 8, 1998 | *Apr. 1, 2003 | X-RAY DIFFRACTION | MHC CLASS I MOLECULE B*3501 COMPLEXED WITH PEPTIDE VPLRPMTY FROM THE NEF PROTEIN (75-82) OF HIV1 |
| B3501 | 1A9B | 3.20 | N | R | 62 | I | 66 | L | 163 | Apr. 3, 1998 | Oct. 21, 1998 | *Nov. 18, 1999 | X-RAY DIFFRACTION | DECAMER LIKE CONFORMATION OF A NANO-PEPTIDE BOUND TO HLA-B3501 DUE TO NONSTANDARD POSITIONING OF THE C TERMINUS |
| B3501 | 1A9E | 2.50 | Y | R | 62 | I | 66 | L | 163 | Apr. 5, 1998 | Oct. 21, 1998 | *Apr. 1, 2003 | X-RAY DIFFRACTION | DECAMER-LIKE CONFORMATION OF A NANO-PEPTIDE BOUND TO HLA-B3501 DUE TO NONSTANDARD POSITIONING OF THE C-TERMINUS |
| B3501 | 1CG9 | 2.70 | Y | R | 62 | I | 66 | L | 163 | Mar. 25, 1999 | Nov. 18, 2003 | *Feb. 24, 2009 | X-RAY DIFFRACTION | COMPLEX RECOGNITION OF THE SUPERTYPIC BW6-DETERMINANT ON HLA-B AND C MOLECULES BY THE MONOCLONAL ANTIBODY SFR8-B5 |
| B3501 | 1XH3 | 1.48 | N | R | 62 | I | 66 | L | 163 | Sep. 17, 2004 | Nov. 23, 2004 | *Jul. 13, 2011 | X-RAY DIFFRACTION | Conformational Restraints and Flexibility of 14-Meric Peptides in Complex with HLA-B*3501 |
| B3501 | 1ZHK | 1.60 | Y | R | 62 | I | 66 | L | 163 | Apr. 25, 2005 | May 17, 2005 | *Jun. 28, 2005 | X-RAY DIFFRACTION | Crystal structure of HLA-B*3501 presenting 13-mer EBV antigen LPEPLPQGOLTAY |

APPENDIX 2-continued

| HLA Allele | PDB ID | Resolution | Bridge | A | Position A | B | Position B | C | Position C | Dep. Date | Rel. Date | Rev. Date | Exp. Method | Structure Title |
|---|---|---|---|---|---|---|---|---|---|---|---|---|---|---|
| B3501 | 1ZSD | 1.70 | N | R | 62 | I | 66 | L | 163 | May 24, 2005 | Jun. 7, 2005 | *Sep. 27, 2005 | X-RAY DIFFRACTION | Crystal Structure Of HLA-B*3501 Presenting an 11-Mer EBV Antigen EPLPQGQLTAY |
| B3501 | 2AXG | 2.00 | Y | R | 62 | I | 66 | L | 163 | Sep. 5, 2005 | Nov. 29, 2005 | *Feb. 24, 2009 | X-RAY DIFFRACTION | The Immunogenicity of a Viral Cytotoxic T Cell Epitope is controlled by its MHC-bound Conformation |
| B3501 | 2CIK | 1.75 | N | R | 62 | I | 66 | L | 163 | Mar. 22, 2006 | Oct. 25, 2006 | *Nov. 22, 2006 *Dec. 20, 2006 *Feb. 24, 2009 | X-RAY DIFFRACTION | INSIGHTS INTO CROSSREACTIVITY IN HUMAN ALLORECOGNITION THE STRUCTURE OF HLA-B35011 PRESENTING AN EPITOPE DERIVED GTOM CYTOCHROME P450. |
| B3501 | 2FYY | 1.50 | N | R | 62 | I | 66 | L | 163 | Feb. 8, 2006 | Dec. 26, 2006 | *Feb. 24, 2009 | X-RAY DIFFRACTION | The role of T cell receptor alpha genes in directing human MHC restriction |
| B3501 | 2FZ3 | 1.90 | N | R | 62 | I | 66 | L | 163 | Feb. 9, 2006 | Dec. 26, 2006 | *Feb. 24, 2009 | X-RAY DIFFRACTION | The role of T cell receptor alpha genes in directing human MHC restriction |
| B3501 | 2H8P | 1.90 | N | R | 62 | I | 66 | L | 163 | May 31, 2006 | Sep. 19, 2006 | *Jun. 3, 2006 *Jul. 13, 2011 | X-RAY DIFFRACTION | Crystal structure of HLA-B*3501 presenting the human cytochrome P450 derived peptide, KPIVVLHGY |
| B3501 | 2NX5 | 2.70 | N | R | 62 | I | 66 | L | 163 | Nov. 16, 2006 | Feb. 27, 2007 | *Feb. 24, 2009 *Apr. 28, 2010 | X-RAY DIFFRACTION | Crystal structure of ELSA TCR bound to HLA-B*3501 presenting EBV peptide EPLPQGQLTAY at 1.7A |
| B3501 | 3LKN | 2.00 | Y | R | 62 | I | 66 | L | 163 | Jan. 27, 2010 | Jul. 7, 2010 | *Jul. 28, 2010 | X-RAY DIFFRACTION | Crystal Structure of HLA-B*3501 in complex with influenza NP418 epitope from 1918 strain |
| B3501 | 3LKO | 1.80 | N | R | 62 | I | 66 | L | 163 | Jan. 27, 2010 | Jul. 7, 2010 | *Jul. 28, 2010 | X-RAY DIFFRACTION | Crystal Structure of HLA-B*3501 in complex with influenza NP418 epitope from 1934 strain |
| B3501 | 3LKP | 1.80 | N | R | 62 | I | 66 | L | 163 | Jan. 27, 2010 | Jul. 7, 2010 | *Jul. 28, 2010 | X-RAY DIFFRACTION | Crystal Structure of HLA-B*3501 in complex with influenza NP418 epitope from 1972 strain |
| B3501 | 3LKQ | 1.80 | N | R | 62 | I | 66 | L | 163 | Jan. 27, 2010 | Jul. 7, 2010 | *Jul. 28, 2010 | X-RAY DIFFRACTION | Crystal Structure of HLA-B*3501 in complex with influenza NP418 epitope from 1977 strain |
| B3501 | 3LKR | 2.00 | N | R | 62 | I | 66 | L | 163 | Jan. 27, 2010 | Jul. 7, 2010 | *Jul. 28, 2010 | X-RAY DIFFRACTION | Crystal Structure of HLA-B*3501 in complex with influenza NP418 epitope from 2009 H1N1 swine origin strain |
| B3501 | 3LKS | 1.90 | Y | R | 62 | I | 66 | L | 163 | Jan. 27, 2010 | Jul. 7, 2010 | *Jul. 28, 2010 | X-RAY DIFFRACTION | Crystal Structure of HLA-B*3501 in complex with influenza NP418 epitope from 1980 strain |
| B3501 | 3MV7 | 2.00 | N | R | 62 | I | 66 | L | 163 | May 3, 2010 | Jun. 9, 2010 | *Jul. 20, 2011 | X-RAY DIFFRACTION | Crystal Structure of the TK3 TCR in complex with HLA-B*3501/HPVG |
| B3501 | 3MV8 | 2.10 | N | R | 62 | I | 66 | L | 163 | May 3, 2010 | Jun. 9, 2010 | *Jul. 20, 2011 | X-RAY DIFFRACTION | Crystal Structure of the TK3-Gln55His TCR in complex with HLA-B*3501/HPVG |
| B3501 | 3MV9 | 2.70 | Y | R | 62 | I | 66 | L | 163 | May 3, 2010 | Jun. 9, 2010 | *Jul. 20, 2011 | X-RAY DIFFRACTION | Crystal Structure of the TK3-Gln55Ala TCR in complex with HLA-B*3501/HPVG |
| B3501 | 4LNR | 2.00 | N | R | 62 | I | 66 | L | 163 | Jul. 12, 2013 | Jul. 23, 2014 | | X-RAY DIFFRACTION | The structure of HLA-B*35:01 in complex with the peptide (RPOVPLRPMTY) |
| B3501 | 4PR5 | 1.80 | N | R | 62 | I | 66 | L | 163 | Mar. 5, 2014 | Apr. 16, 2014 | *Apr. 23, 2014 *Jun. 18, 2014 *Jul. 2, 2014 | X-RAY DIFFRACTION | Crystal Structure of a HLA-B*35:01-HPVG-05 |
| B3501 | 4PRN | 1.65 | N | R | 62 | I | 66 | L | 163 | Mar. 5, 2014 | Apr. 16, 2014 | *Apr. 23, 2014 *Jun. 18, 2014 *Jul. 2, 2014 | X-RAY DIFFRACTION | Crystal Structure of a HLA-B*35:01-HPVG-A4 |
| B3501 | 4QRR | 3.00 | N | R | 62 | I | 66 | L | 163 | Jul. 2, 2014 | Dec. 10, 2014 | *Dec. 17, 2014 *Dec. 31, 2014 | X-RAY DIFFRACTION | Crystal Structure of HLA-B*3501-IPS in complex with a Delta-Bera TCR, clone 12 TCR |
| B3508 | 1ZHL | 1.50 | N | R | 62 | I | 66 | L | 163 | Apr. 26, 2005 | May 17, 2005 | *Jun. 28, 2005 *Apr. 16, 2014 | X-RAY DIFFRACTION | Crystal Structure of HLA-B*3508 presenting 13-mer EBV antigen LPEPLPQGQLTAY |
| B3508 | 2AK4 | 2.50 | Y | R | 62 | I | 66 | L | 163 | Aug. 9, 2005 | Oct. 11, 2005 | *Jan. 31, 2005 *Feb. 24, 2009 | X-RAY DIFFRACTION | Crystal Structure of SB27 TCR in complex with HLA-B*3508-13mer peptide |
| B3508 | 2AXF | 1.80 | Y | R | 62 | I | 66 | L | 163 | Aug. 5, 2005 | Nov. 29, 2005 | *Feb. 24, 2009 | X-RAY DIFFRACTION | The immunogenicity of a Viral Cytotoxic T Cell Epitope is controlled by its MHC-bound Conformation |

APPENDIX 2-continued

| HLA Allele | PDB ID | Resolution | Bridge | A | Position A | B | Position B | C | Position C | Dep. Date | Rel. Date | Rev. Date | Exp. Method | Structure Title |
|---|---|---|---|---|---|---|---|---|---|---|---|---|---|---|
| B3508 | 2NW3 | 1.70 | N | R | 62 | I | 66 | L | 163 | Nov. 14, 2006 | Feb. 27, 2007 | * Feb. 24, 2009 | X-RAY DIFFRACTION | Crystal structure of HLA-B*3508 presenting EOV peptide EPLPQGQLTAY at 1.7A |
| B3508 | 3BW9 | 1.75 | Y | R | 62 | I | 66 | L | 163 | Jan. 8, 2008 | Apr. 22, 2008 | * Feb. 24, 2009 | X-RAY DIFFRACTION | Crystal Structure of HLA-B*3508 in complex with a HCMV 12-mer peptide from the pp55 protein |
| B3508 | 3BWA | 1.30 | N | R | 62 | I | 66 | L | 163 | Jan. 8, 2008 | Apr. 22, 2008 | * Feb. 24, 2009 | X-RAY DIFFRACTION | Crystal Structure of HLA-B*3508 in complex with a HCMV 8-mer peptide from the pp55 protein |
| B3508 | 3KWW | 2.18 | Y | R | 62 | I | 66 | L | 163 | Dec. 1, 2009 | Jun. 9, 2010 | * Feb. 24, 2009 | X-RAY DIFFRACTION | Crystal Structure of the 'restriction triad' mutant of HLA B*3508, beta-2-microglobulin and EBV peptide |
| B3508 | 3KXF | 3.10 | Y | R | 62 | I | 66 | L | 163 | Dec. 1, 2009 | Jun. 9, 2010 | * Apr. 27, 2011 | X-RAY DIFFRACTION | Crystal Structure of SB27 TCR in complex with the 'restriction triad' mutant of HLA B*3508 18-mer |
| B3508 | 3VFS | 1.85 | Y | R | 62 | I | 66 | L | 163 | Jan. 10, 2012 | Feb. 22, 2012 | * Feb. 26, 2014 | X-RAY DIFFRACTION | crystal structure of HLA B*3508LPEP-P5Ala, peptide mutant P5-ala |
| B3508 | 3VFT | 1.95 | Y | R | 62 | I | 66 | L | 163 | Jan. 10, 2012 | Feb. 22, 2012 | * Mar. 7, 2012 Apr. 25, 2012 Aug. 8, 2012 | X-RAY DIFFRACTION | crystal structure of HLA B*3508LPEP-P6Ala, peptide mutant P6-ala |
| B3508 | 3VFU | 1.65 | Y | R | 62 | I | 66 | L | 163 | Jan. 10, 2012 | Feb. 22, 2012 | * Mar. 7, 2012 Apr. 25, 2012 Aug. 8, 2012 | X-RAY DIFFRACTION | crystal structure of HLA B*3508 LPEP-P7Ala, peptide mutant P7-ala |
| B3508 | 3VFV | 1.55 | Y | R | 62 | I | 66 | L | 163 | Jan. 10, 2012 | Feb. 22, 2012 | * Mar. 7, 2012 Apr. 25, 2012 Aug. 8, 2012 | X-RAY DIFFRACTION | crystal structure of HLA B*3508 LPEP-P9Ala, peptide mutant P8-ala |
| B3508 | 3VFW | 2.30 | Y | R | 62 | I | 66 | L | 163 | Jan. 10, 2012 | Feb. 22, 2012 | * Mar. 7, 2012 Apr. 25, 2012 Aug. 8, 2012 | X-RAY DIFFRACTION | crystal structure of HLA B*3508 LPEP-P10Ala, peptide mutant P10-ala |
| B3901 | 4O2C | 1.80 | N | R | 62 | I | 66 | T | 163 | Dec. 17, 2013 | Jul. 23, 2014 | | X-RAY DIFFRACTION | An Nt-acetylated peptide complexed with HLA-B*3901 |
| B3901 | 4O2E | 1.98 | N | R | 62 | I | 66 | T | 163 | Dec. 17, 2013 | Jul. 23, 2014 | | X-RAY DIFFRACTION | A peptide complexed with HLA-B*3901 |
| B3901 | 4O2F | 1.90 | Y | R | 62 | I | 66 | T | 163 | Dec. 17, 2013 | Jul. 23, 2014 | | X-RAY DIFFRACTION | A peptide complexed with HLA-B*3901 |
| B4402 | 1M6O | 1.60 | N | R | 62 | I | 66 | L | 163 | Jul. 17, 2002 | Sep. 2, 2003 | * Feb. 15, 2005 | X-RAY DIFFRACTION | Crystal Structure of HLA B*4402 in complex with HLA DPA*0201 peptide |
| B4402 | 3DX6 | 1.70 | N | R | 62 | I | 66 | L | 163 | Jul. 23, 2008 | Jan. 27, 2009 | * Feb. 24, 2009 | X-RAY DIFFRACTION | Crystal Structure of 0*4402 presenting a 10mer EOV epitope |
| B4402 | 3KPL | 1.96 | N | R | 62 | I | 66 | L | 163 | Nov. 15, 2009 | Dec. 22, 2009 | * Dec. 29, 2009 Apr. 21, 2010 Jul. 13, 2011 | X-RAY DIFFRACTION | Crystal Structure of HLA B*4403 in complex with EEYLQAFTY a self peptide from the ABCD3 protein |
| B4402 | 3KPM | 1.60 | N | R | 62 | I | 66 | L | 163 | Nov. 16, 2009 | Dec. 22, 2009 | * Apr. 21, 2010 Jul. 13, 2011 | X-RAY DIFFRACTION | Crystal Structure of HLA B*4402 in complex with EEYLKAWTF, a mimotope |
| B4402 | 3L3D | 1.80 | N | R | 62 | I | 66 | L | 163 | Dec. 16, 2009 | Mar. 16, 2010 | * Feb. 26, 2014 | X-RAY DIFFRACTION | Crystal structure of HLA B*4402 in complex with the F3A mutant of a self-peptide derived from DPA*0201 |
| B4402 | 3D3G | 2.10 | N | R | 62 | I | 66 | L | 163 | Dec. 16, 2009 | Mar. 16, 2010 | * Feb. 26, 2014 | X-RAY DIFFRACTION | Crystal structure of HLA B*4402 in complex with the R5A mutant of a self-peptide derived from DPA*0201 |
| B4402 | 3L3I | 1.70 | N | R | 62 | I | 66 | L | 163 | Dec. 17, 2009 | Mar. 16, 2010 | * Feb. 26, 2014 | X-RAY DIFFRACTION | Crystal structure of HLA B*4402 in complex with the F7A mutant of a self-peptide derived from DPA*0201 |
| B4402 | 3L3J | 2.40 | N | R | 62 | I | 66 | L | 163 | Dec. 17, 2009 | Mar. 16, 2010 | * Jul. 13, 2011 | X-RAY DIFFRACTION | Crystal structure of HLA B*4402 in complex with the F3A/R5A double mutant of a self-peptide derived from DPA*0201 |
| B4402 | 3L3K | 2.60 | Y | R | 62 | I | 66 | L | 163 | Dec. 17, 2009 | Mar. 16, 2010 | * Feb. 26, 2014 | X-RAY DIFFRACTION | Crystal structure of HLA B*4402 in complex with the R5A/F7A double mutant of a self-peptide derived from DPA*0201 |

APPENDIX 2-continued

| HLA Allele | PDB ID | Resolution | Bridge | A | Position A | B | Position B | C | Position C | Dep. Date | Rel. Date | Rev. Date | Exp. Method | Structure Title |
|---|---|---|---|---|---|---|---|---|---|---|---|---|---|---|
| B4403 | 1N2R | 1.70 | N | R | 62 | I | 66 | L | 163 | Oct. 24, 2002 | Mar. 16, 2004 | *Feb. 24, 2009 | X-RAY DIFFRACTION | A natural selected dimorphism in HLA B*44 alters self peptide repertoire and T cell recognition |
| B4403 | 1SYS | 2.40 | N | R | 62 | I | 66 | L | 163 | Apr. 1, 2004 | Oct. 19, 2004 | *Feb. 24, 2009 | X-RAY DIFFRACTION | Crystal structure of HLA B*4403, and peptide EEPTVSKKY |
| B4403 | 3DX7 | 1.60 | N | R | 62 | I | 66 | L | 163 | Jul. 23, 2008 | Jan. 27, 2009 | *Jul. 13, 2011 | X-RAY DIFFRACTION | Crystal Structure of HLA B*4403 presenting 10mer EOV antigen |
| B4403 | 3KPN | 2.00 | N | R | 62 | I | 66 | L | 163 | Nov. 16, 2009 | Dec. 22, 2009 | *Dec. 29, 2009 *Jan. 12, 2010 *Apr. 21, 2010 *Jul. 13, 2011 | X-RAY DIFFRACTION | Crystal Structure of HLA B*4403 in complex with EEYLQAFTY a self peptide from the ABCD3 protein |
| B4403 | 3KPD | 2.30 | N | R | 62 | I | 66 | L | 163 | Nov. 16, 2009 | Dec. 22, 2009 | *Apr. 21, 2010 *Jul. 13, 2011 | X-RAY DIFFRACTION | Crystal Structure of HLA B*4403 in complex with EEYLKAWTF, a mimotope |
| B4403 | 4JQX | 1.90 | N | R | 62 | I | 66 | L | 163 | Mar. 20, 2013 | May 26, 2013 | *Jul. 17, 2013 | X-RAY DIFFRACTION | HLA B*44:03 in complex with Epstein-Barr virus BZLF i-derived peptide (residues 169-180) |
| B4405 | 1SYV | 1.70 | N | R | 62 | I | 66 | L | 163 | Apr. 2, 2004 | Oct. 19, 2004 | *Feb. 24, 2009 | X-RAY DIFFRACTION | HLA B*4405 complexed to the dominant self ligand EEFGRYGF |
| B4405 | 3DX8 | 2.10 | N | R | 62 | I | 66 | L | 163 | Jul. 23, 2008 | Jan. 27, 2009 | *Jul. 13, 2011 | X-RAY DIFFRACTION | Crystal Structure of B*4405 presenting a 10mer EBV epitope |
| B4405 | 3DXA | 3.50 | Y | R | 62 | I | 66 | L | 163 | Jul. 23, 2008 | Jan. 27, 2009 | *Jul. 13, 2011 | X-RAY DIFFRACTION | Crystal Structure of the OM1 TCR in complex with HLA-B*4405 and decamer EBV antigen |
| B4405 | 3KPP | 1.90 | N | R | 62 | I | 66 | L | 163 | Nov. 15, 2009 | Dec. 22, 2009 | *Dec. 29, 2009 *Apr. 21, 2010 *Jul. 13, 2011 | X-RAY DIFFRACTION | Crystal Structure of HLA B*4405 in complex with EEYLQAFTY a self peptide from the ABCD3 protein |
| B4405 | 3KPO | 1.84 | N | R | 62 | I | 66 | L | 163 | Nov. 16, 2009 | Dec. 22, 2009 | *Dec. 29, 2009 *Apr. 21, 2010 *Nov. 17, 2010 *Jul. 13, 2011 | X-RAY DIFFRACTION | Crystal Structure of HLA B*4405 in complex with EEYLKAWTF, a mimotope |
| B4405 | 3KPR | 2.60 | N | R | 62 | I | 66 | L | 163 | Nov. 16, 2009 | Dec. 22, 2009 | *Dec. 29, 2009 *Apr. 21, 2010 | X-RAY DIFFRACTION | Crystal Structure of the LC13 TCR in complex with HLA B*4405 bound to EEYLKAWTF a mimotope |
| B4405 | 3KPS | 2.70 | N | R | 62 | I | 66 | L | 163 | Nov. 16, 2009 | Dec. 22, 2009 | *Dec. 29, 2009 *Apr. 21, 2010 | X-RAY DIFFRACTION | Crystal Structure of the LC13 TCR in complex with HLA B*4405 bound to EEYLQAFTY a self peptide from the ABCD3 protein |
| B5101 | 1E27 | 2.20 | N | R | 62 | I | 66 | L | 163 | May 15, 2000 | Sep. 12, 2000 | *Feb. 24, 2009 | X-RAY DIFFRACTION | NONSTANDARD PEPTIDE BINDING OF HLA-B*5101 COMPLEXED WITH HIV IMMUNODOMINANT EPITOPE KM1(LPPWAKEI) |
| B5101 | 1E28 | 3.00 | Y | R | 62 | I | 66 | L | 163 | Jun. 18, 2000 | Sep. 12, 2000 | *Feb. 24, 2009 | X-RAY DIFFRACTION | NONSTANDARD PEPTIDE BINDING OF HLA-B*5101 COMPLEXED WITH HIV IMMUNODOMINANT EPITOPE KM2(TAFTIPSI) |
| B5101 | 4MJI | 2.99 | N | R | 62 | I | 66 | L | 163 | Sep. 3, 2013 | May 28, 2014 | | X-RAY DIFFRACTION | T cell response to a HIV reverse transcriptase epitope presented by the protective allele HLA-B*51:01 |
| B5201 | 3W39 | 3.10 | N | R | 63 | I | 67 | L | 164 | Dec. 13, 2012 | Feb. 13, 2013 | | X-RAY DIFFRACTION | Crystal structure of HLA-B*5201 in complexed with HIV immunodominant epitope (TAFTIPSI) |
| B5301 | 1A1M | 2.30 | Y | R | 62 | I | 66 | L | 163 | Dec. 11, 1997 | Apr. 8, 1998 | *Sep. 16, 2003 | X-RAY DIFFRACTION | MHC CLASS I MOLECULE B*5301 COMPLEXED WITH PEPTIDE TPYDINQML FROM GAG PROTEIN OF HIV2 |
| B5301 | 1A1O | 2.30 | N | R | 62 | I | 66 | L | 163 | Dec. 11, 1997 | Apr. 8, 1998 | *Apr. 1, 2003 *Feb. 24, 2009 | X-RAY DIFFRACTION | MHC CLASS I MOLECULE B*5301 COMPLEXED WITH PEPTIDE LS6 (KPIVQYDNF) FROM THE MALARIA PARASITE P. FALCIFARUM |
| B5701 | 2RFX | 2.50 | N | G | 62 | N | 66 | L | 163 | Oct. 2, 2007 | Jul. 8, 2008 | *Feb. 24, 2009 | X-RAY DIFFRACTION | Crystal structure of HLA-B*5701, presenting the self peptide, LSSPVTKSF |
| B5701 | 3UPR | 2.00 | N | G | 62 | N | 66 | L | 163 | Nov. 18, 2011 | Jun. 13, 2012 | *Nov. 14, 2012 | X-RAY DIFFRACTION | HLA-B*57:01 complexed to pep-V and Abacavir |
| B5701 | 3VH8 | 1.80 | N | G | 62 | N | 66 | L | 163 | Aug. 24, 2011 | Oct. 26, 2011 | *Dec. 7, 2011 | X-RAY DIFFRACTION | KIR3DL1 in complex with HLA-B 5701 |
| B5701 | 3VRI | 1.60 | N | G | 62 | N | 66 | L | 163 | Apr. 11, 2011 | May 30, 2012 | *Jul. 4, 2012 | X-RAY DIFFRACTION | HLA-B*57:01-RVAQLENYI in complex with abacavir |

APPENDIX 2-continued

| HLA Allele | PDB ID | Resolution | Bridge | Position A | A | Position B | B | Position C | C | Dep. Date | Rel. Date | Rev. Date | Exp. Method | Structure Title |
|---|---|---|---|---|---|---|---|---|---|---|---|---|---|---|
| B5701 | 3VRJ | 1.00 | N | G | 62 | N | 66 | L | 163 | Apr. 11, 2012 | May 30, 2012 | *Jul. 4, 2012 | X-RAY DIFFRACTION | HLA-B*57:01-LTTKLTNTNI in complex with abacavir |
| B5701 | 3WUW | 2.00 | N | G | 62 | N | 66 | L | 163 | May 8, 2014 | May 28, 2014 | | X-RAY DIFFRACTION | KIR3DL1 in complex with HLA-B 57:01.I80T |
| B5701 | 3X11 | 2.15 | N | G | 62 | N | 66 | L | 163 | Oct. 24, 2014 | Dec. 24, 2014 | *Apr. 8, 2015 | X-RAY DIFFRACTION | Crystal structure of HLA-B*5701.I80N.I_82R.R83G |
| B5701 | 3X12 | 1.80 | N | G | 62 | N | 66 | L | 163 | Oct. 24, 2014 | Dec. 24, 2014 | *Apr. 8, 2015 | X-RAY DIFFRACTION | Crystal structure of HLA-B*5701.I80N |
| B5701 | 5B38 | 2.30 | N | G | 62 | N | 66 | L | 163 | Feb. 12, 2016 | Mar. 30, 2016 | *Apr. 20, 2016 | X-RAY DIFFRACTION | KIR3DL1*005 in complex with HLA-B*57:01 |
| B5701 | 5B39 | 2.50 | N | G | 62 | N | 66 | L | 163 | Feb. 12, 2016 | Mar. 30, 2016 | *Apr. 20, 2016 | X-RAY DIFFRACTION | KIR3DL1*055 in complex with HLA-B*57:01 |
| B5801 | 5INC | 2.88 | N | G | 62 | N | 66 | L | 163 | Mar. 7, 2016 | Oct. 5, 2016 | *Oct. 19, 2016 | X-RAY DIFFRACTION | Crystal structure of HLA-B*5801, a protective HLA allele for HIV-1 infection |
| B5801 | 5IND | 2.13 | N | G | 62 | N | 66 | L | 163 | Mar. 7, 2016 | Oct. 5, 2016 | *Oct. 19, 2016 | X-RAY DIFFRACTION | Crystal structure of HLA-B*5801, a protective HLA allele for HIV-1 infection |

REFERENCES

1. Callahan M K, Postow M A, Wolchok J D. Targeting T Cell Co-receptors for Cancer Therapy. *Immunity.* 2016; 44(5):1069-1078. doi:10.1016/j.immuni.2016.04.023.
2. Gibney G T, Weiner L M, Atkins M B. Predictive biomarkers for checkpoint inhibitor-based immunotherapy. *Lancet Oncol.* 2016; 17(12):e542-e551. doi: 10.1016/S1470-2045(16)30406-5.
3. Snyder A, Makarov V, Merghoub T, et al. Genetic basis for clinical response to CTLA-4 blockade in melanoma. *N Engl J Med.* 2014; 371(23):2189-2199. doi:10.1056/NEJMoa1406498.
4. Van Allen E M, Miao D, Schilling B, et al. Genomic correlates of response to CTLA-4 blockade in metastatic melanoma. *Science.* 2015; 350(6257):207-211. doi: 10.1126/science.aad0095.
5. Rizvi N A, Hellmann M D, Snyder A, et al. Cancer immunology. Mutational landscape determines sensitivity to PD-1 blockade in non-small cell lung cancer. *Science.* 2015; 348(6230):124-128. doi:10.1126/science.aaa1348.
6. Rosenberg J E, Hoffman-Censits J, Powles T, et al. Atezolizumab in patients with locally advanced and metastatic urothelial carcinoma who have progressed following treatment with platinum-based chemotherapy: a single-arm, multicentre, phase 2 trial. *Lancet.* 2016; 387(10031)1909-1920. doi:10.1016/50140-6736(16)00561-4.
7. Hugo W, Zaretsky J M, Sun L, et al. Genomic and Transcriptomic Features of Response to Anti-PD-1 Therapy in Metastatic Melanoma. *Cell.* 2016; 165(1):35-44. doi:10.1016/j.cell.2016.02.065.
8. Cheng D T, Mitchell T N, Zehir A, et al. Memorial Sloan Kettering-Integrated Mutation Profiling of Actionable Cancer Targets (MSK-IMPACT): A Hybridization Capture-Based Next-Generation Sequencing Clinical Assay for Solid Tumor Molecular Oncology. *J Mol Diagn.* 2015; 17(3):251-264. doi:10.1016/j.jmoldx.2014.12.006.
9. Frampton G M, Fabrizio D, Chalmers Z R, et al. Assessment of tumor mutation burden from >60,000 clinical cancer patients using comprehensive genomic profiling. In: *J Clin Oncol*, Vol 34. 2016. 11558
10. Johnson D B, Frampton G M, Rioth M J, et al. Targeted Next Generation Sequencing Identifies Markers of Response to PD-1 Blockade. *Cancer Immunol Res.* 2016; 4(14959-967. doi:10.1158/2326-6066 CIR-16-0143.
11. Zehir A, Benayed R, Shah R H, et al. Mutational Landscape of Metastatic Cancer Revealed from Prospective Clinical Sequencing of 10,000 Patients. *Nat Med.* Submitted.
12. Alexandrov L B, Nik-Zainal S, Wedge D C, et al. Signatures of mutational processes in human cancer. *Nature.* 2013; 500(7463):415-421. doi:10.1038/nature12477.
13. Schumacher T N, Schreiber R D. Neoantigens in cancer immunotherapy. *Science.* 2015; 348(6230):69-74. doi: 10.1126/science.aaa4971.
14. Bouffet E, Larouche V, Campbell B B, et al. Immune Checkpoint Inhibition for Hypermutant Glioblastoma Multiforme Resulting From Germline Biallelic Mismatch Repair Deficiency. *J Clin Oncol.* 2016; 34(19):2206-2211. doi:10.1200/JCO.2016.66.6552.
15. McGranahan N, Furness A J S, Rosenthal R, et al. Clonal neoantigens elicit T cell immunoreactivity and sensitivity to immune checkpoint blockade. *Science.* 2016; 351(6280):1463-1469. doi:10.1126/science.aaf1490.
16. Borghaei H, Paz-Ares L, Horn L, et al. Nivolumab versus Docetaxel in Advanced Nonsquamous Non-Small-Cell Lung Cancer. *N Engl J Med.* 2015; 373(17):1627-1639. doi:10.1056/NEJMoa1507643.
17. Ross D S, Zehir A, Cheng D T, et al. Next-Generation Assessment of Human Epidermal Growth Factor Receptor 2 (ERBB2) Amplification Status: Clinical Validation in the Context of a Hybrid Capture-Based, Comprehensive Solid Tumor Genomic Profiling Assay. *J Mol Diagn.* 2017; 19(2):244-254. doi:10.1016/j.jmoldx.2016.09.010
18. Dyck L, Mills, K H G. Immune Checkpoints and their Inhibition in Cancer and Infectious Diseases. *Eur J Immunol.* 2017; 47(5):765-779. doi: 10.1002/eji.201646875.
19. Riley J L. PD-1 Signaling in Primary T Cells. *Immunol Rev.* 2009; 229(1):114-125. doi: 10.1111/j.1600-065X.2009.00767.x.
20. Larkin A, Chiarion-Sileni V, Gonzalez E, et al. Combined Nivolumab and Ipilimumab or Monotherapy in Untreated Melanoma. *N Engl J Med* 2015; 373(1).23-34. doi: 10.1056/NEJMoa1504030.
21. H. I. V. C. S. International et al., The major genetic determinants of HIV-1 control affect HLA class I peptide presentation. *Science* 330, 1551-1557 (2010).
22. M. Carrington et al., HLA and HIV-1: heterozygote advantage and B*35-Cw*04 disadvantage. *Science* 283, 1748-1752 (1999).
23. J. Fellay et al., A whole-genome association study of major determinants for host control of HIV-1. *Science* 317, 944-947 (2007).
24. X. J. Gao et al., Effect of a single amino acid change in MHC class I molecules on the rate of progression to AIDS. *New England Journal of Medicine* 344, 1668-1675 (2001).
25. E. Trachtenberg et a, Advantage of rare HLA supertype in HIV disease progression. *Nat Med* 9, 928-935 (2003).
26. P. J. R. Goulder, B. D. Walker, HIV and HLA Class I: An Evolving Relationship. *Immunity* 37, 426-440 (2012).
27. A. V. S. Hill et al., Common West African Hla Antigens Are Associated with Protection from Severe Malaria, *Nature* 352, 595-600 (1991).
28. P. Kiepiela et al., Dominant influence of HLA-B in mediating the potential co-evolution of HIV and HLA. *Nature* 432, 769-774 (2004).
29. T. J. T. Pl., *HLA and disease associations.* (Springer Science & Business Media, 2012).
30. P. Parham, T. Ohta, Population biology of antigen presentation by MHC class I molecules. *Science* 272, 67-74 (1996).
31. D. Chowell et al., TCR contact residue hydrophobicity is a hallmark of immunogenic CD8(+) T cell epitopes. *Proceedings of the National Academy of Sciences of the United States of America* 112, E1754-E1762 (2015).
32. P. C. Doherty, R. M. Zinkernagel, A biological role for the major histocompatibility antigens. *Lancet* 1, 1406-1409 (1975).
33. M. M. Gubin et al., Checkpoint blockade cancer immunotherapy targets tumour-specific mutant antigens. *Nature* 515, 577-581 (2014).
34. E. Tran et al., Immunogenicity of somatic mutations in human gastrointestinal cancers. *Science* 350, 1387-1390 (2015).
35. E. Tran et al., T-Cell Transfer Therapy Targeting Mutant KRAS in Cancer. *N Engl J Med* 375, 2255-2262 (2016).
36. N. Riaz, J. J. Havel, V. Makarov, et. al., T. A. Chan, Immunogenomic Dissection of Tumor and Microenvironment Evolution during Immunotherapy with Nivolumab. *In Review,* (2017).

37. K. Kiyotani, T. H. Mai, Y. Nakamura, Comparison of exome-based HLA class I genotyping tools: identification of platform-specific genotyping errors. *J Hum Genet*, (2016).
38. S. A. Shukla et al., Comprehensive analysis of cancer-associated somatic mutations in class I HLA genes. *Nat Biotechnol* 33, 1152-1158 (2015).
39. H. Cao et al., An integrated tool to study MHC region: accurate SNV detection and HLA genes typing in human MHC region using targeted high-throughput sequencing. *PLoS One* 8, e69388 (2013).
40. A. Szolek et al., OptiType: precision HLA typing from next-generation sequencing data. *Bioinformatics* 30, 3310-3316 (2014).
41. D. M. Hyman et al., Precision medicine at Memorial Sloan Kettering Cancer Center: clinical next-generation sequencing enabling next-generation targeted therapy trials. *Drug Discov Today* 20, 1422-1428 (2015).
42. N. Riaz et al., Recurrent SERPINB3 and SERPINB4 mutations in patients who respond to anti-CTLA4 immunotherapy. *Nature Genetics* 48, 1327-1329 (2016).
43. M. A. DePristo et al., A framework for variation discovery and genotyping using next-generation DNA sequencing data. *Nature Genetics* 43, 491-+(2011).
44. H. Li, R. Durbin, Fast and accurate short read alignment with Burrows-Wheeler transform. *Bioinformatics* 25, 1754-1760 (2009).
45. A. McKenna et al., The Genome Analysis Toolkit: a MapReduce framework for analyzing next-generation DNA sequencing data. *Genome Res* 20, 1297-1303 (2010).
46. K. Cibulskis et al., Sensitive detection of somatic point mutations in impure and heterogeneous cancer samples. *Nature Biotechnology* 31, 213-219 (2013).
47. D. C. Koboldt et al., VarScan 2: Somatic mutation and copy number alteration discovery in cancer by exome sequencing. *Genome Research* 22, 568-576 (2012).
48. D. E. Larson et al., SomaticSniper: identification of somatic point mutations in whole genome sequencing data. *Bioinformatics* 28, 311-317 (2012).
49. C. T. Saunders et al., Strelka: accurate somatic small-variant calling from sequenced tumor-normal sample pairs. *Bioinformatics* 28, 1811-1817 (2012).
50. Z. R. Chalmers et al., Analysis of 100,000 human cancer genomes reveals the landscape of tumor mutational burden. *Genome Med* 9, 34 (2017).
51. R. L. Shen, V. E. Seshan, FACETS: allele-specific copy number and clonal heterogeneity analysis tool for high-throughput DNA sequencing. *Nucleic Acids Research* 44, (2016),
52. W. Humphrey, A. Dalke, K. Schulten, VMD: Visual molecular dynamics. *J Mol Graph* Model 14, 33-38 (1996).
53. P. Liu, X. H. Huang, R. H. Zhou, B. J. Berne, Observation of a dewetting transition in the collapse of the melittin tetramer. *Nature* 437, 159-162 (2005).
54. Y. Tu et al., Destructive extraction of phospholipids from *Escherichia coli* membranes by graphene nanosheets. *Nat Nanotechnol* 8, 594-601 (2013).
55. R. H. Zhou, X. H. Huang, C. J. Margulis, B. J. Berne, Hydrophobic collapse in multidomain protein folding. *Science* 305, 1605-1609 (2004).
56. J. C. Phillips et al., Scalable molecular dynamics with NAMD. *J Comput Chem* 26, 1781-1802 (2005).
57. M. J. Abraham, Performance enhancements for GROMACS nonbonded interactions on BlueGene. *J Comput Chem* 32, 2041-2046 (2011).
58. M. R. Thursz, H. C. Thomas, B. M. Greenwood, A. V. Hill, Heterozygote advantage for HLA class-II type in hepatitis B virus infection. *Nat Genet* 17, 11-12 (1997).
59. D. Snary, C. J. Barnstable, W. F. Bodmer, M. J. Crumpton, Molecular structure of human histocompatibility antigens: the HLA-C series. *Eur J Immunol* 7, 580-585 (1977).
60. S. G. Marsh, Parham, P. and Barber, L. D., *The HLA factsbook*. (Academic Press, 1999).
61. M. R. Schaefer et al., A novel trafficking signal within the HLA-C cytoplasmic tail allows regulated expression upon differentiation of macrophages. *J Immunol* 180, 7804-7817 (2008).
62. N. Anfossi et al., Coordinated expression of Ig-like inhibitory MHC class I receptors and acquisition of cytotoxic function in human CD8+ T cells. *J Immunol* 173, 7223-7229 (2004).
63. D. S. Chen, I. Mellman, Elements of cancer immunity and the cancer-immune set point. *Nature* 541, 321-330 (2017).
64. T. N. Schumacher, R. D. Schreiber, Neoantigens in cancer immunotherapy. *Science* 348, 69-74 (2015).
65. D. T. Le et al., PD-1 Blockade in Tumors with Mismatch-Repair Deficiency. *N Engl J Med* 372, 2509-2520 (2015).
66. N. Aptsiauri et al., MHC class I antigens and immune surveillance in transformed cells. *Int Rev Cytol* 256, 139-189 (2007).
67. A. Sette, J. Sidney, Nine major HLA class I supertypes account for the vast preponderance of HLA-A and -B polymorphism. *Immunogenetics* 50, 201-212 (1999).
68. J. Sidney, B. Peters, N. Frahm, C. Brander, A. Sette, HLA class I supertypes: a revised and updated classification. *BMC Immunol* 9, 1 (2008).
69. M. Dibrino et al., Identification of the Peptide Binding Motif for Hla-B44, One of the Most Common Hla-B Alleles in the Caucasian Population. *Biochemistry-Us* 34, 10130-10138 (1995).
70. J. B. Szender et al., HLA superfamily assignment is a predictor of immune response to cancer testis antigens and survival in ovarian cancer. *Gynecol Oncol* 142, 158-162 (2016).
71. H. Pearson et al., MEC class I-associated peptides derive from selective regions of the human genome. *Journal of Clinical Investigation* 126, 4690-4701 (2016).
72. Jordan, E. J. et al. Prospective Comprehensive Molecular Characterization of Lung Adenocarcinomas for Efficient Patient Matching to Approved and Emerging Therapies. *Cancer Discov* 7, 596-609 (2017).
73. Janjigian, Y. Y. et al. Genetic Predictors of Response to Systemic Therapy in Esophagogastric Cancer. *Cancer Discov* (2017). doi:10.1158/2159-8290.CD-17-0787
74. Hellmann, M. D. et al. Molecular determinants of response and resistance to anti-PD-(L)1 blockade in patients with NSCLC profiled with targeted next-generation sequencing (NGS). *J. Clin. Oncol.* 35, 9015-9015 (2017).
75. Chowell, D. et al. Patient HLA class I genotype influences cancer response to checkpoint blockade immunotherapy. *Science* 62, eaao4572 (2017).
76. Balachandran, V. P. et al. Identification of unique neoantigen qualities in long-term survivors of pancreatic cancer. *Nature* 551, 512-516 (2017).
77. Rooney, M. S., Shukla, S. A., Wu, C. J., Getz, G. & Hacohen, N. Molecular and genetic properties of tumors associated with local immune cytolytic activity. *Cell* 160, 48-61 (2015).

78. Topalian, S. L. et al. Safety, activity, and immune correlates of anti-PD-1 antibody in cancer. *N Engl J Med* 366, 2443-2454 (2012).
79. Segal, N. H. et al. Epitope landscape in breast and colorectal cancer. *Cancer Res.* 68, 889-892 (2008).
80. Verdegaal, E. M. E. et al. Neoantigen landscape dynamics during human melanoma-T cell interactions. *Nature* 536, 91-95 (2016).

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method comprising:
   administering immunotherapy to a subject with a tumor that displays a tumor mutational load, wherein the tumor mutational load, when measured after the subject has received immunotherapy, is above a threshold that has been correlated with a statistically significant probability of responding to immunotherapy, wherein the tumor mutational load threshold is selected from the group consisting of:

| Cancer Type | Threshold |
| --- | --- |
| Bladder Cancer | About 7 to about 27 |
| Breast Cancer | About 1 to about 14 |
| Esophagogastric Cancer | About 1 to about 21 |
| Glioma | About 1 to about 15 |
| Head and Neck Cancer | About 1 to about 18 |
| Melanoma | About 1 to about 31 |
| Non-Small Cell Lung Cancer | About 1 to about 29 and |
| Renal Cell Carcinoma | About 1 to about 12 | and wherein the administered immunotherapy is one or more of a PD-1 or PD-L1 blockade therapy or a CTLA-4 blockade therapy.

2. The method of claim 1, wherein the tumor is a solid type tumor selected from the group consisting of bladder cancer, breast cancer, esophagogastric cancer, glioma, head and neck cancer, melanoma, non-small cell lung cancer, renal cell carcinoma.

3. The method of claim 1, wherein the immunotherapy is an antibody or antigen binding fragment thereof.

4. The method of claim 1, wherein the immunotherapy is a combination of one or more of PD-1 or PD-L1 blockade therapy and CTLA-4 blockade therapy.

5. The method of claim 1, wherein the immunotherapy is selected from the group comprising of atezolizumab, avelumab, durvalumab, ipilimumab, nivolumab, pembrolizumab, or tremelimumab, and combinations therein.

6. The method of claim 1, wherein the displayed tumor mutational load is or was determined by use of a targeted sequence panel.

7. The method of claim 1, wherein the tumor mutational load is measured by next-generation sequencing.

8. The method of claim 1, wherein the tumor mutational load is measured by Mutation Profiling of Actionable Cancer Targets (MSK-IMPACT).

9. The method of claim 1, wherein the immunotherapy is demonstrated to have a statistically significant probability of improving overall survival when administered to a population displaying a tumor mutational load above the threshold.

10. A method comprising: administering immunotherapy with an immune checkpoint modulator to a subject who displays HLA class I heterozygosity in a tumor, wherein the immunotherapy is one or more of a PD-1 or PD-L1 blockade therapy or a CTLA-4 blockade therapy.

11. The method of claim 10, wherein the subject displays heterozygosity at one or more HLA class I loci.

12. The method of claim 10, wherein the HLA class I heterozygosity is determined by sequencing.

13. A method comprising:
    administering immunotherapy to a subject with a tumor that displays a tumor mutational load above a threshold that has been correlated with a statistically significant probability of responding to immunotherapy and displays HLA class I heterozygosity, wherein the tumor mutational load threshold is selected from the groups consisting of:

| Cancer Type | Threshold |
| --- | --- |
| Bladder Cancer | About 7 to about 27 |
| Breast Cancer | About 1 to about 14 |
| Esophagogastric Cancer | About 1 to about 21 |
| Glioma | About 1 to about 15 |
| Head and Neck Cancer | About 1 to about 18 |
| Melanoma | About 1 to about 31 |
| Non-Small Cell Lung Cancer | About 1 to about 29 and |
| Renal Cell Carcinoma | About 1 to about 12 | and wherein the immunotherapy is a combination of one or more of a PD-1 blockade therapy and a CTLA-4 blockade therapy.

14. The method of claim 13, wherein the HLA class I heterozygosity is determined by sequencing.

15. The method of claim 13, wherein the immunotherapy is administration of an immune checkpoint modulator.

16. The method of claim 13, wherein the tumor mutational load is measured by Mutation Profiling of Actionable Cancer Targets (MSK-IMPACT).

* * * * *